(12) United States Patent
Chong

(10) Patent No.: US 9,115,094 B2
(45) Date of Patent: Aug. 25, 2015

(54) BIMODAL LIGANDS WITH MACROCYCLIC AND ACYCLIC BINDING MOIETIES, COMPLEXES AND COMPOSITIONS THEREOF, AND METHODS OF USING

(75) Inventor: Hyun-soon Chong, Chicago, IL (US)

(73) Assignee: THE UNITED STATES OF AMERICA, NATIONAL INSTITUTES OF HEALTH (NIH), U.S. DEPT. OF HEALTH AND HUMAN SERVICES (DHHS), Washington, DC (US)

( * ) Notice: Subject to any disclaimer, the term of this patent is extended or adjusted under 35 U.S.C. 154(b) by 622 days.

(21) Appl. No.: 12/806,754

(22) Filed: Aug. 20, 2010

(65) Prior Publication Data

US 2010/0322855 A1    Dec. 23, 2010

Related U.S. Application Data

(63) Continuation-in-part of application No. PCT/US2009/034902, filed on Feb. 23, 2009.

(60) Provisional application No. 61/066,636, filed on Feb. 22, 2008.

(51) Int. Cl.
*C07D 255/02* (2006.01)
*A61K 49/10* (2006.01)

(52) U.S. Cl.
CPC ............ *C07D 255/02* (2013.01); *A61K 49/106* (2013.01)

(58) Field of Classification Search
CPC ............................ C07D 255/02; A61K 49/106
USPC .......... 424/1.11, 1.65, 9.3, 9.36, 9.361, 9.364, 424/9.365
See application file for complete search history.

(56) References Cited

U.S. PATENT DOCUMENTS

| | | | |
|---|---|---|---|
| 5,554,749 A * | 9/1996 | Wallace et al. ............... | 540/474 |
| 6,207,858 B1 | 3/2001 | Chinn et al. | |
| 6,875,866 B2 | 4/2005 | Dahanukar et al. | |
| 7,081,452 B2 * | 7/2006 | Brechbiel et al. ............. | 514/183 |
| 7,163,935 B2 | 1/2007 | Brechbiel et al. | |
| 7,368,100 B2 | 5/2008 | Brechbiel et al. | |
| 7,563,433 B2 | 7/2009 | McBride et al. | |
| 7,597,876 B2 | 10/2009 | McBride et al. | |
| 7,799,934 B2 | 9/2010 | Antilla et al. | |
| 7,993,626 B2 | 8/2011 | McBride et al. | |
| 8,153,101 B2 | 4/2012 | McBride et al. | |
| 2003/0108486 A1 | 6/2003 | Platzek et al. | |
| 2009/0155166 A1 | 6/2009 | McBride et al. | |
| 2011/0110854 A1 | 5/2011 | McBride et al. | |

FOREIGN PATENT DOCUMENTS

| | | | | |
|---|---|---|---|---|
| DE | 3625417 A1 * | 2/1988 | ........... | C07D 257/02 |
| DE | 36 25 417 C2 | 10/1998 | | |
| DE | 198 49 465 A1 | 4/2000 | | |
| EP | 0628316 * | 6/1993 | ............. | A61K 49/00 |
| WO | WO 01/52898 * | 7/2001 | ............. | A61K 47/48 |

OTHER PUBLICATIONS

Cacheris et al., Inorg. Chem., 1987, 26, p. 958-960.*
Chatterton et al., Angew. Chem., 2005, 117, p. 7767-7770.*
Hyun-Soon Chong et al., "Novel synthetic ligands for targeted PET imaging and radiotherapy of copper," Bioorganic & Medical Chemistry Letters, Sep. 2007, vol. 17, No. 22, pp. 6107-6110.
Noah Birch et al., "Expert Opinion—Iron chelators as therapeutic iron depletion agents," Expert Opin. Ther. Patents, 2006, vol. 16, No. 11, pp. 1533-1556.
Hyun-Soon Chong et al., "A novel cholic acid-based contrast enhancement agent for targeted MRI," Bioorganic & Medicinal Chemistry Letters, Jan. 18, 2008, pp. 2505-2508.

* cited by examiner

*Primary Examiner* — Michael G Hartley
*Assistant Examiner* — Leah Schlientz
(74) *Attorney, Agent, or Firm* — Pauley Erickson & Kottis

(57) ABSTRACT

Substituted 1,4,7-triazacyclononane-N,N',N"-triacetic acid and 1,4,7,10-tetraazacyclcododecane-N,N',N",N'"-tetraacetic acid compounds with a pendant amino or hydroxyl group, metal complexes thereof, compositions thereof, and methods of making and use in diagnostic imaging and treatment of cellular disorders.

25 Claims, 7 Drawing Sheets

BIMODAL LIGANDS WITH MACROCYCLIC AND ACYCLIC BINDING MOIETIES, COMPLEXES AND COMPOSITIONS THEREOF, AND METHODS OF USING

CROSS REFERENCE TO RELATED APPLICATION

This patent application is a continuation-in-part of PCT International Patent Application PCT/US2009/034902, internationally filed on 23 Feb. 2009, which claims priority to, and the benefit of, U.S. Provisional Patent Application Ser. No. 61/066,636, filed on 22 Feb. 2008. The co-pending PCT International Patent Application is hereby incorporated by reference herein in its entirety and is made a part hereof, including but not limited to those portions which specifically appear hereinafter.

GOVERNMENT SUPPORT CLAUSE

This invention was made with government support under K22CA102637 and RO1CA112503 awarded by the National Institutes of Health. The government has certain rights in the invention.

BACKGROUND OF THE INVENTION

This invention pertains to substituted 1,4,7-triazacyclononane-N,N',N''-triacetic acid and 1,4,7,10-tetraazacyclcododecane-N,N',N'',N'''-tetraacetic acid compounds with a pendant donor groups, conjugates and metal complexes thereof, compositions thereof and methods of using same.

Radioimmunotherapy (RIT), magnetic resonance imaging (MRI), positron emission tomography (PET), and iron depletion therapy (IDT) are promising techniques for targeted treatment or imaging of numerous diseases including cancers. The success of clinical applications of RIT, MRI, and PET depends heavily on the performance of a synthetic ligand that can bind either radioactive or non-radioactive metals which can be very toxic when deposited in normal tissues in vivo, causing life-threatening side effects.

RIT, an antibody-targeted radiation therapy, holds great promise for treatment of many diseases including cancers, evidenced by Zevalin® (1B4M-DTPA) therapy. However, active clinical exploration of RIT using a variety of antibodies and cytotoxic radionuclides has been challenged by the absence of adequate bifunctional ligands that can bind the radionuclides with clinically acceptable kinetics and in vivo stability. The currently available bifunctional ligands, C-DOTA and 1B4M-DTPA have limitations: C-DOTA forms a stable complex with metals but with clinically unacceptable slow complexation kinetics, while 1B4M-DTPA rapidly forms a less stable complex.

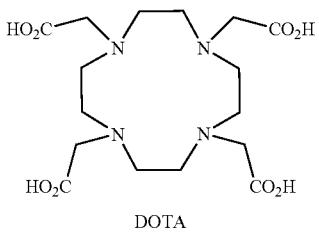

DOTA

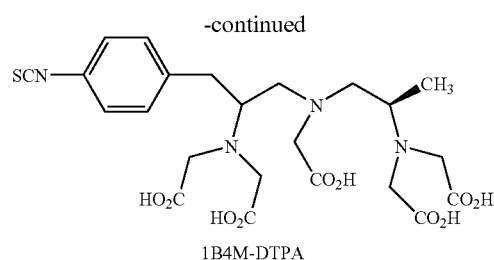

1B4M-DTPA $^{64}$Cu is proven to be effective for PET. Bifunctional ligands possess both binding moieties of Cu(II) and a functional group for conjugation to a targeting moiety are required for PET. Significant research effort has been made to develop $^{64}$Cu-based radiopharmaceuticals. However, less progress has been made on development of clinically viable bifunctional ligand to tightly and rapidly hold the short-lived metal.

MRI is a powerful diagnostic medical tool that provides non-invasive and high resolution imaging for a variety of applications. A number of Gd(III) complexes such as Gd(DOTA) are clinically approved for use in MRI. However, most contrast agents have non-specific extracellular distribution and the disadvantages of low relaxivity, low tissue specificity, and rapid clearance. Considerable research efforts have been directed toward developing safe Gd(III)-based MR contrast agents with high tissue specificity and sensitivity. Development of bifunctional ligands with a functional unit for conjugation to a targeting moiety that can tightly sequester Gd(III) is required for targeted MRI with high sensitivity and specificity.

The enhanced requirement of iron in cancer cells as compared to normal cells makes iron depletion using iron chelators targeting transferrin receptors or other proteins involved in iron uptake one of the most efficient strategies to prevent or suppress the rapid proliferation of cancerous cells. Iron chelators are reported to cause cellular iron depletion and exhibit potent cytotoxic activities on diverse cancer cells. Bifunctional iron chelator that can be linked to many peptides and monoclonal antibodies targeting to various types of tumor cells is a critical component to generate the antitumor conjugates for targeted iron depletion tumor therapy which has been little explored.

The invention provides such compounds. These and other objects and advantages, as well as additional inventive features, will be apparent from the description of the invention provided herein.

SUMMARY OF THE INVENTION

The present invention provides NETA and DEPA analogues and metal ion complexes thereof, as well as conjugates of the compounds and complexes with biomolecules and targeting moieties. One such analogue, NE3TA contains four amines and three carboxylates as potential donor groups. NE3TA-Bn is a heptadentate ligand with a benzyl group which can be further modified for conjugation to a targeting moiety. NE3TA and NE3TA-Bn are converted to a bifunctional ligand C-NE3TA and N-NE3TA, respectively. Further analogues of this invention, hexadentate NBEA and NBPA, possess three amines, two carboxylates, and a hydroxyl group as the donor groups. The design of NBEA and NBPA based on the size-fit between the macrocyclic cavity in NBEA and NBPA and the ionic radius of Cu(II) and Ga(III) provides enhanced complex stability with radioisotope. NBEA and NBPA can produce a neutral Cu(II) complex that would have an advantage of less protein interaction and a potentially more favorable in vivo tissue distribution. NBPA possesses a longer propylene bridge between one of the amino groups and the hydroxyl group compared to the analogous ethylene bridged ligand, NBEA. A bifunctional version of NETA, 3P-2C-NETA contains a functional unit for conjugation to a biomolecule. DOTA and DTPA analogues are the most frequently explored polyaminocarboxylates in RIT. DOTA forms a stable complex with metals but with relatively slow complexation kinetics, while DTPA rapidly bind to a metal but forms a less stable metal complex. 3P-2C-NETA forms a stable complex with a metal by integration of the complexation property of macrocyclic DOTA and acyclic DTPA while being conjugated to a biomolecule. DEPA and its bifunctional version 3P-2C-DEPA are designed for complexing metals having a larger ionic radii such as Lu(III), Bi(III), and Ac(III).

The present invention provides a compound of formula (I):

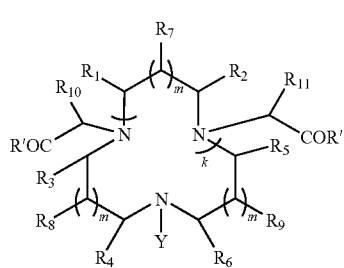

(I)

wherein: R' independently is OH, NH$_2$, or OR", wherein R" independently is alkyl, tert-butyl, allyl, or benzyl; k is 1 or 2; m is 0 or 1; Y is a structure of formula (a-1), (a-2), (a-3), or (a-4):

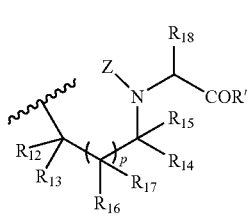

(a-1)

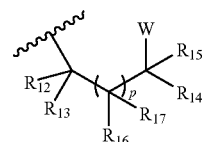

(a-2)

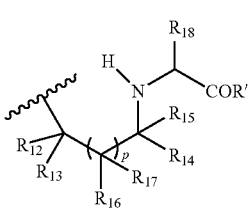

(a-3)

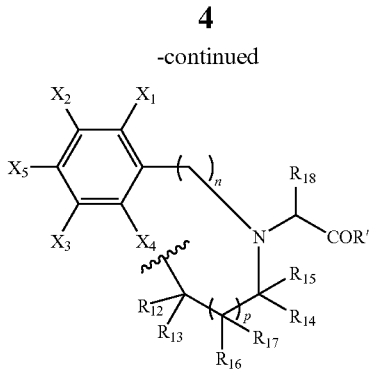

(a-4)

where p is 0 or 1; n is 1 to 10; W is OH, SH, or NZ$_2$; each of R$^{1-18}$ and Z independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, hydroxy, carboxyl, carboxyalkyloxy, amino, carboxylic acid, or holoalkylamido, aldehyde, ester, amido, tosyl, phthalimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, a protecting group, or a group of formula (a-5), (a-6), or (a-7);

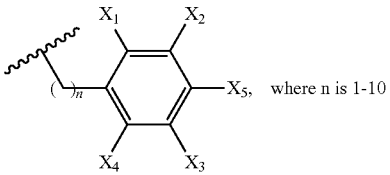

(a-5), where n is 1-10

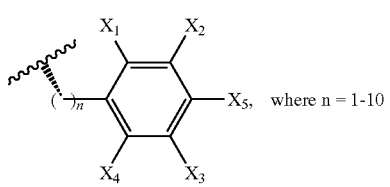

(a-6), where n = 1-10

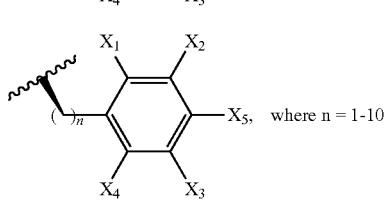

(a-7), where n = 1-10 and X is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydro, alkylamido, holoalkylamido, an ester containing group, an carbonyl containing group, an amide containing group, a thioamide containing group, or an amino acid-containing group;

provided that wherein m is 0, k is 1, R' is OH, Y is (a-1), Z is carboxyalkyl, then one of R$^{14-15}$ is not a compound of the formula of (a-5), (a-6), or (a-7), at least one of R$^{12-17}$ is not a hydrogen, or one of R$^{1-11}$ is a compound of the formula (a-5), (a-6), or (a-7). In one embodiment at least one of R$^{1-9}$ or R$^{12-17}$ forms a cycloalkyl with a neighboring carbon.

The present invention further provides a compound of formula (II):

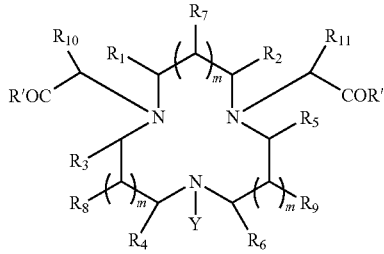
(II)

wherein: R' independently is OH, NH$_2$, or OR", wherein R" independently is alkyl, tert-butyl, allyl, or benzyl; m is 0 or 1; Y is a structure of formula (a-1), (a-2), (a-3), or (a-4):

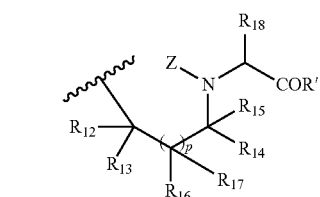
(a-1)

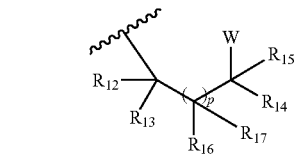
(a-2)

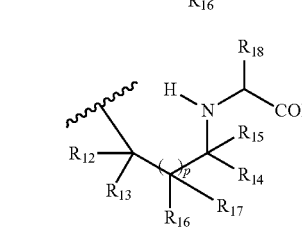
(a-3)

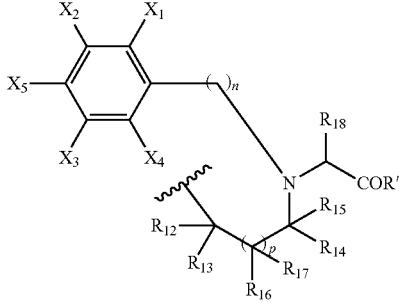
(a-4)

where p is 0 or 1; n is 1 to 10; W is OH, SH, or NZ$_2$; each of R$^{1-18}$ and Z independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, imidazolylalkyl, pyridiylalkyl, benzothiophenylalkyl, thiophenylalkyl, thioalkyl, thioaryl, thiobenzyl, hydroxy, carboxyl, carboxyalkyloxy, amino, carboxylic acid, or holoalkylamido, aldehyde, ester, amido, tosyl, phthalimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, a protecting group, or a group of formula (a-5), (a-6), or (a-7);

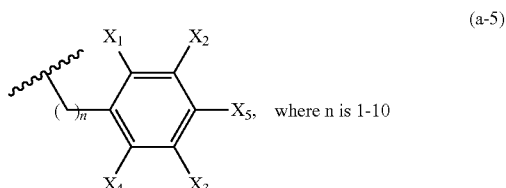
(a-5), where n is 1-10

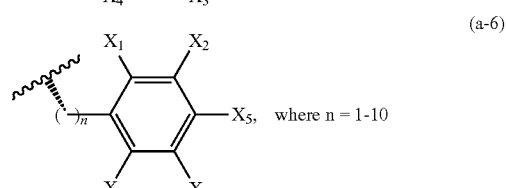
(a-6), where n = 1-10

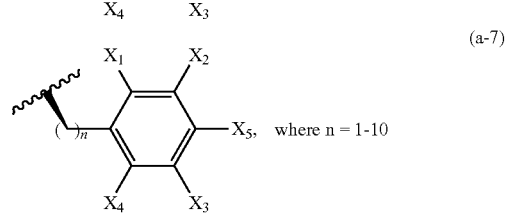
(a-7), where n = 1-10 and X is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydro, alkylamido, holoalkylamido, an ester containing group, an carbonyl containing group, an amide containing group, a thioamide containing group, or an amino acid-containing group;

provided that wherein m is 0, k is 1, R' is OH, Y is (a-1), Z is carboxyalkyl, then one of R$^{14-15}$ is not a compound of the formula of (a-5), (a-6), or (a-7), at least one of R$^{12-17}$ is not a hydrogen, or one of R$^{1-11}$ is a compound of the formula (a-5), (a-6), or (a-7).

The present invention further provides a compound of formula (III):

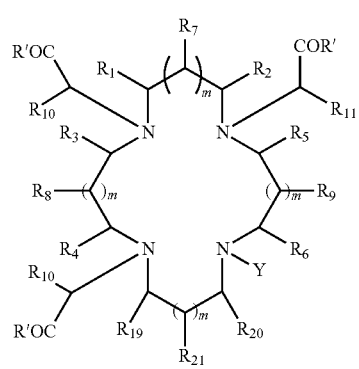
(III)

wherein: R' independently is OH, NH$_2$, or OR", wherein R" independently is alkyl, tert-butyl, allyl, or benzyl; m is 0 or 1; Y is a structure of formula (a-1), (a-2), (a-3), or (a-4):

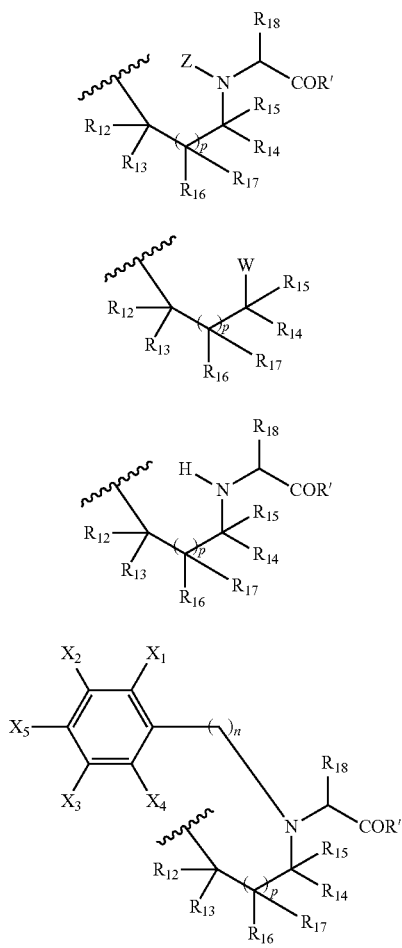

(a-1)

(a-2)

(a-3)

(a-4)

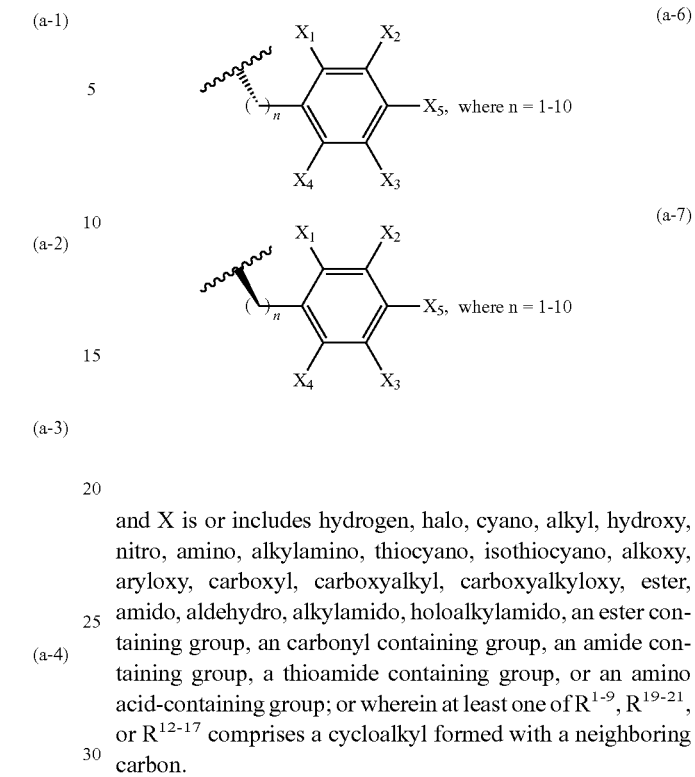

(a-6)

(a-7)

where p is 0 or 1; n is 1 to 10; W is OH, SH, or $NZ_2$; each of $R^{1-21}$ and Z independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, hydroxy, carboxyl, carboxyalkyloxy, amino, carboxylic acid, or holoalkylamido, aldehyde, ester, amido, tosyl, phthalimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, a protecting group, or a group of formula (a-5), (a-6), or (a-7);

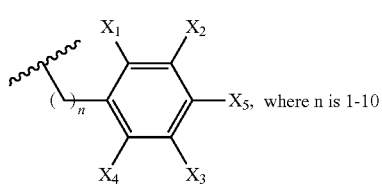

(a-5)

and X is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydro, alkylamido, holoalkylamido, an ester containing group, an carbonyl containing group, an amide containing group, a thioamide containing group, or an amino acid-containing group; or wherein at least one of $R^{1-9}$, $R^{19-21}$, or $R^{12-17}$ comprises a cycloalkyl formed with a neighboring carbon.

Still further provided is a complex comprising the compound of formula (I), (II), or (III) and a metal ion, such as Ac, Bi, Pb, Y, Mn, Cr, Fe, Co, Zn, Ni, Tc, Gd, In, Ga, Cu, Re, Sm, Pm, Ho, Zr, a lanthanide, and an actinide, or a radioactive isotope of carbon, nitrogen, iodine, fluorine, oxygen, or helium.

The invention also provides a conjugate comprising any of the above compounds or complexes and a biomolecule or a targeting moiety, preferably substituted for or at X in the above formulas. Exemplary biomolecules include hormones, bile acids, amino acids, peptides, peptidomimetics, proteins, deoxyribonucleic acids (DNA), ribonucleic acids (RNA), lipids, albumin, receptor molecules, receptor binding molecules, hapten, monoclonal antibodies, polyclonal antibodies, peptides, aptamers, folic acid, estrogens, or transferring.

A pharmaceutical composition comprising a pharmaceutically acceptable carrier and one of the above compounds, complexes, or conjugates thereof is also provided.

A method for obtaining a diagnostic image of a host is further provided. The method comprises administering to the host a compound, complex, or conjugate of formula (I), (II), or (III), in an amount effective to provide an image; and exposing the host to an energy source, whereupon a diagnostic image of the host is obtained.

Still further provided is a method for treating a cellular disorder in a mammal. The method comprises administering to the mammal a compound, conjugate, or complex of formula (I), (II), or (III), in an amount effective to treat the cellular disorder, whereupon the cellular disorder in the mammal is treated.

The invention also provides a method of preparing the compounds of formula (I), (II), or (III) that includes combining a compound of formula (Ib-1) or (Ib-2):

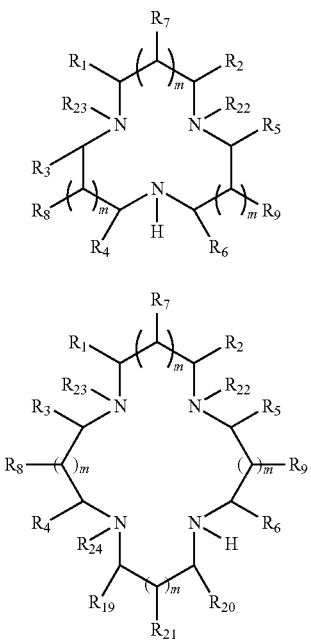

(Ib-1)

(Ib-2)

wherein: m is 0 or 1; each of $R^{1-21}$ is as defined for $R^{1-21}$ in formulas (I)-(IV); each of $R^{22-24}$ is as defined for $R^{1-22}$ in formulas (I)-(IV), or a protecting group or a structure of (a-1), (a-2), (a-3), (a-4), or (a-5), or a structure of formula (b-1), (b-2), or (b-3):

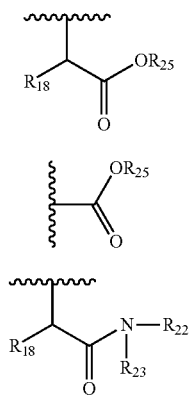

(b-1)

(b-2)

(b-3)

where $R^{18}$ and $R^{22-23}$ are as defined above; $R^{25}$ independently is or includes hydrogen, allyl, alkyl, tert-butyl, benzyl, dimethoxybenzyl, p-methoxybenzyl, p-nitrobenzyl, benzhydryl, trityl, cycloalkyl, aryl, tert-butyldimethylsilyl, or a protecting group; with a compound of formula (Ib-4), (Ib-5), (Ib-6), (Ib-7), (Ib-8), (Ib-9), or (Ib-10):

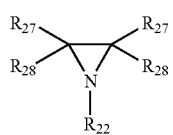

(b-4)

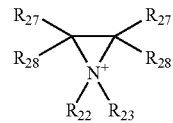

(b-5)

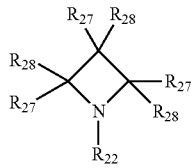

(b-6)

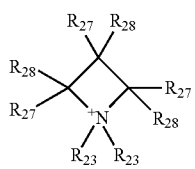

(b-7)

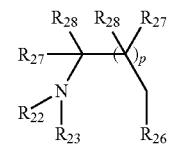

(b-8)

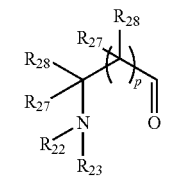

(b-9)

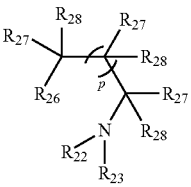

(b-10)

where m is 0 or 1; p is 0 or 1; $R^{22-23}$ are as defined above; $R^{26}$ is a leaving group and includes tosylate, chloride, bromide, mesylate, triflate, or iodide; and $R^{27-28}$ independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, carboxyl, carboxyalkyloxy, aldehyde, ester, amido, an amide containing group, a thioamide containing group, an amino acid-containing group, an ester containing group, a protecting group.

The invention further includes a method of preparing a compound, including chemically reacting a compound of formula (c-1) with a compound of (d-1) or (d-2):

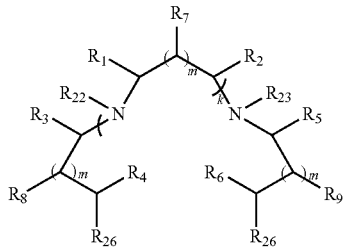
(c-1)

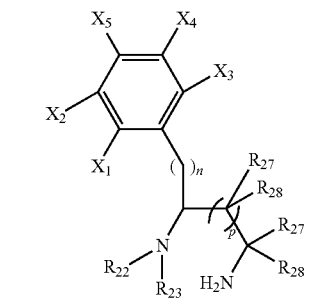
(d-1)

(d-2)

where, k is 0 or 1; m is 0 or 1; n is 1 to 10; p is 0 or 1; $R^{1-9}$ is defined as $R^{1-21}$ in formulas (I)-(IV). $R^{22-23}$ is defined as $R^{1-22}$ in formulas (I)-(IV). $R^{26}$ is a leaving group and includes tosylate, chloride, bromide, mesylate, triflate, or iodide; $R^{27-28}$ is independently is or includes hydrogen, alkyl, allyl, benzyl, cycloalkyl, hydroxyalkyl, aryl, heteroaryl, phenyl, vinyl, or an oxo group; to provide a compound of formula (e-1) or (e-2):

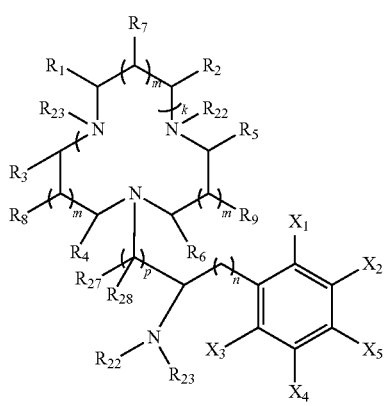
(e-1)

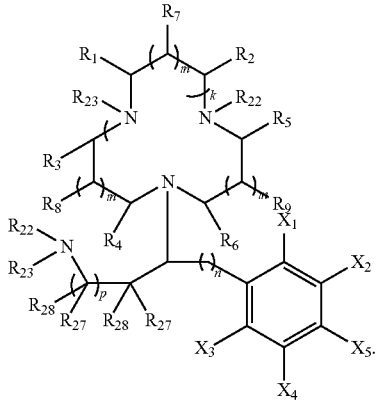
(e-2)

The compound of the formula (e-1) or (e-2), wherein $R^{22-23}$ is a protecting group, is then convertible to a compound of the formula (e-3) or (e-4):

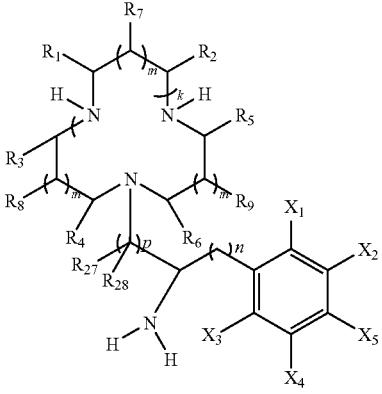
(e-3)

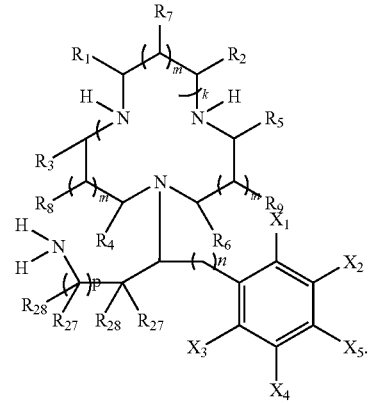
(e-4)

The compounds of the formula (e3) or (e-4) can further be alkylated to provide a desired end compound.

Other objects and advantages will be apparent to those skilled in the art from the following detailed description taken in conjunction with the appended claims and drawings.

DETAILED DESCRIPTION OF PREFERRED EMBODIMENTS

Figure 1:
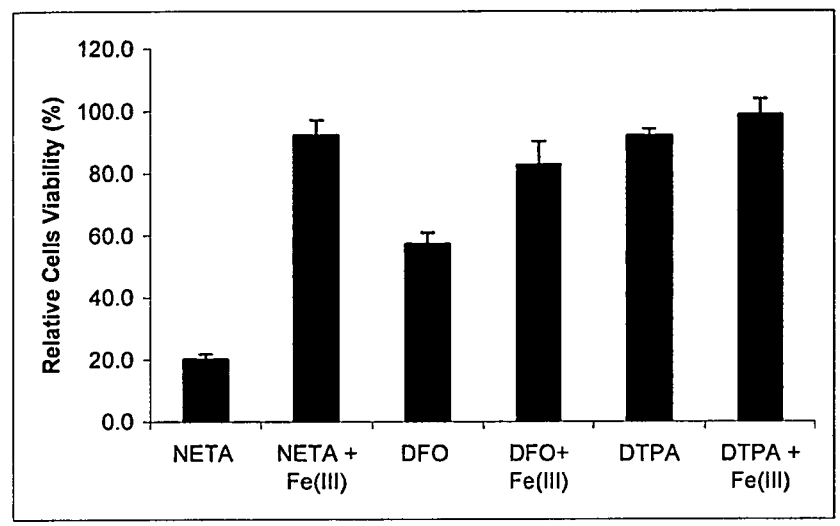
FIG. 1 is a graph illustrating the effects of iron saturation and chelators on Hela cell growth.

The present invention provides a compound of formula (I):

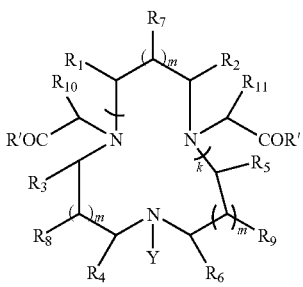
(I)

wherein: R' independently is OH, NH$_2$, or OR", wherein R" independently is alkyl, tert-butyl, allyl, or benzyl; k is 1 or 2; m is 0 or 1; Y is a structure of formula (a-1), (a-2), (a-3), or (a-4):

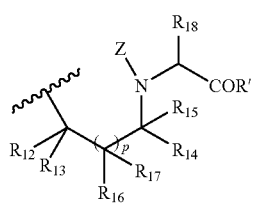
(a-1)

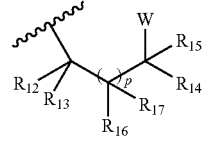
(a-2)

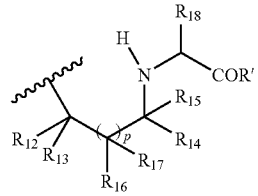
(a-3)

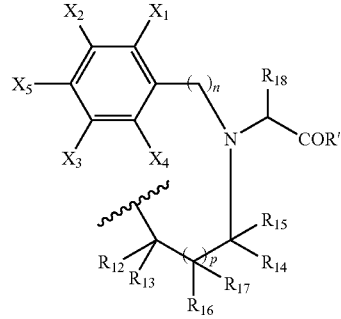
(a-4)

where p is 0 or 1; n is 1 to 10; W is OH, SH, or NZ$_2$; each of R$^{1-18}$ and Z independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, hydroxy, carboxyl, carboxyalkyloxy, amino, carboxylic acid, or holoalkylamido, aldehyde, ester, amido, tosyl, phthalimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, a protecting group, or a group of formula (a-5), (a-6), or (a-7);

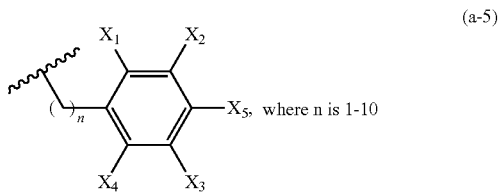
(a-5)

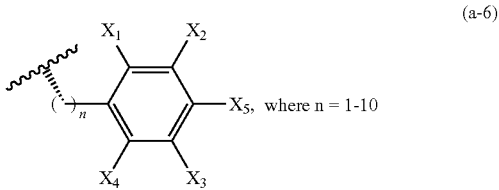
(a-6)

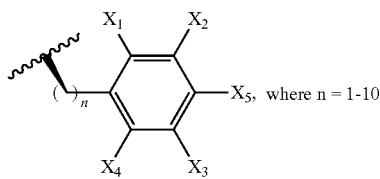

(a-7) where n = 1-10 and X is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydro, alkylamido, holoalkylamido, an ester containing group, an carbonyl containing group, an amide containing group, a thioamide containing group, or an amino acid-containing group;

provided that wherein m is 0, k is 1, R' is OH, Y is (a-1), Z is carboxyalkyl, then one of $R^{14-15}$ is not a compound of the formula of (a-5), (a-6), or (a-7), at least one of $R^{12-17}$ is not a hydrogen, or one $R^{1-11}$ of is a compound of the formula (a-5), (a-6), or (a-7). In one embodiment at least one of $R^{1-9}$ or $R^{12-17}$ forms a cycloalkyl with a neighboring carbon.

The present invention further provides a compound of formula (II):

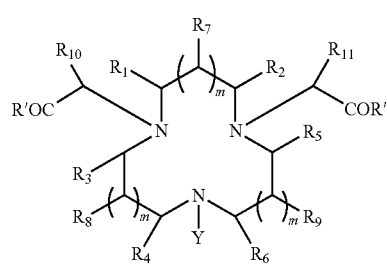

(II)

wherein: R' independently is OH, $NH_2$, or OR", wherein R" independently is alkyl, tert-butyl, allyl, or benzyl; m is 0 or 1; Y is a structure of formula (a-1), (a-2), (a-3), or (a-4):

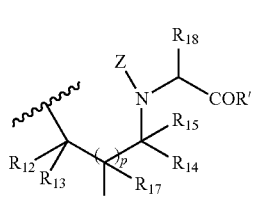

(a-1)

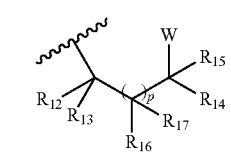

(a-2)

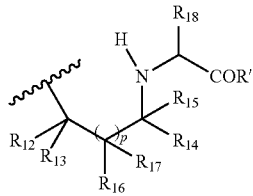

(a-3)

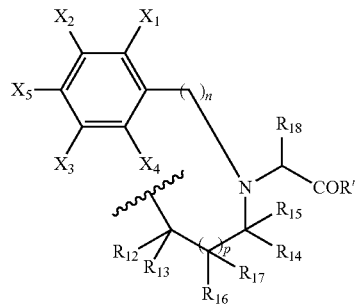

(a-4)

where p is 0 or 1; n is 1 to 10; W is OH, SH, or $NZ_2$; each of $R^{1-18}$ and Z independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, hydroxy, carboxyl, carboxyalkyloxy, amino, carboxylic acid, or holoalkylamido, aldehyde, ester, amido, tosyl, phthalimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, a protecting group, or a group of formula (a-5), (a-6), or (a-7);

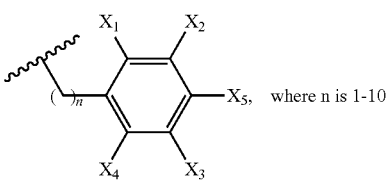

(a-5) where n is 1-10

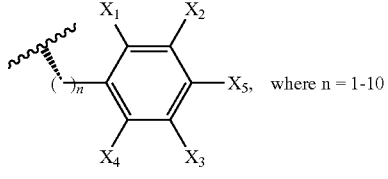

(a-6) where n = 1-10

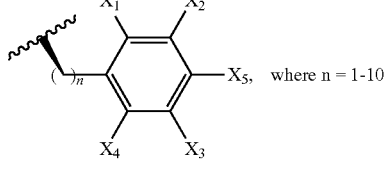

(a-7) where n = 1-10 and X is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydro, alkylamido, holoalkylamido, an ester containing group, an carbonyl containing group, an amide containing group, a thioamide containing group, or an amino acid-containing group;

provided that wherein m is 0, k is 1, R' is OH, Y is (a-1), Z is carboxyalkyl, then one of $R^{14-15}$ is not a compound of the formula of (a-5), (a-6), or (a-7), at least one of $R^{12-17}$ is not a hydrogen, or one of $R^{1-11}$ is a compound of the formula (a-5), (a-6), or (a-7). In one embodiment at least one of $R^{1-9}$ or $R^{12-17}$ forms a cycloalkyl with a neighboring carbon.

Exemplary compounds according to the compound of formula (II) include, formulas (II-a), (II-b), or (II-c), wherein p is 1 or 2 and n is 1 to 10:

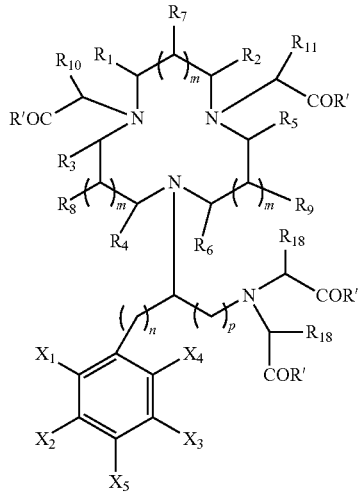

(II-a)

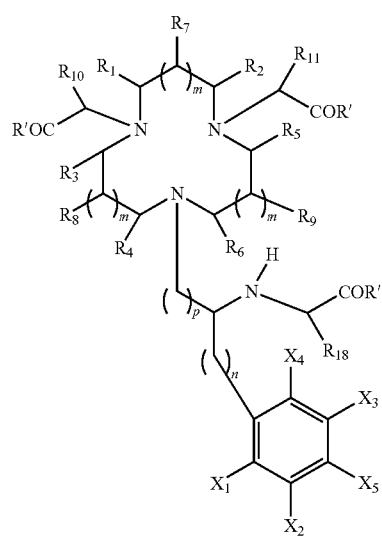

(II-b)

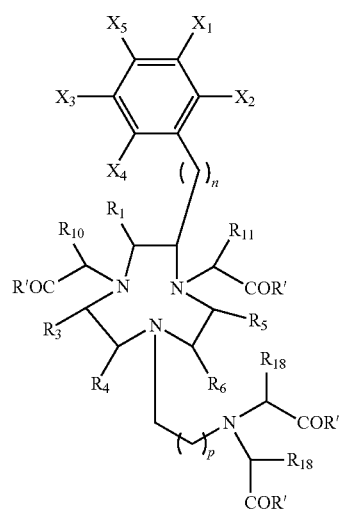

(II-c)

The present invention further provides a compound of formula (III):

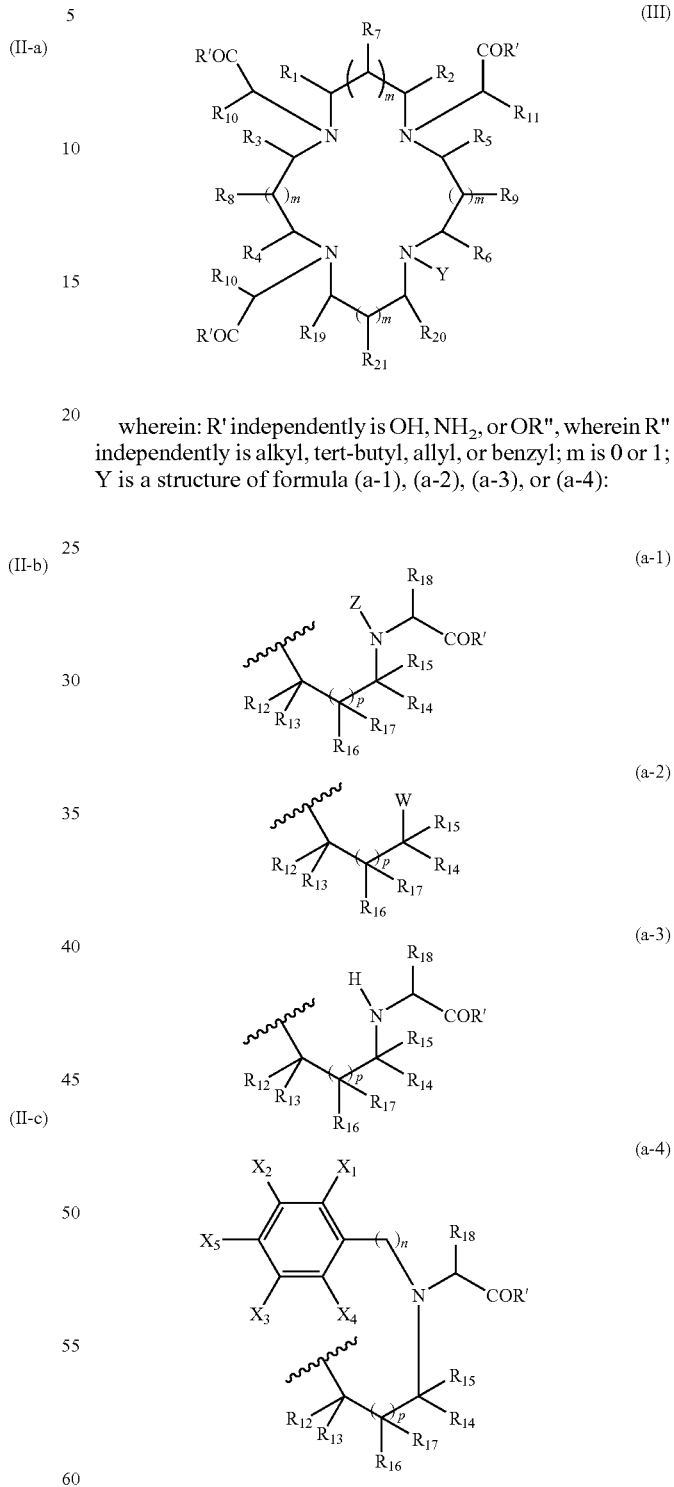

wherein: R' independently is OH, NH$_2$, or OR", wherein R" independently is alkyl, tert-butyl, allyl, or benzyl; m is 0 or 1; Y is a structure of formula (a-1), (a-2), (a-3), or (a-4):

where p is 0 or 1; n is 1 to 10; W is OH, SH, or NZ$_2$; each of R$^{1-21}$ and Z independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, hydroxy, carboxyl, carboxyalkyloxy, amino, carboxylic acid, or holoalkylamido, aldehyde, ester, amido, tosyl, phthalimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, a protecting group, or a group of formula (a-5), (a-6), or (a-7);

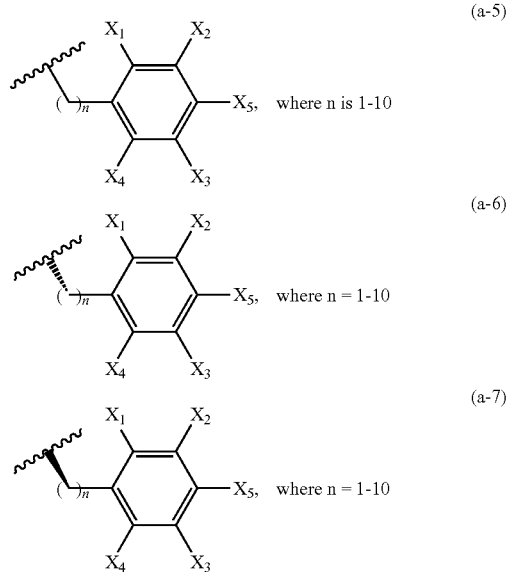

and X is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydro, alkylamido, holoalkylamido, an ester containing group, an carbonyl containing group, an amide containing group, a thioamide containing group, or an amino acid-containing group; and/or wherein at least one of $R^{1-9}$, $R^{19-21}$, or $R^{12-17}$ comprises a cycloalkyl formed with a neighboring carbon.

Exemplary compounds according to the compound of formula (III) include formula (III-a), wherein p is 1 or 2 and n is 1 to 10:

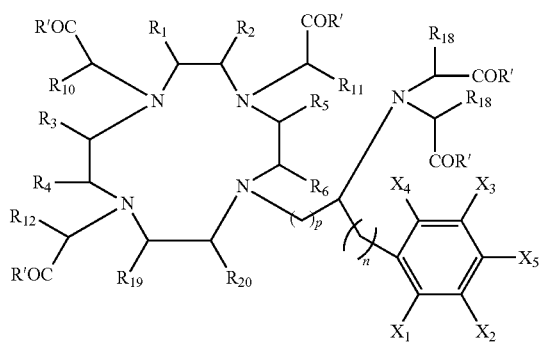

The invention further provides a compound of formula (IV):

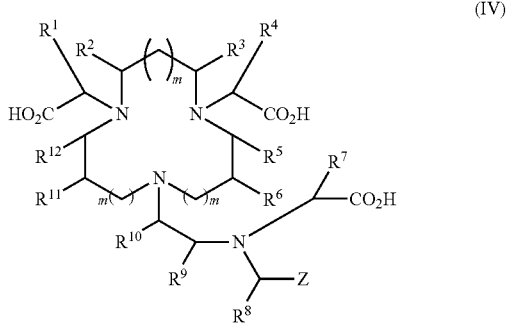

wherein m is 0, 1, or 2; Z is hydrogen, alkyl, alkyloxy, aryloxy, hydroxyalkyl, carboxyalkyl, hydroxyaryl, thioaryl, thioalkyl, benzyl, or includes a group of formula (a-5), (a-6), or (a-7) discussed above, each of $R^{1-12}$ is independently hydrogen, alkyl, cycloalkyl, alkoxy, hydroxyalkyl, aryl, aryloxy, hydroxyaryl, heteroaryl, thioalkyl, thioaryl, alkylamido, holoalkylamido, an amide containing group, a thioamide containing group, an amino acid-containing group, or a group of formula (a-5), (a-6), or (a-7).

The invention still further provides a compound of formula (V):

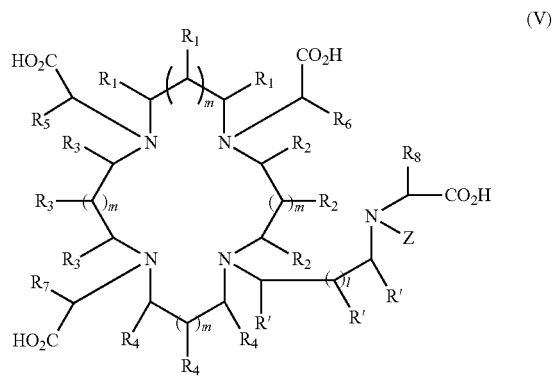

wherein: m is 0 or 1; l is 0 or 1; Z is or includes hydrogen, carboxylic acid, alkyl, benzyl, cycloalkyl, alkoxy, hydroxyalkyl, aryl, aryloxy, hydroxyaryl, heteroaryl, thioalkyl, thioaryl, hydroxyl, carboxyl, carboxyalkyl, carboxyalkyloxy, amido, alkylamido, holoalkylamido, an amide containing group, a thioamide containing group, or an amino acid-containing group, a structure of formula (a-5), (a-6), or (a-7), discussed above, or a structure of formula or (a-8):

where each of $R^{1-8}$ is or includes hydrogen, carboxylic acid, alkyl, benzyl, cycloalkyl, alkoxy, hydroxyalkyl, aryl, aryloxy, hydroxyaryl, heteroaryl, thioalkyl, thioaryl, hydroxy, carboxyl, carboxyalkyl, carboxyalkyloxy, amido, alkylamido, holoalkylamido, an amide containing group, a thioamide containing group, or an amino acid-containing group, or a structure of formula (a-5), (a-6), (a-7), or (a-8); each of R' independently is or includes hydrogen, alkyl, benzyl, cycloalkyl, alkoxy, hydroxyalkyl, aryl, aryloxy, hydroxyaryl, heteroaryl, thioalkyl, thioaryl, hydroxy, carboxyl, carboxyalkyl, carboxyalkyloxy, amido, alkylamido, holoalkylamido, an amide containing group, a thioamide containing group, or an amino acid-containing group, or a structure of formula (a-5), (a-6), or (a-7) where X is or includes hydrogen, halo, alkyl, hydroxy, nitro, amino, alkylamino, thiocyano, isothiocyano, alkoxy, aryloxy, carboxyl, carboxyalkyl, carboxyalkyloxy, amido, alkylamido or holoalkylamido or a structure of formula (c-1), (c-2), or (c-3):

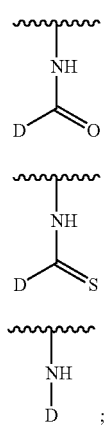

(c-1)

(c-2)

(c-3)

where D is independently hydrogen, alkyl, cycloalkyl, alkoxy, hydroxyalkyl, aryl, aryloxy, hydroxyaryl, heteroaryl, amino, an amino acid-containing group, an antibody, a bile acid, a fluorescent moiety, a nanoparticle, or a biomolecule.

The present invention also provides a compound of formula (VI):

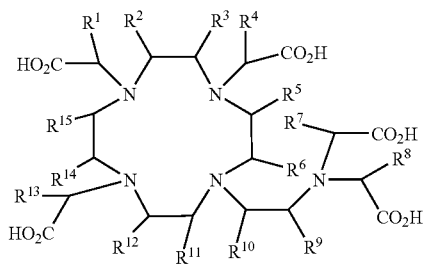

(VI)

wherein each of $R^{1-15}$ is independently hydrogen, alkyl, cycloalkyl, alkoxy, hydroxyalkyl, aryl, aryloxy, hydroxyaryl, heteroaryl, thioalkyl, thioaryl, alkylamido, holoalkylamido, an amide containing group, a thioamide containing group, or an amino acid-containing group, or includes a group of formula (a-5), (a-6), or (a-7) discussed above.

The invention still further provides a compound of formula (VII):

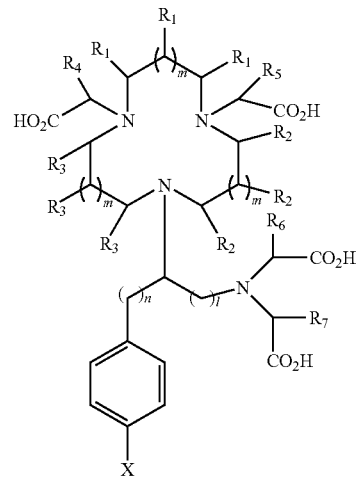

(VII)

wherein: m is 0 or 1; l is 1 or 2; n=1~10; each of $R^{1-7}$ is or includes hydrogen, alkyl, benzyl, cycloalkyl, alkoxy, hydroxyalkyl, aryl, aryloxy, hydroxyaryl, heteroaryl, thioalkyl, thioaryl, hydroxy, carboxyl, carboxyalkyl, carboxyalkyloxy, amido, alkylamido, holoalkylamido, or an amino acid-containing group; and X is or includes hydrogen, halo, alkyl, hydroxy, nitro, amino, alkylamino, thiocyano, isothiocyano, alkoxy, aryloxy, carboxyl, carboxyalkyl, carboxyalkyloxy, amido, alkylamido, holoalkylamido or a structure of formula (c-1), (c-2), or (c-3) discussed above.

The invention still further provides a compound of formula (VIII):

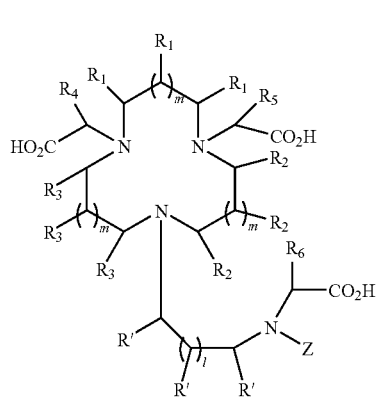

(VIII)

wherein: m is 0 or 1; l is 0 or 1; each of $R^{1-6}$ is or includes hydrogen, alkyl, benzyl, cycloalkyl, alkoxy, hydroxyalkyl, aryl, aryloxy, hydroxyaryl, heteroaryl, thioalkyl, thioaryl, hydroxy, carboxyalkyl, carboxyalkyloxy, amido, alkylamido or holoalkylamido, an amino acid-containing group, or a structure of formula (a-5), (a-6), or (a-7) discussed above; each of R' and Z independently is or includes hydrogen, alkyl, benzyl, cycloalkyl, alkoxy, hydroxyalkyl, aryl, aryloxy, hydroxyaryl, heteroaryl, thioalkyl, thioaryl, hydroxy, carboxyalkyl, carboxyalkyloxy, amido, alkylamido or holoalkylamido, an amino acid-containing group, or a structure of formula (a-5), (a-6), or (a-7) discussed above where X is or includes hydrogen, halo, alkyl, hydroxy, nitro, amino, alkylamino, thiocyano, isothiocyano, alkoxy, aryloxy, carboxyl, carboxyalkyl, carboxyalkyloxy, amido, alkylamido, holoalkylamido, or a structure of formula (c-1), (c-2), or (c-3) discussed above.

The invention still further provides a compound of formula (IX):

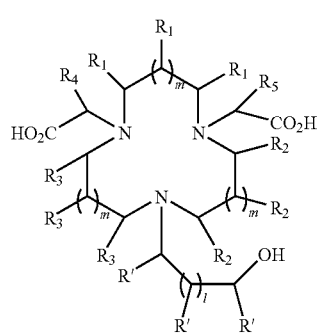

(IX)

wherein: m is 0 or 1; 1 is 0 or 1; each of $R^{1-5}$ is or includes hydrogen, alkyl, benzyl, cycloalkyl, alkoxy, hydroxyalkyl, aryl, aryloxy, hydroxyaryl, heteroaryl, thioalkyl, thioaryl, hydroxy, carboxyl, carboxyalkyl, carboxyalkyloxy, amido, alkylamido, holoalkylamido, an amino acid-containing group, or a structure of formula (a-7), (a-8), or (a-9) discussed above; and each of R' independently is or includes hydrogen, alkyl, benzyl, cycloalkyl, alkoxy, hydroxyalkyl, aryl, aryloxy, hydroxyaryl, heteroaryl, thioalkyl, thioaryl, hydroxy, carboxyl, carboxyalkyl, carboxyalkyloxy, amido, alkylamido or holoalkylamido, an amino acid-containing group, or a structure of formula (a-7), (a-8), or (a-9) discussed above where X is or includes hydrogen, halo, alkyl, hydroxy, nitro, amino, alkylamino, thiocyano, isothiocyano, alkoxy, aryloxy, carboxyl, carboxyalkyl, carboxyalkyloxy, amido, alkylamido, holoalkylamido or a structure of formula (c-1), (c-2), or (c-3) discussed above.

Any of the groups indicated above for $R^{1-24}$ and X can optionally be substituted with suitable substituents such as hydroxy, $C_{1-12}$ alkoxy, acyloxy, halo, benzyl, acetyl, carboxyl, carboxy-$C_{1-12}$ alkyl, such as carboxymethyl, carboxyethyl, carboxy-$C_{1-12}$ alkylamido, carboxy-$C_{1-12}$ dialkylamido, carboxyamido, amino, $C_{1-12}$ alkylamino, $C_{1-12}$ dialkylamino, $C_{1-12}$ alkylcarbonyl, $C_{6-30}$ arylamino, $C_{6-30}$ diarylamino, cyano, tolyl, xylyl, mesityl, anisyl, pyrrolidinyl, formyl, thio, $C_{1-12}$ alkylthio, $C_{6-30}$ aryl, $C_{5-30}$ heteroaryl, such as pyranyl, pyrrolyl, furanyl, thiophenyl, thiazolyl, pyrazolyl, pyridinyl, or pyrimidinyl, phenoxy, benzyloxy, phenylcarbonyl, benzylcarbonyl, nitrophenyl $C_{1-12}$ trialkylsilyl, nitro, sulfonyl, nitrobenzyl, $C_{1-12}$ trialkylammonium, $C_{1-12}$ alkyl, $C_{3-8}$ cycloalkyl, tetrahydrofuranyl, tetrahydropyranyl, piperidinyl and morpholinyl.

Referring now to terminology used generically herein, the term "alkyl" means a straight-chain or branched alkyl substituent containing from, for example, about 1 to about 12 carbon atoms, preferably from about 1 to about 8 carbon atoms, more preferably from about 1 to about 6 carbon atoms. Examples of such substituents include methyl, ethyl, propyl, isopropyl, n-butyl, sec-butyl, isobutyl, tert-butyl, pentyl, isoamyl, hexyl, octyl, dodecanyl, and the like.

The term "cycloalkyl," as used herein, means a cyclic alkyl substituent containing from, for example, about 3 to about 30 carbon atoms, preferably from about 5 to about 14 carbon atoms, more preferably from about 5 to about 10 carbon atoms, and most preferably from about 5 to about 7 carbon atoms. Examples of such substituents include cyclopropyl, cyclobutyl, cyclopentyl, cyclohexyl, and the like.

The term "halo" or "halogen," as used herein, means a substituent selected from Group VIIA, such as, for example, fluorine, bromine, chlorine, and iodine. Preferably, the halo is bromine or iodine.

The term "aryl" refers to an unsubstituted or substituted aromatic carbocyclic substituent, as commonly understood in the art, and includes monocyclic and polycyclic aromatics such as, for example, phenyl, biphenyl, toluenyl, anisolyl, naphthyl, anthracenyl and the like. An aryl substituent generally contains from, for example, about 3 to about 30 carbon atoms, preferably from about 6 to about 18 carbon atoms, more preferably from about 6 to about 14 carbon atoms and most preferably from about 6 to about 10 carbon atoms. It is understood that the term aryl applies to cyclic substituents that are planar and comprise 4n+2 π electrons, according to Hückel's Rule.

The term "heteroaryl" means a substituent defined by an aromatic heterocyclic ring, as is commonly understood in the art, including monocyclic and polycyclic heteroaryls containing from, for example, about 3 to about 30 carbon atoms, preferably from about 5 to about 10 carbon atoms, more preferably from about 5 to about 6 carbon atoms. Monocyclic heteroaryls include, for example, imidazolyl, thiazolyl, pyrazolyl, pyrrolyl, furanyl, pyrazolinyl, thiophenyl, oxazolyl, isoxazolyl, pyridinyl, pyridonyl, pyrimidinyl, pyrazinyl, and triazinyl substituents. Polycyclic heteroaryls include, for example, quinolinyl, isoquinolinyl, indolyl, purinyl, benzimidazolyl, benzopyrrolyl, and benzothiazolyl.

The term "alkoxy" embraces linear or branched alkyl groups that are attached to divalent oxygen. The alkyl group is the same as described herein. Examples of such substituents include methoxy, ethoxy, t-butoxy, and the like. The term "aryloxy" refers to substituents that have an aryl group attached to divalent oxygen. The aryl group is the same as described herein. An example of such substituents is phenoxy.

The term "alkylthio" as used herein, denotes a substituent with an alkyl group directly attached to a divalent sulfur atom. The alkyl group is the same as described herein. Examples of such substituents include methylthio, ethylthio, and the like. Similarly, the term "arylthio" as used herein, denotes a substituent with an aryl group directly attached to a divalent sulfur atom. The aryl group is the same as described herein.

The term "carboxyl" refers to the group —C(O)OH. The term "carboxyalkyl" refers to the group —RC(O)OH that is connected to the compound through the alkyl R group. The term "carboxyalkyloxy" refers to the group —ORC(O)OH, in which the R is an alkyl (e.g., $(CH_2)_n$ alkylene group, where n is 1 to 12) group.

The terms "amine" or "amino" as used herein are represented by the formula $NR^1R^2A^3$, where $R^1$, $R^2$, and $R^3$ can be, for example, independently, hydrogen or substituted or unsubstituted alkyl, cycloalkyl, alkenyl, cycloalkenyl, alkynyl, cycloalkynyl, aryl, or heteroaryl group as described herein. The term "amide" as used herein is generally represented by the formula: $R^1(CO)NR^2R^3$, where either or both $R^2$ and $R^3$ may be hydrogen. An amide is an amine where one of the nitrogen substituents is an acyl group. A "thioamide" as used herein is generally represented by the formula: $R^1(CS)NR^2R^3$, where either or both $R^2$ and $R^3$ may be hydrogen.

The term "alkylamino" refers to a secondary amine substituent with one hydrogen and one alkyl group directly attached to a trivalent nitrogen atom. In addition, the term "alkylamino" also refers to a tertiary amine substituent with two of the same or different alkyl groups directly attached to a trivalent nitrogen atom. The alkyl group is the same as described herein.

The term "alkylamido" refers to substituents of the formula, —C(O)NRR' or —NRC(O)R', in which R and R' are the same or different and each is a hydrogen or alkyl group, as described herein. The term "haloalkylamido" is an alkylamido as described above, in which one or more of the alkyl groups is substituted with a halo moiety, such as, for example, chlorine, bromine or iodine.

The term "amino acid-containing group" refers to substituents that include both a carboxyl group (C(O)OH) and an amino group ($NH_2$). Commonly, such substituents have the generic formula, —RCH($NH_2$)$CO_2$H, in which the substituent bonds to a compound of any of formulas (I)-(IX) through the R group. While any amino acid is to be considered (e.g., glycinyl, alaninyl, leucinyl, etc.) acceptable as a substituent, asparate (—CH($NH_2$)$CO_2$H) and glutamate (—$CH_2$CH($NH_2$)$CO_2$H) are especially preferred. Therefore, when any substituent of (I)-(IX) is asparate or glutamate, the entire nitrogen substituent forms aspartic acid or glutamic acid, respectively.

Also, unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

For sake of brevity, preferred compound backbones are discussed and illustrated hereinafter without the detail of all particular substituent groups, e.g., $R^{1-24}$.

The following are preferred compound backbones according to one embodiment of this invention:

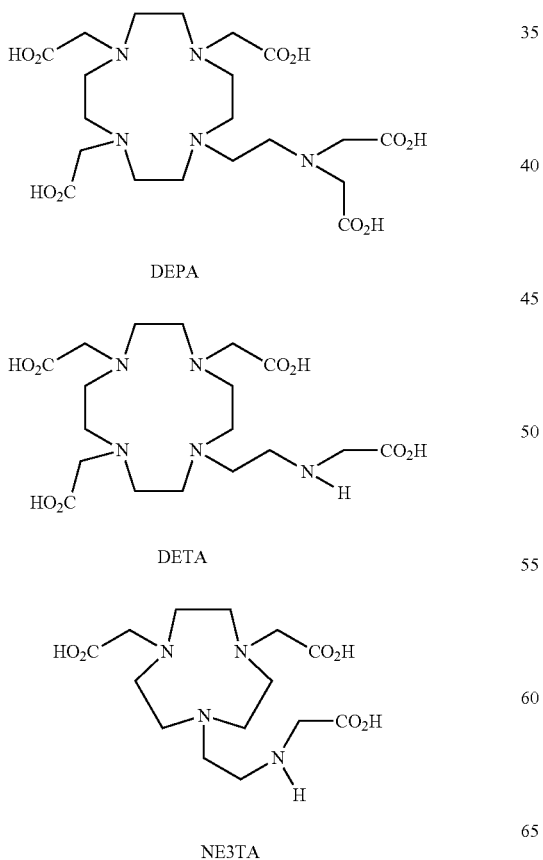

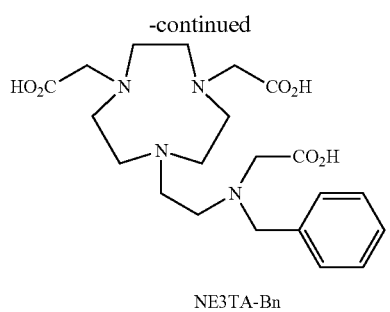

NE3TA-Bn

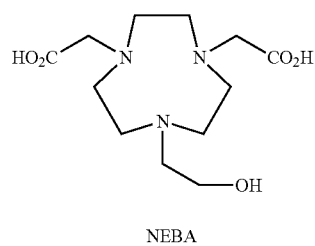

NEBA

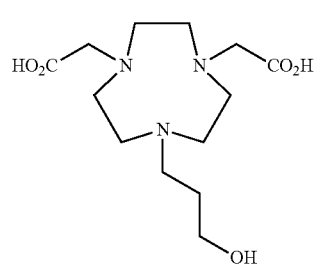

NBPA

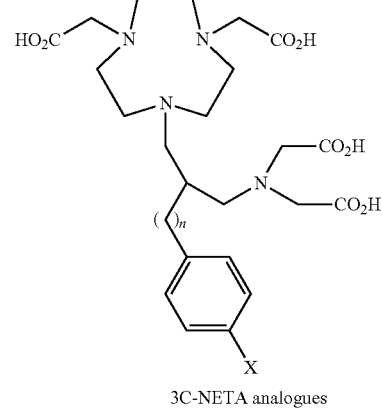

3C-NETA analogues

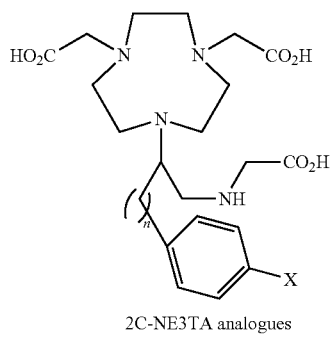

2C-NE3TA analogues

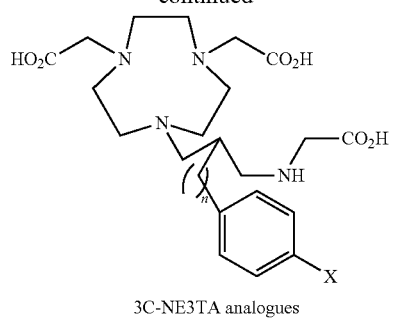
3C-NE3TA analogues
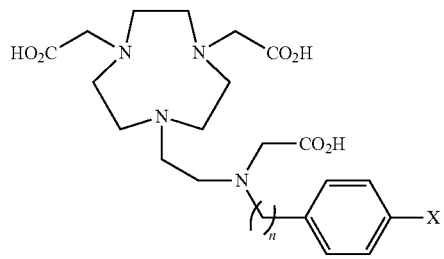
N-NE3TA analogues
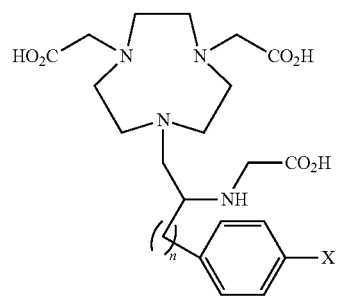
C-NE3TA analogues
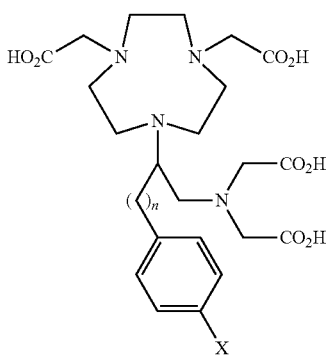
2C-NETA analogues
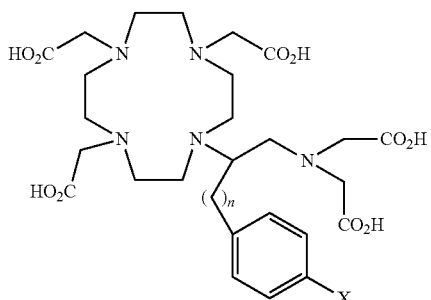
2C-DEPA analogues
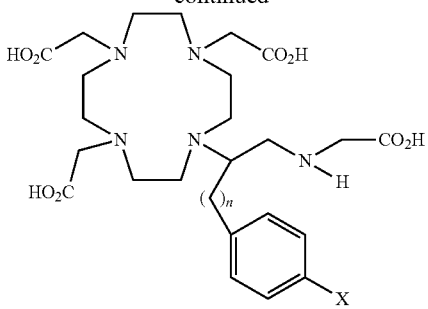
2C-DETA analogues
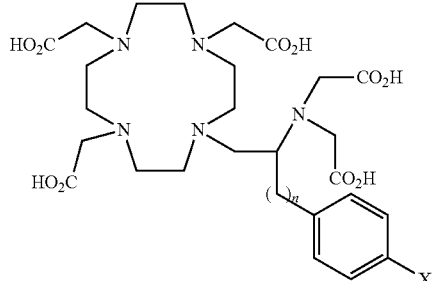
C-DEPA analogues
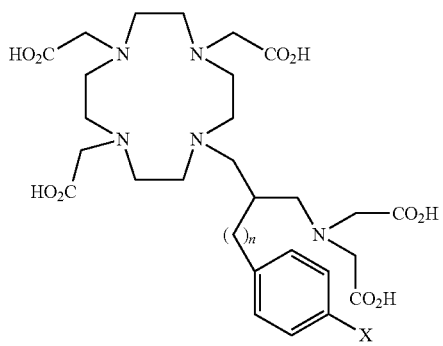
3C-DEPA analogues
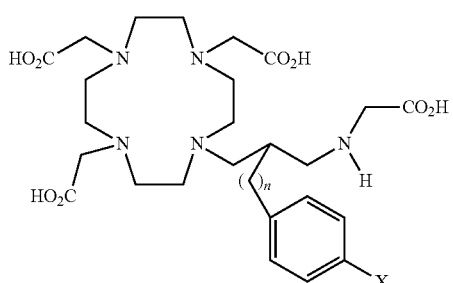
3C-DETA analogues -continued

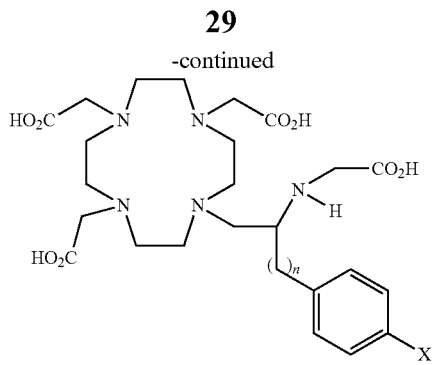

C-DETA analogues

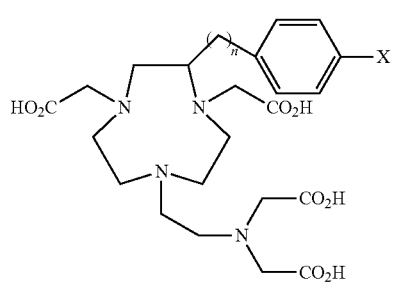

Aanalogues of NETA

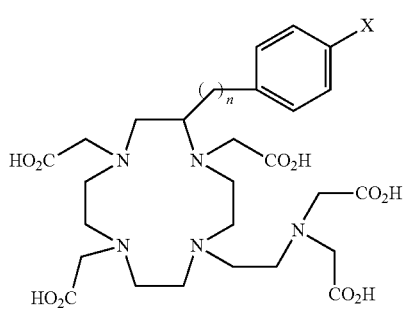

Analogues of DEPA

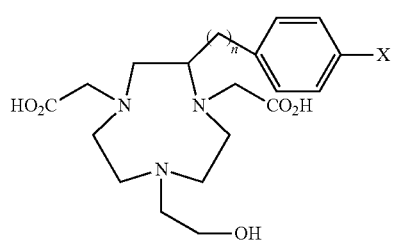

Aanalogues of NEBA

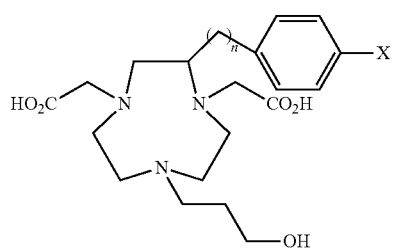

Aanalogues of NBPA

-continued

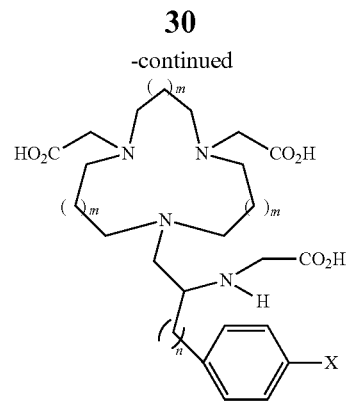

C-NE3TA analogues

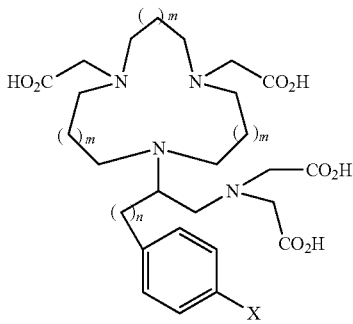

2C-NETA Aanalogues of
m = 0, 1
n = 1~10

The functionality of the substituents (i.e., $R^{1-22}$ and X) of the compounds of the invention allow derivatization to biomolecules or targeting moieties. The term "biomolecule" refers to all natural and synthetic molecules that play a role in biological systems. Biomolecules include hormones, amino acids, peptides, peptidomimetics, proteins, deoxyribonucleic acid (DNA), ribonucleic acid (RNA), lipids, albumins, polyclonal antibodies, receptor molecules, receptor binding molecules, haptens, monoclonal antibodies, and aptamers. In one preferred embodiment of this invention, X in the above compounds is desirably $NO_2$, $NH_2$, or NCS, and can be substituted for a targeting moiety or biomolecule, such as a hormone, a bile acid, an amino acid, a peptide, a peptidomimetic, a protein, deoxyribonucleic acid (DNA), ribonucleic acid (RNA), a lipid, an albumin, a receptor molecule, a receptor binding molecule, a hapten, a monoclonal antibody, a polyclonal antibody, a peptide, an aptamer, a folic acid, an estrogen, or a transferring. Specific examples of biomolecules include insulins, prostaglandins, growth factors, liposomes, and nucleic acid probes. An advantage of using biomolecules is tissue targeting through specificity of delivery.

In one embodiment of this invention, any suitable hapten can be linked with a compound of any of formulas (I)-(IX). Haptens such as hormones, steroids, enzymes and proteins are desirable in some applications because of their site specificity to tumors and/or various organs of the body. A preferred hapten for use in treating cellular disorders or various disease conditions is a monoclonal antibody. Methods of bonding a macrocyclic compound to a hapten are described in U.S. Pat. No. 5,428,154, which are incorporated herein by reference.

Coupling of a compound of any of formulas (I)-(IX) to one or more biomolecules can be accomplished by several known methods (see, for example, Krejcarek et al., Biochem. Biophys. Res. Commun., 1977, 30, 581; Hnatowich et al., Science, 1983, 220, 613). For example, a reactive moiety present in one of the substituents (i.e., $R^{1-24}$ or X) is coupled with a second reactive group located on the biomolecule. Typically, a nucleophilic group is reacted with an electrophilic group to form a covalent bond between the biomolecule and the compound of any of formulas (I)-(IX). Examples of nucleophilic groups include amines, anilines, alcohols, phenols, thiols, and hydrazines. Examples of electrophilic groups include halides, disulfides, epoxides, maleimides, acid chlorides, anhydrides, mixed anhydrides, activated esters, imidates, isocyanates, and isothiocyanates.

Preferably, a compound including the group (a-5), (a-6), or (a-7) is bonded to a biomolecule through the X substituent. It is especially preferred that the X substituent of group (a-5), (a-6), or (a-7) is a substituent that conjugates the compound to a biomolecule. This substituent is desirably a free-end nitro group, which can be reduced to an amine. The amine then can be activated with a compound, such as thionyl chloride, to form a reactive chemical group, such as an isothiocyanate. An isothiocyanate is preferred because it links directly to an amino residue of a hapten, such as an mAb. The aniline group can be linked to an oxidized carbohydrate on the protein and, subsequently, the linkage fixed by reduction with cyanoborohydride. The amino group also can be reacted with bromoacetyl chloride or iodoacetyl chloride to form —$NHCOCH_2Q$, with Q being bromide or iodide. This group reacts with any available amine or sulfhydryl group on a hapten to form a stable covalent bond. If tyrosine is used in the formulation of the macromolecule, a carboxylic acid or methoxy carboxylate group can be in this position of the compound. The most desirable X substituents for compounds of formula (a-5), (a-6), or (a-7) are members selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido. In some preferred instances, X is a haloalkylamido of the formula —$NHCOCH_2Q$, with Q being bromide or iodide. Another preferred substituent for this position is isothiocyano (—NCS).

The invention also provides complex comprising the compound of any of formulas (I)-(IX) and a metal ion, in which is the metal ion is optionally radioactive. The metal ion is any metal ion that is suitable for the desired end use of the complex. Typical metal ions for forming a complex of the invention include Bi, Pb, Y, Mn, Cr, Fe, Co, Zn, Ni, Tc, Gd In, Ga, Cu, Re, Sm, Pm, Ho, Zr, lanthanides (i.e., any element with atomic number 57 to 71 inclusive), and actinides (i.e., any element with atomic number 89 to 103 inclusive). For example, in proton magnetic resonance imaging, paramagnetic metal atoms such as gadolinium(III), manganese(II), manganese(III), chromium(III), iron(II), iron(III), cobalt(II), nickel(II), copper(II), praseodymium(III), neodymium(III), samarium(III), ytterbium(III), terbium(III), dysprosium(III), holmium(III), Europium(III), and erbium(III) (all are paramagnetic metal atoms with favorable electronic properties) are preferred as metals complexed by the ligands of any of formulas (I)-(IX). Gadolinium(III) is the most preferred complexed metal due to the fact that it has the highest paramagnetism, low toxicity when complexed to a suitable ligand, and high lability of coordinated water. For use as x-ray contrast agents, the metal ion must be able to absorb adequate amounts of x-rays (i.e., radio-opaque), such as, for example, indium, yttrium, lead, bismuth, gadolinium, dysprosium, holmium and praseodymium.

Compounds of each of formulas (I)-(IX) also can be complexed with a radioactive metal ion, e.g., Bi, Pb, Y, Mn, Cr, Fe, Co, Zn, Ni, Tc, In, Ga, Cu, Re, Sm, a lanthanide, or an actinide, for use as therapeutic agents (e.g., radiopharmaceuticals). Other suitable radioisotopes include, without limitation, radioactive isotope of carbon, nitrogen, iodine, fluorine, oxygen, or helium. Specific examples of radionuclides suitable for complexing to a compound of formulas (I)-(IX) for various imaging techniques, including single photon emission computed spectroscopy, are, for example, $^{213}Bi$, $^{212}Bi$, $^{212}Pb$, $^{225}Ac$, $^{177}Lu$, $^{111}In$, $^{166}Ho$, $^{90}Y$, $^{153}Sm$, $^{67}Cu$, $^{64}Cu$, $^{153}Gd$, $^{157}Gd$, $^{66}Ga$, $^{68}Ga$, $^{86}Y$, $^{89}Zr$ and $^{67}Ga$.

To prepare metal complexes of the invention, a compound of any of formulas (I)-(IX) are complexed with an appropriate metal or metal ion. This can be accomplished by any methodology known in the art. For example, the metal can be added to water in the form of an oxide, halide, nitrate or acetate (e.g., yttrium acetate, bismuth iodide) and treated with an equimolar amount of a compound of any of formulas (I)-(IX). The compound can be added as an aqueous solution or suspension. Dilute acid or base can be added (where appropriate) to maintain a suitable pH. Heating at temperatures as high as 100° C. for periods of up to 24 hours or more can be employed to facilitate complexation, depending on the metal, the compound, and their concentrations.

Pharmaceutically acceptable salts of the metal complexes of the compounds of any of formulas (I)-(IX) are also useful as imaging agents. These salts can be prepared by using a base (e.g., an alkali metal hydroxide, meglumine, arginine or lysine) to neutralize the above-prepared metal complexes, while they are still in solution. Some of the metal complexes are formally uncharged and do not need cations as counterions. Such neutral complexes may be preferred as intravenously administered x-ray and NMR imaging agents over charged complexes because they may provide solutions of greater physiologic tolerance due to their lower osmolality. However, for use as hepatobiliary agents, negatively charged ligands are preferred.

The above described compounds and complexes can be coupled, e.g., chemically bonded, to a targeting moiety. Exemplary targeting moieties of this invention include bile acids, amino acids, antibodies, peptides, transferrin, or silica amino nanoparticles. Preferably, the X group is or includes a nitro, amino, alkylamino, thiocyano, isothiocyano, alkoxy, aryloxy, carboxyl, carboxyalkyl, carboxyalkyloxy, amido, alkylamido or holoalkylamido attached to the targeting moiety.

In one embodiment of this invention, one or more compounds of formulas (I)-(IX), and the complexes thereof, are conjugated with a bile acid targeting moiety. These bile acid conjugates are useful in, for example, preparing MRI contrast agents, such as liver-specific MRI contrast agents. The bile acid serves as a liver or intestine targeting moiety. The property of amphifacial bile acid to undergo enterohepatic circulation and form helical aggregates makes it a useful shuttle system to deliver various drugs to the liver and intestine with favorable intestine absorption and pharmacokinetic profile. Bile acids are efficiently taken up into the cells by two types of carriers: apical sodium-dependent bile salt transporters (ASBT) carriers and $Na^+$-independent carriers. Studies have demonstrated that bile acids enter liver and colon cancer cells which over express bile acid transporter and carriers.

Exemplary bile acid targeting moieties include cholic acid, deoxycholic acid, chenodeoxycholic acid, glycocholic acid, or ursodeoxycholic acid. Exemplary bile acid antitumor conjugates of bile acids and the above described compounds include the following structures. These structures can be further complexed with the metal ions or isotopes discussed above.

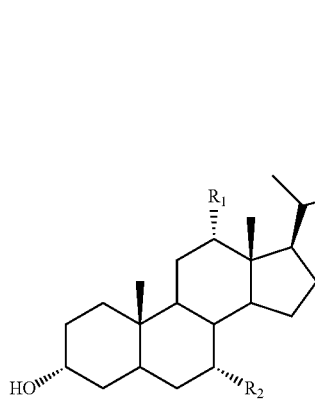
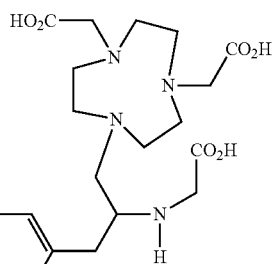

CA-NE3TA; R₁ = R₂ = OH, R₃ = H
DCA-NE3TA; R₁ = OH, R₂ = H, R₂ = H
CDCA-NE3TA; R₁ = H, R₂ = OH, R₃ = H

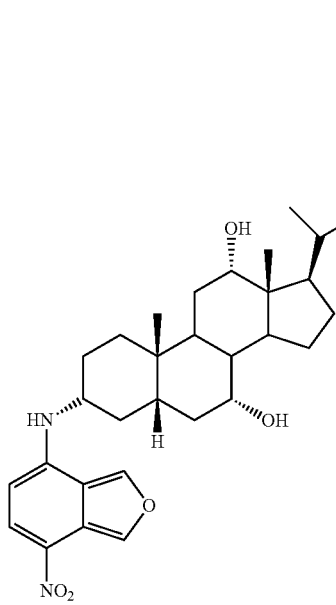

NBD-CA-NE3TA

In another embodiment of this invention, the targeting moiety includes the biomolecule transferrin. Transferrin is a blood plasma protein for iron ion delivery. Transferrin is a glycoprotein, which binds iron very tightly but reversibly. When not bound to iron, it is known as "apotransferrin." When a transferrin protein loaded with iron encounters a transferrin receptor on the surface of a cell, it binds to it and is consequently transported into the cell in a vesicle. The cell will acidify the vesicle, causing transferrin to release its iron ions. The receptor is then transported through the endocytic cycle back to the cell surface, ready for another round of iron uptake. Each transferrin molecule has the ability to carry two iron ions in the ferric form ($Fe^{3+}$). Conjugates of this invention including transferrin will be particularly useful in targeting transferrin receptors, and will help the hydrophilic ligands of this invention to get into the cell (using apotransferrin). The following exemplary conjugates include transferrin (Tf).

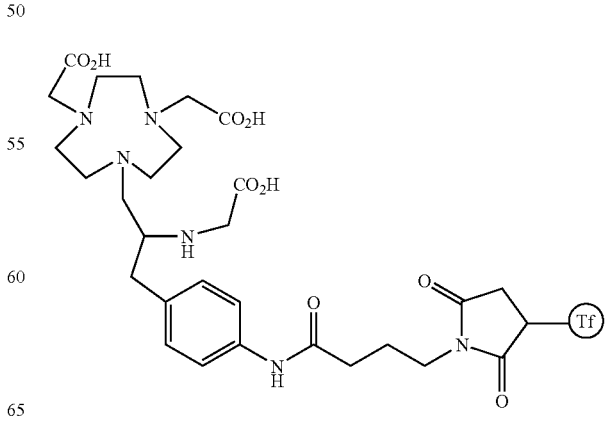

C-NE3TA-Transferrin

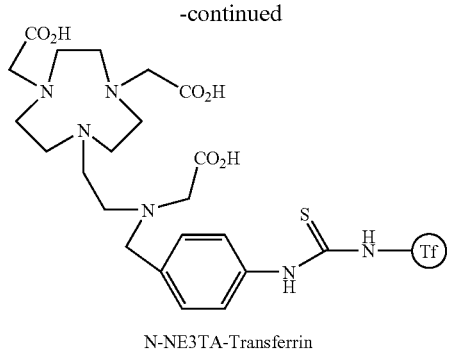

N-NE3TA-Transferrin

The compounds of this invention, and also complexes and conjugates of these compounds, are useful in diagnostic imaging and radiotherapy. In one embodiment of this invention is provided a method for obtaining a diagnostic image of a host by administering to the host a compound, conjugate, or complex of one or more of formulas (I)-(IX), in an amount effective to provide an image; and exposing the host to an energy source, whereupon a diagnostic image of the host is obtained. The diagnostic image can be, for example, a magnetic resonance image (MRI), a fluorescence image (FI), an x-ray contrast image, transmission electron microscopy image, and a positron emission tomography (PET) image, a single photon emission computed spectroscopy (SPECT), or any similar image.

For example, the compounds of any of formulas (I)-(IX) can be complexed with a paramagnetic metal atom and used as relaxation enhancement agents for magnetic resonance imaging. These agents, when administered to a host (e.g., a mammal such as a human) distribute in various concentrations to different tissues, and catalyze the relaxation of protons in the tissues that have been excited by the absorption of radiofrequency energy from a magnetic resonance imager. This acceleration of the rate of relaxation of the excited protons provides for an image of different contrast when the host is scanned with a magnetic resonance imager. The magnetic resonance imager is used to record images at various times, generally either before and after administration of the agents, or after administration only, and the differences in the images created by the presence of the agent in tissues are used in diagnosis. Guidelines for performing imaging techniques can be found in Stark et al., Magnetic Resonance Imaging, Mosbey Year Book: St. Louis, 1992, hereby incorporated by reference.

Accordingly, the present invention provides a method for magnetic resonance imaging of a host (e.g., mammal, such as a human). The method comprises administering to the host a complex of any of formulas (I)-(IX), in which the metal is paramagnetic, in an amount effective to provide an image; and exposing the host to a magnet, whereupon a magnetic resonance image of the host is obtained. Preferably a complex used in obtaining a magnetic resonance image comprises Gd. Paramagnetic metal complexes of the present invention are particularly useful as hepatobiliary agents, i.e., for magnetic resonance imaging of the liver and bile ducts. Exemplary MRI contrast agents according to this invention are complexes of the bile acid conjugates discussed above. Another preferred MRI imaging complex is formed using C-NE3TA.

The compounds and complexes of this invention can further include a fluorescent molecule, moiety, particle or compound, such as for fluorescence imaging (FI). In one embodiment, the compounds or complexes of this invention are attached to a nanoparticle, such as nanoparticles including carbon nanotubes, silica, quantum dots, or dendrimers. The nanoparticles can be, or be attached to, the fluorescent molecule, moiety, particle or compound. Conjugation of, for example, Gd(N-NE3TA) to silica amino nanoparticles containing a fluorescent moiety can be used in both MRI and FI. Exemplary fluorescents include fluorophores such as NBD. N-NE3TA conjugated to a silica nanoparticle and a fluorophore is illustrated below.

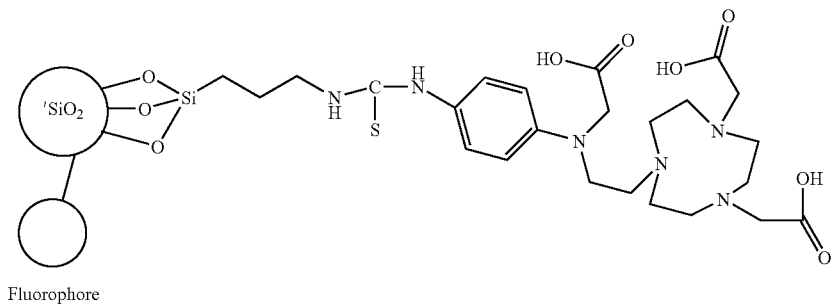

Fluorophore

Radioimmunotherapy (RIT) is a promising technique for targeted treatment or imaging of numerous cancer types. RIT also requires the use of either radioactive or non-radioactive metals, which can be very toxic when deposited in vivo, causing life-threatening side effects. Therefore, the success of clinical applications of both RIT and MRI heavily depends on the performance of the metal-binding ligands. RIT employs tumor-specific monoclonal antibodies (mAb) for selective delivery of a cytotoxic radionuclide to tumor cells to minimize toxicity due to nonselective exposure of the radionuclide. The RIT system generally requires three components: a radionuclide, a mAb, and a bifunctional ligand. The first RIT drug, Zevalin consists of anti-CD20 antibodies, 1B4M-DTPA, and $^{90}$Y, and was proven significant potency in B-cell non-Hodgkin's lymphoma therapy. $^{177}$Lu, $^{90}$Y, $^{212}$Pb, $^{212}$Bi, $^{213}$Bi, and $^{225}$Ac are recognized as promising metallic radionuclides proposed for effective RIT. An adequate bifunctional ligand that can rapidly form a stable complex with a short-lived radionuclide after being conjugated to a sensitive mAb must be employed to minimize toxicity due to dissociation of metal complex and radiolytic damage to protein conjugates resulting from extended exposure of sensitive antibody to reaction mixture during radiolabeling. Bifunctional NE3TA analogues discussed above for MRI is also preferably useful for RIT. Additional preferred RIT complexes according to this invention include the following compound backbones:

37
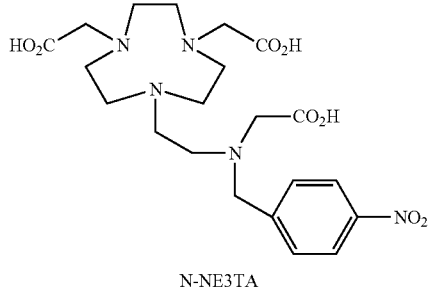
N-NE3TA
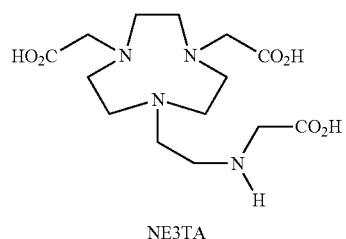
NE3TA
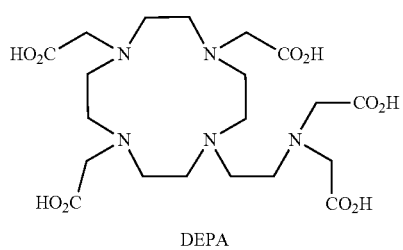
DEPA
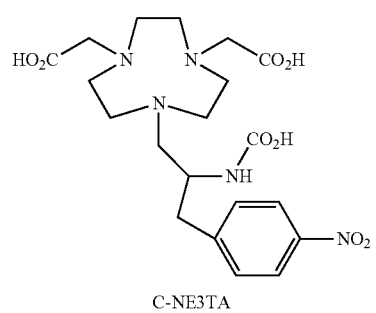
C-NE3TA
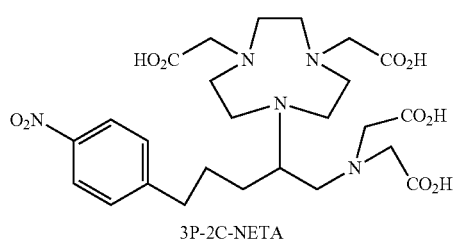
3P-2C-NETA
38
-continued
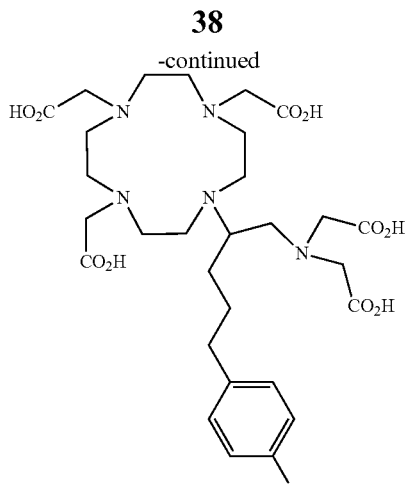
3P-2C-DEPA
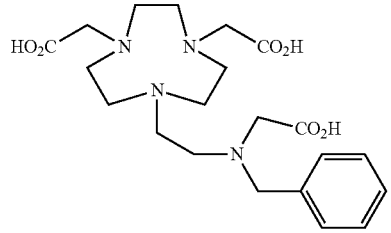
NE3TA-Bn
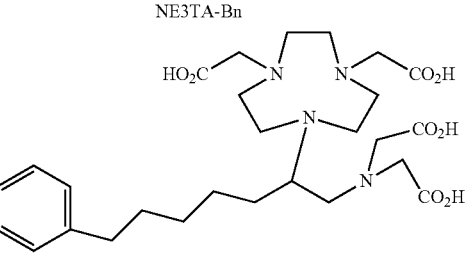
5p-2C-NETA
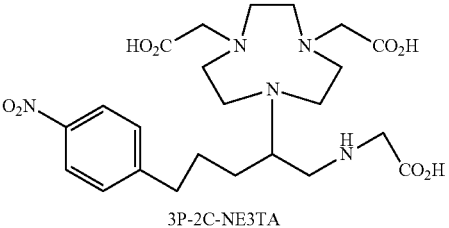
3P-2C-NE3TA
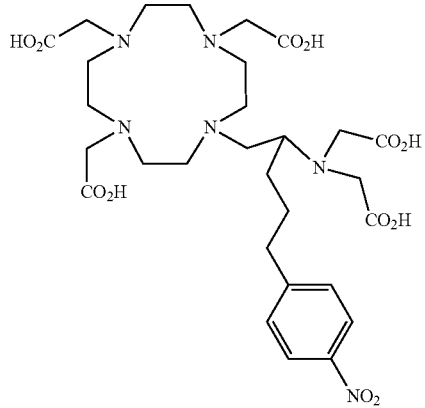
3P-C-DEPA Positron emission tomography, also called PET imaging or a PET scan, is a diagnostic examination that involves the acquisition of physiologic images based on the detection of radiation from the emission of positrons. Positrons are particles emitted from a radioactive substance administered to the patient. The subsequent images of the human body developed with this technique are used to evaluate a variety of diseases. PET scans are used most often to detect cancer and to examine the effects of cancer therapy by characterizing biochemical changes in the cancer. These scans can be performed on the whole body. PET scans of the heart can be used to determine blood flow to the heart muscle and help evaluate signs of coronary artery disease. PET scans of the heart can also be used to determine if areas of the heart that show decreased function are alive rather than scarred as a result of a prior heart attack. Combined with a myocardial perfusion study, PET scans allow differentiation of nonfunctioning heart muscle from heart muscle that would benefit from a procedure, such as angioplasty or coronary artery bypass surgery, which would reestablish adequate blood flow and improve heart function. PET scans of the brain are used to evaluate patients who have memory disorders of an undetermined cause, suspected or proven brain tumors or seizure disorders that are not responsive to medical therapy and are therefore candidates for surgery.

Copper is a preferred metal for PET. Among the available copper radioisotopes, $^{64}$Cu ($t_{1/2}$=12.7 h, $E_{max}^{\beta+}$=656 keV; $E_{max}^{\beta-}$=573 keV) has been shown to be effective for use in positron emission tomography (PET) imaging and targeted radiation therapy applicable to many types of cancer. Bifunctional ligands that possess both binding moieties of Cu(II) and a functional group for conjugation to a targeting moiety are required for the modalities. Research efforts have been directed towards the development of optimal bifunctional ligands that can rapidly form stable complexes with the short-lived $^{64}$Cu while being conjugated to a targeting moiety, either peptide or antibody, to provides an efficient way of generating stable and safe copper radioisotope-labeled drugs for cancer therapy and imaging. Exemplary compounds for use as backbones for use in complexes for PET imaging include NBEA, NBPA, NE3TA, NE3TA-BN.

While the above-described uses for the metal-chelating ligands of the present invention are preferred, those working in the diagnostic arts will appreciate that the ligands also can be complexed with the appropriate metals and used as contrast agents in other imaging techniques, such as x-ray imaging, radionuclide imaging and ultrasound imaging, and in other forms of radiotherapy. Accordingly, the present invention further provides a method for x-ray imaging of a host. The method comprises administering to the host a complex of any of formulas (I)-(IX), in which the metal ion is radio-opaque, in an amount effective to provide an image; and exposing the host to x-rays, whereupon an x-ray contrast image of the host is obtained. The usefulness of metal ions in in vitro and in vivo diagnostic procedures is disclosed in U.S. Pat. No. 4,454,106, hereby incorporated by reference. X-ray contrast imaging procedures can be found in Moss et al., Computed Tomography of the Body, W. D. Saunders Company: Philadelphia, 1992; and M. Sovak, Editor, Radiocontrast Agents, Springer-Verlag: Berlin, 1984, hereby incorporated by reference.

In one desirable embodiment of this invention, a diagnostic process uses $^{111}$In. The radioactive probe $^{111}$In decays with a half life of 2.8 days (67 hours) to an excited state of the daughter nucleus $^{111}$Cd. From this excited state, a cascade of two gamma-rays is emitted, encompassing an isomeric state with a half life of 85 ns. $^{111}$In is useful for single photon emission computed spectroscopy (SPECT), which is a diagnostic tool. Thus, when $^{111}$In is complexed to a compound of any of formulas (I)-(IX) and linked to a biomolecule, such as a hapten, which specifically localizes in a tumor, then that particular localization can be three-dimensionally mapped for diagnostic purposes in vivo by single photon emission tomography. Alternatively, the emission can be used in vitro in radioimmunoassays. The present invention provides a method for SPECT imaging of a host (e.g., mammal, such as a human). The method comprises administering to the host a complex of any of formulas (I)-(IX), in which the metal emits a single photon, in an amount effective to provide an image; and exposing the host to an energy source, whereupon a SPECT image of the host is obtained.

The invention also provides a method for treating a cellular disorder or infectious disease in a mammal, such as treating cancer, iron overload disease, a neurodegenerative, including Alzheuner's disease (AD), Parkinson's disease (PD), tuberculosis, HIV, fungal disease, or amalaria disease. The method includes the steps of administering to the mammal at least one of the compounds, or complexes or conjugates of the compounds, of this invention in an amount effective to treat the cancer, the iron overload disease, the neutrodegenerative or infectious diseases, whereupon the cellular disorder is treated. The treatment can be prophylactic or therapeutic. "Prophylactic" refers to any degree in inhibition of the onset of the cellular disorder, including complete inhibition. "Therapeutic" refers to any degree in inhibition or any degree of beneficial effects on the disorder in the mammal (e.g., human), e.g., inhibition of the growth or metastasis of a tumor.

Preferably, the method includes administration of a metal complex bound to a biomolecule, such as hapten, having a selective binding site on a cell affected by the disorder. For example, the X position of the disclosed compounds of this invention can be bound to an antibody, wherein the antibody is directed and created against an epitope found specifically on tumor cells. Thus, when $^{212}$Pb is transported to the antigen site by the complex, and subsequently decays in secular equilibrium to $^{212}$Bi and its daughters, a beta irradiation is produced from the lead disintegration. In addition, a beta radiation is produced by the bismuth daughters. This beta radiation is similar to the beta radiation from $^{90}$Y but, in addition, each disintegration of bismuth also produces an alpha particle. In this manner, a radiotherapy is provided with a radiation dose from an alpha particle and a beta particle. If desired, only $^{212}$Bi can be introduced in those cases where the disorder to be treated, such as with leukemic cells, can be easily reached within the 1 hour half-life of $^{212}$Bi. Suitable procedures using radiopharmaceuticals can be found in the literature (see, for example, Mettler Jr. et al., Essentials of Nuclear Medicine Imaging, Grune and Stratton, Inc.: New York, 1983).

It is possible to use this method to treat cancer, where the cells are widely differentiated. Cancers suitable for treatment with compounds, conjugates, complexes, and compositions of the invention include, for example, lymphomas, leukemias, colo-rectal cancer, ovarian cancer, breast cancer, and prostate cancer. This method might even be preferred where only a long-range beta emitter, such as $^{90}$Y, is desired. In differing environments in vivo, the $^{212}$Bi is retained inside the chelate after the beta emission in varying amounts. Most desirably, at least 95% of $^{212}$Bi remains in the metal complex. In an acidic medium, such as the stomach, at least about 70% of the $^{212}$Bi is retained. Retaining at least about 80% or 90%, $^{212}$Bi is also desirable depending on the medium.

Compounds and complexes of this invention are useful in radiotherapy of diseases such as cancer. The compounds of this invention are chelators of, for example, copper radioisotopes for use in radiation therapy. As discussed above and further below, ligands of this invention can be radiolabeled with $^{64}$Cu and have demonstrated in vitro stability. Exemplary compound backbones of this invention for use in radiotherapy conjugates and complexes include NBEA, NBPA, NE3TA, and NE3TA-Bn, and conjugates thereof.

Iron is a critical element for the function of the human body, such as for DNA synthesis and regulation of cell cycling. However, free iron, if present in excess, can be dangerous, because it participates in the Haber-Weiss reaction wherein highly reactive oxygen species (ROS) are generated causing life-threatening damage to tissues such as iron overloading diseases and cancers. Many studies indicate that high level of iron accumulated in animals and humans is associated with both the initiation and progression of cancers. It is known that cancer cells require more iron than normal cells and are sensitive to iron depletion. The high demand of iron results from enhanced production of an iron storage protein, ferritin or transferrin receptor (TfR) which governs the uptake of iron into cells from transferrin. The requirement of iron in cancerous cells is also enhanced because iron plays an essential role in the catalytic activity of iron-containing enzyme ribonucleotide reductase (RR). Two dimeric proteins (R1, R2) in RR catalyse the reduction of ribonucleotides to deoxyribonucleotides, the building blocks for DNA synthesis and repair. Cancer cells including Hela and colon cancers and colorectal liver metastates are found to overexpress TfR, RR, or other proteins involved in intracellular iron uptake.

The enhanced requirement of iron in cancer cells as compared to normal cells makes iron depletion using iron chelators targeting TfR, RR, or other proteins involved in iron uptake one of the most efficient strategies to prevent or suppress the rapid proliferation of cancerous cells. Iron chelators are reported to cause cellular iron depletion and exhibit potent cytotoxic activities on diverse cancer cells. Triapine (3-aminopyridine-2-carboxaldehyde thiosemicarbazones), a potent RR inhibitor is a promising iron depleting anti-cancer agent. Cell culture experiments conducted on epithelial ovarian cancer cells indicated that triapine induces apoptosis through an intrinsic pathway. Triapine has been administered intravenously in a number of Phase I and II clinical trials involving patients of various cancers. Hydrophilic iron chelators such as DFO and DTPA have been extensively explored for iron depletion antitumor therapy. DFO has been approved for treatment of iron overload diseases. In addition to its proven iron clearing efficacy, DFO was shown to be effective in inducing apoptotic cell death and exhibited inhibitory and anti-proliferative activity on tumor cells including leukemia, bladder carcinoma, and hepatocelluar carcinoma, most likely due to RR inhibition as a consequence of iron depletion. Two clinical trials involving leukemia patients resulted in the reduction of peripheral blast cell counts, purportedly suggesting significant potential of DFO as an antileukemic agent. Polyaminocarboxylate chelate DTPA is an extracellular iron depletion agent. Antitumor inhibitory activity of DTPA was demonstrated using human neuroblastoma and ovarian carcinoma cell lines. DTPA displayed iron mobilizing capability comparable to DFO in the clinical study of the iron-overloaded thalassaemic patients.

Conjugates and complexes of the backbone compounds of this invention are useful as potent iron chelators for iron depletion therapy (IDT). The polyaminocarboxylate chelators of this invention are thus useful as anti-tumor agents. Exemplary polyaminocarboxylates include NE3TA and NE3TA-Bn and their bifunctional versions C-NE3TA and N-NE3TA.

Additional antitumor agents for targeted IDT include transferrin conjugates, such as C-NE3TA-Transferrin and N-NE3TA-Transferrin, and bile acid based antitumor conjugates, such as CDCA-NE3TA, DCA-NE3TA, CA-NETA, CA-NE3TA, all discussed above.

The invention provides a pharmaceutical composition comprising a pharmaceutically acceptable carrier and one or more compounds of any of formulas (I)-(IX), a conjugate thereof, or a metal complex thereof. The pharmaceutically acceptable carriers described herein, for example, vehicles, adjuvants, excipients, and diluents, are well-known to those skilled in the art and are readily available to the public. The choice of carrier will be determined, in part, by the particular composition and by the particular method used to administer the composition. Accordingly, there are a wide variety of suitable formulations of the pharmaceutical compositions of the present invention.

One skilled in the art will appreciate that suitable methods of administering a composition of the present invention to an animal, e.g., a mammal such as a human, are also known. Although more than one route can be used to administer a particular composition, a particular route can provide a more immediate and more effective result than another route.

Formulations suitable for oral administration can consist of (a) liquid solutions, such as an effective amount of the compound of any of formulas (I)-(IX) dissolved in a diluent, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The compounds of formulas (I)-(IX), alone or in combination with other suitable components, can be made into aerosol formulations to be administered via inhalation. These aerosol formulations can be placed into pressurized acceptable propellants, such as dichlorodifluoromethane, hydrofluorocarbon (such as HFC 134a and/or 227), propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to affect a therapeutic response in the animal over a reasonable time frame or an amount sufficient to allow for diagnostic imaging of the desired tissue or organ. The dose will be determined by the strength of the particular compositions employed and the condition of the animal (e.g., human), as well as the body weight of the animal (e.g., human) to be treated. The size of the dose also will be determined by the existence, nature, and extent of any adverse side effects that might accompany the administration of a particular composition. A suitable dosage for internal administration is 0.01 to 100 mg/kg of body weight per day, such as 0.01 to 35 mg/kg of body weight per day or 0.05 to 5 mg/kg of body weight per day. A suitable concentration of the compound in pharmaceutical compositions for topical administration is 0.05 to 15% (by weight), preferably 0.02 to 5%, and more preferably 0.1 to 3%.

The invention further includes methods of preparing the compounds of formulas (I)-(IX) of this invention. In one embodiment of this invention, the method includes reacting a compound of formula (Ib-1) or (Ib-2):

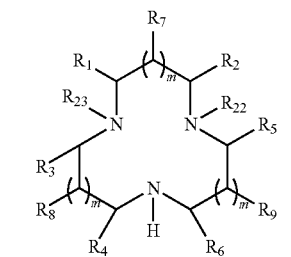
(Ib-1)

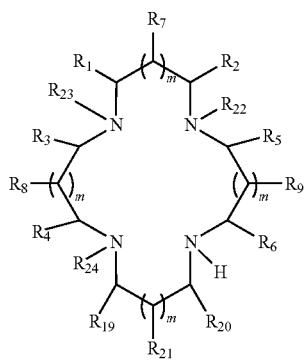
(Ib-2)

wherein: m is 0 or 1; each of $R^{1-21}$ is as defined for $R^{1-21}$ in formulas (I)-(IV); each of $R^{22-24}$ is as defined for $R^{1-22}$ in formulas (I)-(IV), or a protecting group or a structure of (a-1), (a-2), (a-3), (a-4), or (a-5), or a structure of formula (b-1), (b-2), or (b-3):

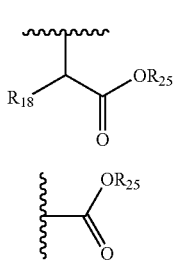
(b-1)

(b-2)

(b-3)

where $R^{18}$ and $R^{22-23}$ are each as defined above; $R^{25}$ independently is or includes hydrogen, allyl, alkyl, tert-butyl, benzyl, dimethoxybenzyl, p-methoxybenzyl, p-nitrobenzyl, benzhydryl, trityl, cycloalkyl, aryl, tert-butyldimethylsilyl, or a protecting group; with a compound of formula (Ib-4), (Ib-5), (Ib-6), (Ib-7), (Ib-8), (Ib-9), or (Ib-10):

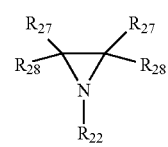
(b-4)

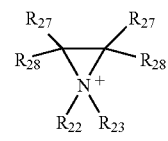
(b-5)

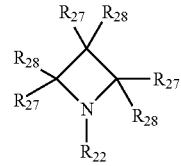
(b-6)

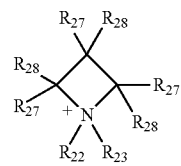
(b-7)

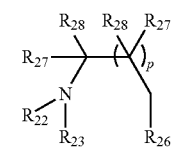
(b-8)

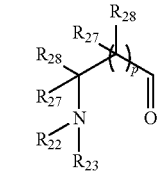
(b-9)

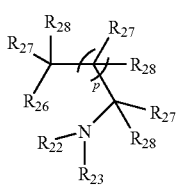
(b-10)

where m is 0 or 1; p is 0 or 1; $R^{1-22}$ are each as defined above; $R^{26}$ is a leaving group and includes tosylate, chloride, bromide, mesylate, triflate, or iodide; and each of $R^{27-28}$ independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, carboxyl, carboxyalkyloxy, aldehyde, ester, amido, an amide containing group, a thioamide containing group, an amino acid-containing group, an ester containing group, a protecting group.

This method is particularly suitable for providing a compound of formula (f-1) or (f-2):

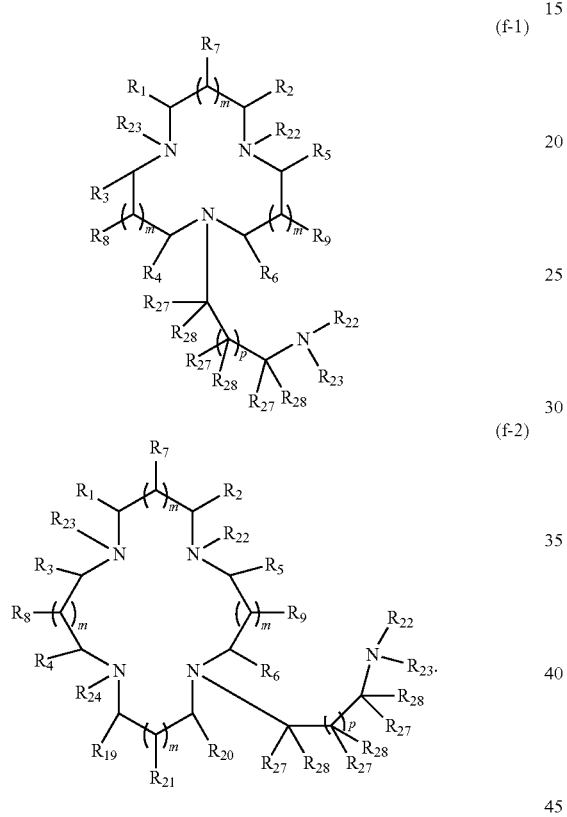

(f-1)

(f-2)

In a further step, the compounds of the formulas (f-1) and (f-2), wherein $R^{22-24}$ is a protecting group, can be converted to a compound of the formula (f-3) or (f-4), respectively:

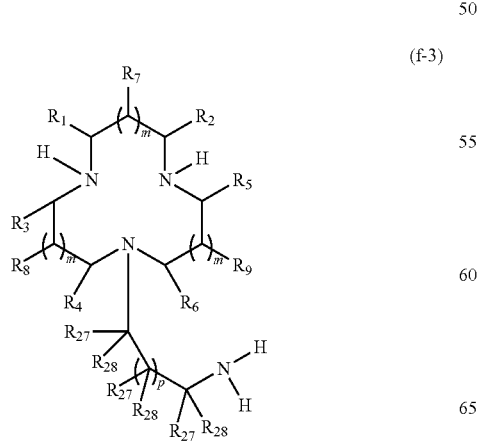

(f-3)

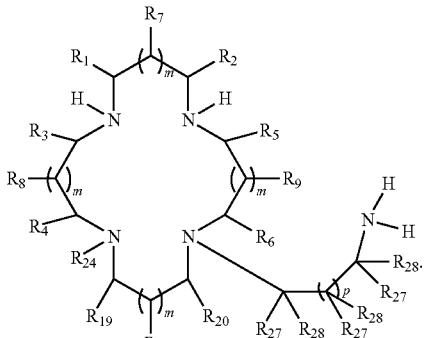

(f-4)

The compounds of (f-3) and (f-4) can then be alkylated, such as to provide a desired compound according to one of formulas (I)-(IV).

Another embodiment of this invention is a method of providing compounds of formula (e-1) or (e-2). The method includes chemically reacting a compound of formula (c-1) with a compound of (d-1) or (d-2):

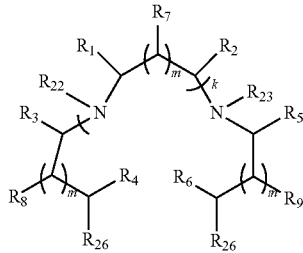

(c-1)

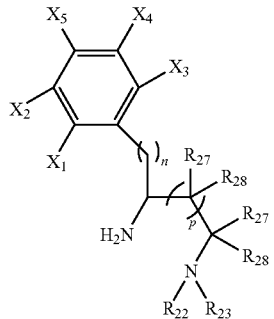

(d-1)

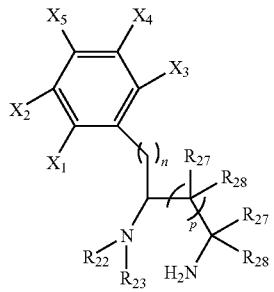

(d-2)

where, k is 0 or 1; m is 0 or 1; n is 1 to 10; p is 0 or 1; $R^{1-9}$ is defined as $R^{1-21}$ in formulas (I)-(IV). $R^{22-23}$ is defined as $R^{1-22}$ in formulas (I)-(IV). $R^{26}$ is a leaving group and includes tosylate, chloride, bromide, mesylate, triflate, or iodide; $R^{27-28}$ is independently is or includes hydrogen, alkyl, allyl, benzyl, cycloalkyl, hydroxyalkyl, aryl, heteroaryl, phenyl, vinyl, or an oxo group; to provide a compound of formula (e-1) or (e-2):

(e-1)
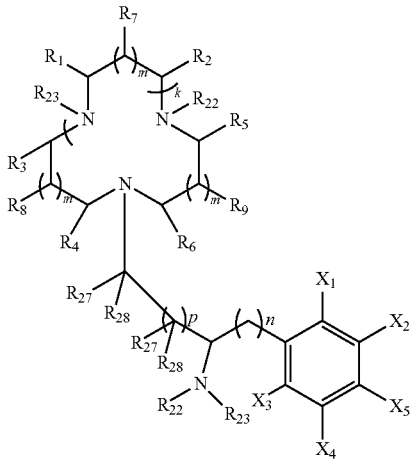

(e-2)
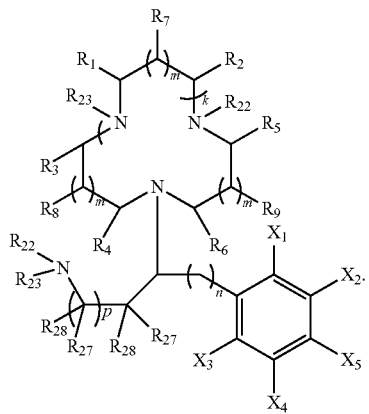

The compound of the formula (e-1) or (e-2), wherein $R^{22-23}$ is a protecting group, can be further converted to a compound of the formula (e-3) or (e-4), respectively:

(e-3)
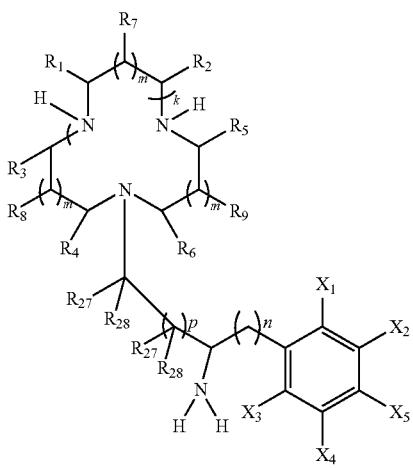

(e-4)
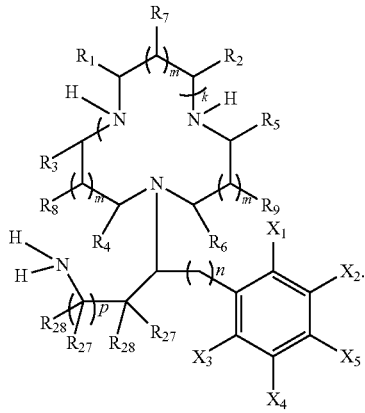

The compounds of (e-3) and (e-4) can then be alkylated, such as to provide a desired compound according to one of formulas (I)-(IV).

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

Example 1

Synthesis and Biological Evaluation of a Novel Decadentate Ligand DEPA

This example provides an efficient and short synthetic route to the novel decadentate ligand 7-[2-(Bis-carboxymethyl-amino)-ethyl]-4,10-bis-carboxymethyl-1,4,7,10-tetra-aza-cyclododec-1-yl-acetic acid (DEPA) with both macrocyclic and acyclic binding moieties being reported. A reproducible and scalable synthetic method to a precursor molecule of DEPA, 1,4,7-tris(tert-butoxycarbonylmethyl)tetraazacyclododecane was developed. DEPA was evaluated as a chelator of $^{177}$Lu, $^{212}$Bi, and $^{213}$Bi for potential use in an antibody-targeted cancer therapy, radioimmunotherapy (RIT) using Arsenazo III based spectroscopic complexation kinetics, in vitro serum stability, and in vivo biodistribution studies.

For a safe and potent RIT, a ligand that can form a stable complex with the radioisotope with clinically acceptable complexation kinetics is required. The ligand DEPA is a hybridized structure of DOTA and DTPA, the most frequently explored polyaminocarboxylates. Macrocyclic DOTA forms a stable complex with various therapeutic metals and is a standard reference ligand for comparison. However, slow formation kinetics of DOTA remains a limitation in RIT applications, particularly involving relatively short-lived radioactive metals (Chong, H. S.; Garmestani, K.; Millenic, D. E.; Brechbiel, M. W. J. Med. Chem. 2002, 45, 3458). Acyclic DTPA rapidly bind to the metals but produces relatively unstable complexes (Harrison, A.; Walker, C. A.; Parker, D.; Jankowski, K. J.; Cox, J. P. Nucl. Med. Biol. 1991). The novel bimodal ligand DEPA is proposed to rapidly form a stable complex with a metal having relatively large ionic radii such as Lu(III), Bi(III), and Ac(III) using the donor system integrating both macrocyclic DOTA and acyclic DTPA. Synthesis and isolation of polar macrocyclic polyaminocarboxylates remains challenging. Chromatographic purification of the polar macrocycles is often complicated due to the formation of polar polyalkylated by-products which are quite indistinguishable from the desired product by TLC. An efficient and short method to prepare DEPA (Scheme 1) is based on a coupling reaction of pre-alkylated precursor molecules 2 and 3. Reaction of trisubstituted cyclen derivative 2 and N-dialkylated bromide 3 was expected to provide the desired macrocycle 4 while minimizing the formation of polyalkylated by-products. The synthetic route to DEPA according to one embodiment of this invention is shown in Scheme 1. The starting material for the coupling reaction, trisubstituted cyclen 2 (Srivastava, S.; Dadachova, E. *Semin Nucl Med.* 2001, 31, 330) was prepared by an efficient synthetic procedure which involves isolation of Compound 2 by simple pH controlled work-up without complicated column chromatography in highly reproducible isolated yield (>45%). The coupling reaction of bisubstituted cyclen derivative 2 and N-dialkylated bromide 3 provided Compound 4, which was further reacted with 6 M HCl to afford the desired chelate DEPA.

Figure 11:
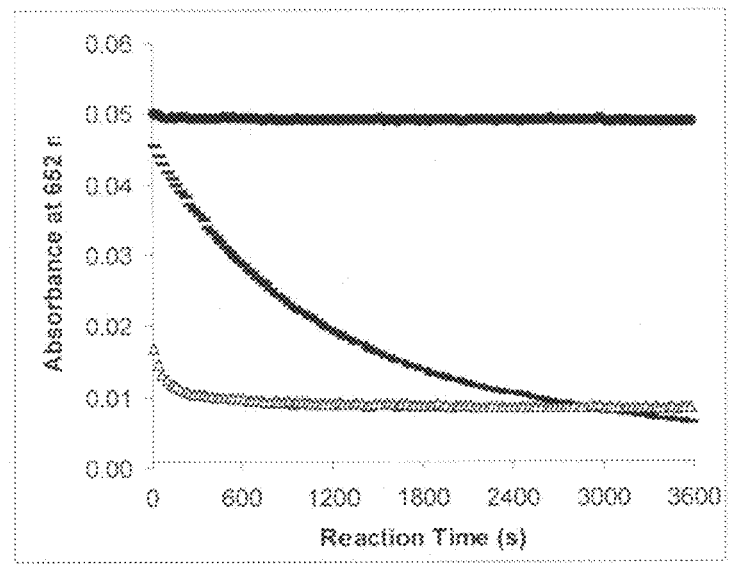
FIG. 11 is a plot of Absorbance (652 nm) vs. Time of Bi(III)-AAIII (●), DOTA (–), DEPA (Δ) at pH 4.0 (0.15M NH$_4$OAc) and 25° C.

The novel ligand DEPA was further evaluated for the complexation kinetics with other metals. The complexation kinetics of the ligand DEPA with Bi(III) was determined using a well-known spectroscopic competing reaction with AAIII according to a modification of the reported procedure (Kodama, M.; Koike, T.; Mahatma, A. B.; Kimura, E. *Inorg. Chem.* 1991, 30, 1270). AAIII is known to form a weak complex with many different metals, which produce a UV absorbance maximum between ~652 nm. However, uncomplexed AAIII absorb little at this wavelength. When introduced to a solution containing the AAIII-metal complex, a chelate can compete with AAIII for the metal. The idea is that if the chelate is more capable of binding the metal than AAIII, the metal will dissociate from the AAIII complex and form a complex with the chelate leading to the decrease in the absorbance at the wavelength. The absorbance ($A_{652}$) for AAIII-Bi(III) complex was measured in the absence and in the presence of the ligands over 1 hour at rt. The complexation kinetics of Bi(III) was determined at pH 4.0 as hydrolysis occurs at a higher pH. The complexation result of the new ligands studied herein was compared to that of DOTA. A plot of absorbance at 652 nm versus time is shown in FIG. 11. The data in FIG. 11 indicate that DOTA displayed sluggish complexation with Bi(III), and the new ligand DEPA displayed quite prompt and substantial binding to Bi(III).

The new ligand DEPA was radiolabeled with $^{177}$Lu and $^{205/6}$Bi (a surrogate of $^{212}$Bi and $^{213}$Bi) and the corresponding radiolabeled complexes were evaluated for in vitro serum stability as described previously. For comparison, DOTA was also radiolabeled with $^{177}$Lu. DEPA and DOTA (0.25 M NH$_4$OAc buffer, pH 4.0) was radiolabeled with $^{177}$Lu at 45° C. for 0.5 h to afford $^{177}$Lu-DEPA ($R_f$=0.6) and $^{177}$Lu-DOTA ($R_f$=0.4) in the respective radiochemical yield of 90% and 95% as determined by radio-TLC. DEPA (0.25 M NH$_4$OAc buffer, pH 5.0) was successfully radiolabeled with $^{205/6}$Bi at room temperature for 1 h to afford $^{205/6}$Bi-DEPA in 96% yield (radio-TLC). $^{177}$Lu-DOTA, $^{177}$Lu-DEPA, and $^{205/6}$Bi-DEPA formed were purified from unbound $^{205/6}$Bi by ion-exchange chromatography using a Chelex-100 column (1 mL volume bed, 100-200 mesh, Na$^+$ form, Bio-Rad, Richmond, Calif.) eluted with PBS (pH 7.4). In vitro serum stability of the purified radiolabeled complexes was performed to determine if DEPA or DOTA radiolabeled with $^{177}$Lu or $^{205/6}$Bi remained stable without loss of the radionuclide in human serum. This was assessed by measuring the transfer of radionuclide from the complex to serum proteins. The data in Table 1 indicate that $^{205/6}$Bi-DEPA was extremely stable in serum, and no radioactivity was released over 14 days. $^{177}$Lu-DEPA remained intact without being dissociated in serum. However, ~10% of the radioactivity was released from $^{177}$Lu-DOTA over 4 days.

TABLE 1

| Time | Radiolabled Complex | | |
|---|---|---|---|
| (h) | $^{177}$Lu-DOTA | $^{177}$Lu-DEPA | $^{205/6}$Bi-DEPA |
| 0 | 100 | 100 | 100 |
| 0.25 | 100.5 | 100 | 100 |
| 0.5 | 99.0 | 100 | 100 |
| 1 | 100.1 | 100 | 100 |
| 2 | 99.3 | 100 | 100 |
| 4 | 97.0 | 100 | 100 |
| 6 | 97.5 | 100 | 100 |
| 24 | 98.2 | 100 | 100 |
| 48 | 91.2 | 100 | 100 |
| 96 | 89.6 | 100 | 100 |
| 120 | — | — | 100 |
| 192 | — | — | 100 |
| 288 | — | — | 100 |
| 336 | — | — | 100 |

Figure 12:
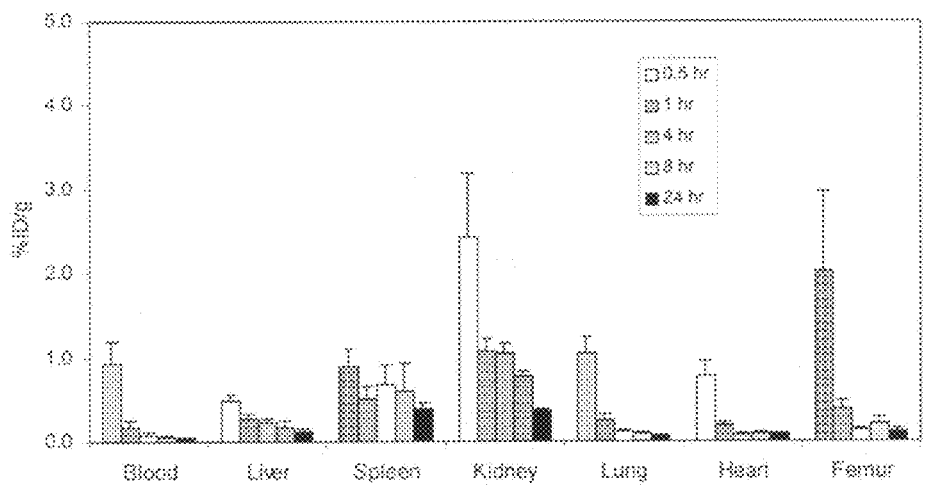
FIG. 12 illustrates the results of a biodistribution study in normal athymic mice of $^{205/6}$Bi-DEPA.

Based on the promising data obtained from the AAIII based spectroscopic complexation kinetics and serum stability experiments, the stability of $^{205/6}$Bi-DEPA was further evaluated by performing a biodistribution study in normal athymic mice as described previously. Blood levels and organ uptake of the radiolabeled complexes in mice were measured at five time points, 0.5, 1, 4, 8, and 24 h post-injection of $^{205/6}$Bi-DEPA. The data in FIG. 12 illustrates that DEPA radiolabeled with $^{205/6}$Bi was essentially inert in vivo and rapidly cleared from the body. Radioactivity that was detected in the blood and the organs was less than 2.44% ID/g at all points. At 24 h post injection, the % ID/g in the kidneys and spleen was 0.36±0.03% and 0.39±0.07%, respectively, which was slightly higher than that observed in other organs. The bone accumulation of the radioactivity was 2.02±0.96% ID/gm at 0.5 h which rapidly decreased to 0.38±0.09% ID/gm at 1 h. Previously, it was reported that $^{177}$Lu-NETA displayed very low organ uptake and rapid blood clearance, while $^{205/6}$Bi-NETA exhibited very high retention in liver at the longer time intervals (5.93±0.78% ID/g at 0 h and 7.31±1.521% ID/g at 24 h) due to possible dissociation of the complex in vivo. Although NETA formed a stable complex with Lu(III) (89 pm), the ligand seems to be inadequate for larger metal Bi(III) (117 pm) due to its smaller cavity size compared to the macrocyclic ring in DEPA. The in vivo biodistribution results suggest that the enhanced in vivo stability of $^{205/6}$Bi-DEPA compared to $^{205/6}$Bi-NETA may result from size-match between Bi(III) and macrocyclic DOTA backbone.

In summary, the novel decadentate ligand DEPA having both macrocyclic and acyclic metal binding moieties was efficiently prepared. The complexation stability and kinetics data suggests that DEPA displayed more rapid and substantial complexation with Bi(III) as compared to DOTA, but appears to be slow in binding Lu(III). $^{177}$Lu-DEPA was found to be stable in serum, while considerable amount of $^{177}$Lu (11%) was released from $^{177}$Lu-DOTA over 4 days. DEPA radiolabeled with $^{205/6}$Bi was very stable in human serum for 2 weeks and display excellent in vivo stability. The complexation kinetics, serum stability, and in vivo biodistribution data confirm the potential of DEPA as a viable chelator of $^{212}$Bi and $^{213}$Bi and validate the synthesis of a bifunctional derivative for RIT.

Example 1

Experimental Information

Instruments and Methods.

Analytical HPLC was performed on an Agilent 1200 equipped with a dioarray detector (λ=254 and 280 nm), thermostat set at 35° C. and a Zorbax Eclipse XDB-C18 column (4.6×150 mm, 80 Å). All absorbance measurements for complexation kinetics were obtained on an Agilent 8453 diode array spectrophotometer equipped with a 8-cell transport system (designed for 1-cm cells). Size exclusion HPLC (SE-HPLC) chromatograms were obtained on a Lab Alliance isocratic system (Model: QGrad) with a Waters 717plus autosampler (Milford, Mass.), a Gilson 112 UV detector (Middleton, Wis.) and an in-line IN/US γ-Ram Model 2 radiodetector (Tampa, Fla.), fitted with a TSK G3000PW column (Tosoh Biosep, Montgomeryville, Pa.).

Reagents.

All reagents were purchased from Aldrich and used as received unless otherwise noted. Lutetium and bismuth atomic absorption standard solution were purchased and used as received. $^{177}$Lu in the chloride form was obtained from NEN Perkin-Elmer. $^{205,6}$Bi was produced using a CS30 cyclotron (PET Dept, Clinical Center, NIH) and purified as described previously. As a note of caution: $^{205/6}$Bi ($t_{1/2}$=15.3/6.2 d) and $^{177}$Lu ($t_{1/2}$=6.7 d) are β, or γ-emitting radionuclides. Appropriate shielding and handling protocols should be in place when using these isotopes.

Scheme 1

1,4,7-Tris(tert-butoxycarbonylmethyl)-1,4,7,10-tetraazacyclododecane-(2)

Reaction of cyclen with 3.0 eq of tert-butyl bromoacetate:

To a solution of cyclen 1 (500 mg, 2.9 mmol) in anhydrous $CHCl_3$ (5 mL) at 0° C. was added a solution of tert-butyl bromoacetate (1.70 g, 8.7 mmol) in anhydrous $CHCl_3$ (10 mL) over 30 min. The resulting mixture was gradually warmed to rt, and continuously stirred for 18 h after which the reaction mixture was filtered while washing with $CH_2Cl_2$ to afford cyclen and mono-substituted cyclen (451 mg) as solid. The filtrate was concentrated in vacuo, and $H_2O$ (7 mL) was added into the residue, and the resulting solution was treated with 0.1 M HCl and 0.5 M NaOH to adjust the pH to 7. The resulting aqueous solution was evaporated, and the residue was dissolved in $CH_2Cl_2$ and filtered to remove NaCl salt. The filtrate was evaporated to dryness and the residue was washed with $H_2O$ to provide pure Compound 2 (696 mg, 47%). The aqueous and ether layers were evaporated and dried to afford bi-substituted cyclen (115 mg, 9.9%) and tetra-substituted cyclen (47 mg, 0.3%), respectively. The $^1$H and $^{13}$C NMR spectra of Compound 2 were essentially identical to data reported previously.

Reaction of cyclen with 2.4 eq of tert-butyl bromoacetate:

To a solution of cyclen 1 (1.00 g, 5.8 mmol) in anhydrous $CHCl_3$ (5 mL) at 0° C. was added a solution of tert-butyl bromoacetate (2.72 g, 13.95 mmol) in anhydrous $CHCl_3$ (10 mL) over 30 min. The resulting mixture was stirred at 0° C. for 1 h, gradually warmed to rt, and continuously stirred for 17 h after which the reaction mixture was concentrated in vacuo. $H_2O$ (15 mL) was added into the residue, and pH of the resulting solution was adjusted to 7. Diethyl ether (15 mL) was added into the aqueous solution, and the white solid that formed was filtered off, washed with water, and dissolved in $CH_2Cl_2$. The organic solution was dried over $MgSO_4$, filtered, and evaporated to the dryness to afford pure Compound 2 (1.34 g, 45%). The $^1$H and $^{13}$C NMR spectra of Compound 2 were essentially identical to data reported previously.

Tert-butyl {7-[2-(Bis-benzyloxycarbonylmethyl-amino)-ethyl]-4,10-bis-tert-butoxycarbonylmethyl-1,4,7,10-tetraaza-cyclododec-1-yl}-acetate (4)

To a solution of Compound 2 (974 mg, 2 mmol) in $CH_3CN$ (40 mL) was added DIPEA (776 mg, 6 mmol) and Compound 3 (882 mg, 2.1 mmol). The resulting mixture was refluxed for 96 h at which time the reaction mixture was cooled to room temperature and evaporated. The residue was purified via column chromatography on silica gel (220-400 mesh) eluting with 7% $CH_3OH/CH_2Cl_2$ (starting from $CH_2Cl_2$ with a gradual increase of 1% polarity) to afford Compound 4 (982 mg, 56%). $^1$H NMR ($CDCl_3$) δ 1.33-1.42 (m, 27H), 2.15-2.50 (m, 8H), 3.82 (t, 4H), 2.95-3.12 (m, 4H), 3.40-3.72 (m, 4H), 5.04 (s, 4H), 7.12-7.32 (m, 10H); $^{13}$C NMR ($CDCl_3$) δ 27.8, 50.7 (2C), 51.9, 52.2, 54.6 (2C), 55.7, 56.3, 66.2, 82.1, 82.4, 128.1, 128.3, 128.5, 135.3, 170.5, 172.5, 173.3. HRMS (Positive ion FAB) Calcd for $C_{46}H_{71}N_5O_{10}$ [M+Na]$^+$ m/z 876.5125. Found: [M+Na]$^+$ m/z 876.5099. A combination of a binary gradient and an isocratic mobile phase (50-100% B/15 min; solvent A=$H_2O$; solvent B=$CH_3CN$ and 100% B/15 min) at a flow rate of 1 mL/min was used for analytical HPLC ($t_R$=9.8 min) of Compound 4.

{7-[2-(Bis-carboxymethyl-amino)-ethyl]-4,10-bis-carboxymethyl-1,4,7,10-tetraazacyclo-dodec-1-yl}-acetic acid (DEPA)

Compound 4 (256 mg, 0.3 mmol) was treated with 6M HCl (10 mL). The resulting mixture was refluxed for 5 h, cooled to room temperature, and washed with $CHCl_3$ (50 mL×3). The aqueous layer was evaporated to provide a waxy solid (184 mg, 89%). $^1$H NMR ($D_2O$) δ 2.70-4.23 (m, 18H); $^{13}$C NMR ($CD_3OD$) δ 46.9, 48.6, 50.8, 51.9, 52.8, 54.7, 55.2, 168.21 (3C). HRMS (Positive ion FAB) Calcd for $C_{20}H_{35}N_5O_{10}$ [M+H]$^+$ m/z 505.2367. Found: [M+H]$^+$ m/z 505.2384.

General Procedure for Complexation Kinetics Using AAIII.

The kinetics experiments were performed as previously described. Ultrapure ammonium acetate (Aldrich, #431311) and hydrochloric acid solution (J. T. Baker, #JT6900-5) were purchased and used as received. All buffer solutions were prepared using deionized water (Milli-Q®, 18 MΩ). Metal-free stock solutions of all $NH_4OAc$ buffers (0.15 M, pH 4 or pH 4.5) were prepared using Chelex-100 resin (100-200 mesh, Bio-Rad Lab, Hercules, Calif.). Chelex resin (5 g) was added into the butter solution (100 mL) and the mixture was shaken for 1 h in a shaker (Eberbach), stored in the refrigerator overnight, and filtered through a Corning filter system (430513, pore size 0.2 μM). A 15 μM AAIII solution in 0.15 M $NH_4OAc$ (pH 4 or pH 4.5) were prepared by adding AAIII (5.82 mg) to the $NH_4OAc$ buffer (500 mL). A solution of Bi(III)-AAIII (7.5 μM) was freshly prepared by mixing AAIII solution (15 μM, 50 mL) in 0.15 M $NH_4OAc$ (pH 4) with Bi(III) atomic absorption standard solution (79 μL, 995 μg/mL). A solution of Lu(III)-AAIII (1.8 μM) was freshly prepared by mixing AAIII solution (5 μM, 50 mL) in 0.15 M $NH_4OAc$ buffer (pH 4.5) with Lu(III) atomic absorption standard solution (15.4 μL, 1014 μg/ml). The resulting solutions were shaken for 2 h in the shaker (Eberbach). The multicell transport of the UV/visible spectrometer was zeroed against a cell filled with 2 mL of AAIII solution. The solution in each sample cell was removed and filled with 2 mL of Bi(III)-AAIII solution or Lu(III)-AAIII solution. 10 μL, of Bi(III)-

AAIII or Lu(III)-AAIII solution was then removed from each sample cell, and each of the ligands, DOTA or DEPA (10 μL, 10 mM) was added into their respective sample cells. Kinetics spectra were collected every 30 sec at 652 nm for 1 h.

Radiolabeling.

Representative conditions for labeling of DEPA and DOTA with $^{177}$Lu are described here. To 18.5 MBq of $^{177}$Lu in 90 μL of 0.25 M NH$_4$OAc (pH 4.0) was added 10 μg of the ligand in 10 uL of H$_2$O. The reaction mixture was incubated at 45° C. for 30 min. Radiometal incorporation and the radiochemical purity were determined by radio-TLC. $^{177}$Lu-DOTA and $^{177}$Lu-DEPA possess the respective R$_f$ values of 0.4 and 0.6. Silica gel TLC plates were developed with MeOH:10% NH$_4$OAc (2:1 v/v). The labeling efficiency $^{177}$Lu-DOTA and $^{177}$Lu-DEPA was 90% and 95% as determined by radio-TLC. DEPA was radiolabeled with $^{205/6}$Bi using previously described conditions. To a solution of DEPA (1 mg, 1.4 μmol) in water (50 μL) was added $^{205/6}$Bi in HI (0.1M, 250 μL, 1.5 mCi). The pH of the mixture was adjusted to 5 with 5M NH$_4$OAc buffer (50 μL, pH 7). The reaction mixture was incubated at room temperature for 1 h. The labeling efficiency (96%) was determined by radio-TLC as the stationary phase and 10% methanol/water as the mobile phase. The complex $^{205/6}$Bi-DEPA possesses an R$_f$ value of 1. $^{177}$Lu-DOTA, $^{177}$Lu-DEPA, and $^{205/6}$Bi-DEPA complex formed were purified from unbound $^{177}$Lu or $^{205/6}$Bi by ion-exchange chromatography using a Chelex-100 column (1 mL volume bed, 100-200 mesh, Na$^+$ form, Bio-Rad, Richmond, Calif.) eluted with PBS (pH 7.4).

In Vitro Serum Stability of the Radiolabeled Metal Complexes.

An aliquot of 3.7 MBq of the purified $^{177}$Lu-labeled ligands was added to 0.5 mL of mouse serum (Sigma, St. Louis, Mo.) and 0.1% NaN$_3$. The resulting mixture was incubated at 37° C. for 96 h. Aliquots of 2 μl, of the resulting mixture were analyzed by radio-TLC and HPLC at different time points, 0, 0.25, 0.5, 1, 2, 4, 6, 24, 48, and 96 h of incubation. The stability of purified $^{205/6}$Bi-DEPA was evaluated in human serum (Gemini Bioproducts, Woodland, Calif.) for 14 days by measuring the transfer of the radionuclide from the complex to serum proteins as monitored by SE-HPLC. Radiolabeled complexes were diluted to an appropriate volume that allowed for preparation of multiple samples containing 5-10 μCi and filter-sterilized using a Millex-GV 0.22 μM filter. 140 μL of this stock solution was then mixed with 1400 μL of sterile normal human serum or saline. Aliquots (200 μL) were drawn and separated into individual tubes for subsequent analysis using aseptic technique. The samples were incubated at 37° C., and at designated intervals, subjected to analysis by SE-HPLC. Samples were loaded onto the HPLC and eluted with PBS, pH 7.4 isocratically at 1 mL/min. Radioactivity still associated with the chelate typically displayed a retention time of 12.5 min at this flow rate. Radioactivity associated with a transfer to serum proteins generally appeared between ~4.5-8 min.

Example 2

Synthesis and Evaluation of 3p-C-DEPA and C-DEPA for Radioimmunotherapy

α-emitting radioisotopes, $^{212}$Bi (t$_{1/2}$=60.6 m) and $^{213}$Bi (t$_{1/2}$=45 m) have been proven to be effective for radioimmunotherapy (RIT) of cancers. The new bifunctional ligands 3p-C-DEPA and C-DEPA is synthesized for use in radioimmunotherapy of Bi(III). The synthetic route to 3p-C-DEPA and C-DEPA is outlined in Schemes 2-6.

Synthesis of 3p-C-DEPA (Scheme 2-4)

Regiospecific ring opening of Compound 8 by nucleophilic attack of bulky tri-substituted CYCLEN 9 occurred at less hindered methylene carbon in Compound 8 to produce Compound 10 which was subsequently treated with HCl(g) in 1,4-Dioxane to afford 3p-C-DEPA (Scheme 2). The regiochemistry observed in the nucleophilic ring opening of the aziridinium ion 8 at the methylene carbon was confirmed by comparing the spectroscopic data of Compound 10 which was prepared separately via other synthetic route starting from Compound 11 (Scheme 3). Reductive amination of Compound 11 with 12 using sodium triacetoxyborohydride provided Compound 13, which was subsequently treated with HCl(g) in 1,4-Dioxane to afford Compound 14. A base-promoted reaction of Compound 14 with t-butyl bromoacetate produced Compound 10, and comparison of the spectroscopic data of Compound 10 that was separately produced via two synthetic routes confirmed regiochemistry in the ring opening of Compound 8. Synthesis of 3p-2C-DEPA having the isothiocyanate (SCN) group for conjugation to an antibody is shown in Scheme 4. The nitro group in Compound 9 was transformed into the amino group to provide Compound 14. The reaction of Compound 14 with thiophosgene provided the desired bifunctional ligand 3p-2C-DEPA-NCS.

Synthesis of C-DEPA (Scheme 5-6)

The key reaction step in the synthesis of C-DEPA is nucleophilic ring opening reaction of N—Boc protected aziridine 2 by macrocyclic tetramine cyclen (1,4,7,10-Tetraazacyclododecane) 1 (Scheme 5). Selective monosubstitution of Compound 1 with aziridine derivative 2 produced 4 by the opening of the aziridine ring in Compound 2 at the less hindered methylene carbon. The isolated yield of Compound 4 was generally low due to formation of polysubstitution byproducts and elimination product 3 and varied on reaction time and temperature and solvent. The best isolated yield of Compound 4 was obtained from the reaction of Compound 1 (1 equiv) and 2 (2 equiv) in MeOH under reflux for 21 h. The same reaction was repeated in CH$_3$OH (reflux, 48 h), a mixture of Compounds 1 and 2 in a 1:1 mole ratio as evidenced by analytical HPLC. When the same reaction mixture in CH$_3$CN was refluxed for ~10 h, the reaction provided 7 in poor yield (12-21%). Considerably higher isolated yield of Compound 4 was accomplished when the reaction mixture was refluxed for 36 h. Reaction of Compound 1 (1 equiv), Compound 2 (1 equiv), and DIPEA (3 equiv) in DMF (45° C., 25 h) provided elimination product 4 as the exclusive product. In order to confirm the regiochemistry observed in the nucleophilic opening of the aziridine ring at the methylene carbon, not the methine carbon, Compound 7 was prepared independently via reductive amination of Compound 5 with Compound 6 followed by removal of BOC groups in Compound 9. Swern oxidation of Compound 6 was smoothly accomplished to provide 7 in good isolated yield. BOC-protected Compound 9 was obtained from reductive amination of Compound 5 with Compound 6 using sodium triacetoxyborohydride. Preparation of Compound 5 via this alternative route was found to be more reliable and practical as compared to the route based on selective substitution which was initially accomplished. The BOC group(s) in both Compounds 4 and 9 were deprotected by the treatment of 4 with 4M HCl in 1,4-dioxane to provide Compound 5. The $^1$H and $^{13}$C NMR spectral data of Compound 5 obtained from two different routes were essentially identical and confirms the regiochemistry observed in the ring opening of the aziridine Compound 2. Synthesis of the target bifunctional ligands C-DEPA and C-DEPA-NCS is shown in Scheme 6. Reaction of Compound 5 in acetonitrile with t-butyl bromoacetate produced Compound 5. This substitution reaction was turned out to be very challenging and provided the desired Compound 9 in poor yield (~10%), and the isolated yield is yet to be improved. Subsequent removal of the tert-butyl groups in 9 using HCl(g) in 1,4-Dioxane provided C-DEPA. The nitro group in Compound 9 was transformed into the amino group to provide Compound 11. Removal of the tert-butyl groups in Compound 11 followed by reaction with thiophosgene provided the desired ligand C-DEPA-NCS with the linker for conjugation to antibody.

Conjugation of 3p-C-DEPA-NCS and C-DEPA with Herceptin.

Herceptin (Trastuzumab), a tumor targeting monoclonal antibody, was conjugated to 3p-C-DEPA-NCS or C-DEPA. The antibody was reported to selectively target the HER2 (human epidermal growth factor receptor 2) protein overproduced in various tumors including colorectal carcinomas (~90% overexpression). 3p-C-DEPA-NCS or C-DEPA was conjugated with trastuzumab, concentration of trastuzumab in the corresponding conjugates was quantified by the method of Lowry. The Cu(II)-AAIII and Pb(II)-AAIII based UV-Vis spectrophotometric assay was used for the determination of the number of 3p-C-DEPA-NCS and C-DEPA linked to trastuzumab (L/P ratio), respectively. The ligand to protein (L/P) ratio for 3p-C-DEPA-Trastuzumab conjugate was measured to be 1.97. The ligand to protein (L/P) ratio for 2C-DEPA-Trastuzumab conjugate was measured to be 0.84. For comparison, C-DOTA-NCS and C-DTPA-NCS (Macrocyclics, TX) were conjugated to Herceptin, and the respective L/P ratio of 1.3 and 1.5 was measured using Pb(II)-AAIII assay.

Radiolabeling of 3p-C-DEPA-Herceptin and C-DEPA with $^{205/6}$Bi.

The purified Herceptin conjugates (30~50 µg) in 0.25M NH$_4$OAc buffer solution at pH 5.5 was labeled with $^{205/6}$Bi (0.1M HI) (60-100 µCi) at room temperature (RT). During the reaction time (1 h), the radiolabeling kinetics was determined by taking aliquots of the reaction mixture at 6 time points. The components were analyzed using SE-HPLC after challenging the reaction mixture with 10 mM DTPA, and the radiolabeling efficiency (%) was determined (Table 2).

TABLE 2

*Radiolabeling efficiency (%) of bifunctional ligands with $^{205/6}$Bi (0.25M NH$_4$OAc, pH 5.5, RT).

| Time (min) | 3p-C-DEPA-trastuzumab | C-DOTA-trastuzumab | C-DTPA-trastuzumab | C-DEPA-trastuzumab |
|---|---|---|---|---|
| 1 | 93.6 ± 0.4 | 8.4 ± 1.9 | 93.6 ± 0.5 | 88.7 ± 1.4 |
| 5 | 94.7 ± 0.9 | 17.2 ± 4.3 | 95.1 ± 0.3 | 90.4 ± 1.0 |
| 10 | 95.0 ± 0.4 | 28.7 ± 4.5 | 95.3 ± 0.6 | 91.2 ± 1.2 |
| 20 | 94.1 ± 0.6 | 38.0 ± 4.9 | 96.0 ± 0.3 | 91.1 ± 1.4 |
| 30 | 94.4 ± 1.6 | 49.7 ± 9.0 | 95.9 ± 0.3 | 92.6 ± 0.8 |
| 60 | 94.5 ± 0.5 | 60.2 ± 8.0 | 95.8 ± 0.1 | 92.7 ± 0.8 |

*Radiolabeling efficiency (mean ± standard deviation) was measured from three different experiments (N = 3).

The data indicate that both 3p-C-DEPA and C-DEPA-Herceptin conjugates were extremely rapid in labeling $^{205/5}$Bi (1 min, >93%) at RT which was comparable to binding of C-DTPA with $^{205/6}$Bi. As expected, radiolabeling of C-DOTA with $^{205/6}$Bi was slow and not complete at 24 h (60.2±8.0%). In Vitro Serum Stability of 205/6Bi-3p-C-DEPA-Herceptin and $^{205/6}$Bi-C-DEPA-Herceptin.

The $^{205/6}$Bi-radiolabeled ligand-Herceptin conjugates were prepared at RT and pH 5.5 and purified on PD-10 column (Sephadex G-25M, GE Healthcare) eluted with PBS, and the fractions containing the radiolabeled antibody conjugate was verified by SE-HPLC and collected. The purified radioimmunoconjugates (30-50 were incubated in human serum (600-900 µL) at 37° C. At each time point (0 h, 1, 2, 3, 4 days), aliquots of the reaction mixture were analyzed using SE-HPLC after challenging the reaction mixture with 10 mM DTPA. $^{205/6}$Bi-3p-C-DEPA-Herceptin and $^{205/6}$Bi-C-DEPA-trastuzumab were found to be stable in human serum without release of the radioactivity for at least 3 days. However, ~25% of the radioactivity was released from $^{205/6}$Bi-C-DTPA-Trastuzumab conjugate in 72 h. (Table 3). The result of the in vitro evaluations suggests both 3p-2C-DEPA and 2C-DEPA as promising bifunctional ligands for use in RIT of $^{212}$Bi and $^{213}$Bi.

TABLE 3

In vitro Serum stability (SE-HPLC) of $^{205/6}$Bi-radiolabeled trastuzumab-ligand conjugates (pH 7 and 37° C.)

| Radioimmunoconjugate | time (h) | purity |
|---|---|---|
| $^{205/6}$Bi-C-DEPA-trastuzumab | 0 | 100 |
| | 24 | 100 |
| | 48 | 100 |
| | 72 | 100 |
| $^{205/6}$Bi-3p-C-DEPA-trastuzumab | 0 | 100 |
| | 24 | 100 |
| | 48 | 100 |
| | 72 | 100 |
| $^{205/6}$Bi-C-DTPA-trastuzumab | 0 | 100 |
| | 24 | 76.7 |
| | 48 | 77.8 |
| | 72 | 77.5 |

Example 2

Experimental Information

Scheme 2

4-nitrophenylpropyl bromide (2)

1-bromo-3-phenylpropane 1 (10.0 g, 50.3 mmol) was dissolved in the mixture of acetic anhydride (10.25 g, 100.6 mmol) and acetic acid (6.04 g, 100.6 mmol), and the resulting mixture was maintained at −40° C. while fuming nitric acid (6.33 g, 100.6 mmol) was added drop wise over 3.5 h. The resulting mixture was allowed to warm to room temperature and then neutralized in ice water with ammonium hydroxide. The reaction mixture was extracted with ethyl acetate (3×100 mL). The combined organic layers were dried over MgSO$_4$, filtered, and concentrated in vacuo to the dryness. The residue was purified via column chromatography on silica gel (220-440 mesh) eluting with 0.1% EtOAc in hexanes to provide the pure product as yellow oil 2 (5.29 g, 53%). $^1$H NMR (CDCl$_3$, 300 MHz) δ 2.15-2.26 (m, 2H), 2.92 (t, J=7.7 Hz, 2H), 3.39 (t, J=6.4 Hz, 2H), 7.35 (d, J=8.7 Hz, 2H), 8.15 (d, J=9.1 Hz, 2H); $^{13}$C NMR (CDCl$_3$, 300 MHz) δ 32.5, 33.5, 33.6, 123.8, 129.4, 146.6, 148.4.

2-Acetylamino-2-[3-(4-nitrophenyl)propyl]malonic acid diethyl ester (3)

To a round bottom flask was added anhydrous EtOH (60 mL). Na (1.58 g, 68.66 mmol) was portion wise added into EtOH. To a clear solution of NaOEt was drop wise added a solution of diethyl acetamido malonate (14.92 g, 68.66 mmol) in Ethanol (140 mL) over 30 min. The resulting mixture was then heated at 50° C. for 1.5 h and then reflux for 10 min. The solution became cloudy and light brownish indicating formation of deprotonated diethyl acetamido malonic ester. To the reaction mixture at reflux was added 2 (16.76 g, 68.66 mmol) in ethanol (120 mL) portionwise over 1 h. The reaction mixture was maintained at reflux for 4.5 days, while monitoring the reaction progress using TLC. The reaction mixture was allowed to cool to room temperature and then evaporated to dryness. To the residue, DI water (100 mL) was added and extracted with diethyl ether (3×150 mL). The combined organic layers were dried over $MgSO_4$, filtered, and concentrated in vacuo to the dryness. The residue was purified via column chromatography on silica gel eluting with 30% EtOAc/hexanes to afford a mixture of 3 and diethyl acetamido malonate (12.3 g) and the mixture was used for the next reaction without further purification. Compound 3 was prepared for characterization in a small quantity. To a round bottom flask was added anhydrous EtOH (10 mL). Na (28.3 mg, 1.23 mmol) was portionwise added into EtOH. To the clear NaOEt solution was added a solution of diethyl acetamido malonate (267 mg, 1.23 mmol) in Ethanol (5 mL) dropwise over 30 min. The resulting mixture was then heated at 50° C. for 1.5 h and then reflux for 10 min. The solution became cloudy and light brownish indicating formation of deprotonated diethyl acetamido malonic ester. To the reaction mixture at reflux was portionwise added 2 (300 mg, 1.23 mmol) in ethanol (5 mL) over 1 h. The reaction mixture was maintained at reflux for 4.5 days while monitoring the reaction progress using TLC. The reaction mixture was allowed to cool to room temperature and then evaporated to dryness. The residue was purified via column chromatography on silica gel eluting with 30% EtOAc/hexanes to afford pure product 3. $^1$H NMR ($CDCl_3$, 300 MHz) δ 1.23 (t, J=7.7 Hz, 6H), 1.45-1.60 (m, 2H), 2.04 (s, 3H), 2.39 (t, J=8.5 Hz, 2H), 2.73 (t, J=7.7 Hz, 2H), 4.22 (q, J=7.2 Hz, 4H), 7.29 (d, J=7.7 Hz, 2H), 8.24 (d, J=8.5 Hz, 2H); $^{13}$C NMR ($CDCl_3$, 300 MHz) δ 13.82, 22.88, 24.91, 31.65, 35.13, 62.44, 66.17, 123.50, 128.98, 146.28, 149.41, 167.78, 169.01.; HRMS (Positive ion FAB) Calcd for $C_{18}H_{24}N_2O_7$ $[M+H]^+$ m/z 381.1662. Found: $[M+H]^+$ m/z 381.1653.

2-Amino-5-(4-nitrophenyl)pentanoic acid (4)

Compound 3 (12.3 g, 32.3 mmol) was dissolved in the mixture of acetic acid (30 mL) and conc. HCl (100 mL), and the resulting solution was maintained under reflux for 24 h. The reaction was allowed to room temperature, and the resulting precipitate was filtered while washing with isopropanol and dried in vacuo to provide pure 3 (6.0 g). The volume of the filtrate was reduced to half and left in the freezer, and white solid formed was filtered. The repeated recrystallization afforded 4 (7.5 g, 46% from 2). $^1$H NMR ($CDCl_3$, 300 MHz) δ 1.75-2.08 (m, 4H), 2.84 (t, J=6.9 Hz, 2H), 4.02 (t, J=5.7 Hz, 1H), 7.47 (d, J=8.5 Hz, 2H), 8.15 (d, J=8.7 Hz, 2H); $^{13}$C NMR ($CDCl_3$, 300 MHz) δ 25.97, 29.61, 34.48, 52.44, 123.22, 129.29, 146.45, 149.50, 170.32. HRMS (Positive ion FAB) Calcd for $C_{11}H_{14}N_2O_4$ $[M+H]^+$ m/z 239.1032. Found: $[M+H]^+$ m/z 239.1029.

2-Amino-5-(4-nitrophenyl)pentanoic acid methyl ester (5)

A solution of Compound 4 (7.1 g, 29.8 mmol) in MeOH (120 mL) at 0-5° C. was saturated with HCl (g) for 2 h, at which time the mixture was allowed to ambient temperature and then was stirred for 24 h. The resulting mixture was concentrated in vacuo to provide technically pure product 5 (7.4 g, 98%) as an acidic salt. $^1$H NMR ($D_2O$, 300 MHz) δ 1.50-1.93 (m, 4H), 2.67 (t, J=7.1 Hz, 2H), 3.68 (s, 3H), 4.03 (t, J=5.9 Hz, 1H), 7.30 (d, J=8.4 Hz, 2H), 8.03 (d, 2H, J=8.2 Hz, 2H); $^{13}$C NMR ($D_2O$, 300 MHz) δ 25.50, 29.26, 34.16, 52.66, 53.50, 123.30, 129.18, 145.50, 149.96, 170.37.

A slurry of the ester salt 5 (10 mmol) in dry methanol (2.5 mL) was treated with $Et_3N$ (10 mL). To the stirred slurry was then added anhydrous ether (100 mL), and the solution was cooled at −10° C. for 1 h. The resulted triethylamine hydrochloride salt was filtered off, and the filtrate was concentrated under vacuum to light yellow oil 5 as free amino ester: $^1$H NMR ($CD_3OD$, 300 MHz) δ 1.65-1.85 (m, 4H), 2.78 (t, J=6.8 Hz, 2H), 3.60 (t, J=5.7 Hz, 1H), 3.73 (s, 3H), 7.45 (d, J=8.4 Hz, 2H), 8.15 (d, J=8.4 Hz, 2H); $^{13}$C NMR (MeOD, 300 MHz) δ 26.54, 32.92, 34.87, 51.68, 53.35, 122.77, 129.26, 146.20, 150.18, 174.32. FIRMS (Positive ion FAB) Calcd for $C_{12}H_{16}N_2O_4$ $[M+H]^+$ m/z 253.1188. Found: $[M+H]^+$ m/z 253.1212.

{tert-butoxycarbonylmethyl-[1-hydroxymethyl-4-(4-nitrophenyl)butyl]amino}acetic acid tert-butyl ester (6) [148]

To a solution of Compound 11a (4.1 g, 18.2 mmol) and $K_2CO_3$ (5.5 g, 39.9 mmol) in $CH_3CN$ (35 mL) at 0-5° C. was added dropwise a solution of tert-butyl bromoacetate (7.3 g, 37.2 mmol) in $CH_3CN$ (15 mL) over 30 min while maintaining the temperature at 0° C. The resulting mixture was allowed to room temperature and stirred for 24 h. After the work-up, Compound 6 (7.6 g, 93%) was obtained as a light yellow oil and used for the next step without further column chromatographic purification. $^1$H NMR ($CDCl_3$, 300 MHz) δ 1.12-1.28 (m, 2H), 1.35-1.57 (m, 18H), 1.60-1.83 (m, 2H), 2.62-2.85 (m, 3H), 3.18-3.30 (m, 1H), 3.72-3.78 (m, 1H), 3.35-3.51 (m, 4H), 7.32 (d, J=8.6 Hz, 2H), 8.14 (d, J=8.7, 2H); $^{13}$C NMR ($CDCl_3$, 300 MHz) δ 27.7 (t), 27.8 (q), 28.3 (t), 35.9 (t), 53.0 (t), 62.6 (d), 65.1 (t), 81.2 (s), 123.5 (d), 129.1 (d), 146.2 (s), 150.1 (s), 172.2 (s). HRMS (Positive ion Calcd for $C_{21}H_{27}NO_3$ $[M+H]^+$ m/z 342.2064. Found: $[M+]^+$ m/z 342.2065.

tert-Butyl 2,2'-(2-bromo-5-(4-nitrophenyl)pentylazanediyl)diacetate (7)

To a solution of Compound 6 (7.6 g, 16.81 mmol) and $PPh_3$ (5.3 g, 20.17 mmol) in $CH_2Cl_2$ (70 mL) at 0° C. was added portionwise NBS (3.6 g, 20.17 mmol) over 30 min. The residue was purified via column chromatography on silica gel (60-230 mesh) eluting with 10% ethyl acetate in hexanes. The product 7 (4.8 g, 66%) was thereby obtained as a yellowish oil. $^1$H NMR ($CDCl_3$, 300 MHz) δ 1.42-1.48 (m, 18H), 1.63-2.20 (m, 4H), 2.65-2.82 (m, 2H), 2.95 (dd, J=14.3, 7.8 Hz, 1H), 3.18 (dd, J=14.3, 6.1 Hz, 1H), 3.31-3.52 (m, 4H), 4.01-4.12 (m, 1H), 7.35 (d, J=8.6 Hz, 2H), 8.12 (d, J=8.6 Hz, 2H); $^{13}$C NMR ($CDCl_3$, 300 MHz) δ 28.0 (q), 28.6 (t), 34.9 (t), 35.2 (t), 55.0 (d), 57.0 (t), 62.3 (t), 80.4 (s), 123.4 (d), 129.1 (d), 146.2 (s), 149.9 (s), 170.3 (s); HRMS (Positive ion FAB) Calcd for $C_{23}H_{35}BrN_2O_6$ $[M+]^+$ m/z 515.1757. Found: $[M+H]^+$ m/z 515.1739. Anal. Calcd for $C_{23}H_{35}BrN_2O_6$: C, 53.59; H, 6.84; N, 5.43. Found: C, 53.32; H, 6.64; N, 5.31.

tert-butyl 2,2',2''-(10-(2-(bis(2-tert-butoxy-2-oxoethyl)amino)-5-(4-nitrophenyl)pentyl)-1,4,7,10-tetraazacyclododecane-1,4,7-triyl)triacetate (10)

To a solution of N,N-bisubstituted amino bromide 8 (547.7 mg, 1.06 mmol) and DIPEA (410.9 mg, 3.18 mmol) in CH$_3$CN (10 mL) was added tri-alkylated cyclen 9 (546.6 mg, 1.06 mmol). The resulting mixture was stirred for 4 weeks at room temperature while monitoring the reaction progress using TLC. The reaction mixture was evaporated to dryness. The residue was purified via column chromatography on silica gel (220-440 mesh) eluting with 3% CH$_3$OH in CH$_2$Cl$_2$. Ether (20 mL) was added to the combined and evaporated fractions having product and filtered to remove the starting material 2. The filtrate was washed with deionized water (2×10 mL). The ether layer was dried over MgSO$_4$, filtered, and concentrated in vacuo to provide pure product 10 (610 mg, 61%). $^1$H NMR (CDCl$_3$, 300 MHz) δ 1.37-1.45 (m, 45H), 1.60-1.78 (m, 2H), 1.81-1.95 (m, 1H), 2.02-2.19 (m, 1H), 2.39-2.50 (m, 3H), 2.56-2.83 (m, 18H), 3.21 (s, 4H), 3.26 (s, 2H), 3.36 (dd, J=16.9, 21.9, 4H), 7.36 (d, J=8.6 Hz, 2H), 8.09 (d, J=8.7 Hz, 2H); $^{13}$C NMR (CDCl$_3$, 300 MHz) δ 27.89 (t), 28.11 (q), 28.22 (q), 30.98 (t), 35.91 (t), 52.04 (t), 52.11 (t), 52.20 (t), 53.09 (t), 53.19 (t), 56.34 (t), 56.44 (t), 58.38 (t), 60.08 (d), 80.41 (s), 80.57 (s), 123.43 (d), 129.30 (d), 146.18 (s), 151.17 (s), 170.98 (s), 171.10 (s), 171.41 (s). HRMS (Positive ion FAB) Calcd for C$_{49}$H$_{85}$N$_6$O$_{12}$ [M+H]$^+$ m/z 949.6225. Found: [M+H]$^+$ m/z 949.6256. Analytical HPLC (t$_R$=42 min, method 1).

Procedure in alkylation.

To a solution of Compound 14 (170.3 mg, 0.45 mmol) in CH$_3$CN (5 mL) was added tert-butylbromoacetate (438.9 mg, 2.25 mmol) and K$_2$CO$_3$ (311.0 mg, 2.25 mmol). The resulting mixture was heated at 65° C. and stirred for 13 h while monitoring the reaction progress by analytical HPLC (method 1, t$_R$=41 min). The reaction mixture was cooled to room temperature, and the solvent was evaporated. The residue was purified by semi-prep HPLC (method 3, 138-143 min) to afford Compound 10 (37 mg, 9%).

Scheme 3 tri-tert-butyl 10-(2-(tert-butoxycarbonyl)-5-(4-nitrophenyl)pentyl)-1,4,7,10-tetraazacyclododecane-1,4,7-tricarboxylate (13)

To a solution of Compound 11 (1.24 g, 3.85 mmol) in 1,2-dichloroethane (30 mL) was added portionwise Compound 12 (1.82 g, 3.85 mmol). The resulted solution was then treated with sodium triacetoxyborohydride (1.14 g, 5.4 mmol). The mixture was stirred at room temperature for overnight while monitoring the reaction progress using TLC. The reaction mixture was quenched by saturated NaHCO$_3$ (40 mL) and the product was extracted while washing with DCM. The combined organic layers were dried over MgSO$_4$, filtered, and concentrated in vacuo. The residue was purified by silica gel (60-230 mesh) column chromatography eluted with 25% EtOAc in hexanes 13 (1.90 g, 63%). $^1$H NMR (CDCl$_3$, 300 MHz) δ 1.03-1.51 (m, 36H), 1.51-2.01 (m, 4H), 2.50-3.99 (m, 21H), 7.30 (d, J=8.5 Hz, 2H), 8.08 (d, J=8.4 Hz, 2H); $^{13}$C NMR (CDCl$_3$, 300 MHz) 24.69 (t), 27.16 (t), 28.57 (q), 28.69 (q), 35.13 (t), 35.68, (t), 36.64 (t), 47.49 (t), 48.46 (d), 50.54 (t), 51.20 (t), 58.18 (t), 58.64 (t), 79.18 (s), 79.28 (s), 79.57 (s), 123.56 (d), 129.19 (d), 146.27 (s), 150.39 (s), 155.14 (s), 155.73 (s), 155.95 (s), 156.72 (s). HRMS (Positive ion ESI) Calcd for C$_{39}$H$_{67}$N$_6$O$_{10}$ [M+H]$^+$ m/z 779.4913. Found: [M+H]$^+$ m/z 779.4890.

5-(4-nitrophenyl)-1-(1,4,7,10-tetraazacyclododecan-1-yl)pentan-2-amine (14)

Compound 13 (1.84 g, 2.36 mmol) at 0-5° C. was treated dropwise with 4M HCl (g) in 1,4-dioxane (18 mL) over 20 min. The resulting mixture was warmed to room temperature. After 22 h, ether (100 mL) was added and continued to stir for 10 min. The resulting mixture was capped and placed in the freezer for 1 h. The solid formed was filtered, washed with ether, and quickly dissolved in DI water. Evaporation of the aqueous solution gave an acidic salt 14 (1.17 g, 89%). $^1$H NMR (D$_2$O, 300 MHz) δ 1.50-1.71 (m, 4H), 2.50-2.80 (m, 6H), 2.82-3.40 (m, 15H), 7.30 (d, J=8.7 Hz, 2H), 8.00 (d, J=8.7 Hz, 2H); $^{13}$C NMR (D$_2$O, 300 MHz) δ 25.65 (t), 30.63 (t), 34.46 (t), 41.30 (t), 42.13 (t), 44.21 (t), 48.56 (t), 48.57 (d), 56.81 (t), 123.66 (d), 129.40 (d), 145.90 (s), 150.21 (s). HRMS (Positive ion ESI) Calcd for C$_{19}$H$_{35}$N$_6$O$_2$ [M+H]$^+$ m/z 379.2816. Found: [M+H]$^+$ m/z 379.2804.

To a solution of acidic salt 14 (670 mg, 1.7 mmol) in DI water (5 mL) was treated with 0.5 M NaOH to adjust pH 7. The aqueous layer was then extracted with CHCl$_3$ (25 mL×2). The aqueous layer was further adjusted to pH 10. At each step, the aqueous layer was extracted with CHCl$_3$ (25 mL×2). The organic layers were combined, dried over MgSO$_4$, filtered, and concentrated in vacuo to provide free amine 14 (452 mg, 100%). $^1$H NMR (CDCl$_3$, 300 MHz) δ 1.20-1.49 (m, 2H), 1.60-1.89 (m, 2H), 2.15-3.00 (m, 21H), 7.33 (d, J=8.6 Hz, 2H), 8.14 (d, J=8.6 Hz, 2H); $^{13}$C NMR (CDCl$_3$, 300 MHz) δ 27.26 (t), 35.00 (t), 35.64 (t), 45.16 (t), 46.01 (t), 46.95 (t), 48.71 (d), 52.10 (t), 62.56 (t), 123.27 (d), 129.00 (d), 145.94 (s), 150.24 (s).

2,2',2"-(10-(2-(bis(carboxymethyl)amino)-5-(4-nitrophenyl)pentyl)-1,4,7,10-tetraazacyclododecane-1,4,7-triyl)triacetic acid Compound 10 (77.0 mg, 0.081 mmol) at 0-5° C. was treated dropwise with 4M HCl(g) in 1,4-dioxane (15 mL) over 20 min. The resulting mixture was allowed to warm to room temperature. After 22 h, ether (~20 mL) was added and continued to stir for 10 min. The resulting mixture was capped and placed in the freezer for 1 h. The solid formed was filtered, washed with ether, and quickly dissolved in DI water. Evaporation of the aqueous solution gave an off-white solid 3p-2C-DEPA (68.0 mg, 97%). $^1$H NMR (D$_2$O, 300 MHz) δ 1.26-1.40 (m, 1H), 1.48-1.70 (m, 3H), 2.52-2.78 (m, 2H), 2.90-3.70 (m, 27H), 3.75-3.98 (m, 2H), 7.35 (d, J=8.3 Hz, 2H), 8.06 (d, J=8.2 Hz, 2H); $^{13}$C NMR (D$_2$O, 300 MHz) δ 27.08 (t), 27.12 (t), 34.64 (t), 48.45 (t), 48.82 (t), 50.22 (t), 51.09 (t), 52.40 (t), 53.58 (t), 54.28 (t), 55.46 (t), 59.43 (d), 123.55 (d), 129.40 (d), 145.71 (s), 150.54 (s), 169.54 (s), 172.97 (s), 173.93 (s); HRMS (Positive ion FAB) Calcd for C$_{29}$H$_{45}$N$_6$O$_{12}$ [M+H]$^+$ m/z 669.3095. Found: [M+]$^+$ m/z 669.3086.

Scheme 4

2,2',2"-(10-(5-(4-aminophenyl)-2-(bis(carboxymethyl)amino)pentyl)-1,4,7,10-tetraazacyclododecane-1,4,7-triyl)triacetic acid (14)

To a solution of 3p-2C-DEPA (46.0 mg, 68.8 μmol) in H$_2$O (12 mL) was added dry 10% Pd/C (14.0 mg) under Argon gas and at room temperature. The reaction mixture was placed under hydrogenation apparatus for 19 h. The resulting mixture was filtered via celite bed and washed thoroughly with H$_2$O. The filtrate was evaporated resulting a light yellow solid 14 (44 mg, 100%). $^1$H NMR (D$_2$O, 300 MHz) δ 1.22-1.38 (m, 1H), 1.43-1.68 (m, 3H), 2.45-2.63 (m, 2H), 2.81-3.70 (m, 27H), 3.80-3.98 (m, 2H), 7.17 (d, J=8.5 Hz, 2H), 7.24 (d, J=8.5 Hz, 2H); $^{13}$C NMR (D$_2$O, 300 MHz) δ 27.04 (t), 27.46 (t), 34.18 (t), 48.50 (t), 48.98 (t), 50.28 (t), 51.12 (t), 52.50 (t), 53.69 (t), 54.50 (t), 55.49 (t), 59.40 (d), 123.01 (d), 127.55 (s), 130.10 (d), 143.28 (s), 169.50 (s), 173.13 (s), 174.22 (s); HRMS (Positive ion ESI) Calcd for $C_{29}H_{47}N_6O_{10}$ [M+H]$^+$ m/z 639.3348. Found: [M+H]$^+$ m/z 639.3342.

2,2',2''-(10-(2-(bis(carboxymethyl)amino)-5-(4-isothiocyanatophenyl)pentyl)-1,4,7,10-tetraazacyclododecane-1,4,7-triyl)triacetic acid To a solution of Compound 14 (7.0 mg, 8.2 μmol) in water (0.1 mL) was added $CSCl_2$ in $CHCl_3$ (7.0 μL). The resulting mixture was stirred at room temperature for 2 hours. The aqueous layer was taken out and concentrated in vacuo to give pure 3p-C-DEPA-NCS as a light yellow solid (8.0 mg, 100%). $^1H$ NMR ($D_2O$, 300 MHz) δ 1.23-1.72 (m, 4H), 2.40-2.58 (m, 2H), 2.80-3.98 (m, 29H), 7.13 (s, 4H). HRMS (Positive ion FAB) Calcd for $C_{30}H_{43}N_6O_{12}S$ [M+H]$^+$ m/z 679.2761. Found: [M+H]$^+$ m/z 679.2747.

Scheme 5 tert-Butyl N-{1-[4-(hydroxynitroso)phenyl]-3-(1,4,7,10-tetraazacyclododecan-1-yl)propan-2-yl}carbamate (4)

To a two neck flask solutions of Compound 2 (1.50 g, 5.4 mmol) in MeOH (100 mL) and cyclen 1 (1.86 g, 10.8 mmol) in MeOH were added simultaneously over 1 h span. The reaction mixture was refluxed for 21 h during the time the reaction was continuously followed by TLC and analytical HPLC. After the completion, the reaction mixture was evaporated to provide dark yellow oil. The crude mixture was then purified by neutral alumina column chromatography eluted with ethyl acetate/n-hexane to afford the pure coupled product as light yellow solid 4 (1.351 g, 56%). Mp 67° C. $^1H$ NMR ($CDCl_3$, 300 MHz) δ 1.34 (s, 9H), 2.52 (dd, J=13.2, 4.9 Hz, 1H), 2.66-3.03 (m, 19H), 3.85 (br s, 1H), 5.80 (br s, 1H of NH), 7.39 (d, J=8.5 Hz, 2H), 8.10 (d, J=8.5 Hz, 2H); $^{13}C$ NMR ($CDCl_3$, 300 MHz) δ 28.38 (q), 38.99 (t), 45.79 (t), 46.27 (t), 47.59 (t), 50.92 (d), 52.37 (t), 59.13 (t), 79.05 (s), 123.37 (d), 130.26 (d), 146.39 (s), 146.97 (s), 155.61 (s). HRMS (positive ion FAB) Calcd for $C_{24}H_{41}N_3O_5$ [M+H]$^+$ m/z 451.3033. Found: [M+]$^+$ m/z 451.3035.

1-(4-nitrophenyl)-3-(1,4,7,10-tetraazacyclododecan-1-yl)propan-2-amine (5)

To Compound 4 (1.251 g, 2.8 mmol) with an ice cooling bath around was added 6 mL of 4 M HCl/dioxane dropwise. After the addition was complete, the reaction mixture was gradually warmed to room temperature and allowed to stir overnight at room temperature for 14 h. After completion 30 mL of ethyl ether was added to the reaction mixture with vigorous stirring and the resulting slurry was kept in the freezer for 2 h. The precipitate was collected and washed with ethyl ether, then immediately lyophilized with water and evaporated to provide pure acidic salt as light yellow solid 5 (1.242 g, 99%). NMR ($D_2O$, 300 MHz) δ 2.44-2.59 (m, 3H), 2.79-3.17 (m, 17H), 3.65-3.67 (m, 1H), 7.38 (d, J=8.4 Hz, 2H), 8.06 (d, J=8.4 Hz, 2H); $^{13}C$ NMR ($D_2O$, 300 MHz) δ 36.61 (t), 40.85 (t), 42.45 (t), 42.69 (t), 48.17 (t), 49.32 (d), 56.28 (t), 123.94 (d), 130.33 (d), 142.67 (s), 146.63 (s). HRMS (positive ion FAB) Calcd for $C_{19}H_{33}N_3O_3$ [M+H]$^+$ m/z 351.2508. Found: [M+H]$^+$ m/z 351.2525.

The hydrochloride salt (500 mg, 1.10 mmol) was dissolved in 10 mL of water and pH of the solution was adjusted to 7 by NaOH (aq) solution, the aqueous solution was the extracted with $CHCl_3$ (15 mL). Then the separated aqueous layer pH was adjusted to 10 and the aqueous solution was the extracted with $CHCl_3$ (15 mL). The separated aqueous layer pH was adjusted to 13 and extracted with $CHCl_3$ (15 mL). The left over aqueous solution was evaporated to dryness on rotavapor and treated with $CHCl_3$ (15 mL). The $CHCl_3$ layer extracted for aqueous solution having pH 7 and 10 showed the pure product (checked by NMR), therefore combined together to provide free amine as light yellow oil 5 (341 mg, 100%). $^1H$ NMR ($CDCl_3$, 300 MHz) δ 2.31-2.38 (m, 3H), 2.43-2.80 (m, 21H), 2.92, (dd, J=13.3, 4.1 Hz, 1H), 3.17-3.26 (m, 1H), 7.36 (d, J=8.5 Hz, 2H), 8.11 (d, J=8.5 Hz, 2H); $^{13}C$ NMR ($CDCl_3$, 300 MHz) δ 42.26 (t), 45.21 (t), 46.26 (t), 47.04 (t), 50.73 (d), 52.51 (t), 62.23 (t), 123.63 (d), 130.06 (d), 146.61 (s), 147.55 (s).

tert-butyl N-{1-[4-(hydroxynitroso)phenyl]-3-oxo-propan-2-yl}carbamate (7)

To the stirred solution of oxalyl chloride (257 mg, 2.03 mmol), and DCM (2 mL) was added dropwise DMSO (277 mg, 3.54 mmol) over a span of 10-15 min while maintaining the temperature −60° C. After 5 min the DCM (1 mL) solution of BOC protected amino alcohol (300 mg, 1.01 mmol) was added dropwise over 10 min at −60° C. After the addition was complete the reaction mixture was allowed to stir at −60° C. for another 1.5 h $Et_3N$ was added and reaction mixture was allowed to stir at same temperature for 30 min. Then the saturated solution of $NH_4Cl$ was added and the resulting aqueous solution was extracted with DCM (25 mL×2). The separated organic layer was treated with $MgSO_4$, filtered and evaporated on rotavapor to provide the aldehyde as a light yellow solid Compound 7 in more then 95% purity (232 mg, 78%). Mp 115° C. $^1H$ NMR ($CDCl_3$, 300 MHz) δ 1.40 (s, 9H), 3.11 (dd, J=13.8, 7.2 Hz, 1H), 3.32 (dd, J=13.8, 5.7 Hz, 1H), 4.40-4.49 (m, 1H), 5.18 (d, J=6.8 Hz, 1H), 7.34 (d, J=8.6 Hz, 2H), 8.14 (d, J=8.6 Hz, 2H), 9.64 (s, 1H); $^{13}C$ NMR ($CDCl_3$, 300 MHz) δ 28.20 (q), 35.01 (t), 60.46 (d), 80.60 (s), 123.80 (d), 130.29 (d), 144.12 (s), 147.05 (s), 155.26 (s), 198.24 (d). HRMS (positive ion ESI) Calcd for $C_{14}H_{18}N_2O_5Na$ [M+Na]$^+$ m/z 317.1108. Found: [M+Na]$^+$ m/z 317.1104.

1,4,7-tri-tert-butyl 10-(2-{[(tert-butoxy)carbonyl]amino}-3-[4 (hydroxynitroso)phenyl]propyl)-1,4,7,10-tetraazacyclododecane-1,4,7-tricarboxylate (9)

To the stirred solution of aldehyde 7 (50 mg, 0.17 mmol) and macrocyclic Compound 8 (80 mg, 0.17 mmol) in dichloro ethane was added sodium triacetoxy borohydride portionwise over 10 min while maintaining the temperature 0° C. After the addition was complete the reaction mixture was gradually warmed to room temperature and allowed to stir at same temperature for 18 h. After which the reaction mixture was treated with saturated $NaHCO_3$ solution (3 mL) and extracted with ethyl acetate (10 mL×2). The separated organic layer was treated with $MgSO_4$, filtered and evaporated on a rotary evaporator to provide Compound 9 as a light yellow oil in more then 99% purity (109 mg, 85%). $^1H$ NMR ($CDCl_3$, 300 MHz) δ 1.32 (s, 9H), 1.40 (s, 9H), 1.42 (s, 18H), 2.52-3.57 (m, 11H), 3.70-4.09 (m, 10H), 5.20 (d, J=6.9 Hz, 1H), 7.34 (d, J=8.4 Hz, 2H), 8.11 (d, J=8.4 Hz, 2H); $^{13}C$ NMR ($CDCl_3$, 300 MHz) δ 28.50 (q), 28.57 (q), 28.66 (q), 41.32 (t), 47.64 (t), 50.33 (d), 50.62 (t), 51.22 (t), 57.50 (t), 57.99 (t), 79.23 (s), 79.56 (s), 79.66 (s), 123.48 (d), 130.31 (d), 146.37 (s), 146.62 (s), 155.12 (s), 155.34 (s), 156.96 (s), 156.76 (s). HRMS (positive ion ESI) Calcd for $C_{37}H_{62}N_6NaO_{10}$ [M+Na]$^+$ m/z 773.4420. Found: [M+Na]$^+$ m/z 773.4398.

1-(4-nitrophenyl)-3-(1,4,7,10-tetraazacyclododecan-1-yl)propan-2-amine (5)

To the coupled product 9 (90 mg, 0.12 mmol) with an ice cooling bath around was added 0.5 mL of 4 M HCl/dioxane dropwise. After the addition was complete, the reaction mixture was gradually warmed to room temperature and allowed to stir overnight at room temperature for 14 h. After completion 5 mL of ethyl ether was added to the reaction mixture with vigorous stirring and the resulting slurry was kept in the freezer for 2 h. The precipitate was collected and washed with ethyl ether, then immediately lyophilized with water and evaporated on rotavapor to provide pure salt as a light yellow solid 5 (59 mg, 93%).

The hydrochloride salt (47 mg, 0.09 mmol) was dissolved in 1 mL of water and pH of the solution was adjusted to Compound 7, the aqueous solution was the extracted with $CHCl_3$ (5 mL). Then the separated aqueous layer pH was adjusted to 10 and the aqueous solution was the extracted with $CHCl_3$ (5 mL). The separated aqueous layer pH was adjusted to 13 and extracted with $CHCl_3$ (5 mL). The left over aqueous solution was evaporated to dryness on rotavapor and treated with $CHCl_3$ (5 mL). The $CHCl_3$ layer extracted for aqueous solution having pH 7 and 10 showed the pure product (checked by NMR), therefore combined together to provide free amine 5 as light yellow oil (28.4 mg, 88%). $^1H$ and $^{13}C$ NMR data of 5 obtained in this reaction is essentially same as those of 5 described above.

Scheme 6 tert-butyl 2-{[2-(tert-butoxy)-2-oxoethyl]({1-[4-(hydroxynitroso)phenyl]-3-{4,7,10-tris[2-(tert-butoxy)-2-oxoethyl]-1,4,7,10-tetraazacyclododecan-1-yl}propan-2-yl})amino}acetate (10)

To the stirred solution of Compound 5 (185 mg, 0.53 mmol) in $CH_3CN$ (5 mL) was added $K_2CO_3$ (365 mg, 2.64 mmol) followed by dropwise addition of tert-butyl bromoacetate (515 mg, 2.64 mmol) over 20 min. The reaction mixture was heated to 65° C. for 8 h, and the progress of the reaction was monitored by analytical HPLC. After the completion of the reaction, the reaction mixture was filtered to remove $K_2CO_3$ while washing with $CH_3CN$. The filtrate was then concentrated on vacuum and purified by semi preparative HPLC (method 2, $t_R$=94-101 min) to provide pure penta-alkylated amine as a light yellow oil 10 (49 mg, 10%). $^1H$ NMR ($CDCl_3$, 300 MHz) δ 1.40 (s, 18H), 1.43 (s, 27H), 2.65 (dd, J=12.6, 9.0 Hz, 1H), 2.47-2.58 (m, 2H), 2.63-2.79 (m, 16H), 3.01-3.09 (m, 1H), 3.14 (dd, J=13.1, 3.6 Hz, 1H), 3.23-3.45 (m, 10H), 7.51 (d, J=8.7 Hz, 2H), 8.11 (d, J=8.7 Hz, 2H); $^{13}C$ NMR ($CDCl_3$, 300 MHz) δ 28.13 (q), 28.23 (q), 39.48 (t), 49.80 (t), 51.76 (t), 51.95 (t), 52.26 (t), 52.75 (t), 56.23 (t), 56.43 (t), 56.90 (t), 62.69 (d), 80.76 (s), 80.80 (s), 123.58 (d), 130.17 (d), 146.52 (s), 147.60 (s), 170.97 (s), 171.08 (s), 171.22 (s). HRMS (positive ion FAB) Calcd for $C_{47}H_{81}N_6O_{12}$ [M+H]$^+$ m/z 921.5912. Found: [M+H]$^+$ m/z 921.5913.

2-[(carboxymethyl)({1-[4-(hydroxynitroso)phenyl]-3-[4,7,10-tris(carboxymethyl)-1,4,7,10-tetraazacyclododecan-1-yl]propan-2-yl})amino]acetic acid (11)

To 10 (4.8 mg, 5.2 µmol) with an ice cooling bath around was added 0.5 mL of 4 M HCl/dioxane dropwise. After the addition was complete, the reaction mixture was gradually warmed to room temperature and allowed to stir overnight at room temperature. After completion 5 mL of ethyl ether was added to the reaction mixture with vigorous stirring and the resulting slurry was kept in the freezer for 2 h. The precipitate was collected and washed with ethyl ether, then immediately lyophilized with water and evaporated to provide pure salt as a light yellow solid Compound 11 (4.1 mg, 98%). $^1H$ NMR ($D_2O$, 300 MHz) δ 2.42-3.10 (m, 6H), 3.16-3.64 (m, 23H), 3.79-3.96 (m, 2H), 7.41 (d, J=8.6 Hz, 1H), 8.11 (d, J=8.6 Hz, 1H). HRMS (positive ion FAB) Calcd for $C_{27}H_{41}N_6O_{12}$ [M+H]$^+$ m/z 641.2782. Found: [M+H]$^+$ m/z 641.2773.

2,2',2"-(10-(3-(4-aminophenyl)-2-(bis(carboxymethyl)amino)propyl)-1,4,7,10-tetraazacyclododecane-1,4,7-triyl)triacetic acid (12)

To a solution of Compound 11 (15.0 mg, 18.2 µmol) in $H_2O$ (6.5 mL) was added dry 10% Pd/C (3.8 mg) under Argon gas and at room temperature. The reaction mixture was placed under hydrogenation apparatus for 14 h. The resulting mixture was filtered via celite bed and washed thoroughly with $H_2O$. The filtrate was evaporated resulting a light yellow solid Compound 12 (13.4 mg, 92.7%). $^1H$ NMR ($D_2O$, 300 MHz) δ 2.40-2.71 (m, 2H), 2.80-3.15 (m, 8H), 3.15-3.3.81 (m, 18H), 3.81-4.32 (m, 5H), 7.21-7.45 (dd, 4H).

2-[(carboxymethyl)[1-(4-isothiocyanatophenyl)-3-[4,7,10-tris(carboxymethyl)-1,4,7,10-tetraazacyclododecan-1-yl]propan-2-yl]amino]acetic acid (13)

To a solution of Compound 10 (4.6 mg, 5.55 mop in water (0.15 mL) was added $CSCl_2$ in $CHCl_3$ (6.9 µL). The resulting mixture was stirred at room temperature for 4 hours. The aqueous layer taken out and concentrated in vacuo gave pure Compound 13 (C-DEPA-NCS) as a light brownish solid (3.3 mg, 71%). $^1H$ NMR ($D_2O$, 300 MHz) δ 2.40-2.51 (m, 2H), 2.80-4.01 (m, 29H), 7.11-7.23 (s, 4H); HRMS (positive ion FAB) Calcd for $C_{28}H_{41}N_6O_{10}S$ [M+H]$^+$ m/z 653.2605. Found: [M+H]$^+$ m/z 653.2626.

Experimental for Evaluation of 3p-C-DEPA and C-DEPA

Tables 2 and 3
Conjugation of 3p-C-DEPA-NCS and C-DEPA-NCS to Trastuzumab.

All absorbance measurements were obtained on an Agilent 8453 diode array spectrophotometer equipped with an 8-cell transport system (designed for 1 cm cells). Metal-free stock solutions of all buffers were prepared using Chelex®-100 resin (200-400 mesh, Bio-Rad Lab, Hercules, Calif., Cat#142-2842). Chelex resin (3.0 g) was added into the buffer solution (300 mL) and the mixture was shaken overnight in a shaker and filtered through a Corning filter system (Cat#430513, pore size 0.2 µm). Disposable PD-10 Sephadex™ G-25M columns (GE Healthcare, #17-0851-01) were rinsed with 25 mL of the appropriate buffer prior to addition of antibody or its ligand conjugates. Centricon C-50 (50,000 MWCO) Centrifugal Filter Devices (Cat# UFC805008) were purchased from Amicon Bioseparations (Millipore, Bedford, Mass.). Trastuzumab was obtained from Dr. Martin Brechbiel's lab (NIH) as a gift. The initial concentration of trastuzumab was determined by the Lowry method (24). Phosphate buffered saline (PBS, 1×, 11.9 mM Phosphates, 137 mM NaCl, and 2.7 mM KCl, pH 7.4) was purchased from Fisher and was used as received. Conjugation buffer (50 mM HEPES, 150 mM NaCl, pH 8.6) were prepared as 1× solutions, chelexed, and filtered through the Corning filter. Trastuzumab (5.924 mg) was diluted to 2.5 mL using conjugation buffer (1:1.8), and the resulting solution was added to the PD-10 column. Conjugation buffer (3.5 ml) was added into the PD-10 column to exchange the buffer solution of the antibody and collected in a sterile test tube and checked for the presence of trastuzumab via analysis of the UV/VIS spectrum at 280 nm. To a sterile test tube containing the recovered trastuzumab (5.91 mg) was added a 10-fold excess of the ligand. The resulting solution was gently agitated overnight at room temperature and placed on a Centricon C-50 membrane and spun down to reduce volume. PBS (3×2 mL) was added to the remaining solution of the Trastuzumab conjugate, followed by centrifugation in order to remove unreacted ligand. The volume of purified conjugate antibody was brought to 1.0 mL with PBS. To measure [Trastuzumab] in C-DEPA-Trastuzumab conjugate, A UV/Vis spectrometer was zeroed against a cuvette filled with 2.0 mL of PBS with a window open from 190 nm to 1100 nm. 50 µl of PBS was removed and discarded, and 50 µl of C-DEPA-trastuzumab conjugate was added and absorbance at 280 nm was noted. Beer's Law was used to calculate [trastuzumab] in the conjugate with molar absorptivity of 1.42.

Spectroscopic Determination of Ligand to Protein (L/P) Ratio.

A stock solution of the Pb-AAIII or Cu-AAIII reagent was prepared in 0.15 M $NH_4OAc$, pH 7.0 by adding an aliquot of Pb atomic absorption solution (4.9×M) into a 12.5 µM solution of AAIII to afford a 4 µM solution of Pb. This solution was stored in the dark to avoid degradation over time. A UV/Vis spectrometer was zeroed against well-dried blank 8 cuvettes with a window open from 190 nm to 1100 nm. A cuvette was filled with AAIII solution (2 mL), and the other seven cuvettes with the AAIII-Pb or -Cu solution (2 mL). The AAIII-Pb or Cu solution (50 µL) from the seven cuvettes was removed and discarded. Milli-Q water (50 µL) was added to the second cuvette, and from one to five 10 µL additions of ligand (0.1 mM) were added to the five cuvettes to give a series of five different concentrations (2 mL total volume). The solutions in the third to the sixth cuvette were diluted to 2.0 mL by adding an aliquot of milli-Q water. Ligand-trastuzumab conjugate (50 µL) was added to the eighth cuvette containing Pb-AAIII or Cu-AAIII reagent (1950 µL). After addition of ligand-trastuzumab conjugate to the AAIII-Pb or Cu solution, the resulting solution was equilibrated for 10 min. The absorbance of the resulting solution at 652 nm was monitored every 30 second over 6 min. The average of the absorbance of each solution was calculated, and the absorbance data from the AAIII-Pb or -Cu solutions containing six different concentrations were used to construct a calibration plot of $A_{652}$ versus [ligand].

Radiolabeling of 3p-C-DEPA or C-DEPA-Trastuzumab Conjugate with $^{205/6}Bi$.

All HCl solutions were prepared from ultra pure HCl (Fisher, Cat# A466-500). For metal-free radiolabeling, plasticware including pipette tips, tubes, and caps was soaked in 0.1N HCl overnight and washed thoroughly with Milli-Q (18.2 MΩ) water, and air-dried overnight. Ultra pure $NH_4OAc$ (Aldrich, #372331) was purchased from Aldrich and used to prepare buffer solutions (0.1 M) at pH 7. The buffer solutions were treated with Chelex-100 resin (Biorad, #142-2842, 1 g/100 ml buffer solution), shaked overnight at room temperature, and filtered through 0.22 µm filter (Corning, #430320) prior to use. $^{205/6}Bi$ (0.1M HI) was provided by NIH. To a buffer solution (120 µL) at pH 7 in a capped microcentrifuge tube (1.5 mL, Fisher Scientific #05-408-129) was sequentially added a solution of ligand-trastuzumab (60 µg) in PBS (10 µL) and $^{205/6}Bi$ (0.1M HI, 60.5 µCi, 12.7 µL). The final volume of the resulting solution was 142.7 µL, and the pH of the reaction mixture was 5.5. The reaction mixture was agitated on the thermomixer (Eppendorf, #022670549) set at 1,000 rpm at room temperature for 1 h. The labeling efficiency was determined by SE-HPLC (Biorad, Bio Silect SEC 250-5, 7.8×30 cm, Cat#125-0062). A solution of radiolabeled mixture (10 was withdrawn at the designated time points (1 min, 5 min, 10 min, 20 min, 30 min, and 60 min) and DTPA solution (10 mM, 1 µL) was added to the mixture and 20 min was given to quench labeling reaction. Peaks for bound and unbound radioisotope appeared around 8.3 min and 11 min, respectively.

In Vitro Stability of Radiolabeled Complexes.

$^{205/6}Bi$-2C-DEPA-Trastuzumab and $^{205/6}Bi$-3p-2C-DEPA-Trastuzumab conjugates were prepared at 37° C. (5M $NH_4OAc$ buffer, pH 7; reaction chromatography using PD-10 column (Disposable PD-10 Sephadex™ G-25M columns, GE Healthcare, Cat#17-0851-01) eluted with PBS (pH 7.4, Fisher Scientific, Cat# BP2438-4). The fractions containing pure metal complex (~10,300 kcpm, 0.5 mL) were combined and added into human serum (0.5 mL, Gemini Bioproducts, #100110) in a microcentrifuge tube (Fisher Scientific, #05-408-129). $^{205/6}Bi$-2C-DEPA-Trastuzumab or $^{205/6}Bi$-3p-2C-DEPA-Trastuzumab conjugates in 5M $NH_4OAc$ (14 µL, pH 7) were prepared by reaction of $^{205/6}Bi$-2C-DEPA-Trastuzumab or $^{205/6}Bi$-3p-2C-DEPA-Trastuzumab conjugates (42 µg) with $^{205/6}Bi$ (98 µCi) at 37° C. until radiolabeling was complete. Pure antibody-ligand conjugate (~10,300 kcpm, 0.5 mL) complex as evidenced by SE-HPLC (Biorad, Bio Silect SEC 250-5, 7.8×30 cm, Cat#125-0062) using PBS at pH 7.4 as the mobile phase was added into human serum (0.5 mL) in a microcentrifuge. The stability of the purified radiolabeled complexes was evaluated for 11 days. The serum stability of the radiolabeled complexes was assessed by measuring the transfer of the radionuclide from each complex to serum proteins using SE-HPLC. A solution of the radiolabeled complex in serum (~20-80 µL) was withdrawn at the designated time point, treated with DTPA (10 mM, 1~2.5 µL), incubated at room temperature for 20 min and then diluted with PBS at pH 7.4 (60~80 µL) before injection in SE-HPLC. Sample was run with PBS at pH 7.4 as the mobile phase.

Example 3

PET Imaging and Radiotherapy of Copper

Ligands NBEA, NBPA, NE3TA, and NE3TA-Bn were synthesized and evaluated as potential chelators of copper radioisotopes for use in targeted positron emission tomography (PET) imaging or radiation therapy. The ligands were radiolabeled with $^{64}Cu$, and in vitro stability of the radiolabeled complexes was assessed in rat serum. Serum stability results suggest that among the ligands tested, NE3TA, and NE3TA-Bn form stable complexes with $^{64}Cu$.

NE3TA contains four amines and three carboxylates as potential donor groups. NE3TA-Bn is a heptadentate ligand with a benzyl group which can be further modified for conjugation to a targeting moiety. Hexadentate NBEA and NBPA each possess three amines, two carboxylates, and a hydroxyl group as the donor groups. The hypothesis for the design of NBEA and NBPA was that the size-fit between the macrocyclic cavity in NBEA and NBPA and the ionic radius of Cu(II) might provide enhanced radioisotope complex stability while producing a neutral Cu(II) complex that would have an advantage of less protein interaction and a potentially more favorable in vivo tissue distribution. NBPA possesses a longer propylene bridge between one of the amino groups and the hydroxyl group compared to the analogous ethylene bridged ligand, NBEA.

As shown in Scheme 7, the ligands NBEA and NBPA are efficiently synthesized starting from starting Compounds 1 and 2, respectively. The base-promoted reaction of Compounds 1 or 2 with tert-butylbromoacetate afforded alkylated ligand 3 or 4 in good yield (~50%). Removal of tert-butyl groups in Compounds 3 and 4 was efficient with TFA to provide NBEA and NBPA in high yields (>90%) without any further purification. Synthesis of NE3TA (Scheme 8) and NE3TA-Bn (Scheme 8) involves a coupling reaction between two precursor molecules, a pre-alkylated amino ethyl bromide and a bisubstituted 1,4,7-triazatricyclononane (tacn) derivative. The key coupling step was very efficiently achieved while minimizing formation of polyalkylated byproducts.

The radiolabeling reactions of the ligands with $^{64}$Cu were performed at elevated temperatures to ensure complete complex formation. At the no-carrier-added (NCA) level, all ligands were successfully labeled with $^{64}$Cu in quantitative radiochemical yields (100%) as determined by radio-TLC. The ligands displayed rapid labeling reaction kinetics with $^{64}$Cu. The $^{64}$Cu complexes of NE3TA, NE3TA-Bn, NBEA, and NBPA possessed the respective $R_f$ values of 0.63, 0.53, 0.62 and 0.59. The $^{64}$Cu-labeled complexes were freshly prepared for their serum stability evaluation, which was assessed by measuring the transfer of radionuclide from the complex to serum proteins over 24 hours or 48 hours. The results determined by radio-TLC are shown in Table 4. The stability of the complexes is comparable to that of $^{64}$Cu-DOTA, which was used as a positive control. DOTA is known to bind Cu(II) using the four nitrogens in the macrocyclic ring and two pendant carboxylate oxygens as demonstrated by a X-ray crystallography (Smith, S. V. J. Inorg. Biochem. 2004, 98, 1874-1901).

Among the ligands tested, $^{64}$Cu-labeled complexes of NE3TA, NE3TA-Bn were stable in rat serum for 48 hours with no measurable loss of radioactivity. However, the $^{64}$Cu complexes of NBPA and NBEA appeared to be less stable in rat serum. Significant amounts of $^{64}$Cu dissociated from the NBPA and NBEA complexes ($^{64}$Cu—NBPA: 29%; $^{64}$Cu—NBEA: 54%. See $R_f1$ values in Table 4) in 24 hours as determined by radio-TLC. It appears that the serum stability of the Cu(II) complexes has some dependency on the length of the carbon chain between the pendant donor groups and the macrocyclic ring. It is interesting to note that NBPA possessing the hydroxyl group connected to the amino group via a longer propyl chain that can form six-membered chelate ring with the metal is more effective in holding $^{64}$Cu compared to NBEA. The serum stability data suggest that the bidentate aminocarboxylate groups in NE3TA and NE3TA-Bn more effectively serve as the donor group, tightly holding $^{64}$Cu in serum than the monodentate hydroxyl group in NBEA and NBPA, and that the introduction of a benzyl group into one of the tertiary amines in the side arm (NE3TA-Bn) does not impact the complex stability. That no measurable loss of radioactivity from $^{64}$Cu—NE3TA-Bn was recorded out to 48 hours (nearly 4 half lives of $^{64}$Cu) demonstrates the potential of utilizing the NE3TA-Bn backbone as a basis for bifunctional chelators for targeted PET imaging or radiation therapy.

TABLE 4

In Vitro Serum Stability of $^{64}$Cu-Labeled New Ligands in Rat Serum

| Complex | Incubation Time | $R_f1$ | $R_f2$ | Purity |
|---|---|---|---|---|
| $^{64}$Cu-NBEA | 1 h | | 0.60 | 100 ± 0.0 |
| | 4 h | | 0.61 | 100 ± 0.0 |
| | 24 h | 0.12 | 0.60 | 45.3 ± 9.8 |
| $^{64}$Cu-NBPA | 1 h | | 0.55 | 99.6 ± 0.7 |
| | 4 h | | 0.55 | 97.5 ± 4.4 |
| | 24 h | 0.09 | 0.55 | 70.5 ± 6.5 |
| $^{64}$Cu-NE3TA | 1 h | | 0.60 | 100 ± 0.0 |
| | 4 h | | 0.60 | 100 ± 0.0 |
| | 24 h | | 0.58 | 100 ± 0.0 |
| | 48 h | | 0.57 | 100 ± 0.0 |
| $^{64}$Cu-NE3TA-Bn | 1 h | | 0.53 | 100 ± 0.0 |
| | 4 h | | 0.51 | 100 ± 0.0 |
| | 24 h | | 0.55 | 100 ± 0.0 |
| | 48 h | | 0.53 | 100 ± 0.0 |

Example 3

Experimental Information

Scheme 7

General Synthetic Procedure to Compound 3 and 4:

To a suspension of alcohol 1 or 2 (1 mmol) and $K_2CO_3$ (2 mmol) in $CH_3CN$ (5 mL) under argon was added dropwise tert-butyl bromoacetate (2 mmol), and the resulting mixture was stirred at room temperature for 1 h, followed by heating at 40° C. for 8 hours. The reaction mixture was allowed to cool gradually to ambient temperature and was filtered, and the filtrate was concentrated in vacuo. The residue was purified via column chromatography on silica gel (220-400 mesh) eluting with 8% $CH_3OH$ in $CH_2Cl_2$. Compound 3 or 4 was obtained as a waxy white solid: Compound 3 (Yield: 65%) $^1$H NMR (300 MHz, $CDCl_3$) δ 4.51 (t, J=6.5 Hz, 2H), 3.77 (t, J=6.32 Hz, 2H), 3.45 (br, 8H), 3.2 (m, 6H), 2.99 (s, 2H), 1.27 (s, 18H). $^{13}$C NMR (300 MHz, $CDCl_3$) δ 28.14, 47.91, 52.09, 54.67, 56.25, 61.72, 81.72, 170.82. HRMS (positive ion FAB) Calcd for $C_{22}H_{42}O_6$: [M+H]$^+$ m/z 402.2692. Found: [M+H]$^+$ m/z 402.2968. Compound 4 (Yield: 50%) $^1$H NMR (300 MHz, $CDCl_3$) δ 1.42 (s, 18H), 2.10-2.25 (m, 2H), 2.60-2.85 (m, 4H), 2.90-3.20 (m, 4H), 3.30-3.55 (m, 10H), 4.15 (t, 2H); $^{13}$C NMR (300 MHz, $CDCl_3$) δ 28.15, 48.23, 51.58, 52.29, 53.61, 56.92, 64.24, 81.76, 170.84. HRMS (positive ion FAB) Calcd for $C_{23}H_{44}O_6$: [M+H]$^+$ m/z 416.3129. Found: [M+H]$^+$ m/z 416.3124.

General Procedure for Deprotection of tert-Butyl Groups in 3 and 4:

To either Compound 3 or 4 (2 mmol) was added TFA (3 mL) at room temperature. The reaction mixture was stirred for 3 h. TFA was removed under vacuo and the residue obtained was treated with diethyl ether (10 mL). The precipitated product was filtered, washed with diethyl ether (30 mL) and immediately dissolved in water (5 mL). The aqueous layer was washed with $CH_2Cl_2$ (3×10 mL) and concentrated under vacuo to obtain the desired product 5 or 6: (Compound 5: Yield 86%) $^1$H-NMR (300 MHz, $D_2O$) δ 4.51 (t, J=6.5 Hz, 2H), 3.87 (s, J=6.3 Hz, 4H), 3.75 (br, 6H), 3.54 (m, 4H), 3.22 (s, 4H); $^{13}$C NMR (300 MHz, $D_2O$) δ 49.25, 50.31, 51.34, 56.21, 56.50, 62.44, 172.70 HRMS (positive ion FAB) Calcd for $C_{14}H_{26}O_6$: [M+H]$^+$ m/z 290.1716. Found: [M+H]$^+$ m/z 290.1715. (Compound 6: Yield 92%) $^1$H NMR (300 MHz, $CDCl_3$) δ 2.05-2.20 (m, 2H), 3.13-3.25 (m, 4H), 3.26-3.44 (m, 6H), 3.45-3.60 (m, 4H), 3.70-3.85 (m, 4H), 4.05 (t, 2H); $^{13}$C NMR (300 MHz, $CDCl_3$) δ 23.80, 49.22, 50.59, 50.98, 54.88, 56.89, 65.66, 173.13. HRMS (positive ion FAB) Calcd for $C_{15}H_{28}O_6$: [M+H]$^+$ m/z 304.1872. Found: [M+H]$^+$ m/z 304.1880.

General Radiolabeling Procedure:

Nitric acid (10-20%) used for acid wash was prepared by diluting 70% nitric acid with mini-Q water (18 MΩ-cm). The ammonium acetate buffer (0.4 M, pH 7.0) was pretreated with Chelex 100 resin (Bio-Rad, Hercules, Calif.) before use. Silica gel 60 $F_{254}$ plates were purchased from Merck & Co (Whitehouse Station, N.J.). Copper-64 ($^{64}$CuCl$_2$ in 0.1N HCl) was purchased from Trace Life Sciences (Denton, Tex.). Radio-TLC analysis was performed on a Rita Star Radioisotope TLC Analyzer (Straubenhardt, Germany). Prior to labeling, all reaction vials were acid washed with 10-20% nitric acid overnight. To 100 μL of each ligand solution (5 mM in 0.4 M NH$_4$OAc buffer, pH 7.0), 0.5 μL of $^{64}$CuCl$_2$ (420-450 μCi) was added. The resulting solutions were incubated at 60° C. for 1 h in an Eppendorf thermomixer with 1,000 rpm. The radiochemical yields and purity were determined by radio-TLC (Raytest, VA) with silica gel plate as the static phase and 10% NH$_4$OAc/MeOH=1/1 (v/v) as the mobile phase. Under this TLC condition, free $^{64}$Cu$^{2+}$ or $^{64}$Cu-associated proteins stay at the origin.

In Vitro Serum Stability:

To 100 μL of rat serum, 10 μL of each $^{64}$Cu-labeled complex was added (n=3 per complex). DOTA labeled with $^{64}$Cu was used as a positive control. The resulting solutions were incubated at 37° C. in a water-bath. At 1 h, 4 h, 24 h and 48 h after the complex addition to rat serum, the solutions were sampled and analyzed by radio-TLC.

Example 4

Synthesis and Evaluation of Polyaminocarboxylate-Based Antitumor Agents

Figure 2:
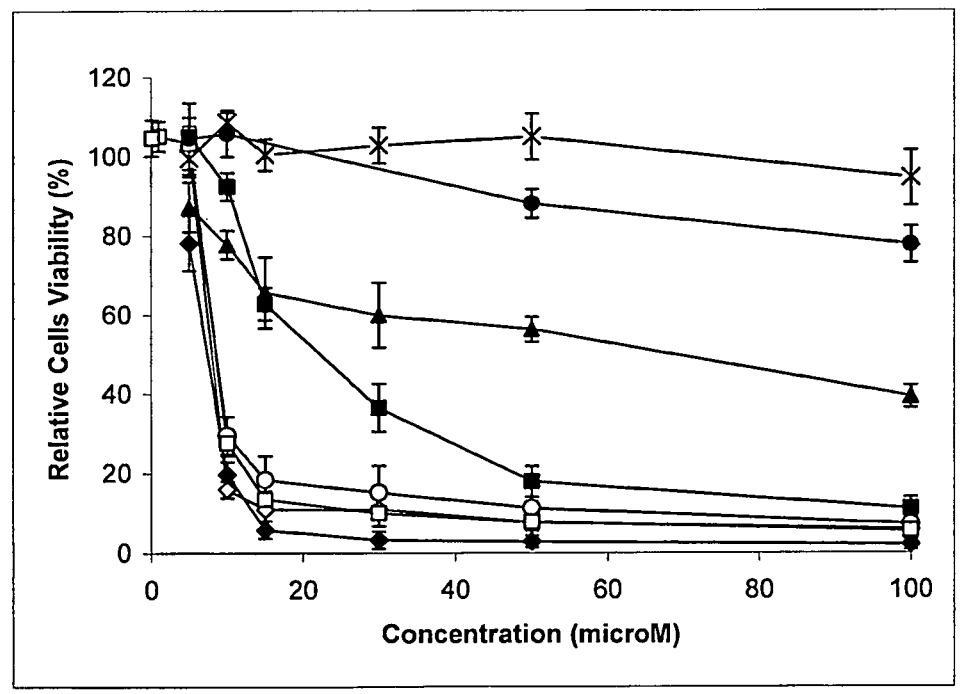
FIG. 2 is a graph illustrating the effects of chelators DFO (▲), DTPA (●), NETA (■), NE3TA (◇), C-NETA (*), N-NE3TA (□), NE3TA-Bn (◆), C-NE3TA (○) on viability of Hela cancer cells.

This example provides the synthesis and evaluation of the polyaminocarboxylates NETA, NE3TA, and NE3TA-Bn and their bifunctional versions C-NETA (Chong H S, Ma X, Le T, Kwamena B, Milenic D E, Song H A, Brady E D, Brechbiel M W. J. Med. Chem. 2008, 51, 118-125), C-NE3TA (Scheme 12), and N-NE3TA (Scheme 9). Cytotoxicity of the new chelators was measured in the HeLa and HT29 cancer cells and compared to that of the clinically used iron chelators DFO and DTPA. A potent bifunctional ligand C-NE3TA containing a fluorescent moiety NBD was synthesized and evaluated for cellular uptake of the chelator. Octadentate NETA possesses both macrocyclic and acyclic moiety and is proposed to form a stable complex with fast complexation kinetics based on bimodal binding approach using both moieties (Chong, H. S.; Garmestani, K.; Ma. D.; Milenic, D. E.; Overstreet, T.; Brechbiel, M. W. J. Med. Chem. 2002, 45, 3458-64). The preliminary cell culture experiments were performed to see if NETA is an effective cytotoxic agent. As shown in FIG. 1, NETA (50 μM) as the free ligand was toxic to the HeLa cell, and almost 80% of the cancer cells died, while almost all HeLa cells incubated with DTPA (50 μM) survived. NETA also displayed a three-fold increased antiproliferative activity compared to DFO. In order to investigate the effect of the chelators on the cellular growth, the Hela cancer cells saturated with Fe(III)-citrate (50 μM) were incubated with each of the chelators (50 μM). Inspection of FIG. 1 indicates that almost no anti-proliferative activity was observed with NETA and DTPA, while DFO resulted in a modest increase in cell viability as compared to non-saturated cancer cells. The result suggests that the anti-proliferative activity of NETA may result from iron chelation. Cytotoxicity of NETA in a series of concentrations was evaluated using the HeLa cell line and compared to the clinically available DFO and DTPA (FIG. 2). NETA exhibited significantly enhanced cytotoxicity, while DTPA resulted in almost no cytotoxicity in the HeLa cells. NETA and DTPA possess the respective IC$_{50}$ of 30.8±4.0 and 264.5±36.2 μM (Table 5). Cytotoxicity of DFO is not concentration-dependent and was much lower than that of NETA.

With the promising cytotoxicity data of NETA, a NETA analogue, NE3TA, was evaluated. NE3TA possesses seven coordinating group that may be more effective in binding to the hexacoordinate iron than the eight coordination groups in NETA. An efficient and short method to prepare NE3TA is shown in Scheme 8. The key step is the coupling reaction of macrocyclic and acyclic backbones, i.e., N-Bn protected mono-alkylated bromide 5 and bisubstituted tacn derivative 6 (Huskens, J.; Sherry, A. D. J. Am. Chem. Soc. 1996, 118, 4396-4404) in the ratio of 1 to 1. Compound 5 was prepared starting from the readily available ethanol amine. Reaction of ethanol amine with benzaldehyde and further reductive amination provided N-benzyl ethanol amine 2 (Richard, H. Smith, Jr.; Wladkowski, B. D.; Taylor, J. E.; Thompson, E. J.; Pruski, B.; Klose, J. R.; Andrews, A. W.; Michejdat, C. J. J. Org. Chem. 1993, 58, 2097-2103). Reaction of Compound 2 with t-butyl bromoacetate provided the alkylated product 4 which was then further converted to bromide 5. The reaction of Compounds 5 and 6 successfully provided Compound 7 in good yield (71%). Isolation of the polar and tailing Compound 7, which can be readily monitored by HPLC and TLC analysis due to the presence of a benzylic UV chromophore, was achieved by simple flash column chromatography eluting with 5-6% CH$_3$OH/CH$_2$Cl$_2$. t-butyl groups in Compound 7 were removed by 6M HCl to provide NE3TA-Bn (8) which was then subjected to hydrogenation to remove the benzyl protecting group, thereby affording the desired chelate NE3TA (9).

Figure 3:
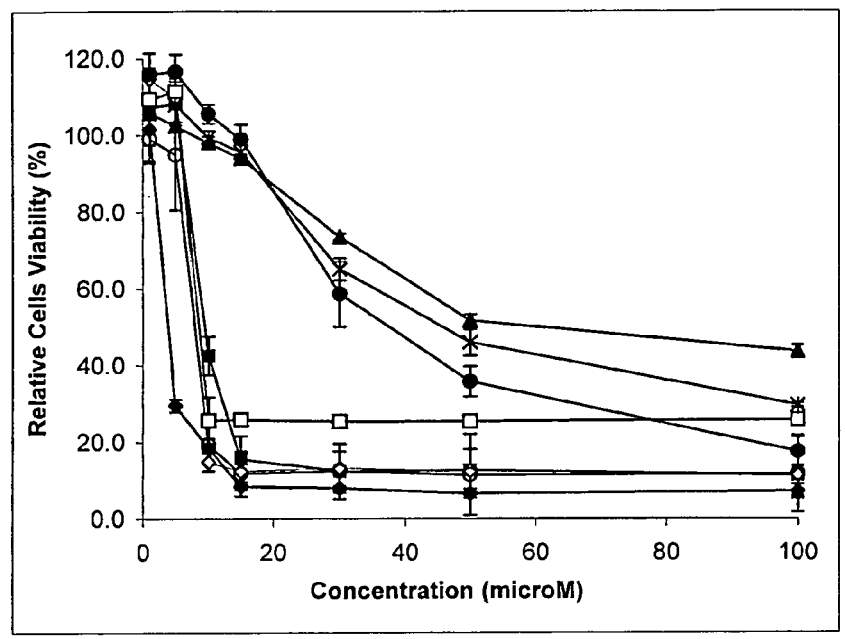
FIG. 3 is a graph illustrating the effects of chelators DFO (▲), DTPA (●), NETA (■), NE3TA (◇), C-NETA (*), N-NE3TA (□), NE3TA-Bn (◆), C-NE3TA (○) on viability of HT29 cancer cells.
Figure 4:
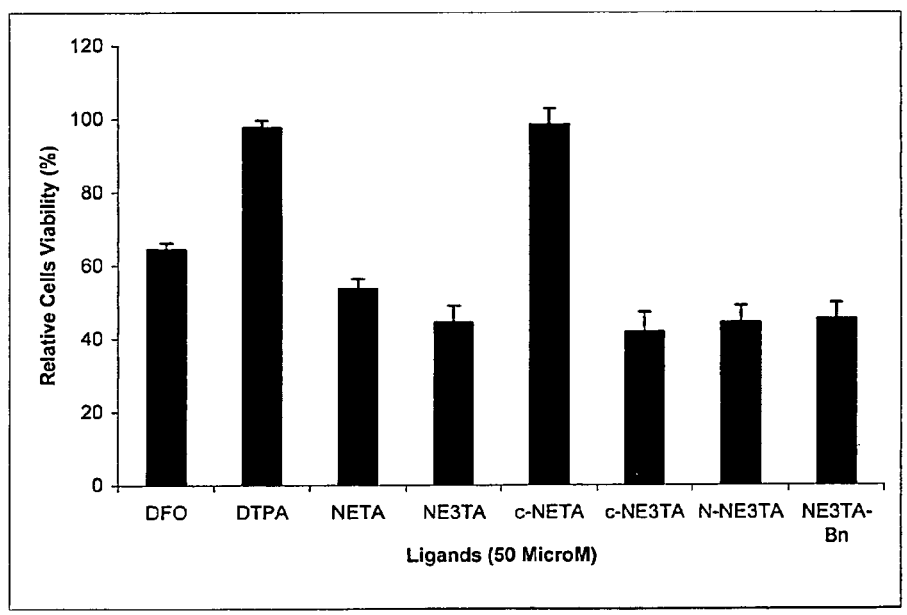
FIG. 4 is a graph illustrating the antiproliferative activity of ligands against MRC-5 cells.

NE3TA and NE3TA-Bn were evaluated for cytotoxicity using the HeLa cell (FIG. 2). Among all non-functionalized ligands, NE3TA-Bn displayed the highest activity against HeLa cells. Replacement of hydrogen in NE3TA by a benzyl group resulted in a slight increase in cytotoxicity. It seems that the presence of lipophilic benzyl group in NE3TA-Bn may result in some increase in cellular permeation, thus leading to enhanced cytotoxicity. NETA and NE3TA-Bn possess the respective IC$_{50}$ of 5.7±0.3 and 4.4±0.9 (Table 5). NE3TA and NE3TA-Bn were further evaluated for cytotoxicity in the HT29 cancer cells (FIG. 3) and compared to NETA, DTPA, and DFO. NE3TA and NE3TA-Bn produced higher antiproliferative activity in HT29 cells with the respective IC$_{50}$ value of 4.7±0.3 and 2.6±0.2 (Table 2) than other chelators evaluated. All chelators tested produced enhanced activity in HT29 cancer cells compared to HeLa cells (FIGS. 3 and 4). NETA possesses significantly increased IC$_{50}$ value in HT29 cells compared to the HeLa cells (7.3±1.5 vs 30.8±4.0, Table 2).

TABLE 5

| | IC50 (μM) | |
|---|---|---|
| Ligand | Hela | HT29 |
| NETA | 30.8 ± 4.0 | 7.3 ± 1.5 |
| NE3TA | 5.7 ± 0.3 | 4.7 ± 0.3 |
| Bn-NE3TA | 4.4 ± 0.9 | 2.6 ± 0.2 |
| C-NETA | >100 | 45.7 ± 4.0 |
| C-NE3TA | 7.1 ± 0.1 | 5.0 ± 0.7 |
| N-NE3TA | 8.4 ± 0.4 | 6.8 ± 0.4 |

TABLE 5-continued

| | IC50 (μM) | |
|---|---|---|
| Ligand | Hela | HT29 |
| DFO | >50 | 36.1 ± 1.4 |
| DTPA | 264.5 ± 36.2 | 39.1 ± 4.0 |

The result prompted evaluation of a bifunctional version of NETA, NE3TA, and NE3TA-Bn that can be employed for targeted iron depletion therapy (IDT) by conjugation of the bifunctional iron chelator to a tumor targeting moiety such as antibody or peptide. The structure of bifunctional chelators, C-NETA, C-NE3TA, and N-NE3TA are shown above. The bifunctional ligands possess the nitro group which can be further converted to amino ($NH_2$) or isothiocyante (NCS) group for conjugation to a tumor targeting peptide or antibody possessing lysine amine. N-functionalized NETA (N-NE3TA) was prepared, Scheme 9, based on the strategy involving the key coupling reaction that was used for the preparation of NE3TA.

Reaction of Compound 10 with t-butyl bromoacetate and subsequent bromindation provided the precursor molecule 12 for the coupling reaction. Reaction of bisubstituted tacn 6 with Compound 12 provided the desired product 13. Removal of t-butyl groups in Compound 13 with 4M HCl afforded the desired ligand N-NE3TA (14).

The cytotoxicity of the bifunctional ligands C-NETA, C-NE3TA, and N-NE3TA was evaluated using the HeLa and HT29 cell lines. Inspection of the data in FIGS. 2 and 3 indicates that introduction of a functional unit, p-nitro-benzyl group into NE3TA backbone via carbon substitution (C-NE3TA) or nitrogen substitution (N-NE3TA) is well tolerated and resulted in minimal decrease in cytotoxicity as compared with NE3TA. An $IC_{50}$ value of 7.1±0.1 μM and 8.4±0.4 μM using the Hela cells was observed with C-NE3TA and N-NE3TA, respectively. Both compounds displayed a slight increase in $IC_{50}$ value in HT29 cells (5.0±0.7 μM and 6.8±0.4 μM for C-NE3TA and N-NE3TA, respectively) as compared to the HeLa cells. However, C-functionalized NETA (C-NETA) displayed virtually no inhibitory activity against the HeLa cells over all the entire concentration range evaluated (FIG. 2), while the anti-proliferative activity of C-NETA ($IC_{50}$=45.7±4.0 μM) which is similar to that of DFO and DTPA was observed in HT29 cells (FIG. 3).

The cytotoxicity of the chelators in the cancer cells was compared to their cytotoxicities in non-cancer cells using human lung fibroblast cell (MRC-5). As shown in FIG. 4, there was little change in cell viability of the normal cells treated with DFO as compared to that of the HeLa and HT29 cancer cells. DTPA resulted in much enhanced viability of normal cells compared to HT29 cancer cells. The chelators displayed about 2-8 times enhanced antiproliferative activity in normal cells as compared to the HeLa and HT29 cancer cells. This result demonstrates the proposed hypothesis that the cancer cells require more iron than the normal cells and overexpress TfR or RR. Comparison of the cytotoxicity data of cancer cells to normal cells indicate that all new polyaminocarboxylate chelators were more selective in removing iron from the cancer cells than DFO.

Figure 5:
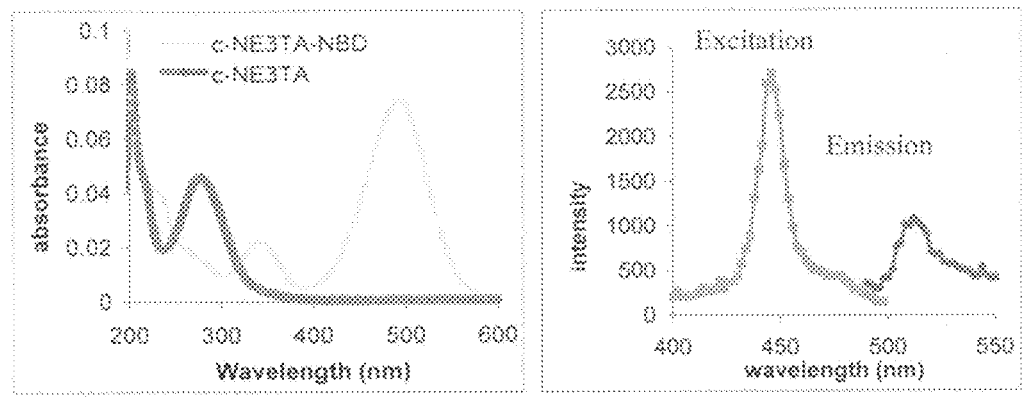
FIG. 5 illustrates the UV and Fluorescence spectra of C-3NETA and C-NE3TA-NBD (10 μM, H$_2$O).
Figure 14:
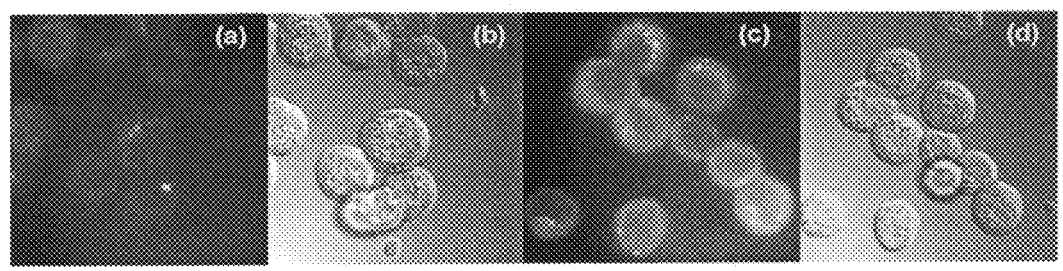
FIG. 14 is a TEM images of the fluorescent bile acid-based NE3TA conjugate NBD-CA-NE3TA.

In order to visualize cellular uptake using fluorescence imaging, C-NE3TA was conjugated with an organic fluorescent moiety, NBD to produce C-NE3TA-NBD (Scheme 10). Thus, the starting material 15 was reacted with NBD-Cl to provide the fluorescent conjugate 16. t-Butyl groups in Compound 16 were removed by treating 4M HCl in 1,4-dioxane. UV and fluorescence spectra of C-NE3TA-NBD (10 μM, $H_2O$) are shown in FIG. 5, respectively. C-NE3TA has the respective excitation and emission wavelength of 446 nm and 512 nm. Fluorescence and phase contrast images of control HT29 cells or HT29 cells incubated with C-NE3TA-NBD (50 μM) were obtained using a confocal microscope with a band-pass filter set at 436/20 nm (excitation) and 535/30 nm (emission). Fluorescence images were taken and indicated that C-NE3TA-NBD does accumulate in the HT29 cancer cells (FIG. 14). It was noted that the control HT29 colon cancer cells also emit auto-fluorescence at the wavelength of excitation. While polyaminocarboxylate NE3TA is too hydrophilic to enter the cancer cells, C-NE3TA-NBD containing lipophilic moieties, both benzyl and NBD group is proposed to penetrate into the cells resulting in the punctuate present in the cancer cells.

The cytotoxicity data indicated that the novel non-functionalized polyamine-carboxylates display significantly enhanced inhibitory activity against the HeLa and HT29 cancer cells as compared to the clinically available iron depleting agent DFO. Introduction of a bifunctional unit (p-nitrobenzyl) to the NE3TA backbone (C-NE3TA and N-NE3TA) was achieved without compromising the cytotoxic activity of NE3TA. C-NE3TA conjugated with NBD was taken up into HT29 cancer cells.

Thus, the polyaminocarboxylate chelators NETA, NE3TA, and NE3TA-Bn were found to display antiproliferative activity which is much greater than the clinically available agents DFO and DTPA in both cancer cells. The promising antitumor polyaminocarboxylate-based chelators were functionalized via introduction of a nitro group which can be further modified to either amino or thiocyanate group for use in targeted therapies. The result of the cytotoxicity measurements demonstrates that while NE3TA and NE3TA-Bn was substituted with a nitro group without compromising their cytotoxic activities (C-NE3TA and N-NE3TA, respectively), introduction of a nitro group into NETA backbone resulted in significantly decreased activity of NETA (C-NETA). The fluorescent cellular uptake study of C-NE3TA-NBD indicates that C-NE3TA is taken up into HT29 cancer cells. Both the nonfunctionalized chelators (NETA, NE3TA, and NE3TA-Bn) and the bifunctional chelators (C-NE3TA and N-NE3TA) possess great promise as cancer therapeutics. The two potent bifunctional ligands C-NE3TA and N-NE3TA can be linked to many peptides and monoclonal antibodies targeting to various types of tumor cells to generate the antitumor conjugates for use in targeted iron depletion tumor therapy which has been little explored.

Example 4

Experimental Information

General.

$^1H$, $^{13}C$, and NMR spectra were obtained using a Bruker 300 instrument and chemical shifts are reported in ppm on the δ scale relative to TMS, TSP, or solvent. Elemental microanalyses were performed by Galbraith Laboratories, Knoxville, Tenn. All reagents were purchased from Aldrich and used as received unless otherwise noted. Arsenazo III (AAIII, 2,2-(1,8-dihydroxy-3,6-disulfonaphthylene-2,7-bisazo)bis-benzenearsonic acid), and copper, lutetium, and bismuth atomic absorption standard solution were purchased and used as received. Fast atom bombardment (FAB) high resolution mass spectra (HRMS) were obtained on JEOL double sector JMS-AX505HA mass spectrometer (University of Notre Dame, Ind.). The analytical HPLC was performed on Agilent 1200 equipped with a dioarray detector (λ=254 and 280 nm), thermostat set at 35° C. and a Zorbax Eclipse XDB-C18 column (4.6×150 mm, 80 Å). The mobile phase of a binary gradient (0-100% B/40 min; solvent A=0.05 M AcOH/Et$_3$N, pH 6.0; solvent B=CH$_3$CN) at a flow rate of 1 mL/min was used for analytical method 1. A combination of a binary gradient and an isocratic mobile phase (50-100% B/15 min; solvent A=H$_2$O; solvent B=CH$_3$CN and 100% B/15 min) at a flow rate of 1 mL/min was used for analytical HPLC method 2. Fluorescence Spectra were recorded on a PC1 Photon counting spectrofluorometer (ISS, Inc., Champaign, Ill.) with excitation at 446 nm and bandwidth of 8 nm. Fluorescence images were obtained using Olympus DSU Spinning disk confocal microscope (Olympus America Inc., Melville, N.Y.) with a band-pass filter set at 436/20 nm (Excitation) and 535/30 nm (Emission). All UV absorbance measurements were obtained on an Agilent 8453 diode array spectrophotometer equipped with a 8-cell transport system (designed for 1-cm cells).

Schemes 8-10

(E)-2-(benzylideneamino)ethanol (1)

To a solution of ethanolamine (1.23 g, 20.1 mmol) in anhydrous MeOH (50 mL) at 0° C. was added benzaldehyde (2.13 g, 20.0 mmol) and molecular sieves (10 pieces). The resulting mixture was gradually warmed to room temperature and stirred for 120 h. The reaction mixture was filtered while rinsing with CH$_2$Cl$_2$. The filtrate was evaporated, and the residue was dried under vacuum overnight to afford off-white oily Compound 1 (2.63 g, 87%). The compound was used for the next step without further purification. $^1$H NMR (CDCl$_3$) δ 2.40 (s, 1H), 3.70 to 3.80 (m, 2H), 3.85 to 4.0 (m, 2H), 7.35 to 7.50 (m, 3H), 7.68 to 7.79 (m, 2H), 8.32 (s, 1H); 8.11 (d, 2H); $^{13}$C NMR (CDCl$_3$) δ 62.28, 63.17, 128.1, 128.52, 130.78, 135.72, 163.10.

2-(Benzylamino)ethanol (2)

To a solution of Compound 1 (2.62 g, 17.3 mmol) in anhydrous EtOH (55 mL) was portionwise added NaBH$_4$ (0.67 g, 17.7 mmol) at 0° C. over 1 h period. The resulting mixture was gradually warmed to room temperature and was stirred for 20 h. The resulting mixture was filtered to eliminate excess NaBH$_4$, and the solvent was evaporated. The residue was dissolved in CH$_2$Cl$_2$ (50 mL) and filtered, and the filtrate was concentrated in vacuo to afford Compound 2 (1.86 g, 61.3%). $^1$H NMR (CDCl$_3$) δ 2.60 to 2.70 (m, 2H), 3.60 to 3.73 (m, 2H), 7.24 to 7.27 (m, 5H); $^{13}$C NMR (CDCl$_3$) δ 50.62, 53.44, 60.45, 126.98, 128.11, 128.36, 139.73. HRMS (Positive ion FAB) Calcd for C$_9$H$_{13}$NO [M+H]$^+$ m/z 152.2163. Found: [M+H]$^+$ m/z 152.1075.

4-benzyl-morpholin-2-one (3)

To a mixture of Compound 2 (355.8 mg, 2.353 mmol) and K$_2$CO$_3$ (565 mg, 4.09 mmol) in anhydrous CHCl$_3$ (12 mL) at 0° C. was dropwise added Benzyl-2-bromoacetate (540 mg, 2.36 mmol) over 0.5 h. The reaction mixture was gradually warmed to room temperature and stirred for 36 h. The resulting reaction mixture was filtered while washing with CH$_2$Cl$_2$, and the filtrate was concentrated to give Compound 3. $^1$H NMR (CDCl$_3$) δ 2.7 (t, 2H), 3.3 (s, 2H), 3.6 (s, 2H) 4.4 (t, 2H), 7.2-7.4 (m, 5H); $^{13}$C NMR (CDCl$_3$) δ 48.49, 55.64, 61.59, 68.69, 127.67, 128.48, 128.87, 136.04, 167.37. HRMS (Positive ion FAB) Calcd for C$_{11}$H$_{13}$NO$_2$ [M+H]$^+$ m/z 192.0900. Found: [M+H]$^+$ m/z 192.1032.

Tert-butyl 2-(benzyl(2-hydroxyethyl)amino)acetate (4)

To a solution of Compound 2 (1.86 g, 12.3 mmol) and potassium carbonate (1.70 g, 12.3 mmol) in CH$_3$CN anhydrous (50 mL) at 0° C. was dropwise added t-Butyl-bromoacetate (2.41 g, 12.4 mmol) over 45 minute. The reaction mixture was gradually warmed to room temperature and stirred for 66 h. The resulting reaction mixture was filtered, and the filtrate was concentrated to give a white oily compound. The residue was then dissolved in CH$_2$Cl$_2$ (50 mL), and the resulting solution was filtered, and the filtrate was concentrated to afford white Compound 4 (2.94 g, 90%), $^1$H NMR (CDCl$_3$) δ 1.45 (s, 9H), 2.86 (t, 2H), 3.23 (s, 2H), 3.54 to 3.62 (m, 2H), 3.82 (s, 2H), 7.23 to 7.34 (m, 5H); $^{13}$C NMR (CDCl$_3$) δ 28.00, 55.27, 26.52, 58.47, 58.84, 81.29, 127.28, 128.36, 128.81, 138.27, 171.02. HRMS (Positive ion FAB) Calcd for C$_{15}$H$_{24}$NO$_3$ [M+H]$^+$ m/z 266.3605. Found: [M+H]$^+$ m/z 266.1756.

Tert-butyl 2-(benzyl(2-bromoethyl)amino)acetate (5)

To a solution of Compound 4 (2.94 g, 11.1 mmol) in anhydrous CH$_2$Cl$_2$ (40 mL) at 0° C. was added PPh$_3$ (3.49 g, 13.3 mmol). NBS (2.37 g, 13.3 mmol) was added portionwise into the reaction mixture over 1 h. The resulting mixture was stirred at 0° C. for 30 minute after which the ice bath was removed, and the reaction mixture was stirred for 3 h. The resulting mixture was evaporated into an orange solid. The residue was dissolved in ether (100 mL). The solution was filtered, and the filtrate was evaporated and washed with ether again (3 times). The resulting clear filtrate was evaporated to give a white solid. The residue was then dissolved in ether (100 mL) and was passed through a short silica gel column to eliminate as much of the leftover PPh$_3$ as possible. The resulting pure fractions (according to TLC analysis) were collected and dried overnight. The residue was on column chromatography eluted with 5% EtOAc in hexanes to provide Compound 5 (1.83 g, 50.4%) was collected at the ratio ethyl acetate to hexane as 1:11. $^1$H NMR (CDCl$_3$) δ 1.47 (s, 9H), 3.10 to 3.18 (m, 2H), 3.31 (s, 2H), 3.30 to 3.40 (m, 2H), 3.88 (s, 2H), 7.20 to 7.38 (m, 5H); $^{13}$C NMR (CDCl$_3$) δ 28.12, 30.47, 55.14, 55.85, 57.99, 80.96, 127.17, 128.26, 128.69, 138.74, 170.48. HRMS (Positive ion FAB) Calcd for C$_{15}$H$_{23}$N$_4$O$_2$Br [M+H]$^+$ m/z 328.0929. Found: [M+Na]$^+$ m/z 328.0912.

4-[2-(Benzyl-tert-butoxycarbonylmethyl-amino)-ethyl]-7-tert-butoxycarbonyl-methyl-[1,4,7]triazonan-1-yl)-acetic acid tert-butyl ester (7)

To a solution of Compound 6 (0.74 g, 2.1 mmol) in CH$_3$CN (60 mL) was added DIPEA (0.91 g, 7.1 mmol) and Compound 5 (0.88 g, 2.77 mmol). The reaction mixture was stirred under reflux condition and monitored by TLC analysis for 72 h. The resulting solution was evaporated into a yellow reddish residue (1.49 g). This residue is purified via column chromatography with silica gel (60 mesh) eluting with 3% of methanol in dichloromethane. Final residue after evaporation was a yellow solid Compound 7 (0.88 g, 70.6%). $^1$H NMR (CDCl$_3$) δ 1.41 (d, 27H), 2.80 to 3.80 (m, 24H), 7.26 to 7.29 (m, 5H); $^{13}$C NMR (CDCl$_3$) δ 28.04, 49.07, 49.31, 52.57, 53.73, 55.26, 57.68, 58.27, 81.48, 81.59, 127.58, 128.46, 129.10, 137.47, 170.24, 170.44. HRMS (Positive ion FAB) Calcd for C$_{33}$H$_{57}$N$_4$O$_6$ [M+H]$^+$ m/z 605.8388. Found: [M+H]$^+$ m/z 605.4278. Analytical HPLC=3.6 min, Method 2).

(4-[2-Benzyl-carboxymethyl-amino)-ethyl]-7-carboxymethyl-[1,4,7]-triazonan-1-yl)-acetic acid (8)

To a solution of Compound 7 (0.09 g, 0.15 mmol) in 1,4-dioxane (5 mL) in an ice-bath was added 4M HCl in 1,4-dioxane (3 mL). The resulting mixture was gradually warmed to room temperature and stirred for 18 h. Ether (15 mL) was added to the reaction mixture, and the resulting mixture was stirred for 30 min. The resulting mixture was placed in the freezer for 2 h, and the solid residue was quickly filtered, washed with ether (10 mL), and dissolved in 18 MΩ deionized water. Evaporation of the aqueous solution provided an off-white solid Compound 8 (0.07 g, 80%). $^1$H NMR (D$_2$O) δ 2.93 to 3.03 (m, 4H), 3.15 to 3.22 (m, 6H), 3.32 (s, 4H), 3.40 to 3.50 (m, 2H), 3.90 (s, 4H), 3.97 (s, 2H), 4.35 (s, 2H), 7.20 to 7.40 (m, 5H); $^{13}$C NMR (D$_2$O) δ 48.75, 49.75, 50.04, 50.19, 51.16, 53.68, 56.44, 59.55, 127.87, 129.47, 130.67, 131.40, 168.13, 170.36. HRMS (Positive ion FAB) Calcd for C$_{21}$H$_{33}$N$_4$O$_6$ [M+H]$^+$ m/z 437.5162. Found: [M+H]$^+$ m/z 437.2400.

(4-Carboxymethyl-7-[2-(carboxymethyl-amino)-ethyl]-[1,4,7]-trizonan-1-yl)-acetic acid (9)

To a solution of Compound 8 (0.10 g, 0.17 mmol) in MeOH (10 mL) was added wet 10% Pd/C (30 mg) under argon gas and at room temperature. The reaction mixture was placed under debenzylation apparatus for 60 h. The resulting mixture was filtered via celite bed and washed thoroughly with MeOH and water. The filtrate was evaporated resulting a moisture sensitive yellow solid 9 (0.08 g, 94.8%). NMR (D$_2$O) δ 3.10 to 3.18 (m, 4H), 3.28 to 3.35 (m, 12H), 3.58 to 3.63 (m, 2H), 3.88 to 3.94 (m, 6H); $^{13}$C NMR (D$_2$O) δ 43.75, 43.88, 47.59, 48.77, 48.99, 49.17, 49.40, 50.05, 50.48, 50.69, 51.05, 51.93, 52.03, 52.99, 55.79, 56.29, 168.72, 171.40, 171.66. HRMS (Positive ion FAB) Calcd for C$_{20}$H$_{30}$N$_6$O$_9$ [M+H]$^+$ m/z 347.1931. Found: [M+H]$^+$ m/z 347.1964.

2-(4-nitrobenzylamino)Ethanol (10)

To a solution of ethanolamine (1.22 g, 20.0 mmol) in anhydrous MeOH (50 mL) at 0° C. was added 4-nitrobenzaldehyde (3.02 g, 20.0 mmol) and molecular sieves (10 pieces). The resulting mixture was gradually warmed to room temperature and stirred for 120 h. The reaction mixture was filtered while rinsing with CH$_2$Cl$_2$. The filtrate was evaporated, and the residue was dried under vacuum overnight to afford yellowish oily imine compound (2.624 g, 87%). The compound was used for the next step without further purification. $^1$H NMR (CDCl$_3$) δ 2.17 (s, 1H), 3.82 to 3.86 (m, 2H), 3.94 to 3.99 (m, 2H), 7.90-7.93 (d, 2H), 8.26 (d, 2H); $^{13}$C NMR (CDCl$_3$) δ 61.81, 63.52, 123.78, 124.25, 128.84, 130.49, 141.22, 148.92, 160.90.

To a solution of the obtained imine compound (1.962 g, 10.0 mmol) in anhydrous EtOH (30 mL) was portionwise added NaBH$_4$ (0.378 g, 10.0 mmol) at 0° C. over 1 h period. The resulting mixture was gradually warmed to room temperature and was stirred for 20 h. The resulting mixture was filtered to eliminate excess NaBH$_4$, and the solvent was evaporated. The residue was dissolved in CH$_2$Cl$_2$ (50 mL) and filtered, and the filtrate was concentrated in vacuum to afford Compound 10 (1.86 g, 61%). $^1$H NMR (CDCl$_3$) δ 2.71 (t, 2H), 3.61 (t, 2H), 3.84 (s, 2H), 7.42 (d, 2H), 8.05 (d, 2H); $^{13}$C NMR (CDCl$_3$) δ 50.71, 52.71, 60.87, 123.59, 128.68, 146.93, 147.78.

t-Butyl [(2-Hydroxy-ethyl)-(4-nitro-benzyl)-amino] ester (11)

To a solution of Compound 10 (1.78 g, 9 mmol) and potassium carbonate (1.24 g, 9 mmol) in CH$_3$CN anhydrous (50 mL) at 0° C. was dropwise added t-Butyl-bromoacetate (1.78 g, 9 mmol) over 60 minute. The reaction mixture was gradually warmed to room temperature and stirred for 21 h. The resulting reaction mixture was filtered, and the filtrate was concentrated to give a yellowish oily compound. The residue was then dissolved in CH$_2$Cl$_2$ (50 mL), and the resulting solution was filtered, and the filtrate was concentrated to afford yellowish oily Compound 11 (2.94 g, 90%). $^1$H NMR (CDCl$_3$) δ 1.44 (s, 9H), 2.83 (t, 2H), 3.23 (s, 2H), 3.59 (t, 2H), 3.91 (s, 2H), 7.51 (d, 2H), 8.15 (d, 2H); $^{13}$C NMR (CDCl$_3$) δ 28.01, 55.71, 56.93, 58.68, 59.29, 81.67, 123.59, 129.30, 146.05, 147.18, 171.12. HRMS (Positive ion FAB) Calcd for C$_{15}$H$_{22}$N$_2$O$_5$ [M+H]$^+$ m/z 311.1594. Found: [M+H]$^+$ m/z 311.1607.

t-Butyl [(2-Bromo-ethyl)-(4-nitro-benzyl)-amino] ester (12)

To a solution of Compound 11 (1.873 g, 6.03 mmol) in anhydrous dichloromethane (40 mL) at 0° C. was added triphenylphosphine (1.899 g, 7.24 mmol). NBS (1.289 g, 7.24 mmol) was added portionwise into the reaction mixture over 1 h. The resulting mixture was stirred at 0° C. for 30 minute after which the ice bath was removed, and the reaction mixture was stirred for 3 h. The solvent was evaporated, and the residue was dissolved in ether (100 mL). The solution was filtered, and the filtrate was evaporated and washed with ether (3×100 mL). The filtrate was evaporated to give an oily compound which was then dissolved in ether (100 mL) and was passed through a short silica gel column to eliminate triphenylphosphine. The fractions containing the desired product were collected and dried overnight. Further purification was performed using column chromatography eluted with 30% ethyl acterate in hexane to afford Compound 12 (1.83 g, 50.4%). $^1$H NMR (CDCl$_3$) δ 1.44 (s, 9H), 3.12-3.15 (m, 2H), 3.30 (s, 2H), 3.30-3.40 (m, 2H), 3.98 (s, 2H), 7.54 (d, 2H), 8.14 (d, 2H); $^{13}$C NMR (CDCl$_3$) δ 28.20, 30.38, 55.08, 55.82, 57.50, 81.55, 123.66, 129.20, 146.95, 147.33, 170.22. HRMS (Positive ion FAB) Calcd for C$_{15}$H$_{22}$N$_2$O$_4$Br [M+H]$^+$ m/z 373.0763. Found: [M+H]$^+$ m/z 373.0789.

t-Butyl (4-tert-Butoxycarbonylmethyl-7-{2-[tert-butoxycarbonylmethyl-(4-nitro-benzyl)-amino] ethyl}-[1,4,7]triazonan-1-yl)ester (13)

To a solution of Compound 6 (200 mg, 0.56 mmol) in CH$_3$CN (5 mL) was added N,N'-Diisopropylethylamine (217.14 g, 7.1 mmol) and Compound 12 (219 mg, 0.587 mmol). The reaction mixture was refluxed for 6 days. The resulting solution was evaporated into a yellow reddish residue. This residue is purified via column chromatography with silica gel (220 mesh) eluting with 3% methanol in dichloromethane to afford a yellow oily Compound 13 (0.88 g, 70.6%). $^1$H NMR (CDCl$_3$) δ 1.41 (d, 27H), 2.80-3.75 (m, 24H), 7.26 (d, 2H), 8.19 (d, 2H); $^{13}$C NMR (CDCl$_3$) δ 28.15, 49.28, 49.92, 52.66, 53.59, 55.07, 57.37, 57.37, 81.81, 81.59, 123.64, 129.64, 145.78, 147.40, 169.99, 170.56. HRMS (Positive ion FAB) Calcd for $C_{33}H_{56}N_5O_8$ [M+H]$^+$ m/z 650.4129. Found: [M+H]$^+$ m/z 650.4100. Analytical HPLC ($t_R$=25 min, Method 1).

6.(4-Carboxymethyl-7-{2-[carboxymethyl-(4-nitrobenzyl)-amino]-ethyl}-1,4,7]triazonan-1-yl)-acetic acid (14)

To a solution of Compound 5 (13 mg, 0.02 mmol) in an ice-bath was added 4M HCl in 1,4-dioxane (5 mL). After the addition, the ice bath was taken out and the reaction mixture was gradually increased to room temperature and stirred for 18 h To this solution, ether (~15 mL) was added and was continuously stirred for 30 min. The resulting mixture was and placed in the refrigerator for 2 h. Solid residue from recrystallization was quickly filtered and washed with ethyl ether (~50 mL), and immediately dissolved in water and lyophilized to provide pure Compound 14 as a yellow solid (0.07 g, 80%). $^1$H NMR (D$_2$O) δ 2.82 to 2.85 (m, 4H), 2.94 to 2.96 (m, 2H), 3.12 to 3.14 (m, 4H), 3.28 (s, 4H) 3.38 to 3.40 (m, 2H), 3.81 (s, 6H), 4.50 (s, 2H), 7.70 (2, 2H), 8.22 (d, 2H); $^{13}$C NMR (D$_2$O) δ 48.37, 48.83, 49.53, 50.44, 51.03, 52.00, 55.01, 56.38, 58.22, 124.33, 132.58, 135.89, 148.71, 169.55, 171.53. HRMS (Positive ion FAB) Calcd for $C_{21}H_{31}N_5O_8$ [M+H]$^+$ m/z 481.2173. Found: [M+H]$^+$ m/z 481.2170.

t-Butyl (4-tert-Butoxycarbonylmethyl-7-{2-(tert-butoxycarbonylmethyl-amino)-3-[4-(7-nitro-benzo[1,2,5]oxadiazol-4-ylamino)-phenyl]-propyl}-[1,4,7]triazonan-1-yl)-acetate (16)

To a solution of Compound 15 (94 mg, 0.15 mmol) in DCM (2 mL) was portionwise added NBD-Cl (30.3 mg, 0.15 mmol). The resulting mixture was stirred for 4 h while monitoring the progress by TLC analysis. During the reaction whole apparatus were wrapped with aluminum foil for dark condition. The resulting solution was evaporated and purified via column chromatography with silica gel (220 mesh) eluting with 1% of methanol in dichloromethane. The fractions containing product 16 were collected and evaporated to provide Compound 16 (31 mg, 26%). NMR (CDCl$_3$) δ 1.41-1.49 (m, 27H), 2.65-2.92 (m, 16H), 3.25-3.42 (m, 6H), 3.62-3.67 (m, 1H), 6.64 (d, 1H), 7.23-7.38 (m, 4H), 8.42 (d, 1H). HRMS (Positive ion FAB) Calcd for $C_{39}H_{58}N_8O_9$ [M+H]$^+$ m/z 783.4405. Found: [M+H]$^+$ m/z 783.4434.

(4-Carboxymethyl-7-{2-(carboxymethyl-amino)-3-[4-(7-nitro-benzo[1,2,5]oxadiazol-4-ylamino)-phenyl]-propyl}-[1,4,7]triazonan-1-yl)-acetic acid (17)

To a solution of Compound 16 (15.7 mg, 0.02 mmol) in 1,4-dioxane (1 mL) at 0-5° C. was added 4M HCl(g) in 1,4-dioxane (1 mL) dropwise over ~15 min. The resulting mixture was allowed to warm to room temperature. Ether (~15 mL) was added to the reaction mixture and stirred for 10 min. The resulting mixture was placed in the freezer for 1 h. The solid residue was filtered and washed with ether and quickly dissolved in 18μΩ deionized water. Evaporation of the aqueous solution gave pure Compound 17 (12.4 mg, 90%) as an orange solid. $^1$H NMR (CD$_3$OD) δ 2.82-3.48 (m, 13H), 3.78-4.08 (m, 10H), 6.76 (d, 1H), 7.40-7.55 (m, 4H), 8.51 (d, 1H). HRMS (Positive ion FAB) Calcd for $C_{27}H_{34}N_8O_9$ [M+H]$^+$ m/z 615.2527. Found: [M+H]$^+$ m/z 615.2520. Analytical HPLC ($t_R$=3.6 min, Method 2).

Cell Culture

Human cervix HeLa cell line was obtained from ATCC (Rockville, Md.) and cultured in minimum essential medium (MEM) with L-glutamine (2 mM), Earle's BSS and sodium bicarbonate (1.5 g/L), supplemented with 10% fetal bovine serum (FBS), non-essential amino acids (0.1 mM), sodium pyruvate (1 mM) and antibiotic/antimycotic solution in a humidified atmosphere with 5% $CO_2$ at 37° C. Human colon cancer cell line HT29 was maintained in a humidified atmosphere with 5% $CO_2$ at 37° C. in RPMI-1640 medium, containing 10% FBS with L-glutamine and antibiotic/antimycotic. Lung fibroblast MRC-5 cell line was obtained from ATCC (Rockville, Md.) and cultured in ATCC formulated EMEM, supplemented with 10% fetal bovine serum (FBS) in a humidified atmosphere with 5% $CO_2$ at 37° C.

Antiproliferative Activity.

Cells were seeded onto 96-well plate at density of 2,000 cells for Hela cells or 5,000 cells for HT29 cells or 5,000 cells for MRC-5 per well in 0.1 mL complete medium and allowed to attach for 24 h. Varying concentrations of the test compounds in the final volume of 0.1 mL complete medium were then added in at least five series dilutions and incubated for 72 h. To measure cell proliferation, the Cell Titer 96 aqueous nonreactive cell proliferation assay (Promega Life Sciences, Madison, Wis.) was used according to the manufacturer's instructions. Briefly, MTS (2 mg/mL) and PMS (0.92 mg/ml) were mixed in a ratio of 20:1. An aliquot (20 μL) of the MTS/PMS mixture was added into each well, and the plate was incubated for 3 h at 37° C. Optical absorbance at 490 nm was then recorded with an enzyme-linked immunosorbent assay (ELISA) microtiter plate reader (Biotek). Each experiment was done at least in triplicate. Antiproliferative activity of the test compounds was expressed as the fraction of optical densities of treated the cells relative to the untreated solvent controls.[31] The data were plotted in GraphPad Prizm 3.0. Nonlinear regression analysis was used to determine IC$_{50}$ values. IC$_{50}$ of the compounds was expressed as the concentration of the drugs inhibiting cell growth by 50%.

Iron Saturation Experiment

Hela Cells were inoculated onto 96-well plates at density of 2,000 per well in 0.1 mL complete medium and incubated for 24 h. The aqueous solution (50 μM) of the chelators, NETA, DFO, or DTPA was prepared and mixed with stoichiometric amount of aqueous solution (50 μM) of ferric citrate in complete medium, and the resulting mixture was then added into the triplicate plates. Control samples containing no ferric citriate were also tested. Plates were incubated at 37° C. in 5% $CO_2$/95% air for 72 hours. After the incubation, cells proliferation rates were evaluated by MTS assay.

Fluorescence and UV Spectra of C-NE3TA-NBD.

Fluorescence Spectra were recorded on a PC1 Photon counting spectrofluorometer (ISS, Inc., Champaign, Ill.) with excitation at 446 nm, bandwidth of 8 nm, data collection every 1 nm at 20° C. Stock solution (1 mM) of NBD-NE3TA was prepared by dissolving sample in H$_2$O. UV-Vis measurements were carried out by adding 10 μL aliquots of the stock solution via a micropipette into 2 mL of H$_2$O in a quartz cuvette, while the measurement of fluorescence was carried out by adding 1 μL aliquots of the stock solutions into 1 mL H$_2$O in a quartz cuvette. The mixtures were stirred briefly for equilibration prior to data acquisition.

Fluorescence Imaging of Live Cancer Cells.

HT29 cancer cells were plated in glass cover slips which placed in 6-well plates, and were incubated with growth media in a humidified atmosphere with 5% $CO_2$ at 37° C. overnight. Control cells or cells containing C-NE3TA-NBD (50 μM, H$_2$O) were incubated with media for 0.5 h under 5% $CO_2$ at 37° C. At the end of the incubation time, cells were rinsed with PBS three times and subsequently observed under the Olympus DSU Spinning disk confocal microscope with a band-pass filter set at 436/20 nm (Excitation) and 535/30 nm (Emission).

Example 5

A Novel Cholic Acid-Based Contrast Enhancement Agent for Targeted MRI

Gd(III) complexes of heptadentate ligands NE3TA and NE3TA-Bn were prepared, and their relaxivities were measured and favorably compared to the commercially available MRI contrast enhancement agent Gd(DOTA). NE3TA was conjugated with cholic acid (CA) to produce CA-NE3TA. As discussed further below, TEM images of Gd(CA-NE3TA) indicate that the complex self-assembles forming nano-sized micelles and displays an over 3-fold increased relaxivity compared to Gd(DOTA).

Magnetic resonance imaging (MRI) is a non-invasive and high resolution imaging technique that has become a powerful diagnostic tool in the clinic. The images due to the MR signal of water protons provide a sharp contrast between tissues with different proton relaxation times ($T_1$ or $T_2$). Signal intensity, i.e., relaxivity ($1/T_1$ or $1/T_2$) results from proton exchange between a slowly exchanging gadolinium-bound water molecule and bulk water. In order to enhance contrast between tissues, paramagnetic metal complexes have been introduced in vivo. The lanthanide Gd(III) is known to be an optimal paramagnetic metal for MRI due to its high electronic spin (7/2) and slow electronic relaxation rate. A number of Gd(III) complexes such as Gd(DOTA) and Gd(DTPA) are clinically approved for use in MRI (Caravan, P.; Ellison, J. J.; McMurry, T. J.; Lauffer, R. B. *Chem. Rev.* 1999, 99, 2293-2352). However, most contrast agents have non-specific extracellular distribution and the disadvantages of low relaxivity, low tissue specificity, and rapid clearance (Aime, S.; Botta, M.; Fasano, M.; Terreno, E. *Chem. Soc. Rev.* 1998, 27, 19-29). Considerable research efforts have been directed towards developing safe Gd(III)-based MR contrast agents with high tissue specificity and sensitivity. MRI is proven to be more sensitive and specific than other medical tests for detecting liver malignancies and for distinguishing them from benign lesions (Reimer, P.; Schneider, G.; Schima, W. *Eur. Radiol.* 2004, 14, 559-578). The gadolinium complexes of two DTPA analogues, benzyloxypropionictetraacetate (BOPTA) and ethoxybenzyl-diethylenetriaminepentaacetic acid (EOB-DTPA) are the clinically approved hepatobiliary agents (Vogl, T. J.; Lencioni, R.; Hammerstingl, R. M.; Bartolozzi, C. Chapter 4. Contrast agents; Georg Thieme Verlag Publisher, Stuttgart, Germany. 2003). The Gd(III) complexes provide low detection and characterization of metastatic lesions, although the agents are useful in detection and characterization of hepatocelluar lesions (Vogl, T. J.; Hammerstingl, R.; Schwarz, W. Radiology 1996, 198, 881-887).

The compounds of this invention are useful in preparing MRI contrast agents, such as liver-specific MRI contrast agents. Bile acid can be used as a liver or intestine targeting moiety. The property of amphifacial bile acid to undergo enterohepatic circulation and form helical aggregates makes it a useful shuttle system to deliver various drugs to the liver and intestine with favorable intestine absorption and pharmacokinetic profile. Bile acids are efficiently taken up into the cells by two types of carriers: apical sodium-dependent bile salt transporters (ASBT) carriers and $Na^+$-independent carriers. Experimental studies demonstrate that bile acids enter liver and colon cancer cells which over express bile acid transporter and carriers (Ballestero, M. R.; Monte, M. J.; Briz, O.; Jimenez, F.; Martin, F. G. S.; Marin, J. J. G. *Biochem. Pharmacol.* 2006, 72, 729-738; Powell, A. A.; LaRue, J. M.; Batta, A. K.; Martinez, J. D. *Biochem. J.* 2001, 356, 481-6).

The Gd(III) complexes of NETA and NPTA are stable in both serum and mice and possess enhanced relaxivity compared to those of DOTA Chong, H. S.; Garmestani, K.; Bryant Jr., L. H.; Milenic, D. E, Overstreet, T.; Birch, N.; Le, T.; Brady, E. D.; Brechbiel, M. W. *J. Med. Chem.* 2006, 49, 2055-2062). In the present example, the Gd(III) complexes of heptadentate NE3TA and NE3TA-Bn were prepared as potential MRI contrast agents. Heptadentate NE3TA contains four amines and three carboxylates as potential donor groups. NE3TA-Bn is a heptadentate ligand with a benzyl group which can be further modified for conjugation to a targeting moiety. Both NE3TA and NE3TA-Bn can produce neutral Gd(III) complexes that have an advantage of less protein interaction and a potentially more favorable in vivo tissue distribution, and the corresponding Gd(III) complexes may provide enhanced relaxivity due to increase in hydration number (q) when compared to that of DOTA and DTPA.

The present example includes the synthesis and characterization of Gd(III) complexes: Gd(NE3TA), Gd(NE3TA-Bn), and Gd(CA-NE3TA). Transmission electron microscopy (TEM) images of cholic acid analogues, CA-NE3TA and Gd(CA-NE3TA) were obtained.

Figure 6:
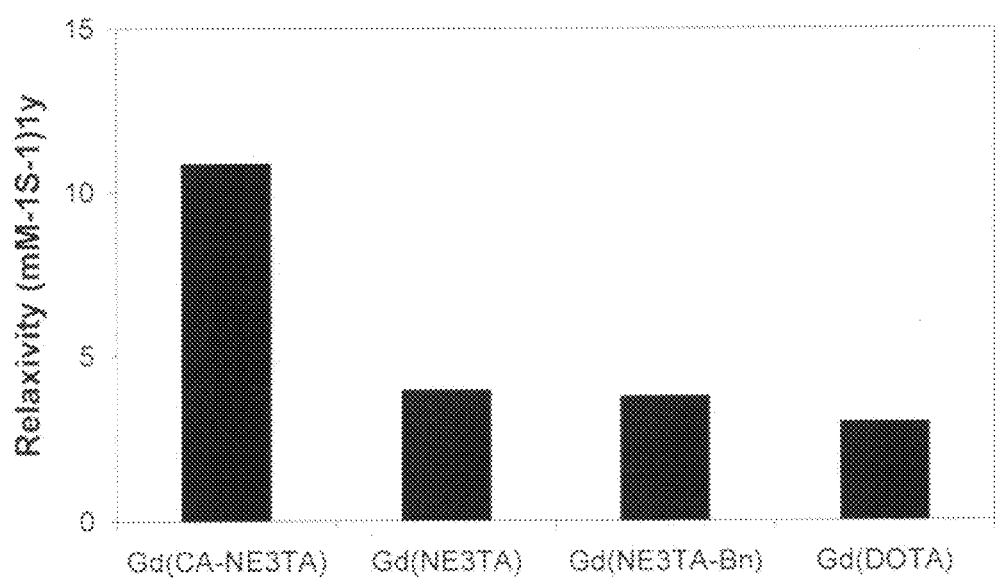
FIG. 6 is a graph illustrating the relaxivity of the Gd(III) complexes of one embodiment of this invention.

Gd(NE3TA) and Gd(NE3TA-Bn) were synthesized by reacting $GdCl_3$ with NE3TA and NE3TA-Bn, respectively. NE3TA or NE3TA-Bn were mixed with $GdCl_3$ in a molar ratio of 1 to 0.9, and the resulting mixture at pH 7 was heated to 90° C. and stirred until no free Gd(III) ions were detected using an ArsenazoIII (AAIII) assay. Relaxivity of the aqueous Gd(III) complexes (pH 7) was measured on a Bruker MQ60 NMR analyzer, and the concentration of the Gd(III) complexes was measured by ICP-MS. The relaxivity data shown in FIG. 6 indicate that the Gd(III) complexes of NE3TA (3.94 $mM^{-1}$ $s^{-1}$) and NE3TA-Bn 3.74 $mM^{-1}$ $s^{-1}$) provided higher relaxivity as compared to Gd(DOTA) (2.97 $mM^{-1}$ $s^{-1}$), probably due to increase in q. NE3TA was successfully conjugated with the most common bile acid, cholic acid (Scheme 11).

Figure 7:
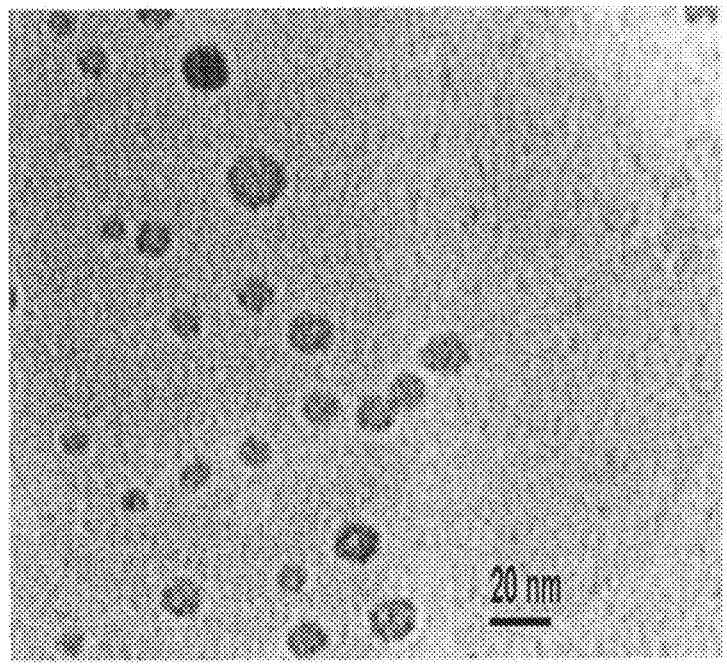
FIG. 7 is a TEM image of unstained CA-NE3TA (10 μM aqueous solution).
Figure 8:
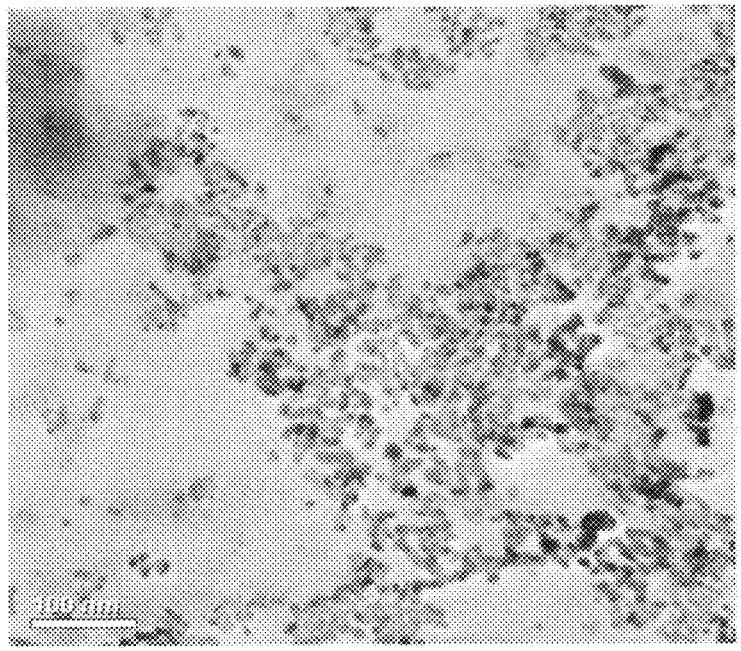
FIG. 8 is a TEM image of unstained Gd(CA-NE3TA) (100 μM aqueous solution) (inset, scale bar in 10 nm).
Figure 9:
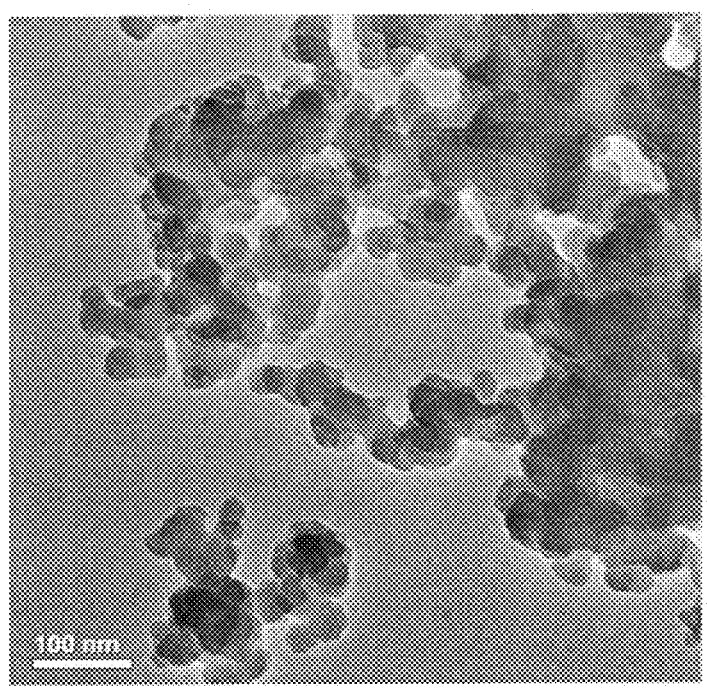
FIG. 9 is a TEM image of unstained Gd(CA-NE3TA) (10 μM aqueous solution).

Amphifacial cholic acid is a good targeting moiety, and its conjugation to MR contrast agent is expected to form helical globular aggregates with a favorable pharmacokinetic and relaxivity profile. In Scheme 11, cholic acid was converted to an activated amide 1, which was further reacted with a functionalized NE3TA (2) containing an amino group to provide Compound 3. The t-butyl group of Compound 3 was removed by treatment with 4M HCl in 1,4-dioxane to provide CA-NE3TA (4). The TEM image of CA-NE3TA in FIG. 7 (10 µM aqueous solution) indicates that the bile acid conjugated NE3TA forms discrete spherical micells in nanometer size (~10-50 nm) due to the presence of hydrophobic cholic acid moiety surrounded by hydrophilic NE3TA ligand. The Gd(III) complex of CA-NE3TA was prepared as described above. Gd(CA-NE3TA) self-assembles into nano-sized micells as evidenced by TEM measurement (~10 nm, FIG. 8). Interestingly, when the complex Gd(CA-NE3TA) was taken in low concentration (10 µM aqueous solution), it was shown to rapidly agglomerate into stacked spherical micells (FIG. 9). Aggregation of Gd(CA-NE3TA) as evidenced by TEM images is proposed to result from heating during the complexation reaction and/or gadolinium induced cross linking. $T_1$ relaxivity of Gd(CA-NE3TA) in aqueous solution (0.2 mM) was measured to 10.85 $mM^{-1}$ $s^{-1}$. The relaxivity data indicates that incorporation of cholic acid with NE3TA produced more than 3-fold increase in $T_1$ relaxivity. This increase in relaxivity may be a result of slower molecular rotation due to aggregation of the complex as evidenced by the TEM image.

Relaxivity of the Gd(NE3TA) and Gd(NE3TA-Bn) are high when compared to that of the commercially available MR contrast agent Gd(DOTA). Both the cholic acid-based CA-NE3TA and the corresponding Gd(III) complex (Gd (CA-NE3TA)) self assemble forming nano-sized micells as shown by the TEM images. Gd(CA-NE3TA) displayed much increased relaxivity as compared to Gd(DOTA). The bile acid-conjugated Gd(III) complexes of this invention, e.g., Gd(CA-NE3TA) possess promise for use in targeted MRI.

Example 5

Experimental Information

Scheme 11

General.

The analytical HPLC was performed on Agilent 1200 equipped with a dioarray detector ($\lambda$=254 and 280 nm), thermostat set at 35° C. and a Zorbax Eclipse XDB-C18 column (4.6×150 mm, 80 Å). A combination of a binary gradient and an isocratic mobile phase (50-100% B/15 min; solvent A=$H_2O$; solvent B=$CH_3CN$ and 100% B/15-30 min) at a flow rate of 1 mL/min was used for analytical HPLC method.

3-[4-(3,7,12-Trihydroxy-10,13-dimethyl-hexadecahydro-cyclopenta[a]phenanthren-17-yl)-pentanoyl]-thiazolidin-2-one (1)

To a vigorously stirred solution of cholic acid (2 g, 4.89 mmol) in $CH_2Cl_2$ (20 mL) was added DCC (1.1 g, 5.38 mmol), 2-mercaptothiazoline (0.64 g, 5.38 mmol), and catalytic amount (42 mg) of N,N-dimethyl amino pyridine (DMAP). The reaction mixture was stirred for 24 h at room temperature, and the white precipitate of dicyclohexyl urea was filtered off. The yellowish filtrate was diluted to 40 mL with $CH_2Cl_2$ and sequentially washed with 0.5N NaOH solution (20 mL), 0.1N HCl (20 mL), and brine (20 mL). The organic layer was dried over $MgSO_4$, filtered, and concentrated in vacuo to provide pure activated Compound 1 (2.05 g, 85%) which was used for next step without further purification. $^1H$ NMR (300 MHz, $CDCl_3$) δ 0.66 (s, 3H), 0.87 (s, 3H), 0.98 (d, 3H), 1.12-2.03 (m, 22H), 2.20 (t, 2H), 3.27 (t, 2H), 3.33-3.48 (m, 1H), 3.82 (s, 1H), 3.94 (s, 1H), 4.56 (t, 2H); $^{13}C$ NMR (300 MHz, $CDCl_3$) δ11.81, 18.55, 20.60, 22.82, 23.71, 28.22, 28.28, 30.65, 30.78, 32.82, 34.61, 35.05, 35.35, 35.43, 35.62, 39.41, 39.63, 39.80, 41.50, 42.71, 50.42, 55.94, 56.11, 68.49, 71.96, 72.92, 175.46, 201.52.

t-Butyl [4-tert-Butoxycarbonylmethyl-7-(2-(tert-butoxycarbonylmethyl-amino)-3-{4-[4-(3,7,12-trihydroxy-10,13-dimethyl-hexadecahydro-cyclopenta[a] phenanthren-17-yl)-pentanoylamino]-phenyl}-propyl)-[1,4,7]-triazonan-1-yl]acetate (3)

To a solution of Compound 2 (86 mg, 0.14 mmol) in $CH_2Cl_2$ (5 mL) was added $Et_3N$ (14 mg, 0.14 mmol) and Compound 1 (71 mg, 0.14 mmol). The reaction mixture was refluxed for 2 days. The resulting solution was evaporated, and the residue was purified via column chromatography with neutral alumina eluting with 1% methanol starting from $CH_2Cl_2$ to afford pure Compound 3 as a creamy solid (0.95 g, 67%). $^1H$ NMR (300 MHz, MeOD) δ 0.72 (s, 3H), 0.91 (s, 3H), 0.97-1.15 (m, 7H), 1.18-1.65 (m, 36H), 1.70-2.06 (m, 7H), 2.08-3.13 (m, 20H), 3.15-3.54 (m, 8H), 3.80 (s, 1H), 3.98 (s, 1H), 7.18 (d, 2H), 7.50 (d, 2H). $^{13}C$ NMR (300 MHz, $CD_3OD$) δ 11.61, 16.39, 21.77, 22.84, 26.48, 27.02, 27.08, 27.32, 28.20, 29.36, 29.78, 31.80, 33.57, 34.50, 35.09, 35.56, 39.06, 39.61, 41.61, 41.79, 46.09, 46.65, 46.63, 71.47, 72.65, 80.69, 80.94, 120.06, 129.17, 134.13, 137.03, 170.98, 171.48, 173.78. HRMS (Positive ion FAB) Calcd for $C_{57}H_{95}N_5O_{10}$ $[M+H]^+$ m/z 1010.7157. Found: $[M+H]^+$ E m/z 1010.7154. Analytical HPLC ($t_R$=11 min).

[4-Carboxymethyl-7-(2-(carboxymethyl-amino)-3-{4-[4-(3,7,12-trihydroxy-10,13-dimethyl-hexadecahydro-cyclopenta[a]phenanthren-17-yl)-pentanoylamino]-phenyl}-propyl)-[1,4,7]triazonan-1-yl]-acetic acid (4). To a solution of Compound 3 (20 mg, 0.02 mmol) in a ice-bath was added 4M HCl in 1,4-dioxane (5 mL). After the addition, the reaction mixture was gradually increased to room temperature and stirred for 24 h. To this solution, ether (30 mL) was added and continuously stirred for 30 min. The resulting mixture was placed in the freezer for 2 h. Solid residue was quickly filtered, washed with ethyl ether (5 mL), immediately dissolved in $H_2O$ and $CH_3OH$, and lyophilized to provide pure Compound 4 as a light brownish solid (19 mg, 97%). $^1H$ NMR ($CD_3OD$) 0.71 (s, 3H), 0.58-0.95 (m, 6H), 0.96-1.17 (m, 5H), 1.21-2.05 (m, 26H), 2.10-2.52 (m, 5H), 2.55-3.09 (m, 4H), 3.15-4.12 (m, 10H), 7.27 (d, 2H), 7.56 (d, 2H). HRMS (Positive ion FAB) Calcd for $C_{45}H_{72}N_5O_{10}$ $[M+H]^+$ m/z 842.5279. Found: $[M+H]^+$ m/z 842.5265.

TEM Measurement.

Stock solutions of compounds CA-NE3TA and Gd(CA-NE3TA) were prepared in 18 MΩ $H_2O$ and diluted to the final concentrations of CA-NE3TA (10 μM, pH=5) and Gd(CA-NE3TA) (100 μM or 10 μM, pH=7). In triplicate, a 5 μL aliquot of CA-NE3TA solution was placed on a gold-coated grid (300 mesh, formvar support film, Cat # FF300-Au, Electron Microscopy Sciences, PA). The sample on the grid was air-dried for 5-10 min after each deposition. The grid was air-dried overnight, transferred into a desiccator, and further dried in vacuo for 1.5 days. The sample of Gd(CA-NE3TA) (10 μM) was prepared as described above. A 5 μL aliquot of Gd(CA-NE3TA) solution (100 μM) was added to a cavity of a Micro-Test Staining Dish (Cat#71564, Electron Microscopy Sciences, PA), and a gold-coated grid was inverted into the solution in the plate and air-dried for 10 min. The grid was further dipped into a drop of the solution (10 μL) in a cavity of the plate and air-dried overnight. The grid was transferred into a desiccator and further dried in vacuo for 1.5 days. TEM images were obtained at room temperature on a Hitachi HF-2000 High resolution TEM (Hitachi) operated at 80 kV, equipped with a charged-coupled device (CCD) camera.

General Procedure for the Preparation of Gd(III) Complex Using Simple Ligands (DOTA, NETA, or NE3TA-Bn).

Simple Ligands (2 mM, 1 mL) and $GdCl_3$ (2 mM, 0.9 mL) were mixed and heated at 90° C., while pH of the solution was constantly maintained at pH 7 by adding 1N NaOH. The heating was continued until no free $Gd^{3+}$ was detected using arsenazo III (AAIII) solution. The complex solution without free $Gd^{3+}$ was further evaluated for T1 relaxivity.

Procedure for the Preparation of Gd(CA-NE3TA).

CA-NE3TA (2 mM, 1 mL) was mixed with $GdCl_3$ (2 mM, 0.9 mL). The pH of the solution was slowly adjusted to 7 using 1N NaOH. Gd(CA-NE3TA) was precipitated as the complexation proceeded and pH of the mixture solution was adjusted to 7. The suspension was further heated at 90° C. until no free $Gd^{3+}$ detected as evidenced by AAIII assay. The resulting mixture was spun down at 1000×g, and the pellets were dissolved in DMSO (50 μL) and then make up 5% DMSO aqueous solution (1 mL) for further evaluation for T1 relaxivity.

Procedure for Detection of Free Gadolinium Using AAIII Assay.

AAIII assay was used for the determination of the free Gd(III) in the complex solution. A solution of AAIII (10 μM) was prepared in the acetate buffer (NH$_4$OAc, 0.15 M, pH 7). Droplets of AAIII (100 μL) were arranged in a 96 well plate, and a droplet of reaction mixture (100 μL) was added to AAIII solution in each well. The presence of free Gd$^{3+}$ was indicated by the immediate color change from pink to green.

ICP-MS.

To verify the concentration of Gadolinum ICP-MS was performed using a computer-controlled Thermo Elemental (Now Thermo Fisher) PQ ExCell Inductively Coupled Plasma Mass Spectrometer. Samples were prepared by nitric acid digestion (9:1=nitric acid:sample) in a 65° C. water bath. The digested samples were diluted into 15 mL conical vials with a final concentration of 3% (v/v) nitric acid. Gd standards were prepared in 3% (v/v) nitric acid with values 0.1, 0.25, 0.5, 1, 5, 10, 25, and 50 ng/mL Gd. Indium was spiked into every sample (including standards) for a final indium concentration of 5 ng/mL. Isotopes $^{157}$Gd and $^{115}$In were used for determination.

Relaxivity Measurements.

Relaxivity measurements were acquired by taking the slope of a plot of 1/T1 (s$^{-1}$) versus concentration (mM). The longitudinal water proton relaxation times (T1) were determined using a Bruker mq60 NMR (Bruker Canada, Milton, ON, Canada) analyzer operating at 59.97 MHz and 37° C. The agent was added to Millipore water and serially diluted by 0.5 to give a series of 5 concentrations (500 μL total volume) for each relaxivity trial. The $T_1$ was determined using an inversion recovery pulse sequence with 10 different pulse separations per sample, 4 repetitions per echo time, phase cycling, and a recycle delay that is ≥5 times the $T_1$ of each given sample. All curves were fit using a monoexponential curve fitting formula.

Example 6

Bimodal Bifunctional Ligands for Radioimmunotherapy and Targeted MRI

The bifunctional ligand C-NE3TA, possessing both acyclic and macrocyclic moieties, was prepared and evaluated as potential chelates for radioimmunotherapy (RIT) and targeted magnetic resonance imaging (MRI). An optimized synthetic method to C-NE3TA including purification of the polar and tailing reaction intermediates, t-butyl C-NE3TA (2) using semi-prep HPLC is shown in Scheme 12. Gd(III) complex of C-NE3TA as contrast enhancement agents for use in targeted MRI were prepared. T1 Relaxivity data indicate that Gd(C-NE3TA) possess higher relaxivity than C-DOTA, a bifunctional version of a commercially available MRI contrast agent, Gado®. C-NE3TA was radiolabeled with $^{177}$Lu, $^{90}$Y, $^{203}$Pb, $^{205/6}$Bi, and $^{153}$Gd, and in vitro and in vivo stability of the radiolabeled corresponding complexes was assessed in human serum and athymic mice, respectively. The in vitro studies indicate that all radiolabeled complexes except $^{203}$Pb complexes of C-NE3TA which were dissociated in serum were stable in serum for 11 days. C-NE3TA radiolabeled $^{177}$Lu, $^{90}$Y, $^{205/6}$Bi, or $^{153}$Gd possess excellent or acceptable in vivo biodistribution profile. C-NE3TA was further modified for conjugation to a monoclonal antibody Herceptin®. The ratio of ligand to protein (L/P) of C-NE3TA-Herceptin based on Arsenazo assay was determined to be 2.5.

C-NE3TA contains four amines and three carboxylates as potential donor groups. The heptadentate C-NE3TA forms a neutral complex with Y(III), Lu(III), Bi(III), and Gd(III) that requires no counterion and thus have an advantage of less protein interaction and a potentially more favorable in vivo tissue distribution. Synthesis of C-NE3TA is shown in Scheme 6. To prepare t-butyl C-NE3TA 2, the starting material 1 as an HCl salt instead of free amine was reacted with t-butyl bromoacetate in DMF at 50° C. (Scheme 12). The reaction provided t-butyl C-NE3TA 2 in 68% yield as the major product. With the challenge encountered in isolation of Compound 2 in a high purity, a purification method was developed that is available for efficient preparation of the ligands in high purity which can produce water soluble peracid form after deprotection of t-butyl groups. The desired ligand C-NE3TA was obtained by removal of t-Butyl groups of Compound 2 by HCl(g). Synthesis of C-NE3TA-NCS having a functional linker for conjugation to an antibody is shown in Scheme 13. The nitro group in Compound 2 was transformed into the amino group to provide Compound 3. Removal of tert-butyl groups in Compound 3 followed by reaction with thiophosgene provided the desired ligands with the linker for conjugation to antibody C-NE3TA-NCS (6).

The Gd(III) complexes of the chelates in the nitro form were prepared as described previously. T1 relaxivity of the Gd(III) complexes, Gd(C-NETA) and Gd(C-NE3TA) was measured and compared to that of Gd(C-DOTA). The Gd(III) complex of non-functionalized bimodal ligand NETA has been reported as stable in both serum and mice, and displays considerably enhanced T1 relaxivity compared to Gd(DOTA) where the Gd(III) is coordinated to the eight donor atoms of the ligands with one vacant coordination site available to bind a water molecule (q=1). It was proposed that the increase in relaxivities of Gd(NETA) compared to Gd(DOTA) may be ascribed to a decrease in the ligand denticity from eight to seven-coordinate by one of the flexible acyclic pendant coordinating groups not being coordinated at all or from an "on"-"off" mechanism of one of the pendant coordinating groups and thus an increase in q value of Gd(NETA) complex to an intermediate between one coordinated water molecule (q=1) and two coordinated water molecules (q=2) (Chong H S, Garmestani K, Bryant Jr., L H, Milenic D E, Overstreet T, Birch N, Le T, Brady E D, Brechbiel M W. *J. Med. Chem.* 2006, 49, 2055-2062). In the present example, the Gd(III) complexes of bifunctional ligands C-NETA and heptadentate C-NE3TA were prepared as potential MRI contrast agents. Heptadentate C-NE3TA is expected to provide enhanced relaxivity due to increase in hydration number (q) when compared to C-NETA and C-DOTA. The Gd(III) complexes of the bifunctional ligands were prepared and purified using semi-prep HPLC, while the presence of free Gd(III) ions was detected using an ArsenazoIII (AAIII) assay.

Figure 10:
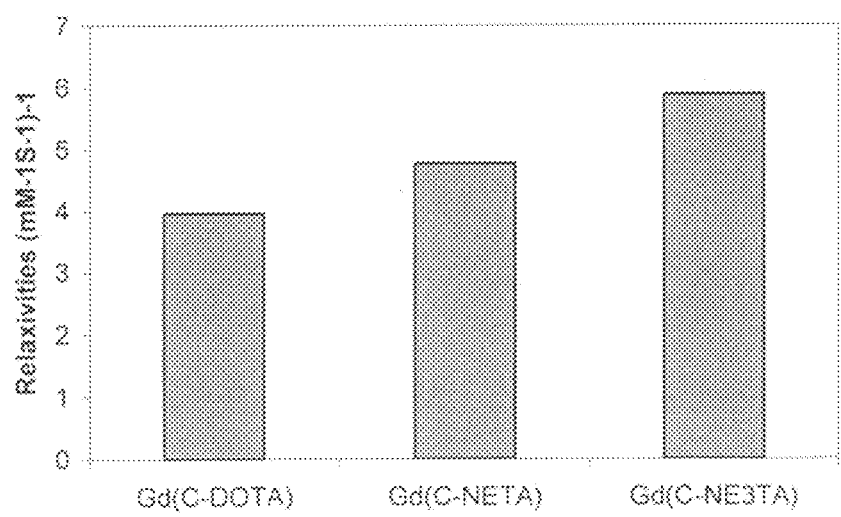
FIG. 10 is a graph illustrating relaxivity data of Gd(C-DOTA), Gd(C-NETA), Gd(C-NE3TA).

Relaxivity of the aqueous Gd(III) complexes (~pH 7) were measured on a Bruker MQ60 NMR analyzer, and the concentration of the Gd(III) complexes were measured by ICP-MS. The relaxivity data (FIG. 10) indicate that C-NETA (4.77 mM$^{-1}$ s$^{-1}$) and C-NE3TA (5.89 mM$^{-1}$ s$^{-1}$) provided higher relaxivity as compared to DOTA (3.96 mM$^{-1}$ s$^{-1}$). Introduction of a functional nitro group into the NETA backbone didn't affect T1 relaxivity of NETA. The difference of T1 relaxivity (~1 MHz) between C-DOTA and C-NETA was similar to that between DOTA and NETA. As mentioned above, the on and off binding to Gd(III) of one of the pendant coordinates would have resulted enhanced relaxivity of Gd(C-NETA) compared to Gd(C-DOTA). Among the evaluated Gd(III) complexes, Gd(C-NE3TA) gives the highest T1 relaxivity at 60 MHz, probably due to increase in q. The relaxation rates for the Gd(III) chelates are dominated by the inner-sphere dipolar coupling between the coordinated water molecule and the paramagnetic Gd(III). The measured relaxivities arise from the exchange between the coordinated water molecule and the surrounding water molecules in solution. An increase in the number of coordinated water molecules to the Gd(III), which could have occurred with dissociation of Gd(III) from the chelate in solution, would have resulted in a significant increase in the measured relaxivities. No indication of Gd(III) dissociation is evident from the relaxivity data, which is in agreement with the in vitro serum stability and in vivo biodistribution studies.

C-NE3TA was radiolabeled with $^{90}$Y, $^{177}$Lu, $^{203}$Pb, $^{205/6}$Bi, or $^{153}$Gd as previously described (Chong, H. S.; Milenic, D. E.; Garmestani, K.; Brady, E. D.; Arora, H.; Pfiester, C.; Brechbiel, M. W., *Nucl. Med. Biol.* 2006, 33, 459-67; Chong H S, Garmestani K, Bryant Jr., L H Milenic D E, Overstreet T, Birch N, Le N, Brady E D, Brechbiel M W. *J. Med. Chem.* 2006, 49, 2055-2062). In vitro serum stability of the radiolabeled complexes purified via ion-exchange chromatography was performed to determine if C-NE3TA labeled with the radioisotopes remained stable without transchelation or loss of their respective radionuclide in human serum. This was assessed by measuring the transfer of radionuclide from the complex to serum proteins over the course of 11 days. C-NE3TA radiolabeled with $^{90}$Y, $^{177}$Lu, $^{203}$Pb, $^{205/6}$Bi, or $^{153}$Gd were stable in serum for up to 11 days with no measurable loss of radioactivity. $^{203}$Pb—C-NE3TA remains unstable dissociating significant amount of $^{203}$Pb (~40%) in 1 day.

The in vivo stability of the radiolabeled complexes was evaluated by performing biodistribution studies in normal athymic mice. The results of the biodistribution studies for the radiolabeled complexes are shown in Tables 3-6. Selected organs and the blood were harvested at five time points, 0.5, 1, 4, 8, and 24 h post-injection and the radioactivity measured. C-NETA and C-NE3TA radiolabeled with $^{177}$Lu have similar biodistribution profiles, and both complexes were rapidly cleared from the blood and displayed low radioactivity levels in all organs (<0.8% ID/g at 24 h, Table 6). $^{90}$Y—C-NE3TA resulted in rapid blood and liver clearance (Table 7). C-NE3TA radiolabeled with $^{205/6}$Bi was rapidly cleared from the blood, lung, heart, and femur and displayed a higher radioactivity level in the kidney compared to other organs (Table 8). Radioactivity level of $^{205/6}$Bi—C-NE3TA in the kidney peaked at 5.05±0.24% ID/gm at 0.5 hh was decreased to 0.73±0.19% ID/gm at 24 hours. C-NE3TA radiolabeled with $^{153}$Gd was almost completely cleared from blood, liver, spleen, lung, heart, and femur in less than 4 hours, and radioactivity level in the kidney was 0.16%±0.11 ID/g at 24 hour post-injection (Table 9).

TABLE 6

Biodistribution of C-NE3TA radiolabeled with $^{177}$Lu in Non-Tumor Bearing Mice

| Ligand | Tissue | Timepoints (hr) | | | | |
|---|---|---|---|---|---|---|
| | | 0.50 | 1.00 | 4.00 | 8.00 | 24.00 |
| $^{177}$Lu-C-NE3TA | Blood | 0.93 ± 0.30 | 0.31 ± 0.04 | 0.12 ± 0.02 | 0.06 ± 0.01 | 0.01 ± 0.00 |
| | Liver | 0.82 ± 0.27 | 0.69 ± 0.20 | 0.50 ± 0.02 | 0.36 ± 0.05 | 0.31 ± 0.04 |
| | Spleen | 0.33 ± 0.08 | 0.28 ± 0.20 | 0.19 ± 0.07 | 0.13 ± 0.02 | 0.12 ± 0.05 |
| | Kidney | 2.78 ± 0.99 | 1.57 ± 0.52 | 1.34 ± 0.09 | 1.16 ± 0.19 | 0.84 ± 0.08 |
| | Lung | 0.87 ± 0.22 | 0.42 ± 0.16 | 0.17 ± 0.03 | 0.15 ± 0.03 | 0.07 ± 0.03 |
| | Heart | 0.37 ± 0.08 | 0.19 ± 0.09 | 0.08 ± 0.02 | 0.10 ± 0.11 | 0.02 ± 0.01 |
| | Femur | 1.06 ± 1.35 | 0.39 ± 0.13 | 0.36 ± 0.11 | 0.28 ± 0.15 | 0.38 ± 0.10 |

Values are the percent injected dose per gram (% ID/g) ± standard deviation

TABLE 7

Biodistribution of C-NE3TA radiolabeled with $^{90}$Y in Non-Tumor Bearing Mice

| Ligand | Tissue | Timepoints (hr) | | | | |
|---|---|---|---|---|---|---|
| | | 0.50 | 1.00 | 4.00 | 8.00 | 24.00 |
| $^{90}$Y-C-NE3TA | Blood | 1.86 ± 1.92 | 0.76 ± 1.09 | 0.05 ± 0.05 | 0.02 ± 0.00 | 0.00 ± 0.00 |
| | Liver | 1.65 ± 0.59 | 0.88 ± 0.59 | 0.17 ± 0.05 | 0.20 ± 0.16 | 0.10 ± 0.03 |
| | Spleen | 0.70 ± 0.15 | 0.47 ± 0.26 | 0.13 ± 0.08 | 0.07 ± 0.02 | 0.07 ± 0.02 |
| | Kidney | 2.58 ± 1.04 | 2.00 ± 2.32 | 0.74 ± 0.15 | 0.49 ± 0.10 | 0.35 ± 0.05 |
| | Lung | 1.64 ± 0.99 | 1.16 ± 0.65 | 0.10 ± 0.04 | 0.16 ± 0.22 | 0.23 ± 0.36 |
| | Heart | 0.79 ± 0.52 | 0.38 ± 0.31 | 0.06 ± 0.02 | 0.05 ± 0.01 | 0.02 ± 0.01 |
| | Femur | 1.19 ± 0.48 | 0.82 ± 0.26 | 0.30 ± 0.04 | 0.22 ± 0.06 | 0.08 ± 0.02 |
| | Liver | 0.48 ± 0.08 | 0.32 ± 0.07 | 0.29 ± 0.03 | 0.22 ± 0.03 | 0.17 ± 0.02 |

Values are the percent injected dose per gram (% ID/g) ± standard deviation

TABLE 8

Biodistribution of ligands radiolabeled with $^{205/6}$Bi in Non-Tumor Bearing Mice

| Ligand | Tissue | Timepoints (hr) | | | | |
|---|---|---|---|---|---|---|
| | | 0.50 | 1.00 | 4.00 | 8.00 | 24.00 |
| $^{205/6}$BiC-NE3TA | Blood | 0.46 ± 0.18 | 0.13 ± 0.02 | 0.03 ± 0.00 | 0.02 ± 0.01 | 0.01 ± 0.00 |
| | Liver | 1.01 ± 0.15 | 0.80 ± 0.16 | 0.52 ± 0.13 | 0.37 ± 0.08 | 0.14 ± 0.03 |
| | Spleen | 0.45 ± 0.24 | 0.25 ± 0.02 | 0.18 ± 0.01 | 0.12 ± 0.02 | 0.13 ± 0.01 |
| | Kidney | 5.05 ± 0.24 | 4.69 ± 0.55 | 3.42 ± 0.55 | 1.99 ± 0.32 | 0.73 ± 0.19 |
| | Lung | 0.56 ± 0.13 | 0.25 ± 0.03 | 0.16 ± 0.01 | 0.13 ± 0.04 | 0.09 ± 0.01 |
| | Heart | 0.36 ± 0.09 | 0.19 ± 0.02 | 0.12 ± 0.01 | 0.09 ± 0.01 | 0.08 ± 0.02 |
| | Femur | 0.62 ± 0.27 | 0.26 ± 0.05 | 0.23 ± 0.06 | 0.14 ± 0.02 | 0.13 ± 0.01 |

Values are the percent injected dose per gram (% ID/g) ± standard deviation

TABLE 9

Biodistribution of ligands radiolabeled with $^{153}$Gd in Non-Tumor Bearing Mice

| Ligand | Tissue | Timepoints (hr) | | | | |
|---|---|---|---|---|---|---|
| | | 0.50 | 1.00 | 4.00 | 8.00 | 24.00 |
| $^{153}$Gd-C-NE3TA | Blood | 1.41 ± 0.57 | 0.20 ± 0.08 | 0.00 ± 0.00 | 0.00 ± 0.00 | 0.00 ± 0.00 |
| | Liver | 1.74 ± 0.69 | 0.58 ± 0.22 | 0.03 ± 0.01 | 0.02 ± 0.00 | 0.02 ± 0.01 |
| | Spleen | 0.50 ± 0.37 | 0.24 ± 0.05 | 0.02 ± 0.00 | 0.02 ± 0.00 | 0.01 ± 0.01 |
| | Kidney | 4.28 ± 1.33 | 1.13 ± 0.12 | 0.52 ± 0.04 | 0.38 ± 0.06 | 0.16 ± 0.11 |
| | Lung | 0.91 ± 0.28 | 0.32 ± 0.09 | 0.03 ± 0.00 | 0.02 ± 0.00 | 0.01 ± 0.01 |
| | Heart | 0.43 ± 0.16 | 0.14 ± 0.06 | 0.01 ± 0.00 | 0.01 ± 0.00 | 0.13 ± 0.27 |
| | Femur | 0.43 ± 0.14 | 1.30 ± 0.58 | 0.02 ± 0.01 | 0.02 ± 0.00 | 0.01 ± 0.00 |

Values are the percent injected dose per gram (% ID/g) ± standard deviation

HER2 receptors overproduced in a variety of epithelial tumors are a target of cancer drugs. Herceptin which selectively targets the HER2 protein and blocks its overexpression function and has been shown to enhance a survival rate of metastatic breast cancer patients was chosen as a tumor targeting biomolecule for the present study. C-NETA was conjugated with Herceptin by the method in Brady, E. D.; Chong, H. S.; Milenic, D. E.; Brechbiel, M. W. *Nucl. Med. Biol.* 2004, 31, 795-802. Protein concentration was quantified by the method of Lowry, O. H.; Rosebrough, N. J.; Rarr, A. L.; Randall, A. J. *J. Biol. Chem.* 1951, 193, 265-75. The AAIII-Cu(II) based UV-Vis spectrophotometric assay as described in Brady, E. D.; Chong, H. S.; Milenic, D. E.; Brechbiel, M. W. *Nucl. Med. Biol.* 2004, 31, 795-802 was used for the determination of the number of C-NETA ligands linked to Herceptin (L/P ratio). The L/P ratio for C-NETA-Herceptin and C-NE3TA conjugates was found to be 1 and 2.5, respectively.

At clinically relevant field strength, the relaxivities of Gd(C-NE3TA) are higher than that of a bifunctional version of Gd(C-NETA) and the clinically used contrast agent, Gd(DOTA). The in vitro serum stability and in vivo biodistribution data of the $^{153}$Gd-labeled complex, Gd(C-NE3TA) indicate that C-NE3TA bind to $^{153}$Gd with high complex stability. C-NE3TA was radiolabeled with $^{177}$Lu, $^{90}$Y, $^{203}$Pb, and $^{205/6}$Bi, the radioisotopes for RIT applications. C-NE3TA radiolabeled with $^{177}$Lu, $^{90}$Y, $^{203}$Pb, and $^{205/6}$Bi were extremely stable without leaking any radioactivity from the metal complex in human serum for up to 11 days, while $^{203}$Pb—C-NE3TA underwent significant dissociation of the metal from the complexes. In vivo biodistribution of the radiolabeled complexes using athymic mice indicate that C-NE3TA is the adequate chelates to effectively hold all radioisotopes ($^{177}$Lu, $^{90}$Y, and $^{205/6}$Bi, and $^{153}$Gd) evaluated in vivo. All of the radiolabeled complexes exhibited rapid blood clearance and relatively low radioactivity levels in the normal organs and possess a favorable biodistribution profile. The bifunctional ligands, C-NE3TA were successfully conjugated to Herceptin with the respective L/P product ratio of 2.5 as determined using UV/Vis spectrophotometric AAIII assay. The result of T1 relaxivity, in vitro serum stability, and in vivo biodistribution studies suggests that the bifunctional ligands, C-NETA and C-NE3TA are promising bifunctional ligands for disease-specific Gd(III)-based MRI and RIT of $^{177}$Lu, $^{90}$Y, and $^{205/6}$Bi.

Example 6

Experimental Information

Instruments and Methods.

Analytical HPLC was performed on Agilent 1200 equipped with a dioarray detector ($\lambda$=254 and 280 nm), thermostat set at 35° C. and a Zorbax Eclipse XDB-C18 column (4.6×150 mm, 80 Å). The mobile phase of a binary gradient (0-100% B/40 min; solvent A=0.05 M AcOH/Et$_3$N, pH 6.0; solvent B=CH$_3$CN for method 1 or solvent A=0.05 M AcOH/Et$_3$N, pH 6.0; solvent B=CH$_3$OH for Method 2) at a flow rate of 1 mL/min was used. Semi-prep HPLC was performed on an Agilent 1200 equipped with a dioarray detector ($\lambda$=254 and 280 nm), thermostat set at 35° C., and a Zorbax Eclipse XDB-C18 column (9.4×250 mm, 80 Å). The mobile phase of a binary gradient (0-100% B/40 min; solvent A=0.05 M AcOH/Et$_3$N, pH 6.0; solvent B=CH$_3$CN for method 3 or 0-50% B/30 min, solvent A=H$_2$O, pH 6.0; solvent B=methanol for Method 4) at a flow rate of 3 mL/min was used. Size exclusion HPLC (SE-HPLC) chromatograms were obtained on a Lab Alliance isocratic system (Model: QGrad) with a Waters 717plus autosampler (Milford, Mass.), a Gilson 112 UV detector (Middleton, Wis.) and an in-line IN/US γ-Ram Model 2 radiodetector (Tampa, Fla.), fitted with a TSK G3000PW column (Tosoh Biosep, Montgomeryville, Pa.). Reagents.

All reagents were purchased from Aldrich and used as received unless otherwise noted. Phosphate buffered saline (PBS), 1×, pH 7.4 consisted of 0.08 M $Na_2HPO_4$, 0.02 M KH2PO4, 0.01 M KCl, and 0.14 M NaCl. $^{88}Y$ was obtained from Los Alamos National Laboratory and purified as previously reported in Hyun-soon Chong, Kayhan Garmestani, L. Henry Bryant Jr. Diane E. Milenic, Terrish Overstreet, Noah Birch, Thien Le, Erik D. Brady, Martin W. Brechbiel *J. Med. Chem.* 2006, 49, 2055-2062. $^{90}Y$ in the chloride form was purchased from Perkin Elmer Life Sciences (Shelton, Conn.). $^{177}Lu$ in the chloride form was obtained from NEN Perkin-Elmer. $^{86}Y$, $^{205,6}Bi$, and $^{203}Pb$ were produced using a CS30 cyclotron (PET Dept, Clinical Center, NIH) and purified as described in Hyun-soon Chong, Kayhan Garmestani, L. Henry Bryant Jr. Diane E. Milenic, Terrish Overstreet, Noah Birch, Thien Le, Erik D. Brady, Martin W. Brechbiel *J. Med. Chem.* 2006, 49, 2055-2062, and Chong, H. S.; Milenic, D. E.; Garmestani, K.; Brady, E. D.; Arora, H.; Pfiester, C.; Brechbiel, M. W. *Nucl. Med. Biol.* 2006, 33, 459-67. $^{64}Cu$ was obtained as an acid solution from Washington University Medical School.

Schemes 12 and 13

Tert-butyl{4-tert-Butoxycarbonylmethyl-7-[2-(tert-butoxycarbonylmethyl-amino)-3-(4-nitro-phenyl)-propyl]-[1,4,7]-triazonan-1-yl}-acetic acetate (2)

To a slurry of Compound 1, HCl (2.27 g, 5 mmol) in DMF (50 mL) at 0° C. was added diisopropylethyl amine (6.5 g, 50.25 mmol), KI (996 mg, 6 mmol). tert-butyl bromoacetate (3.22 g, 16.5 mmol) was added dropwise over 20 min. The resulting mixture was stirred for 2 hours at 0° C. and for 2 h at room temperature. The reaction mixture was heated to 50° C. and stirred for 19 h after which time the reaction mixture was cooled to room temperature and then to 0° C. 6 M HCl (3.5 mL) and heptane (30 mL) were sequentially added to the solution. The resulting solution was vigorously stirred for 5 min, and the heptane layer was separated. The aqueous layer was extracted with heptane (2×30 mL), and treated with 10% $Na_2CO_3$ (45 mL). Additional heptane was added into the aqueous solution, and the resulting mixture was stirred for 30 min, and the heptane layer was separated. The combined heptane layers were washed with water (10 mL), dried, filtered, and concentrated in vacuo. The residue was on silica gel (220-400 mesh) column eluted with 20%-30% $CH_3OH/CH_2Cl_2$ and 0.5 mL $Et_3N$ in 20%-30% $CH_3OH/CH_2Cl$ starting from $CH_2Cl_2$ to provide pure 2 (2.21 g, 68%): $^1H$ NMR ($CDCl_3$) δ 1.41 (s, 27H), 2.30-2.52 (m, 3H), 2.63-2.94 (m, 16H), 3.20-3.36 (m, 6H), 7.36 (d, J=8.01 Hz, 2H), 8.15 (d, J=8.01 Hz, 2H); $^{13}C$ NMR ($CDCl_3$) δ 28.98, 28.09, 39.32, 49.83, 55.84, 56.04, 56.92, 59.48, 62.62, 80.36, 80.76, 123.32, 130.11, 146.36, 147.47, 171.07, 171.40; HRMS (Positive ion FAB) Calcd for $C_{33}H_{56}N_5O_8$ $[M+H]^+$ m/z 650.4129. Found: $[M+H]^+$ m/z 650.4110. Analytical HPLC ($t_R$=24.78 min, method 1). Isolation of Compound 3 from the reaction mixture was dissolved in 1 mL of $CH_3OH$, and the fraction from 79-101 min (3 mL/min) was collected, evaporated, dissolved in $CH_2Cl_2$, and washed with $H_2O$. The organic layer was dried, filtered, evaporated, and concentrated in vacuo to afford the desired Compound 2.

{4-Carboxymethyl-7-[2-(carboxymethyl-amino)-3-(4-nitro-phenyl)-propyl]-[1,4,7]-triazonan-1-yl}-acetic acid (C-NE3TA)

Compound 2 (60 mg, 0.09 mmol) was treated with 4M HCl in 1,4-dioxane (5 mL) at 0° C. The resulting mixture was gradually warmed to room temperature and stirred for 18 h. Diethyl ether (100 mL) was added into the reaction mixture, and the resulting mixture was placed in the freezer for 2 hours. The precipitate was filtered, immediately dissolved in water (10 mL), and washed with diethyl ether (20 mL). The aqueous layer was lyophilized to provide pure C-NE3TA as a light brownish solid (54 mg, 95%): $^1H$ NMR ($D_2O$) δ 2.42-2.60 (m, 1H), 2.80-3.39 (m, 14H), 3.68-3.92 (m, 8H), 7.45 (d, J=7.9 Hz, 2H), 8.16 (d, J=7.9 Hz, 2H); $^{13}C$ NMR ($D_2O$) δ 36.6, 47.5, 51.4, 52.3, 54.3, 58.6, 61.1, 126.8, 132.9, 145.7, 149.6, 171.6, 174.0. HRMS (Positive ion FAB) Calcd for $C_{21}H_{32}N_5O_8$ $[M+H]^+$ m/z 482.2251. Found: $[M+H]^+$ m/z 482.2274. Analytical HPLC ($t_R$=9.96 min, method 2).

Tert-butyl {4-[3-(4-Amino-phenyl)-2-(tert-butoxycarbonylmethyl-amino)-propyl]-7-tert-butoxycarbonylmethyl-[1,4,7]triazonan-1-yl}-acetate (3)

To a solution of Compound 2 (180 mg, 0.28 mmol) in MeOH (20 mL) was added 10% Pd/C catalyst (36 mg). The resulting mixture was subjected to hydrogenolysis by agitation with excess H2 (g) at 20 psi in a Parr hydrogenartor apparatus at ambient temperature for 14 h. The reaction mixture was filtered through Celite, and the filtrate was concentrated in vacuo to provide pure Compound 3 (167 mg, 97%). $^1H$ NMR ($CDCl_3$) δ 1.37-1.50 (m, 36H), 2.24-2.49 (m, 5H), 2.61-2.94 (m, 12H), 3.28-3.47 (m, 8H), 6.60 (d, 2H), 6.92 (d, 2H) $^{13}C$ NMR ($CDCl_3$) 28.05, 28.15, 38.23, 49.53, 55.09, 55.41, 56.74, 59.11, 62.23, 80.60, 80.75, 115.19, 128.38, 129.91, 144.76, 171.16, 171.41; HRMS (Positive ion FAB) Calcd for $C_{33}H_{58}N_5O_6$ $[M+H]^+$ m/z 620.4387. Found: $[M+H]^+$ m/z 620.4385. Analytical HPLC ($t_R$=27.46 min, method 1).

{4-[3-(4-Amino-phenyl)-2-(carboxymethyl-amino)-propyl]-7-carboxymethyl-[1,4,7]triazonan-1-yl}-acetic acid (7)

Compound 5 (55 mg, 0.09 mmol) was treated with 4M HCl in 1,4-dioxane (5 mL) at 0° C. The resulting solution was lyophilized to provide pure Compound 5 as a yellow solid (48 mg, 97%). $^1H$ NMR ($D_2O$) δ 2.42-2.53 (m, 2H), 2.75-3.22 (m, 14H), 3.51 (s, 1H), 3.75-3.95 (m, 8H), 7.29 (dd, 4H); $^{13}C$ NMR ($D_2O$) δ 33.7, 44.9, 48.7, 49.5, 50.9, 51.6, 55.9, 56.3, 56.7, 58.7, 123.7, 129.1, 130.8, 136.4, 169.1, 171.1, 171.8; HRMS (Positive ion FAB) Calcd for $C_{21}H_{34}N_5O_6$ $[M+H]^+$ m/z 452.2509. Found: $[M+H]^+$ m/z {4-Carboxymethyl-7-[2-(carboxymethyl-amino)-3-(4-isothiocyanato-phenyl)-propyl]-[1,4,7]-triazonan-1-yl}-acetic acid (6)

To a solution of Compound 5 (20 mg, 0.031 mmol) in water (2 mL) was added a 1M solution of thiophosgene in $CHCl_3$ (0.39 mL). The resulting mixture was stirred for 2 h at room temperature. The aqueous layer was decanted, and $CHCl_3$ layer was separated and washed with water (2×1 mL). The combined aqueous layers were lyophilized to provide Compound 6 (19 mg, 88%). $^1$H NMR (D$_2$O) δ $^1$H NMR (D$_2$O) δ 2.52-2.60 (m, 2H), 2.85-3.32 (m, 15H), 3.74-3.88 (m, 8H), 7.21 (dd, 4H); HRMS (Positive ion FAB) Calcd for C$_{22}$H$_{32}$N$_5$O$_6$S [M+H]$^+$ m/z 494.2073. Found: [M+H]$^+$ m/z 494.2081. Analytical HPLC (t$_R$=16.0 min, method 1).

General Procedure for the Preparation of Gd(III) Complexes (C-DOTA, C-NETA, or C-NE3TA).

Ligand (2 mM, 1 mL) and GdCl$_3$ (2 mM, 0.9 mL) were mixed and heated at 90° C., while pH of the solution was constantly maintained at pH 7 by adding 1N NaOH. The heating was continued until no free Gd$^{3+}$ was detected using arsenazo III (AAIII) solution. The Gd complexes were prepared by reacting the aqueous solution of the appropriate ligand (2 mM, 1 mL, C-NETA, C-NE3TA, or C-DOTA) and GdCl$_3$ (2 mM, 0.9 mL) at a 1:0.9 mole ratio at 90° C. overnight, and the pH of the resulting solution was adjusted to ~7 using 1M NaOH. No unbound Gd(III) was detected in the solution as evidenced by AAIII assay and TLC analysis. The Gd complexes were purified using semi-HPLC (Method 4). Fractions at 20.4 min, 18.0 min, 14.5-15.1 min were collected to provided C-NETA, C-NE3TA, and C-DOTA, respectively.

Procedure for Detection of Free Gadolinium Using AAIII Assay.

AAIII assay was used for the determination of the free Gd(III) in the complex solution. A solution of AAIII (10 µM) was prepared in the acetate buffer (NH$_4$OAc, 0.15 M, pH 7). Droplets of AAIII (100 µL) were arranged in a 96 well plate, and a droplet of reaction mixture (100 µL) was added to AAIII solution in each well. The presence of free Gd$^{3+}$ was indicated by the immediate color change from pink to green.

ICP-MS.

To verify the concentration of gadolinum in the purified complexes, ICP-MS was performed using a computer-controlled Thermo Elemental (Now Thermo Fisher) PQ ExCell Inductively Coupled Plasma Mass Spectrometer. Samples were prepared by nitric acid digestion (9:1 nitric acid:sample) in a 65° C. water bath. The digested samples were diluted into 15 mL conical vials with a final concentration of 3% (v/v) nitric acid. Gd standards were prepared in 3% (v/v) nitric acid with values 0.1, 0.25, 0.5, 1, 5, 10, 25, and 50 ng/mL Gd. Indium was spiked into every sample (including standards) for a final indium concentration of 5 ng/mL. Isotopes $^{157}$Gd and $^{115}$In were used for determination.

Relaxivity Measurements.

Relaxivity measurements were acquired by taking the slope of a plot of 1/T1 (s$^{-1}$) versus concentration (mM). The longitudinal water proton relaxation times (T1) were determined using a Bruker mq60 NMR (Bruker Canada, Milton, ON, Canada) analyzer operating at 59.97 MHz and 37° C. The agent was added to Millipore water and serially diluted by 0.5 to give a series of 5 concentrations (500 µL total volume) for each relaxivity trial. The T$_1$ relaxivity was determined using an inversion recovery pulse sequence with 10 different pulse separations per sample, 4 repetitions per echo time, phase cycling, and a recycle delay that is ≥5 times the T$_1$ of each given sample. All curves were fit using a monoexponential curve fitting formula.

Radiolabeling of Ligands.

Each of the radioisotopes (1-3 mCi in 10-20 µl of 0.1 M HCl solution) was added to 100 µL of 0.15 M NH$_4$OAc buffer solution (pH 4.5). 5M NH$_4$OAc was added as needed to adjust pH to 4.5; solution volumes were brought up to 200 µL. Separate tubes containing 7 µmol of each of the ligands were prepared and the solids were dissolved in 200 µL of NH$_4$OAc, pH 4.5. The ligand solution was added to the radionuclide solution and the resulting tube was capped. The reactions were heated at 80° C. for 12 hours, after which they were loaded onto a column of Chelex-100 resin (100-200 mesh, Na$^+$ form, Biorad, Richmond, Calif.; 1 mL volume bed, equilibrated with PBS, pH 7.4). The complexes were eluted from the resin with PBS, pH 7.4 while the resin retained the free metals.

In Vitro Stability of the Radiolabeled Metal Complexes.

The stability of the purified radiolabeled complexes was evaluated in human serum (Gemini Bioproducts, Woodland, Calif.) for up to 11 days. The serum stability of the radiolabeled complexes was assessed by measuring the transfer of the radionuclide from each complex to serum proteins using SE-HPLC methods. Radiolabeled complexes were diluted to an appropriate volume that allowed for preparation of multiple samples containing 5-10 µCi and were filter-sterilized using a Millex-GV 0.22 µm filter. This stock solution was then mixed with 1400 µL of sterile normal human serum. Aliquots (200 µL) were drawn and separated into individual tubes for subsequent analysis using aseptic technique. The samples were incubated at 37° C., and at designated intervals, subjected to analysis by SE-HPLC. Samples were loaded onto the HPLC and eluted with PBS, pH 7.4 isocratically at 1 mL/min. Radioactivity still associated with the chelate typically displayed a retention time of ~8.5 min at this flow rate. Radioactivity associated with a transfer to serum proteins generally appeared at ~6 min.

In Vivo Biodistribution Studies Oh the Radiolabeled Metal Complexes.

Female athymic mice were obtained from Charles River Laboratories (Wilmington, Mass.) at 4-6 weeks of age. The pH of the radiolabeled ligands was adjusted to pH ~7.0 with 0.5 M sodium bicarbonate (pH 10.5) and diluted in phosphate-buffered saline. The radiolabeled ligands (5-10 µCi for $^{86}$Y, $^{205/6}$Bi, $^{177}$Lu, and $^{203}$Pb) were administered to the mice in 200 µL of solution via tail vein injection. The mice (5 per data point) were sacrificed by exsanguination at 0.5, 1, 4, 8, and 24 h. Blood and the major organs were harvested, wet-weighed and the radioactivity measured in a γ-scintillation counter (1480 Wizard, Perkin Elmer). The percent injected dose per gram (% ID/g) was determined for each tissue. The values presented are the mean and standard deviation for each tissue.

General Procedure for Spectroscopic Determination of Ligand to Protein Ratio.

A stock solution of the copper arsenazo III reagent was prepared in 0.15 M NH$_4$OAc, pH 7.0 by adding an aliquot of a 5.00×10$^{-4}$ M copper atomic absorption solution (to afford a 5 µM solution of copper) to a 10 µM solution of arsenazo III. This solution was stored in the dark to avoid degradation over time. A UV/Vis spectrometer was zeroed against a cuvette filled with 1.000 mL of a 0.15 M NH$_4$OAc solution at pH 7.0 with a window open from 250 nm to 700 nm. The acetate solution was removed and replaced with 1.000 mL of the copper arsenazo III reagent, a spectrum was collected and the absorbance values at 280 and 652 nm noted. 50 µL of the copper arsenazo reagent were removed and discarded. The ligand-antibody conjugate of interest was added (50 µL) and the spectrum was immediately collected. Spectra were then collected periodically until no further change was noted for the peaks at 280 and 652 nm (less than 30 min for the copper arsenazo III reagent with the ligands detailed in this paper). A series of calculations detailed in the discussion allow for the determination of the concentration of ligand in the sample.

Spectroscopic Determination of Ligand to Protein Ratio.

All absorbance measurements were obtained on an Agilent 8453 diode array spectrophotometer equipped with a 8-cell transport system (designed for 1-cm cells). Metal-free stock solutions of all buffers were prepared using Chelex-100 resin (100-200 mesh, Bio-Rad Lab, Hercules, Calif.). Chelex resin (5 g) was added into the buffer solution (500 mL) and the mixture was shaken for 1 h in a shaker, stored in the refrigerator overnight, and filtered through a Corning filter system (#430513, pore size 0.2 µM). Disposable PD-10 Sephadex™ G-25M columns (GE Healthcare, Piscataway, N.J.) were rinsed with 25 mL of the appropriate buffer prior to addition of antibody or its ligand conjugates. Centricon C-50 (50,000 MWCO) Centrifugal Filter Devices were purchased from Amicon Bioseparations (Millipore, Bedford, Mass.) and were rinsed several times with DI $H_2O$ prior to use. Herceptin was purchased from Genentech Inc. (South San Francisco, Calif.). The initial concentration of Herceptin was determined by the Lowry method. Phosphate buffered saline (PBS) was purchased from Gibco as a 1× solution at pH 7.4 and was used as received. Ammonium acetate (0.15 M, pH 7.0 and 0.15 M, pH 4.5), conjugation buffer (50 mM HEPES, 150 mM NaCl, pH 8.6) were prepared as 10× solutions, chelexed and then diluted to 1× solutions for use as needed with DI $H_2O$. Phosphate buffered saline (PBS), 1×, pH 7.4 consisted of 0.08 M $Na_2HPO_4$, 0.02 M $KH_2PO_4$, 0.01 M KCl, and 0.14 M NaCl.

Conjugation of C-NE3TA-NCS to Herceptin.

Herceptin (6.0 mg, 2.5 mL) was added to a PD-10 column previously charged with conjugation buffer. Additional conjugation buffer (3.5 mL) was added to PD-10 column to exchange the buffer solution of the antibody. The collected antibody solution (5.9 mg, 98.0%) was then added a 10-fold excess of C-NE3TA-NCS. The solution was gently agitated for 24 h at room temperature. The reaction solution was then placed on a centricon C-50 membrane and spun down to reduce volume. PBS (3×2 mL) was added to the remaining solution of the C-NE3TA-Herceptin conjugate, followed by centrifugation to remove unreacted ligand. The volume of purified conjugate antibody was brought to 1 mL with PBS. The analysis of the absorbance of the solution at 280 nm indicated that 5.71 mg ($38.8 \times 10^{-5}$ M, 96.8%) of the Herceptin remained after the processing.

A stock solution of the Cu AAIII reagent was prepared in 0.15 M $NH_4OAc$, pH 7.0 by adding an aliquot of a 5 µM Cu(II) atomic absorption solution to a 10 µM solution of AAIII. This solution was stored in the dark to avoid degradation over time. A UV/Vis spectrometer was zeroed against a cuvette filled with 2.000 mL of a 5 µM AIII solution at pH 4.5 with a window open from 200 nm to 1100 nm. The AAIII solution was removed and replaced with 2.000 mL of the CuAAIII reagent, a spectrum was collected and the absorbance values at 610 nm noted. Solutions of $C-NE3TA-NO_2$ were then used for generating the calibration graph. Various concentration of $C-NE3TA-NO_2$ solution (50 µL) was reacted with 1950 µL of CuAAIII reagent at room temperature. Absorbance measurements at 610 nm were taken after 5 min. An aliquot of the C-NE3TA-Herceptin conjugate (50 µL) was added to a cuvette containing the CuAAIII reagent (1950 µL) and the absorbance at 610 nm was monitored over time. Spectra were then collected periodically until no further change was noted for the peaks at 280 and 610 nm. The reaction was complete after 30 min, and the concentration of C-NE3TA was calculated ($9.7 \times 10^{-5}$ M). The L/P for the C-NE3TA-Herceptin conjugate was found to be 2.5 to 1.

Example 7

Bile Acid-Based Polyaminocarboxylate Conjugates as Targeted Antitumor Agents

This example presents the novel bile acid-polyaminocarboxylate conjugates (CDCA-NE3TA, CA-NE3TA, DCA-NE3TA, and NBD-CA-NE3TA) that were prepared by conjugation of NE3TA, a potential iron depleting cytotoxic chelator to bile acid, and the conjugates were found to self assemble forming nano-sized micells and display significantly enhanced cytotoxicities in both Hela and HT29 colon cancer cells as compared to the clinically explored iron depletion agents DFO and DTPA, and CA-NE3TA attached to an organic fluorophore NBD was shown to enter the colon cancer cells as evidenced by fluorescence-microscopic examinations. Many reports suggest that high level of iron accumulated in animals and humans is associated with both the initiation and progression of cancers. Although there are iron chelators being evaluated in clinical and preclinical settings, including Triapine (3-aminopyridine-2-carboxaldehyde thiosemicarbazone), DFO (desferoxamine), and DTPA (diethylenepentaacetic acid), no iron chelators that can target to the specific cancer cells (N. Birch, X. Wang, X, and H-. S. Chong, *Expert Opinion.* 2006, 16, 1533).

As an ongoing effort to develop targeted iron depleting antitumor agents, bile acid-based NE3TA conjugates were designed. Amphiphilic bile acid including cholic acid (CA), deoxycholic acid (DCA), and chenodeoxycholic acid (CDCA) is known to form helical globular aggregates with a favorable pharmacokinetic profile and proven to be a useful shuttle system for selective delivery of various drugs. The experimental studies demonstrate that highly hydrophobic bile acid such as deoxycholic acid and chenodeoxycholic acid enter colon cancer cells which over-produce bile acid transporter and carriers, receptor proteins, or nuclear receptors for bile acids. Although a number of iron chelators have been prepared and evaluated as antitumor agents, their use in targeted iron depletion anticancer therapy has been little explored. The bile acid-NE3TA conjugates reported herein are the first examples of targeted iron depleting antitumor agents evaluated on tumor cells. The synthesis of the novel bile acid-based chelators CA-NE3TA, DCA-NE3TA, and CDCA-NE3TA is shown in Scheme 14. CA-NE3TA was prepared by a known procedure as reported previously. Bile acids (CA, DCA, and CDCA) were preactivated with 2-mercaptothiazoline to provide bile acid analogues 1-3, respectively. The desired bile acid-NE3TA conjugates 7-9 were prepared by the reaction of the activated bile acid analogues 1, 2, or 3 with the bifunctional ligand NE3TA (4) containing the amino group. t-butyl groups in conjugates 6-9 were removed by 4MHCl in 1,4-dioxane to provide bile acid conjugated chelators CA-NE3TA, CDCA-NE3TA, and DCA-NE3TA, respectively. The cytotoxicity of the bile-acid based NE3TA conjugates CA-NE3TA, CDCA-NE3TA, and DCA-NE3TA using MTS assay was evaluated using the HeLa and HT29 cell line. Inspection of the cytotoxicity data indicates that all bile acid-NE3TA conjugates possess higher inhibitory activity against the HaLa and HT29 cancer cells compared to the clinically available chelators DFO and DTPA over the entire concentration range evaluated. This result is significant as there are reports that structural modification to a chelator for introduction of a functional unit could significantly affect it's complexation with metal. $IC_{50}$ values of bile acid-chelator conjugate are shown in Table 10. Among all the compounds evaluated, DCA-NE3TA is the most potent inhibitor against both HeLa and HT29 cells. The respective $IC_{50}$ values of 6.3±0.1 µM and 7.5±0.3 µM in HeLa and HT29 cancer cells were observed with DCA-NE3TA. It should be noted that conjugation of NE3TA to DCA is well tolerated and has little impact on cytotoxicity of the parent chelator NE3TA. The HeLa cells were approximately 40-fold more sensitive to DCA-NE3TA than DTPA. CA-NE3TA and CDCA-NE3TA possess similar cytotoxicity in HeLa cell (24.0±2.7 µM vs 24.6±1.0 μM), while CA-NE3TA (8.3±2.4 μM) possesses a two-fold increased cytotoxicity in HT29 cancer cells compared to CDCA-NE3TA (15.5±3.2 μM).

TABLE 10

| Ligand | IC$_{50}$ (μM) | |
|---|---|---|
| | Hela | HT29 |
| NE3TA* | 5.7 ± 0.3 | 4.7 ± 0.3 |
| CA-NE3TA | 24.0 ± 2.7 | 8.3 ± 2.4 |
| DCA-NE3TA | 6.3 ± 0.1 | 7.5 ± 0.3 |
| CDCA-NE3TA | 24.6 ± 1.0 | 15.5 ± 3.2 |
| DFO* | >50 | 36.1 ± 1.4 |
| DTPA* | 264.5 ± 36.2 | 39.1 ± 4.0 |

Figure 13:
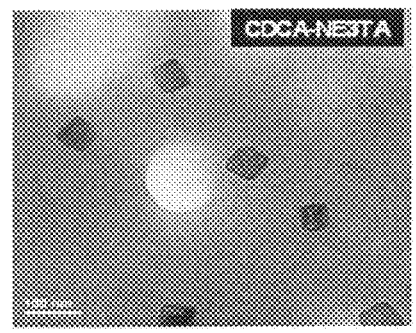
FIG. 13 is a TEM image of CDCA-NE3TA.

TEM images of CDCA-NE3TA indicate that the hydrophobic bile acid conjugated to NE3TA forms discrete semi-square micelles in nanometer size (~15-60 nm, FIG. 13). Self-assembly of the conjugate results from the presence of hydrophobic cholic acid moiety surrounded by hydrophilic NE3TA ligand. NE3TA was successfully conjugated to an organic fluorescent moiety NBD (4-nitrobenzo-2-oxa-1,3-diazole) to produce NBD-CA-NE3TA (Scheme 15). The key step of the synthesis of NBD-CA-NE3TA is the reaction of bifunctional analogue 4 with cholic acid analogue containing amino group 11. Aza cholic acid 10 was prepared starting from the readily available cholic acid according to the literature. Compound 10 was preactivated with 2-mercaptothiazoline to produce Compound 11. Coupling reaction of Compound 11 with Compound 4 provided compound 12 in 53% yield. tert-Butyl groups in 12 were removed by treating 4M HCl in 1,4-dioxane to provide Compound 13 in 95% yield. The azide group in Compound 13 was reduced to the amino group using hydrogenation to provide Compound 14 which was further reacted with NBD-Cl to provide the fluorescent bile acid-based NE3TA conjugate NBD-CA-NE3TA (FIG. 14).

Example 7

Experimental Information

Schemes 14-15

4-(3,12-Dihydroxy-10,13-dimethyl-hexadecahydro-cyclopenta[a]phenanthren-17-yl)-1-(2-thioxo-thiazo-lidin-3-yl)-pentan-1-one (2)

To a vigorously stirred solution of cholic acid (1 g, 2.6 mmol) in CH$_2$Cl$_2$ (60 mL) was added DCC (684 mg, 3.6 mmol), 2-mercaptothiazoline (354 mg, 3 mmol), and catalytic amount (40 mg) of N,N-dimethyl amino pyridine (DMAP). The reaction mixture was stirred for 24 h at room temperature at which time the reaction mixture was transferred to a separate-funnel and sequentially washed with 0.5N NaOH solution (100 mL×2), and 0.1N HCl (100 mL×2). The organic layer was dried over MgSO$_4$, filtered, and concentrated in vacuo to provide pure yellow solid 2 (1.07 g, 82%). $^1$H NMR (CDCl$_3$) δ 0.68 (s, 3H), 0.90 (s, 3H), 0.98 (d, 3H), 1.10-1.95 (m, 23H), 3.25-3.35 (m, 4H), 3.53-3.67 (m, 1H), 3.98 (s, 1H), 4.57 (t, 2H); $^{13}$C NMR (CDCl$_3$) δ12.73, 17.49, 23.16, 23.76, 26.17, 27.21, 27.63, 28.33, 28.60, 30.40, 30.74, 33.52, 34.11, 35.32, 35.48, 35.87, 36.00, 36.40, 42.08, 46.52, 47.44, 48.09, 53.59, 56.16, 71.53, 72.99, 175.35, 201.52. HRMS (Positive ion FAB) Calcd for C$_{27}$H$_{44}$N$_3$O$_2$ [M+H]$^+$ m/z 494.2763. Found: [M+H]$^+$ m/z 494.2744.

4-(3,7-Dihydroxy-10,13-dimethyl-hexadecahydro-cyclopenta[a]phenanthren-17-yl)-1-(2-thioxo-thiazo-lidin-3-yl)-pentan-1-one (3)

To a vigorously stirred solution of chenodeoxycholic acid (2 g, 5.1 mmol) in CH$_2$Cl$_2$ (30 mL) was added DCC (1.26 g, 6.1 mmol), followed by the addition of 2-mercaptothiazoline (730 mg, 6.1 mmol) and catalytic amount (50 mg) of N,N-dimethyl amino pyridine (DMAP). The reaction mixture was stirred for 24 h, the white precipitate of dicyclohexyl urea was filtered off and the filtrate volume was adjusted to 100 mL with DCM. The DCM layer was washed with 0.1N NaOH solution (3×50 mL) and water (50 mL), dried over anhydrous magnesium sulfate, filtered and concentrated in vacuo to yield the crude product. Purification by column chromatography on silica gel using ethyl acetate and hexane (1:3) afforded activated cholic acid derivative 3 (2.24 g, 89%) as a yellow crystalline solid. $^1$H NMR (300 MHz, CDCl$_3$) δ 0.65 (s, 3H), 0.90 (s, 3H), 0.95 (d, 3H), 1.10-2.30 (m, 28H), 3.15-3.35 (m, 2H), 3.26 (t, 2H), 3.35-3.60 (m, 1H), 3.85 (s, 1H), 4.56 (t, 2H).; $^{13}$C NMR (300 MHz, CDCl$_3$) δ11.81, 18.55, 20.60, 22.82, 23.71, 28.22, 28.28, 30.65, 30.78, 32.82, 34.61, 35.05, 35.35, 35.43, 35.62, 39.41, 39.63, 39.80, 41.50, 42.71, 50.42, 55.94, 56.11, 68.49, 71.96, 175.46, 201.52. HRMS (Positive ion FAB) Calcd for C$_{27}$H$_{42}$NO$_2$S$_2$ [M+H]$^+$ m/z 476.2657. Found: [M+H]$^+$ m/z 476.2656.

[4-tert-butoxycarbonylmethyl-7-(2-(tert-butoxycar-bonylmethyl-amino)-3-{4-[4-(3,12-dihydroxy-10,13-dimethyl-hexadecahydro-cyclopenta[a]phenanthren-17-yl)-pentanoylamino]-phenyl}-propyl)-[1,4,7] triazonan-1-yl]-acetic acid tert-butyl ester (8)

To a solution of Compound 4 (270 mg, 0.44 mmol) in CH$_2$Cl$_2$ (6 mL) was added Et$_3$N (44 mg, 0.44 mmol) and Compound 2 (191 mg, 0.44 mmol). The reaction mixture was refluxed for 2 days. The resulting solution was evaporated, and the residue was purified via column chromatography with neutral alumina eluting with 1.5% CH$_3$OH starting from CH$_2$Cl$_2$ to afford pure Compound 8 as a creamy solid (223 mg, 54%). $^1$H NMR (300 MHz, CDCl$_3$) δ 0.68 (s, 3H), 0.91 (s, 3H), 0.93-1.93 (m, 54H), 2.20-2.93 (m, 20H), 3.20-3.45 (m, 6H), 3.52-3.68 (m, 1H), 3.98 (s, 1H), 7.10 (d, 2H), 7.43 (d, 2H). $^{13}$C NMR (300 MHz, CDCl$_3$) δ 12.67, 17.49, 23.16, 23.79, 26.22, 27.29, 27.61, 28.10, 28.21, 28.46, 33.56, 33.76, 34.20, 35.20, 35.38, 36.05, 36.39, 38.88, 42.15, 46.52, 47.90, 49.89, 53.43, 55.58, 55.90, 59.40, 71.63, 73.11 80.63, 80.86, 119.81, 129.56, 129.97, 136.78, 171.26, 171.64, 172.48. FIRMS (Positive ion FAB) Calcd for C$_{57}$H$_{96}$N$_5$O$_9$ [M+H]$^+$ m/z 994.7208. Found: [M+H]$^+$ m/z 994.7182. Analytical HPLC (t$_R$=11 min, method 1).

[4-tert-Butoxycarbonylmethyl-7-(2-(tert-butoxycar-bonyl methyl-amino)-3-{4-[4-(3,7-dihydroxy-10,13-dimethyl-hexadecahydro-cyclopenta[a]phenanthren-17-yl)-pentanoylamino]-phenyl}-propyl)-[1,4,7] triazonan-1-yl]-acetic acid tert-butyl ester (9)

To a solution of Compound 4 (92 mg, 0.15 mmol) in CH$_2$Cl$_2$ (5 mL) was added Et$_3$N (15 mg, 0.15 mmol) and Compound 3 (73 mg, 0.15 mmol). The reaction mixture was refluxed for 2 days. The resulting solution was evaporated, and the residue was purified via column chromatography with neutral alumina eluting with 2.5% methanol starting from CH$_2$Cl$_2$ to afford pure Compound 9 as a creamy solid (36 mg, 24%). $^1$H NMR (300 MHz, CDCl$_3$) δ 0.70 (s, 3H), 0.93-3.50 (m, 82H) 3.80 (s, 1H), 3.80 (s, 1H), 7.16 (d, 2H), 7.50 (d, 2H).

¹³C NMR (300 MHz, CDCl₃) δ 10.81, 17.59, 20.39, 22.00, 23.25, 27.08, 27.91, 29.36, 29.96, 31.82, 32.66, 33.58, 34.52, 34.82, 35.16, 35.58, 39.07, 39.36, 39.67, 41.76, 42.30, 50.16, 55.95, 67.63, 71.44, 81.01, 120.10, 129.19, 129.20, 136.80, 171.01, 173.71. HRMS (Positive ion FAB) Calcd for $C_{57}H_{96}N_5O_9$ [M+H]⁺ m/z 994.7208. Found: [M+H]⁺ m/z 994.7234. Analytical HPLC ($t_R$=26 min, Method 1).

[4-Carboxymethyl-7-(2-(carboxymethyl-amino)-3-{4-[4-(3,12-dihydroxy-10,13-dimethylhexadecahydro-cyclopenta[a]phenanthren-17-yl)-pentanoylamino]-phenyl}-propyl)-[1,4,7]triazonan-1-yl]-acetic acid (DCA-NE3TA)

To a solution of Compound 8 (20 mg, 0.02 mmol) in 1,4-dioxane (1 mL) was dropwise added 4M HCl in 1,4-dioxane (1 mL) at 0-5° C. After the addition, the reaction mixture was gradually increased to room temperature and stirred for 1.8 h. To this solution, ether (30 mL) was added and continuously stirred for 30 min. The resulting mixture was placed in the freezer for 2 h. Solid residue was quickly filtered, washed with ethyl ether (5 mL), and immediately dissolved in DI H₂O and lyophilized to provide pure DCA-NE3TA as a light brownish solid (19 mg, 98%). ¹H NMR (CD₃OD) 0.71 (s, 3H), 0.92-3.90 (m, 55H), 3.97 (s, 1H), 4.09 (s, 1H), 7.28 (d, 2H), 7.57 (d, 2H); ¹³C NMR (CD₃OD) 11.86, 16.39, 22.35, 23.50, 26.09, 27.02, 27.33, 28.53, 29.68, 31.79, 33.43, 33.63, 33.73, 33.91, 35.04, 35.55, 35.79, 36.05, 42.21, 44.44, 46.17, 71.16, 72.65, 120.41, 129.55, 130.54, 167.99, 173.96 HRMS (Positive ion FAB) Calcd for $C_{45}H_{72}N_5O_9$ [M+H]⁺ m/z 826.5330. Found: [M+H]⁺ m/z 826.5355.

[4-Carboxymethyl-7-(2-(carboxymethyl-amino)-3-{4-[4-(3,7-dihydroxy-10,13-dimethylhexadecahydro-cyclopenta[a]phenanthren-17-yl)-pentanoylamino]phenyl}-propyl)-[1,4,7]triazonan-1-yl]-acetic acid (CDCA-NE3TA)

To a solution of Compound 3 (16 mg, 0.016 mmol) in 1,4-dioxane (1 mL) was dropwise added 4M HCl in 1,4-dioxane (1 mL) at 0-5° C. After the addition, the reaction mixture was gradually increased to room temperature and stirred for 18 h. To this solution, ether (30 mL) was added and continuously stirred for 30 min. The resulting mixture was placed in the freezer for 2 h. Solid residue was quickly filtered, washed with ethyl ether (5 mL), and immediately dissolved in DI H₂O and lyophilized to provide pure CDCA-NE3TA as a light brownish solid (15 mg, 97%). ¹H NMR (CD₃OD) δ 0.69 (s, 3H), 0.93 (s, 3H), 0.80-3.40 (m, 55H), 3.79 (s, 1H), 4.08 (s, 1H), 7.28 (d, 2H), 7.57 (d, 2H); ¹³C NMR (CD₃OD) δ 10.76, 17.56, 20.38, 21.97, 23.23, 27.90, 29.94, 31.75, 32.66, 33.54, 34.50, 34.81, 35.13, 35.59, 39.06, 39.34, 39.66, 41.75, 42.29, 50.16, 55.92, 67.64, 71.44, 120.40, 129.28, 130.67, 138.07, 168.05, 173.87. HRMS (Positive ion FAB) Calcd for $C_{45}H_{72}N_5O_9$ [M+H]⁺ m/z 826.5330. Found: [M+H]⁺ m/z 826.5349.

1-[(2S,5S,9R,15R,16S)-9,16-dihydroxy-2,15-dimethyl-14-[5-oxo-5-(3-sulfanylidene-1,2-thiazolidin-2-yl)pentan-2-yl]tetracyclo[8.7.0.0²,⁷.0¹¹,¹⁵]heptadecan-5-yl]triaz-2-yn-2-ium-1-ide (11)

To a vigorously stirred solution of azacholic acid 10 (50 mg, 0.12 mmol) in CH₂Cl₂ (5 mL) was added EDC (33 mg, 0.17 mmol) followed by the addition of 2-mercaptothiazoline (17 mg, 0.14 mmol) and catalytic amount (2 mg) of N,N-dimethyl amino pyridine (DMAP). The reaction mixture was stirred for 24 h and diluted with CH₂Cl₂ (20 mL). The organic layer was washed with water (10 mL), 0.1N aq. NaOH solution (3×10 mL), 2M HCl (5 mL), water (5 mL) and brine (5 mL). The organic layer was dried over anhydrous magnesium sulfate, filtered and concentrated in vacuo to yield the crude product 11 (50 mg, 82%) as yellow oil. ¹H NMR (300 MHz, CDCl₃) δ 0.7 (s, 3H), 0.9 (s, 3H), 1.0 (d, 3H), 1.1-2.45 (m, 24H), 3.1-3.4 (m, 1H), 3.3 (t, 2H), 3.85 (s, 1H), 4.0 (s, 1H), 4.56 (t, 2H). ¹³C NMR (300 MHz, CDCl₃) δ12.53, 17.57, 22.61, 23.23, 26.62, 26.81, 27.58, 28.28, 30.74, 34.50, 34.77, 35.40, 35.47, 35.83, 39.46, 41.83, 41.94, 46.62, 47.62, 56.14, 61.35, 68.26, 72.98, 175.39, 201.58. HRMS (Positive ion FAB) Calcd for $C_{27}H_{43}N_4O_3S_2$ [M+H]⁺ m/z 535.2777. Found: [M+H]⁺ m/z 535.2764.

1-[(2S,5S,9R,15R,16S)-14-(4-{[4-(3-{4,7-bis[2-(tert-butoxy)-2-oxoethyl]-1,4,7-triazo-nan-1-yl]-2-{bis[2-(tert-butoxy)-2-oxoethyl]amino}propyl)phenyl]carbamoyl}-butan-2-yl)-9,16-dihydroxy-2,15-dimethyltetracyclo[8.7.0.0.0]heptadecan-5-yl]triaz-2-yn-2-ium-1-ide (12)

To a solution of Compound 4 (245 mg, 0.40 mmol) in CH₂Cl₂ (5 mL) was added Et₃N (40 mg, 0.440 mmol) and Compound 11 (211 mg, 0.40 mmol). The reaction mixture was refluxed for 2 days. The resulting solution was evaporated, and the residue was purified via column chromatography (SiO₂, 220-400 mesh) eluting with 1%-20% CH₃OH/CH₂Cl₂ and 1-2 mL Et₃N in 20% CH₃OH/CH₂Cl₂ to afford pure Compound 12 as a creamy solid (220 mg, 53%). ¹H NMR (CDCl₃) δ 0.65 (s, 3H), 0.87 (s, 3H), 0.92-1.15 (m, 3H), 1.20-2.05 (m, 20H), 2.15-2.90 (m, 10H), 3.10-3.56 (m, 5H), 3.85 (s, 1H), 3.96 (s, 1H), 7.02 (d, 2H), 7.53 (d, 2H); ¹³C NMR (CDCl₃) δ 11.3, 12.4, 17.5, 22.4, 23.5, 26.4, 27.0, 28.1, 29.7, 31.2, 33.0, 34.8, 35.6, 38.7, 39.1, 42.0, 45.9, 46.2, 46.5, 49.8, 52.3, 55.2, 55.8, 59.2, 61.4, 63.2, 68.1, 73.2, 80.71 (2C), 80.9, 120.15, 129.42, 135.2, 139.13, 171.25, 171.57, 173.33. (Et₃N peak present). FIRMS (Positive ion FAB) Calcd for $C_{57}H_{95}N_8O_9$ [M+H]⁺ m/z 1035.7222. Found: [M+]⁺ m/z 1035.7218.

1-[(2S,5R,9R,15R,16S)-14-{4-[(4-{3-[4,7-bis(carboxymethyl)-1,4,7-triazonan-1-yl]-2-[bis(carboxymethyl)amino]propyl}phenyl)carbamoyl]butan-2-yl}-9,16-dihydroxy-2,15-dimethyltetracyclo[8.7.0.0.0]heptadecan-5-yl]triaz-2-yn-2-ium-1-ide (13)

To a solution of Compound 12 (20 mg, 0.019 mol) in 1,4-dioxane (2 mL) was dropwise added 4M HCl in 1,4-dioxane (1 mL) at 0-5° C. After the addition, the reaction mixture was gradually warmed to room temperature and stirred for 24 h. To the resulting mixture was added ether (30 mL), and the resulting mixture was continuously stirred for 30 min. The resulting mixture was placed in the freezer for 2 h. Solid residue was quickly filtered, immediately dissolved in MeOH, lyophilized to provide 13 as a white solid (16 mg, 95%). ¹H NMR (CD₃OD) δ 0.72 (s, 3H), 0.93 (s, 3H), 1.06-1.08 (m, 3H), 1.28-2.10 (m, 24H), 2.20-2.48 (m, 4H), 2.85-3.62 (m, 23H), 3.80-4.13 (m, 7H), 7.23 (d, 2H), 7.62 (d, 2H). HRMS (Positive ion FAB) Calcd for $C_{45}H_{71}N_8O_9$ [M+H]⁺ m/z 867.5344. Found: [M+H]⁺ m/z 867.5364.

2-{[1-(4-{4-[(2S,5R,9R,15R,16S)-5-amino-9,16-dihydroxy-2,15-dimethyltetracyclo-[8.7.0.0.0]heptadecan-14-yl]pentanamido}phenyl)-3-[4,7-bis(carboxymethyl)-1,4,7-triazonan-1-yl]propan-2-yl](carboxymethyl)amino}acetic acid (14)

To a solution of Compound 13 (20 mg, 0.023 mmol) in MeOH (10 mL) in a reaction bottle for hydrogenation was added dry 10% Pd/C (10 mg). The reaction mixture was subject to hydrogenation for 14 h in a Parr hydrogenator and filtered via celite bed and washed thoroughly with EtOH and $H_2O$. The filtrate was concentrated in vacuo to provide Compound 14 as a white waxy solid (22 mg, 96%). $^1H$ NMR ($CD_3OD$) δ 0.73 (s, 3H), 0.96 (s, 3H), 1.06-3.80 (m, 61H), 3.82 (s, 1H), 4.01 (s, 1H), 7.23 (d, 2H), 7.62 (d, 2H). FIRMS (Positive ion FAB) Calcd for $C_{45}H_{73}N_6O_9$.5HCl $[M+H]^+$ m/z 10214273. Found: $[M+H]^+$ m/z 1021.4321.

NBD-CA-NE3TA.

To a solution of Compound 14 (43 mg, 0.051 mmol) in MeOH (3 mL) in an ice-bath was added 7-chloro-4-nitrobenzo-2-oxa-1,3-diazole (NBD-Cl, 16 mg, 0.08 mmol). The resulting mixture was stirred for 1 day, and $Et_3N$ (11 μL, 0.08 mmol) was added to the reaction mixture which was further stirred for 1 day. The reaction mixture was concentrated in vacuo. Pure NBD-CA-NE3TA (19 mg, 38%) was isolated using prep-TLC eluted with $CH_3CN$: $H_2O$ (30:8). $^1H$ NMR ($CD_3OD$) 0.65 (s, 3H), 0.82-3.80 (m, 63H), 3.90 (s, 1H), 6.68 (d, 1H), 7.12 (d, 2H), 7.47 (d, 2H), 8.52 (d, 1H). HRMS (Positive ion FAB) Calcd for $C_{51}H_{73}N_9O_{12}$ ($NH_3)_3$ $[M+H]^+$ m/z 1054.6175. Found: $[M+H]^+$ m/z 1054.6177. Analytical HPLC ($t_R$=1.5 min, Method 2)

Cell Culture.

Human cervix HeLa cell line was obtained from ATCC (Rockville, Md.) and cultured in minimum essential medium (MEM) with L-glutamine (2 mM), Earle's BSS and sodium bicarbonate (1.5 g/L), supplemented with 10% fetal bovine serum (FBS), non-essential amino acids (0.1 mM), sodium pyruvate (1 mM) and antibiotic/antimycotic solution in a humidified atmosphere with 5% $CO_2$ at 37° C. Human colon cancer cell line HT29 was maintained in a humidified atmosphere with 5% $CO_2$ at 37° C. in RPMI-1640 medium, containing 10% FBS with L-glutamine and antibiotic/antimycotic.

Antiproliferative Activity.

Cells were seeded onto 96-well plate at density of 2,000 cells for Hela cells or 5,000 cells for HT29 cells per well in 0.1 mL complete medium and allowed to attach for 24 h. Varying concentrations of the test compounds in the final volume of 0.1 mL complete medium were then added in at least five series dilutions and incubated for 72 h. To measure cell proliferation, the Cell Titer 96 aqueous nonreactive cell proliferation assay (Promega Life Sciences, Madison, Wis.) was used according to the manufacturer's instructions. Briefly, MTS (2 mg/mL) and PMS (0.92 mg/ml) were mixed in a ratio of 20:1. An aliquot (20 μL) of the MTS/PMS mixture was added into each well, and the plate was incubated for 3 h at 37° C. Optical absorbance at 490 nm was then recorded with an enzyme-linked immunosorbent assay (ELISA) microtiter plate reader (Biotek). Each experiment was done at least in triplicate. Antiproliferative activity of the test compounds was expressed as the fraction of optical densities of treated the cells relative to the untreated solvent controls. The data were plotted in GraphPad Prizm 3.0. Nonlinear regression analysis was used to determine $IC_{50}$ values. $IC_{50}$ of the compounds was expressed as the concentration of the drugs inhibiting cell growth by 50%.

TEM Measurement.

Stock solutions of compounds CA-NETA and CDCA-NE3TA were prepared in 18 MΩ $H_2O$ and diluted to the final concentrations of CA-NETA (1 mM, pH=7) and CDCA-NE3TA (10 mM, pH=7). A 5 μL aliquot of CDCA-NE3TA solution was added to a cavity of a Micro-Test Staining Dish (Cat#71564, Electron Microscopy Sciences, PA), and a gold-coated grid was inverted into the solution in the plate and air-dried for 10 min. The grid was further dipped into a drop of the solution (10 μL) in a cavity of the plate and air-dried overnight. The grid was transferred into a desiccator and further dried in vacuo for 1.5 days. TEM images were obtained at room temperature on a Hitachi HF-2000 High resolution TEM (Hitachi) operated at 80 kV, equipped with a charged-coupled device (CCD) camera.

Fluorescence and UV Spectra of NBD-CA-NE3TA.

Fluorescence Spectra were recorded on a PC1 Photon counting spectrofluorometer (ISS, Inc., Champaign, Ill.) with excitation at 446 nm, bandwidth of 8 nm, data collection every 1 nm at 20° C. Stock solution (1 mM) of NBD-CA-NE3TA was prepared by dissolving sample in 0.005% $DMSO-H_2O$. UV-Vis measurements were carried out by adding 10 μL aliquots of the stock solution via a micropipette into 2 mL of $H_2O$ in a quartz cuvette, while the measurement of fluorescence was carried out by adding 1 μL aliquots of the stock solutions into 1 mL $H_2O$ in a quartz cuvette. The mixtures were stirred briefly for equilibration prior to data acquisition.

Fluorescence Imaging of Live Cancer Cells.

HT29 cancer cells were plated in glass cover slips which placed in 6-well plates, and were incubated with growth media in a humidified atmosphere with 5% $CO_2$ at 37° C. overnight. Control cells or cells containing NBD-CA-NE3TA (50 μM) were incubated with media for 0.5 h under 5% $CO_2$ at 37° C. At the end of the incubation time, cells were rinsed with PBS three times and subsequently observed under the Olympus DSU Spinning disk confocal microscope with a band-pass filter set at 436/20 nm (Excitation) and 535/30 nm (Emission).

Example 8

Synthesis of C-NE3TA-Transferin and N-NE3TA-Transferin Conjugates for Iron Depletion Therapy Many different types of cancers including HeLa and colon cancers and colorectal liver metastates are reported to display overexpression of transferrin receptor (TfR). The iron binding protein transferrin has been employed for selective delivery of an antitumor agent in cancer therapy. (Qian M Z, Li H, Sun H, Ho K. Targeted drug delivery via the transferring receptor-mediated endocytosis pathway. *Phamacol Rev* 2002, 54, 561-587). Recently, it was reported that polyaminocarboxylate-based NE3TA analogues exhibit antiproliferative activity against HeLa and colon cancer cells. Although the mechanism of the cytotoxic activity of the NE3TA analogues is not clearly understood, the antitumor activity of the NE3TA analogues is speculated to result from their chelating capability of biologically important metals in the cancer cells. The NE3TA analogues that can form a neutral complex with Fe(III) displayed significantly enhanced antitumor activity as compared to the clinically available iron depleting agent DFO. This example provides a synthesis of NE3TA-based transferrin conjugate for targeted antitumor therapy. Combination of NE3TA as potential iron chelator with iron-binding transferrin is proposed to better penetrate and target the cancer cells and chelate iron in intercellular labile iron pools (LIP) as compared to NE3TA treatment alone. C-NE3TA-NCS (Scheme 13) and N-NE3TA-NCS (Scheme 17) as the respective bifunctional version of NE3TA (Scheme 8) and NE3TA-Bn (Scheme 8) were synthesized and conjugated to transferrin. The corresponding transferrin conjugates were evaluated for antiproliferative activity in HeLa cancer cells. The bifunctional ligands N-NE3TA-NCS and C-NE3TA-NCS possess an isothiocyanate group for conjugation to transferrin. Synthesis of N-NE3TA-NCS is shown in Scheme 17. Synthesis of C-NE3TA was accomplished by a modification of the synthetic procedure reported by our group (Scheme 16). A highly practical and cost effective synthesis of the precursor molecule 4 to C-NE3TA-NCS is shown in Scheme 16. Swern oxidation of 1 provided 2 followed by reductive amination 2 with 3 to provided 4. t-butyl groups in 5 were removed using TFA to produce 5. The improved synthetic route to 5 appears to be very efficient. The key precursor molecule 8 to N-NE3TA-NCS was prepared via a modification of the synthetic procedure that was previously reported. Compound 7 was readily produced from swern oxidation of 6, and reductive amination of Compound 7 provided the desired macrocyclic compound 8 in excellent yield. The nitro group in Compound 8 was converted to the amino group using hydrogenolysis. Removal of t-butyl groups in Compound 9 by the treatment of 9 with 4M HCl/1,4-dioxane provided the bifunctional ligand 10 which was reacted with thiophosgene to provide the desired bifunctional ligand in the isothiocyanate form.

TABLE 11

IC50 value of ligand-transferin conjugates

| Ligand | IC50 (µM) Hela |
|---|---|
| N-NE3TA | 8.4 ± 0.4 |
| C-NE3TA | 7.1 ± 0.1 |
| Apo-C-NETA | 9.15 ± 1.18 |
| Holo-C-NE3TA | 7.03 ± 0.09 |
| Apo-N-NE3TA | 8.85 ± 1.43 |
| Holo-N-NE3TA | 11.48 ± 0.21 |
| DTPA | 264.5 ± 36.2 |

Example 8

Experimental Information tert-butyl 1-(4-nitrophenyl)-3-oxopropan-2-ylcarbamate (2)

Oxalyl chloride (237 mg, 2.0 mmol) in dry dichloromethane (8 mL) at −60° C. was added dropwise dry DMSO (277 mg, 3.5 mmol) over 10 min. After 5 min, N—BOC-amino alcohol 1 (300 mg, 1.0 mmol) in dichloromethane (2 ml) was added dropwise and the mixture was stirred intensively for 1 h, while the temperature was maintained between −50~60° C. At which time, distilled triethylamine (511 mg, 5.1 mmol) was added and the mixture was stirred for additional 15 min. Saturated NH$_4$Cl solution (10 mL) and deionized water (10 mL) were added, and the mixture was stirred for additional 5 min. The mixture was warmed to room temperature. The organic layer was washed with 5% citric acid solution (2×10 ml), deionized water (10 mL), and brine (10 mL). Standard work-up of the organic phase gave desired product 2 (232 mg, 78%) as yellowish oil which was immediately used for the next step without further purification. $^1$H NMR (CDCl$_3$, 300 MHz) δ1.43 (s, 18H), 3.15 (dd, J=13.8, 7.0 Hz, 1H), 3.33 (dd, J=14.0, 6.1 Hz, 1H), 4.39-4.51 (m, 1H), 7.35 (d, J=8.6 Hz, 2H), 8.18 (d, J=8.6 Hz, 2H), 9.66 (s, 1H); $^{13}$C NMR (CDCl$_3$, 300 MHz) δ 28.2 (q), 35.1 (t), 60.5 (d), 80.7 (s), 123.9 (d), 130.3 (d), 147.2 (d), 155.0 (s), 198.0 (s). HRMS (Positive ion ESI) Calcd for C$_{14}$H$_{18}$N$_2$O$_5$Na [M+H]$^+$ m/z 317.1104. Found: [M+H]$^+$ m/z 317.1108.

Di-tert-butyl 7-[2-tert-Butoxycarbonylamino-3-(4-nitrophenyl)-propyl][1,4,7]-triazanonane-1,4-dicarboxylate (4)

To a solution of Compound 2 (792 mg, 2.7 mmol) in 1,2-dichloroethane (35 mL) at 0° C. was added portionwise Compound 3 (886 mg, 2.7 mmol) over 20 min. The resulted solution was then treated with sodium triacetoxyborohydride (801 mg, 3.8 mmol). The mixture was stirred at room temperature for overnight while monitoring the reaction progress using TLC. The reaction mixture was quenched by adding saturated NaHCO$_3$ (20 mL) and the product was extracted and washed with CH$_2$Cl$_2$. The combined organic layers were dried over MgSO$_4$, filtered, and concentrated in vacuo to provide pure Compound 4 (1.65 g, 100%) as a yellowish waxy solid. $^1$H and $^{13}$C NMR spectral data of Compound 4 is essentially identical to the date reported in the literature. (Hyuna)

1-(4-Nitrobenzyl)-2-[1,4,7]triazanonan-1-ylethylamine (5)

$^1$H and $^{13}$C NMR spectral data of Compound 5 is essentially identical to the date reported in the literature.

tert-butyl 2-({[4-(hydroxynitroso)phenyl]methyl}(2-oxoethyl)amino)acetate (7)

To the stirred solution of oxalyl chloride (245.5 mg, 1.93 mmol), and DCM (2 mL) was added dropwise DMSO (264.3 mg, 3.38 mmol) over a span of 10-15 min while maintaining the temperature −60° C. After 5 min the DCM (4 mL) solution of protected amino alcohol 6 (300 mg, 0.97 mmol) was added dropwise over 10 min at −60° C. After the addition was complete the reaction mixture was allowed to stir at −60° C. for another 2 h. Et$_3$N was added and reaction mixture was allowed to stir at same temperature for 30 min. Then the saturated solution of NH$_4$Cl was added and the resulting aqueous solution was extracted with DCM (30 mL×3). The separated organic layer was treated with MgSO$_4$, filtered and evaporated on rotavapor to provide the aldehyde as light yellow solid 7 in more than 95% purity (251 mg, 84%). $^1$H NMR (CDCl$_3$, 300 MHz) δ 1.46 (s, 9H), 3.37 (s, 23), 3.57 (s, 2H), 3.98 (s, 2H), 7.58 (d, J=8.6 Hz, 2H), 8.19 (d, J=8.6 Hz, 2H), 9.65 (s, 1H); $^{13}$C NMR (CDCl$_3$, 300 MHz) δ 28.16 (q), 55.70 (t), 57.92 (t), 63.73 (t), 81.74 (s), 123.73 (d), 29.46 (d), 146.02 (s), 147.53 (s), 169.86 (s), 200.66 (d).

tert-butyl 2-[(2-{4,7-bis[2-(tert-butoxy)-2-oxoethyl]-1,4,7-triazonan-1-yl}ethyl)({[4-(hydroxynitroso)phenyl]methyl})amino]acetate (8)

To the stirred solution of aldehyde 7 (86.2 mg, 0.28 mmol) and macrocyclic compound (100 mg, 0.28 mmol) in dichloro ethane was added sodium triacetoxy borohydride (83 mg, 0.39 mmol) portionwise over 10 min while maintaining the temperature 0° C. After the addition was complete the reaction mixture was gradually warmed to room temperature and allowed to stir at same temperature for 18 h after which the reaction mixture was treated with saturated NaHCO$_3$ solution (20 mL) and extracted with ethyl acetate (30 mL×3). The separated organic layer was treated with MgSO$_4$, filtered and evaporated on a rotary evaporator to provide Compound 8 as light yellow oil in more then 99% purity (157 mg, 86%). $^1$H and $^{13}$C NMR data of Compound 3 was essentially identical to that of the compound reported in the literature. (Jmedchem 2008)

tert-butyl 2-{[(4-aminophenyl)methyl](2-{4,7-bis[2-(tert-butoxy)-2-oxoethyl]-1,4,7-triazonan-1-yl}ethyl)amino}acetate (9)

To a solution of Compound 8 (48.0 mg, 73.9 pump in EtOH (7.0 mL) was added dry 10% Pd/C (9.5 mg) under Argon gas and at room temperature. The reaction mixture was placed under hydrogenation apparatus for 14 h. The resulting mixture was filtered via celite bed and washed thoroughly with EtOH. The filtrate was then concentrated on vacuum and purified by semi preparative HPLC (method 2, $t_R$=100-120 min) to provide pure product as light yellow oil 9 (41.0 mg, 90%). $^1$H NMR (CDCl$_3$, 300 MHz) δ 2.60-2.76 (m, 8H), 2.83 (s, 8H), 3.20 (s, 2H), 3.29 (s, 4H), 3.63-3.66 (m, 4H), 6.61 (d, J=Hz, 2H), 7.08 (d, J=Hz, 2H). HRMS (Positive ion FAB) Calcd for $C_{33}H_{58}N_5O_6$ [M+H]$^+$ m/z 620.4387. Found: [M+H]$^+$ m/z 620.4410.

2-{[(4-aminophenyl)methyl]({2-[4,7-bis(carboxymethyl)-1,4,7-triazonan-1-yl]ethyl})amino}acetic acid (10)

To Compound 9 (39 mg, 62.9 μmol) with an ice cooling bath around was added 6 mL of 4 M HCl/dioxane dropwise. After the addition was complete, the reaction mixture was gradually warmed to room temperature and allowed to stir overnight at room temperature. After completion 50 mL of ethyl ether was added to the reaction mixture with vigorous stirring and the resulting slurry was kept in the freezer for 2 h. The precipitate was collected and washed with ethyl ether, then immediately lyophilized with water and evaporated to provide pure salt as light yellow solid Compound 10 (34 mg, 85%). NMR (D$_2$O, 300 MHz) δ 2.97 (m, 4H), 3.21 (m, 6H), 3.33 (s, 4H), 3.48 (t, J=5.4 Hz, 2H), 3.93 (s, 4H), 3.99 (s, 2H), 4.46 (s, 2H), 7.40 (d, J=6.4 Hz, 2H), 7.59 (d, J=6.4 Hz, 2H).

2-({2-[4,7-bis(carboxymethyl)-1,4,7-triazonan-1-yl]ethyl}[(4-isothiocyanatophenyl)methyl]amino)acetic acid To a solution of Compound 10 (20.1 mg, 31.7 μmol) in water (0.3 mL) was added CSCl$_2$ in CHCl$_3$ (39.4 μL). The resulting mixture was stirred at room temperature for 4 hours. The aqueous layer taken out and concentrated in vacuo gave pure compound 6 (N-NE3TA-NCS) as a yellow solid (20 mg, 99%). $^1$H NMR (D$_2$O, 300 MHz) δ 2.97 (m, 4H), 3.02-3.36 (m, 12H), 3.44 (t, J=5.4 Hz, 2H), 3.93 (s, 4H), 3.98 (s, 2H), 4.36 (s, 2H), 7.29 (d, J=6.1 Hz, 2H), 7.47 (d, J=6.1 Hz, 2H). HRMS (Positive ion ESI) Calcd for $C_{22}H_{32}N_5O_6S$ [M+H]$^+$ m/z 494.2073. Found: [M+H]$^+$ m/z 494.2098.

Example 9

Aziridinium Salts as Versatile Reactive Intermediates

A variety of aziridinium cations have been generated in situ as precursor molecules of enantiomerically pure organic compounds and biological active agents. Several aziridinium cations are proposed as intermediates involved in the reaction of nitrogen mustard family with interstrand cross-linked DNA (S. M. Rink, M. S. Solomon, M. J. Taylor, S. B. Rajur, L. W. McLaughlin, P. B. Hopkins, *J. Am. Chem. Soc.*, 1993, 115, 2551-2557). Ring opening of substituted aziridinium cations have been recognized as an efficient synthetic route to chiral 1,2- and 1,3-diamines, 3,4-diamino nitrites, nitrogen containing heterocycles, and α,β-diaminoesters (J. M. Concellón, E. Riego, J. R. Suarez, S. Garcia-Granda, M. R. Diaz, *Org. Lett.* 2004, 6, 4499-4501). The synthetic methods to generate quaternary aziridinium cations as reactive intermediates involve N-alkylation of aziridines, intramolecular substitution reaction of β amino halides, and mesylation of β-amino alcohols (M. D'hooghe, V. V. Speybroeck, M. Waroquier, N. D. Kimpe, *Chem. Commun.* 2006, 1554-1556). Research efforts have been made to characterize aziridinium salts, and formation of several aziridinium salts was induced by using heavy counter anions such as fluoroborate or perchlorate (N. Leonard, J. Paukstelis, *J. Org. Chem.* 1965, 30, 821-825; b) C. Lillocci. *J. Org. Chem.* 1988, 53, 1733-1736).

In this example, synthesis and characterization of a series of aziridinium salts from bromination of N,N-dialkylated β-amino alcohols was described. Scheme 18 shows N,N-bisubstituted amino bromides 3 that have been isolated by reaction of N,N-dialkylated β-amino alcohols 2 with N-bromosuccinimide (NBS) and triphenylphosphine (PPh$_3$). As a typical procedure of bromination, β-amino ethanols 2 (1 equiv) in CH$_2$Cl$_2$ was reacted with a 1.2 equiv/1.2 equiv mixture of NBS and PPh$_3$ at 0° C. However, instead of obtaining the desired S$_N$2 product 4, the reaction led to the secondary β-amino bromide as the ring opening product of the aziridinium bromide salt 3 that was formed as the reactive intermediate. Aziridinium salt was isolated by sequestering bromide in the secondary β-amino bromide 3 with either silver perchlorate or silver tetrafluoroborate and completely characterized by NMR. The scope of the reaction using various backbone substituted N,N-dialkylated β-amino alcohols was investigated. It appears that introduction of any R substituent into the β-amino alcohol backbone generates steric hindrance preventing nucleophilic attack of bromide at the less hindered methylene carbon via a S$_N$2 pathway. Compound 2a (t-Bu) and Compound 2b (Bn) containing no C-substituent led to the respective normal intermolecular substitution product Compounds 4a and 4b, and no aziridinium salts were formed (Table 12, entries 1 and 2). All backbone substituted β-amino ethanols 2 including compound 2c having the sterically less demanding methyl group were transformed to aziridinum salts via intramolecular rearrangement. Then, the attack of the counter anion bromide to the electron deficient methine carbon in the aziridinium cation generated led to the formation of Compound 5. The aziridinium ions in Table 12 were successfully isolated and characterized by sequestering bromide in the secondary amino bromide using AgClO$_4$.

TABLE 12

| Entry | Substrate | R | R' | Product | Yield |
|---|---|---|---|---|---|
| 1 | 2a | H | t-Bu | 4a | 86% |
| 2 | 2b | H | Bn | 4b | 85% |
| 3 | 2c | (S)-methyl | t-Bu | 5c | 44% |
| 4 | 2d | rac-benzyl | t-Bu | 5d | 51% |
| 5 | 2e | (S)-4-nitrobenzyl | t-Bu | 5e | 55% |
| 6 | 2f | rac-4-nitrobenzyl | t-Bu | 5f | 67% |
| 7 | 2g | rac-3-(4-nitrophenyl)-propyl | t-Bu | 5g | 66% |
| 8 | 2h | (S)—CO$_2$CH$_3$ | t-Bu | 5h | 23% |
| 9 | 5c | (S)-methyl | t-Bu | 3c' | * |
| 10 | 5d | rac-benzyl | t-Bu | 3d' | * |
| 11 | 5e | (S)-4-nitrobenzyl | t-Bu | 3e' | * |
| 12 | 5f | rac-4-nitrobenzyl | t-Bu | 3f' | * |
| 13 | 5g | rac-3-(4-nitrophenyl)-propyl | t-Bu | 3g' | * |

* quantitative yield

Example 9

Experimental Information

Scheme 18/Table 12

General Procedure for Synthesis of Compound 5.

To a solution of N,N-dialkylated alcohol 2 (1 equiv) and PPh$_3$ (1.2 equiv) in CH$_2$Cl$_2$ was portionwise added NBS (1.2 equiv) at 0° C. over 30 min. The resulting mixture was stirred for 3 h while being maintained at 0° C. The ice bath was removed, and the reaction mixture was warmed to RT and stirred for 1 h and evaporated to dryness. The residue was purified via column chromatography on silica gel (60-230 mesh) eluting with 10% EtOAc in hexanes.

(R)-tert-butyl 2,2'-(2-bromopropylazanediyl)diacetate (5c)

To a solution of Substrate 2c (378 mg, 1.25 mmol) and PPh$_3$ (393 mg, 1.50 mmol) in CH$_2$Cl$_2$ (6 mL) at 0° C. was added NBS portionwise (267 mg, 1.50 mmol). The residue was purified by silica gel column chromatography eluted with EtOAc/hexanes (1:20) to afford the pure product as colorless oil 5c (203 mg, 44%). $^1$H NMR (CDCl$_3$, 300 MHz) δ 1.46 (s, 18H), 1.72 (d, J=6.6 Hz, 3H), 2.91 (dd, J=14.2, 7.6 Hz, 1H), 3.18 (dd, J=14.2, 6.2 Hz, 1H), 3.41-3.54 (m, 4H), 3.95-4.19 (m, 1H); $^{13}$C NMR (CDCl$_3$, 300 MHz) δ 23.7 (q), 28.2 (q), 48.8 (d), 57.2 (t), 64.0 (t), 81.2 (s), 170.7 (s). HRMS (positive ion FAB) Calcd for C$_{15}$H$_{28}$NO$_4$Br [M+H]$^+$ m/z 366.1280. Found: [M+H]$^+$ m/z 366.1256. [α]$^{26}_D$=−7.89° (c=1.0, CHCl$_3$).

tert-Butyl 2,2'-(2-bromo-3-phenylpropylazanediyl) diacetate (5d)

To a solution of Substrate 2d (279 mg, 0.73 mmol) and PPh$_3$ (231 mg, 0.88 mmol) in CH$_2$Cl$_2$ (5 mL) at 0° C. was added NBS (156.8 mg, 0.88 mmol). The residue was purified by silica gel column chromatography eluted with EtOAc/hexanes (1:20) to afford colorless oil 5d (163 mg, 51%). $^1$H NMR (CDCl$_3$, 300 MHz) δ 1.45 (s, 18H), 2.92-3.09 (m, 2H), 3.22-3.33 (m, 1H), 3.41-3.59 (m, 5H), 4.19-4.32 (m, 1H), 7.17-7.38 (m, 5H); $^{13}$C NMR (CDCl$_3$, 300 MHz) δ 28.2 (q), 42.4 (t), 55.4 (d), 57.2 (t), 62.1 (t), 81.2 (s), 126.6 (d), 128.3 (d), 129.3 (d), 138.7 (s), 170.6 (s). HRMS (positive ion FAB) Calcd for C$_{21}$H$_{33}$NO$_4$Br [M+H]$^+$ m/z 442.1593. Found: [M+H]$^+$ m/z 442.1596.

(R)-tert-butyl 2,2'-(2-bromo-3-(4-nitrophenyl)propylazanediyl)diacetate (5e)

To a solution of Substrate 2e (473 mg, 1.1 mmol) and PPh$_3$ (350 mg, 1.3 mmol) in CH$_2$Cl$_2$ (4 mL) at 0° C. was added NBS (238 mg, 1.3 mmol). The residue was purified by silica gel column chromatography eluting with EtOAc/hexanes (1:20) to afford colorless liquid 5e (298 mg, 55%). $^1$H NMR (CDCl$_3$, 300 MHz) δ 1.47 (s, 18H), 2.98 (dd, J=14.2, 9.1 Hz, 2H), 3.37 (dd, J=14.2, 5.3 Hz, 1H), 3.41-3.57 (m, 4H), 3.81 (dd, J=14.2, 3.1 Hz, 1H), 4.14-4.23 (m, 1H), 7.46 (d, J=8.7 Hz, 2H), 8.29 (d, J=8.7 Hz, 2H); $^{13}$C NMR (CDCl$_3$, 300 MHz) δ 28.2 (q), 41.9 (t), 53.9 (d), 57.5 (t), 62.6 (t), 81.5 (s), 123.5 (d), 130.3 (d), 146.7 (s), 146.9 (s), 170.6 (s). HRMS (positive ion FAB) Calcd for C$_{21}$H$_{31}$N$_2$O$_6$Br [M+H]$^+$ m/z 487.1444. Found: [M+H]$^+$ m/z 487.1459. [α]$^{26}_D$=+11.87 (c=1.0, CHCl$_3$).

tert-butyl 2,2'-(2-bromo-3-(4-nitrophenyl)propylazanediyl)diacetate (5f)

To the stirred solution of Substrate 2f (3.2 g, 7.6 mmol) and PPh$_3$ (2.4 g, 9.1 mmol) in CH$_2$Cl$_2$ (30 mL) at 0° C. was added NBS (1.6 mg, 9.1 mmol). The residue was purified via column chromatography on silica gel eluted with 10% EtOAc in hexanes to afford colorless oil 5f (2.5 g, 67%). $^1$H NMR (CDCl$_3$, 300 MHz) δ 1.46 (s, 18H), 2.91-3.03 (m, 2H), 3.32-3.58 (m, 5H), 3.75-3.85 (m, 1H), 4.12-4.23 (m, 1H), 7.44 (d, J=8.6 Hz, 2H), 8.15 (d, J=8.6 Hz, 2H); $^{13}$C NMR (CDCl$_3$, 300 MHz) δ 28.2 (q), 41.9 (t), 53.9 (d), 57.5 (t), 62.6 (t), 81.4 (s), 123.5 (d), 130.3 (d), 146.7 (s), 146.8 (s), 170.6 (s). HRMS (Positive ion FAB) Calcd for C$_{21}$H$_{31}$N$_2$O$_6$Br [M+H]$^+$ m/z 487.1444. Found: [M+H]$^+$ m/z 487.1443.

tert-Butyl 2,2'-(2-bromo-5-(4-nitrophenyl)pentylazanediyl)diacetate (5g)

To a solution of Substrate 2g (7.6 g, 16.81 mmol) and PPh$_3$ (5.3 g, 20.17 mmol) in CH$_2$Cl$_2$ (70 mL) was portionwise added NBS (3.6 g, 20.17 mmol) at 0° C. over 30 min. The residue was purified via column chromatography on silica gel eluting with 10% EtOAc in hexanes. The product 5g was thereby obtained as yellowish oil (4.8 g, 66%). $^1$H NMR (CDCl$_3$, 300 MHz) δ 1.42-1.48 (m, 18H), 1.63-2.20 (m, 4H), 2.65-2.82 (m, 2H), 2.95 (dd, J=14.3, 7.8 Hz, 1H), 3.18 (dd, J=14.3, 6.1 Hz, 1H), 3.31-3.52 (m, 4H), 4.01-4.12 (m, 1H), 7.35 (d, J=8.6 Hz, 2H), 8.12 (d, J=8.6 Hz, 2H); $^{13}$C NMR (CDCl$_3$, 300 MHz) δ 28.0 (q), 28.6 (t), 34.9 (t), 35.2 (t), 55.0 (d), 57.0 (t), 62.3 (t), 80.4 (s), 123.4 (d), 129.1 (d), 146.2 (s), 149.9 (s), 170.3 (s); HRMS (Positive ion FAB) Calcd for C$_{23}$H$_{34}$N$_2$O$_6$Br [M+H]$^+$ m/z 515.1757. Found: [M+H]$^+$ m/z 515.1739. Anal. Calcd for C$_{23}$H$_{34}$N$_2$O$_6$Br: C, 53.59; H, 6.84; N, 5.43. Found: C, 53.32; H, 6.64; N, 5.31.

General Synthesis of Isolable Aziridinium Ions 3' or 3".

To a vial containing a solution of N,N-bisubstituted β-amino bromide 5 (1 eq) in CDCl$_3$ or CHCl$_3$ at 0° C., −10° C. or −20° C. was added AgClO$_4$ (5 eq) or AgBF$_4$ (1 eq). The resulting mixture was continuously stirred at 0° C., −10° C. or −20° C., while the reaction progress using TLC was monitored. After completion of the reaction, AgBr was filtered off, and the resulting solution containing an aziridinium salt 3' or 3" was concentrated in vacuo and/or directly characterized by $^1$H and $^{13}$C NMR.

(S)-1,1-bis(2-tert-butoxy-2-oxoethyl)-2-methylaziridinium perchlorate ((S)-3c)

To a vial containing a solution of (R)-5c (24 mg, 0.065 mmol) in CDCl$_3$ (0.5 mL) at −10° C. was added AgClO$_4$ (67.9 mg, 0.33 mmol). The resulting mixture was stirred at −10° C. for 14 min. Silver bromide was filtered, and the filtrate was concentrated to dryness in vacuo to provide pure (S)-3c as a white solid in a quantitative yield. $^1$H NMR (CDCl$_3$, 300 MHz) δ 1.41-1.53 (m, 18H), 1.78 (d, J=5.9 Hz, 3H), 3.42 (dd, J=7.7 Hz, J=4.2 Hz, 1H), 3.60-3.78 (m, 2H), 4.00 (q, J=17.3 Hz, 2H), 4.16 (q, J=12.9 Hz, 2H); $^{13}$C NMR (CDCl$_3$, 300 MHz) δ12.1 (q), 27.9 (q), 48.5 (t), 53.2 (d), 53.3 (t), 60.4 (t), 85.8 (s), 86.1 (s), 163.8 (s), 164.0 (s). [α]$^{26}_D$=+4.40° (c=1.0, CHCl$_3$).

2-benzyl-1-(2-tert-butoxy-2-oxoethyl)-1-(2-(tert-butylperoxy)ethyl)aziridinium perchlorate (3d')

To a vial containing a solution of 5d (100 mg, 0.23 mmol) in CDCl$_3$ (0.5 mL) at −10° C. was added AgClO$_4$ (234 mg, 1.13 mmol). The resulting mixture was stirred at −10° C. for 55 min. Silver bromide was filtered off, and the filtrate containing 3d' was immediately characterized by NMR. $^1$H NMR (CDCl$_3$, 300 MHz) δ 1.38-1.53 (m, 18H), 3.17 (dd, J=13.9 Hz, J=9.4 Hz, 1H), 3.42-3.52 (m, 2H), 3.53-3.61 (m, 1H), 3.73-3.38 (m, 1H), 4.00-4.28 (m, 4H), 7.25-7.35 (m, 5H); $^{13}$C NMR (CDCl$_3$, 300 MHz) δ 27.9 (q), 27.9 (q), 32.2 (t), 47.5 (t), 53.9 (t), 56.0 (d), 60.5 (t), 85.8 (s), 85.9 (s), 127.8 (d), 129.2 (d), 129.2 (d), 133.0 (s), 163.8 (s), 163.9 (s).

Synthesis of 3d' in CHCl$_3$

To a vial containing a solution of 5d (100 mg, 0.23 mmol) in CHCl$_3$ (1 mL) at 0° C. was added AgClO$_4$ (234 mg, 1.13 mmol). The resulting mixture was stirred at 0° C. for 43 min. Silver bromide was filtered off and filtrate was concentrated to dryness to provide 3d' as a white sold in a quantitative yield. 3d' was immediately characterized by NMR. The $^1$H and $^{13}$C NMR data of 3d" was essentially identical to those of 3d' reported above.

2-benzyl-1-(2-tert-butoxy-2-oxoethyl)-1-(2-(tert-butylperoxy)ethyl)aziridinium tetrafluoro-borate (3d")

To a vial containing a solution of 5d (100 mg, 0.23 mmol) in CDCl$_3$ (1 mL) at 0° C. was added AgBF$_4$ (44.8 mg, 0.23 mmol). The resulting mixture was stirred at 0° C. for 53 min. Silver bromide was filtered off, and the filtrate was immediately characterized by NMR. The $^1$H and $^{13}$C NMR data of 3d" was identical to those of 3d' reported above which can be explained by the same aziridinium cation present in both salts. $^1$H NMR (CDCl$_3$, 300 MHz) δ 1.43-1.49 (m, 18H), 3.07-3.15 (m, 1H), 3.40-3.56 (m, 2H), 3.70-3.77 (m, 1H), 3.99-4.21 (m, 4H), 7.25-7.35 (m, 5H); $^{13}$C NMR (CDCl$_3$, 300 MHz) δ 27.8 (q), 32.1 (t), 47.3 (t), 53.7 (t), 55.9 (d), 60.4 (t), 85.5 (s), 85.6 (s), 127.7 (d), 128.7 (d), 129.1 (d), 129.2 (d), 129.5 (d), 133.2 (s), 163.9 (s), 164.0 (s).

(S)-1,1-bis[2-(tert-butoxy)-2-oxoethyl]-2-[(4-nitrophenyl)methyl]aziridin-1-ium perchlorate (3e')

To a round bottom flask containing a solution of Substrate 5e (50 mg 0.1 mmol) in CDCl$_3$ (0.5 ml) at –20° C. was added AgClO$_4$ (103.7 mg, 0.5 mmol). The reaction mixture was stirred at –20° C. for 2.5 h. Silver bromide was filtered off, and the filtrate was concentrated to dryness in vacuo to provide 3e' in a quantitative yield. $^1$H NMR (CDCl$_3$, 300 MHz) δ1.49 (d, J=11.2 Hz, 18H), 3.33-3.42 (m, 1H), 3.55-3.71 (m, 3H), 3.95-4.31 (m, 4H), 7.47 (t, J=9.0 Hz, 0.5H), 7.57 (d, J=8.3 Hz, 1.5H), 8.14 (d, J=7.38 Hz, 2H); $^{13}$C NMR (CDCl$_3$, 300 MHz) δ 27.9 (q), 28.1 (q), 31.8 (t), 47.4 (t), 53.8 (t), 55.0 (d), 60.6 (t), 86.0 (s), 86.1 (s), 123.6 (d), 123.7 (d), 124.1 (d), 130.4 (d), 130.6 (d), 141.0 (s), 147.4 (s), 163.7 (s), 163.8 (s). [α]$^{26}_D$=–1.79 (c=1.0, CDCl$_3$).

1,1-bis[2-(tert-butoxy)-2-oxoethyl]-2-[(4-nitrophenyl)methyl]aziridin-1-ium perchlorate (3f')

To a round bottom flask containing a solution of Substrate 5f (50 mg 0.1 mmol) in CDCl$_3$ (0.5 ml) at –20° C. was added AgClO$_4$ (103.7 mg, 0.5 mmol). The reaction mixture was stirred at –20° C. for 2.5 h at which time the reaction was completion. Silver bromide was filtered off, and the filtrate containing 3f was directly characterized by NMR. $^1$H NMR (CDCl$_3$, 300 MHz) δ1.49 (m, 18H), 3.33-3.42 (m, 1H), 3.55-3.71 (m, 3H), 3.95-4.31 (m, 4H), 7.47 (t, J=9.0 Hz, 0.5H), 7.57 (d, J=8.3 Hz, 1.5H), 8.14 (d, J=7.38 Hz, 2H); $^{13}$C NMR (CDCl$_3$, 300 MHz) δ 27.9 (q), 28.1 (q), 31.8 (t), 47.6 (t), 53.8 (t), 55.0 (d), 60.6 (t), 86.0 (s), 86.1 (s), 123.6 (d), 123.7 (d), 124.1 (d), 130.4 (d), 130.6 (d), 141.0 (s), 147.4 (s), 163.7 (s), 163.8 (s).

1,1-bis[2-(tert-butoxy)-2-oxoethyl]-2-[3-(4-nitrophenyl)propyl]aziridin-1-ium perchlorate (3g')

To a vial containing a solution of Substrate 5g (30 mg 0.06 mmol) and CDCl$_3$ (0.5 ml) at –10° C. was added AgClO$_4$ (62.2 mg, 0.3 mmol). The reaction mixture was stirred at –10° C. for 1 h. Silver bromide was filtered off, and the filtrate containing Substrate 3g' was directly characterized by NMR. $^1$H NMR (CDCl$_3$, 300 MHz) δ1.46-1.49 (m, 18H), 1.95-2.19 (m, 4H), 2.72-2.90 (m, 2H), 3.43 (dd, J=7.9 Hz, J=4.3 Hz, 1H), 3.59 (dd, J=7.7 Hz, J=4.3 Hz, 1H), 3.70-3.74 (m, 1H), 3.94-4.08 (m, 3H), 4.17-4.29 (m, 1H), 7.38 (d, J=8.6 Hz, 2H), 8.09 (d, J=8.6 Hz, 2H); $^{13}$C NMR (CDCl$_3$, 300 MHz) δ 36.1 (t), 27.1 (t), 27.9 (q), 27.9 (q), 28.1 (q), 34.5 (t), 47.9 (t), 53.3 (t), 56.0 (d), 60.4 (t), 85.9 (s), 86.0 (s), 123.6 (d), 123.7 (d), 129.4 (d), 129.5 (d), 146.5 (s), 149.2 (s), 163.8 (s), 164.0 (s).

Example 10

Synthetic Route to Bifunctional Ligands Via Ring Opening of Aziridinium Ions

This example provides a new synthetic method to macrocyclic bifunctional ligands based on nucleophilic substitution reaction of aziridinium ions by a macrocyclic polyamino nucleophile (Scheme 19). A series of key precursor molecules 7 and 8 to bifunctional ligands was prepared by a practical coupling reaction of 3 or 4 with 5 or 6 as shown in Scheme 19. The regiochemistry in the ring opening of aziridinium ions 3 or 4 was found to be affected by counter anions (halide or perchlorate, or tetrafluoroborate).

Example 10

Experimental Information

Scheme 19

General Procedure for the Reaction of 2 with 5 or 6:

To a solution of Compound 2 (1 eq) and DIPEA (3 eq) in CH$_3$CN (5 mL) was added Compound 5 or 6 (1 eq). The resulting mixture was stirred for 5 days at room temperature while monitoring the reaction progress using TLC. The reaction mixture was evaporated to dryness. To the residue, DI water (5 mL) was added and extracted with CH$_2$Cl$_2$ (2×10 mL). The combined organic layers were dried over MgSO$_4$, filtered, and concentrated in vacuo to the dryness. The residue was purified via column chromatography on silica gel (220-440 mesh) eluting with 2~15% CH$_3$OH in CH$_2$Cl$_2$. The product was thereby obtained.

General Procedure for the Reaction of 4 with 5 or 6:

To a vial containing a solution of N,N-bisubstituted β-amino bromide 5 (1 eq) in CH$_3$CN at 0° C., –10° C. or –20° C. was added AgClO$_4$ (1 eq) or AgBF$_4$ (1 eq). The resulting mixture was stirred for 5 min at 0° C., and a solution of Compound 5 (1 eq) or 6 (1 eq) in CH$_3$CN was added to the mixture which was gradually warmed to room temperature and stirred while the reaction progress using TLC was monitored. After completion of the reaction, the reaction mixture was evaporated to dryness. DI water (5 mL) was added to the residue, and the product was extracted with CH$_2$Cl$_2$ (2×10 mL). The combined organic layers were dried over MgSO$_4$, filtered, and concentrated in vacuo to the dryness. The residue was purified via column chromatography on silica gel (220-440 mesh) eluting with 2-15% CH$_3$OH in CH$_2$Cl$_2$. The desired product was thereby obtained.

(R)-tert-butyl 2,2'-(2-(4,7-bis(2-tert-butoxy-2-oxoethyl)-1,4,7-triazonan-1-yl)-1-phenylethylazanediyl)diacetate (7a)

To a solution of Compound 2a (103.0 mg, 0.24 mmol) and DIPEA (93.0 mg, 0.72 mmol) in $CH_3CN$ (5 mL) at 0° C. was added portionwise compound 5 (86.1 mg, 0.24 mmol) over 20 min. The resulting mixture was stirred at room temperature for 19 h while monitoring the reaction progress using TLC. The reaction mixture was concentrated and $CH_2Cl_2$ (10 mL) was added. The resulting mixture was filtered and concentrated in vacuo. The residue was purified via column chromatography on silica gel (220-440 mesh) eluting with 4% $CH_3OH$ in $CH_2Cl_2$. The product 7a (94.7 mg, 56%) was thereby obtained as a yellowish oil. $^1H$ NMR ($CDCl_3$, 300 MHz) δ 1.44 (s, 36H), 2.59-3.12 (m, 13H), 3.17-3.30 (m, 5H), 3.42 (s, 4H), 3.83 (t, J=7.2 Hz, 0.8H), 4.30 (t, J=7.7 Hz, 0.2H), 7.15-7.38 (m, 5H); $^{13}C$ NMR ($CDCl_3$, 300 MHz) δ 28.2 (q), 44.7 (t), 46.5 (t), 47.1 (t), 50.2 (t), 50.8 (t); 52.4 (t), 52.8 (t), 56.3 (t), 63.1 (d), 81.6 (s), 81.8 (s), 82.2 (s), 128.9 (d), 129.0 (d), 135.3 (s), 168.0 (s), 170.1 (s), 170.4 (s). HRMS (Positive ion ESI): Calcd for $C_{38}H_{65}N_4O_8$ $[M+H]^+$ m/z 705.4797. Found: $[M+H]^+$ m/z 705.4794. $[α]^{26}_D$=−16.6° (c 1.0, $CHCl_3$). Analytical HPLC ($t_R$=39.2 min, method 4).

(R)-tert-butyl 2,2'-(1-(4,7-bis(2-tert-butoxy-2-oxoethyl)-1,4,7-triazonan-1-yl)propan-2-ylazanediyl)diacetate (7b)

To a solution of (R)-2b (105.0 mg, 0.29 mmol) and DIPEA (112.4 mg, 0.87 mmol) in $CH_3CN$ (5 mL) at 0° C. was added portionwise 5 (102.5 mg, 0.29 mmol) over 20 min. The resulting mixture was stirred at room temperature for 19 h while monitoring the reaction progress using TLC. The reaction mixture was concentrated and $CH_2Cl_2$ (10 mL) was added. The resulting mixture was filtered and concentrated in vacuo. The residue was purified via column chromatography on silica gel (220-440 mesh) eluting with 4% $CH_3OH$ in $CH_2Cl_2$. The product (R)-7b was thereby obtained (60 mg, 32%) as a yellowish oil. $^1H$ NMR ($CDCl_3$, 300 MHz) δ 1.03-1.24 (m, 3H), 1.41 (s, 36H), 2.73 (s, 5H), 2.99-3.45 (m, 23H); $^{13}C$ NMR ($CDCl_3$, 300 MHz) δ 28.1 (d), 28.1 (q), 28.2 (q), 44.7 (d), 49.1 (d), 51.9 (d), 53.0 (d), 56.8 (d), 81.3 (s), 81.9 (s), 170.8 (s), 170.9 (s), 171.2 (s). HRMS (Positive ion ESI): Calcd for $C_{33}H_{63}N_4O_8$ $[M+H]^+$ m/z 643.4640. Found: $[M+H]^+$ m/z 643.4643. $[α]^{26}_D$=−1.8° (c 1.0, $CHCl_3$).

Example 11

Synthesis of 2p-2C-NETA, 3p-2C-NETA, and 5p-2C-NETA for Antibody Targeted Radiation Cancer Therapy In this example, 2p-2C-NETA, 3p-2C-NETA, and 5p-2C-NETA were synthesized for use in RIT. The key reaction step for preparation of the bifunctional ligands involves regiospecific ring opening of an aziridinium salt that was prepared from bromination of N,N'-dialkylated β amino alcohol prepared starting from Compound 1, 2 or 3. An efficient synthetic route is presented in Scheme 20. The opening of aziridinum cations by the bulky and less nucleophilic bisubstituted TACN 10 occurred at the more substituted methine carbon to provide Compound 7, 8, or 9. t-Butyl groups in 7, 8, or 9 were removed by treatment of 7, 8, or 9 with HCl(g) to provide the desired ligands.

Scheme 1: Synthesis of DEPA

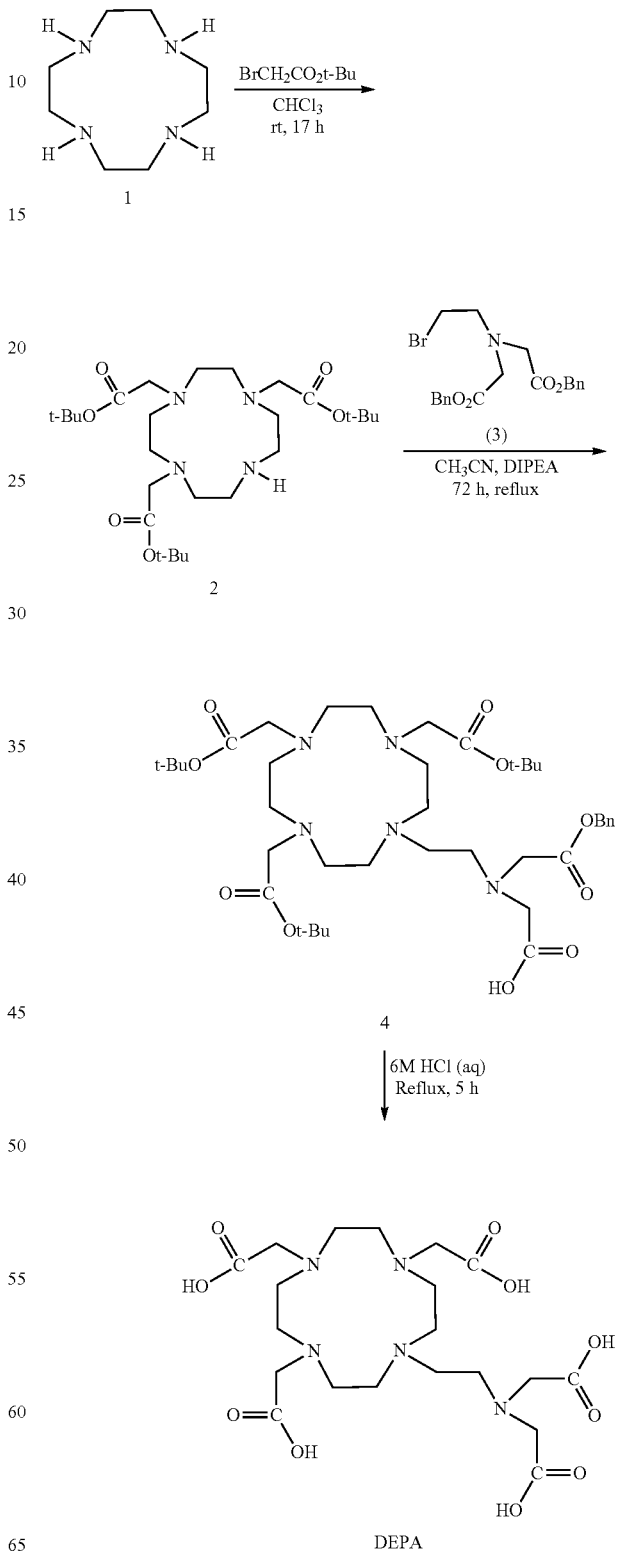

Scheme 2: Synthesis of bifunctional ligand 3p-2C-DEPA
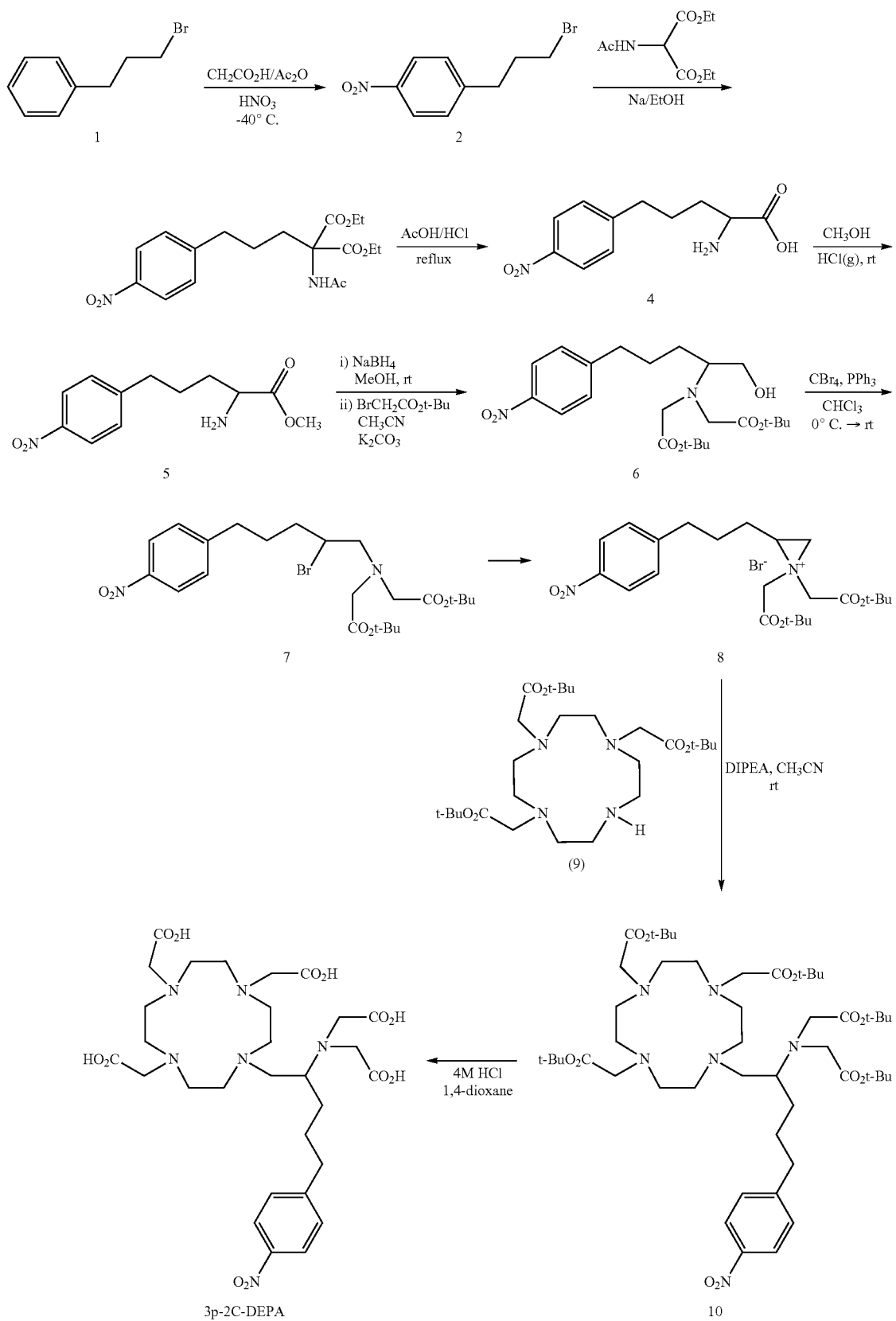

Scheme 3: Confirmation of regiochemistry in ring opening of aziridinium ion 7: an Alternative synthetic route to 3p-2C-DEPA.
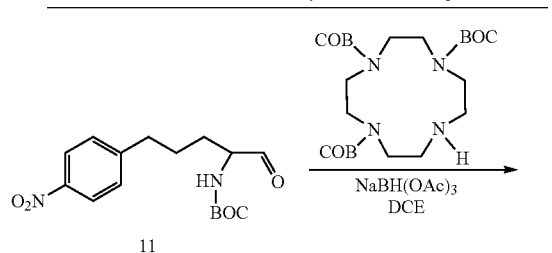
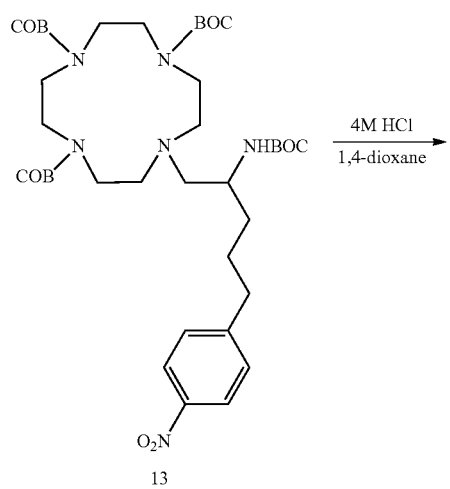
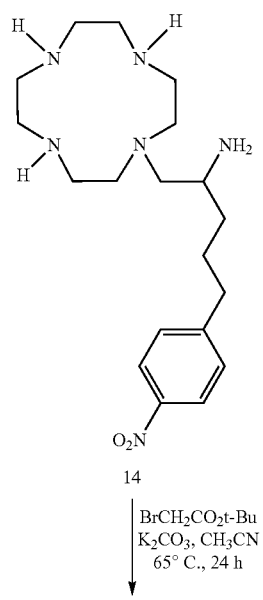
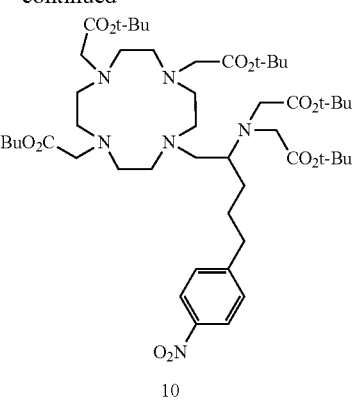
Scheme 4: Synthesis of 3p-2C-DEPA-NCS for conjugation to an antibody
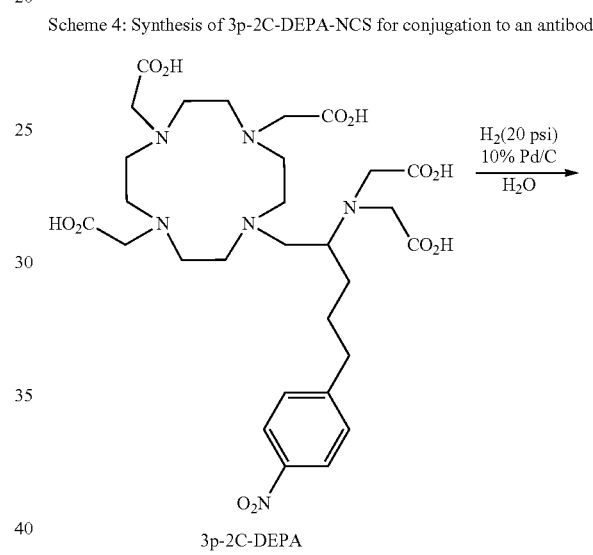
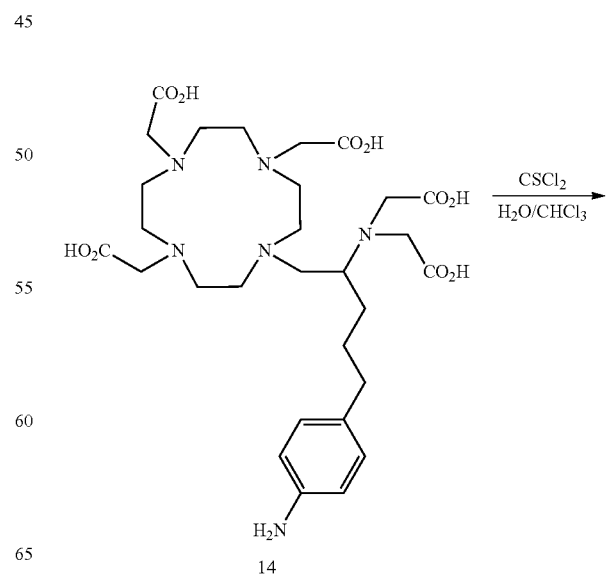

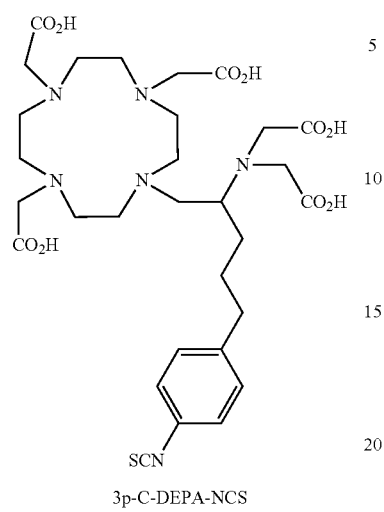
3p-C-DEPA-NCS
Scheme 5: Synthesis of precursor molecule 5 to C-DEPA
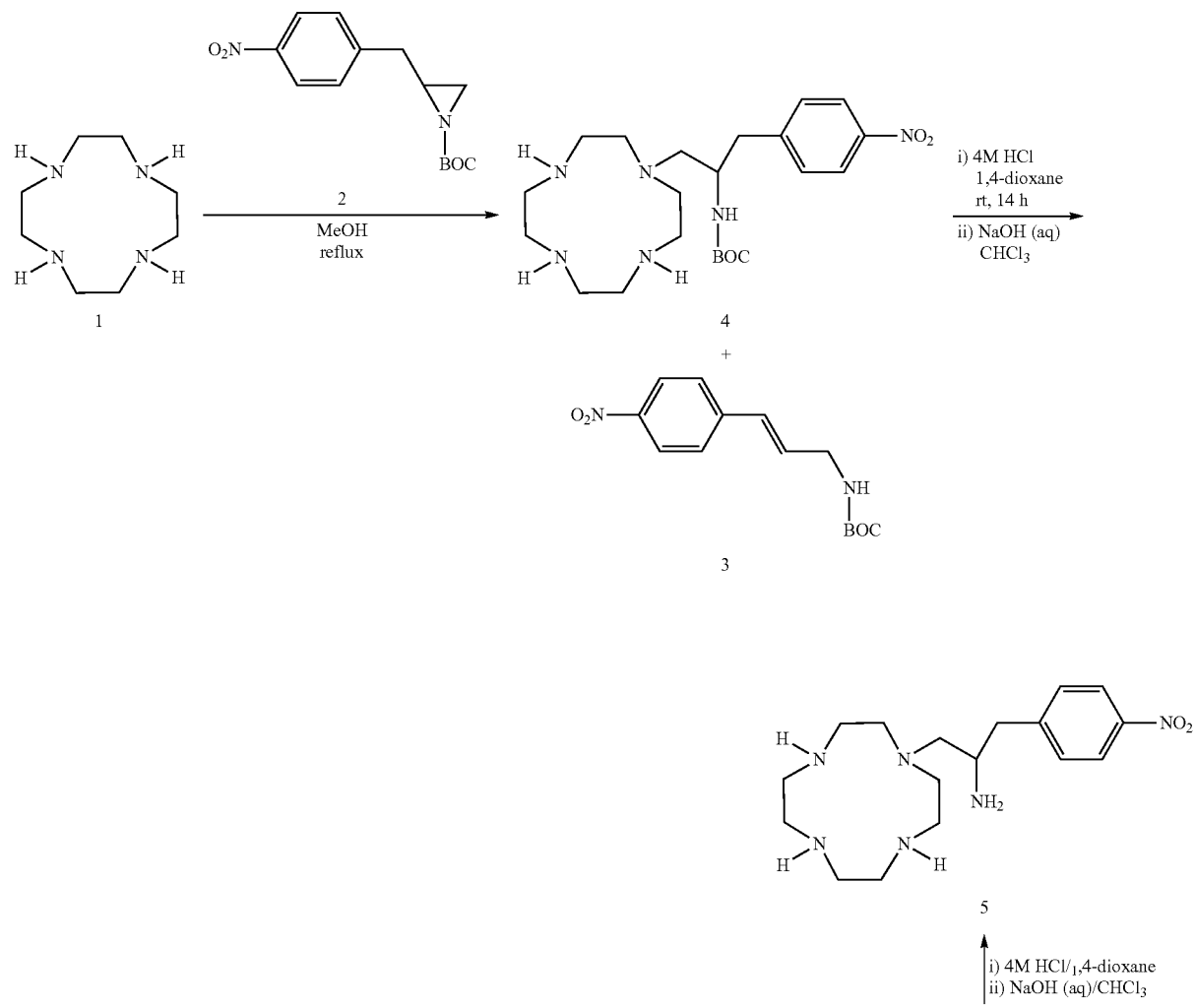

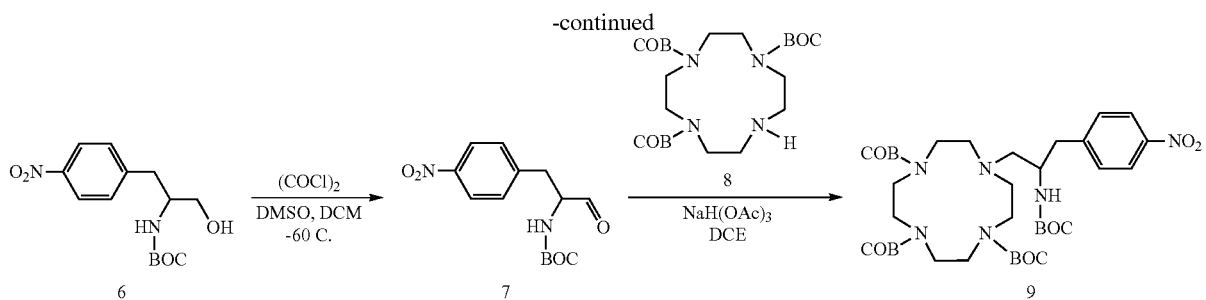
Scheme 6: Synthesis of C-DEPA and C-DEPA-NCS
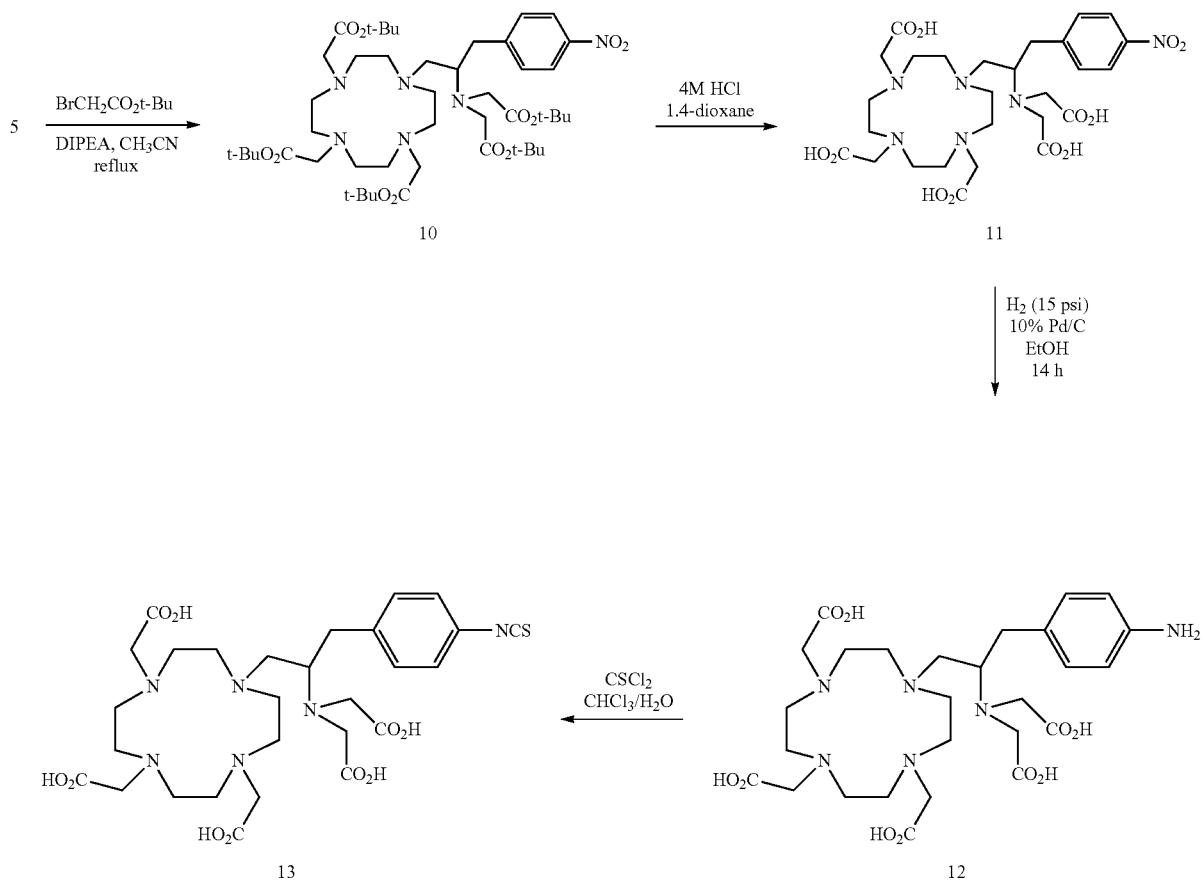
Scheme 7: Synthesis of NBEA and NBPA
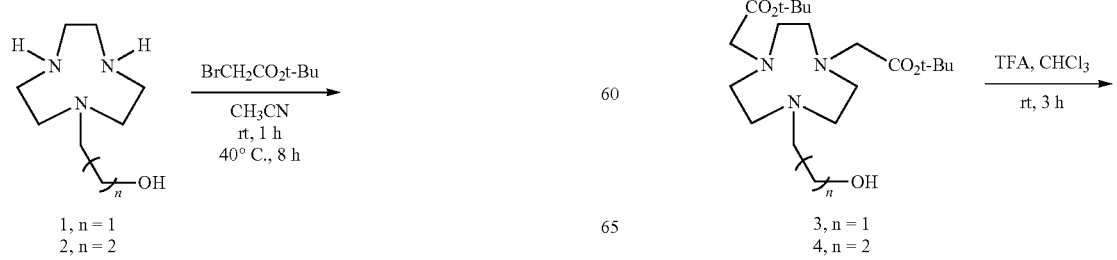

-continued
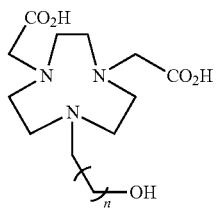
5. NBEA, n = 1
6. NBPA, n = 2
Scheme 8: Synthesis of NE3TA and NE3TA-Bn
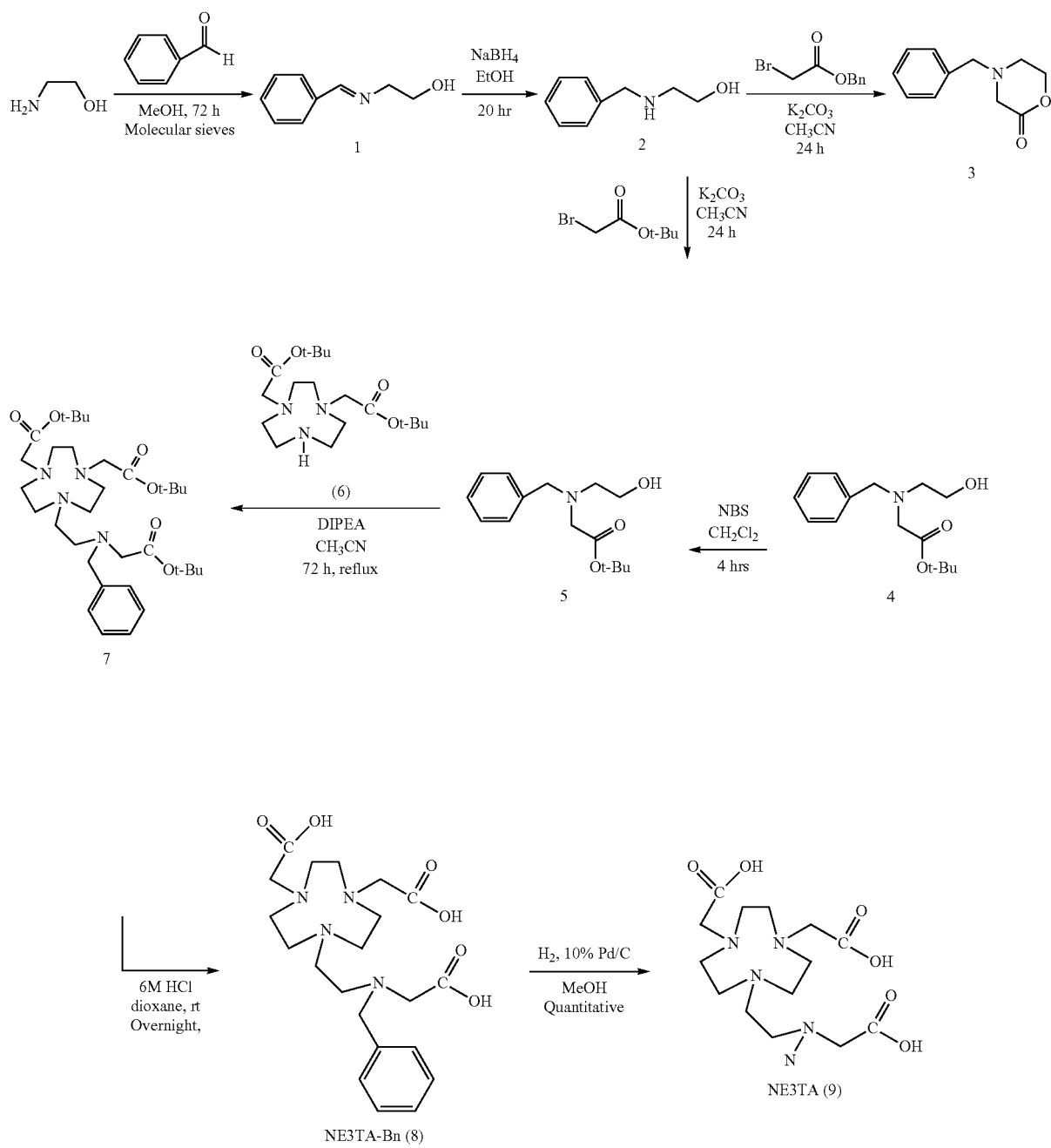

Scheme 9: Synthesis of N-NE3TA
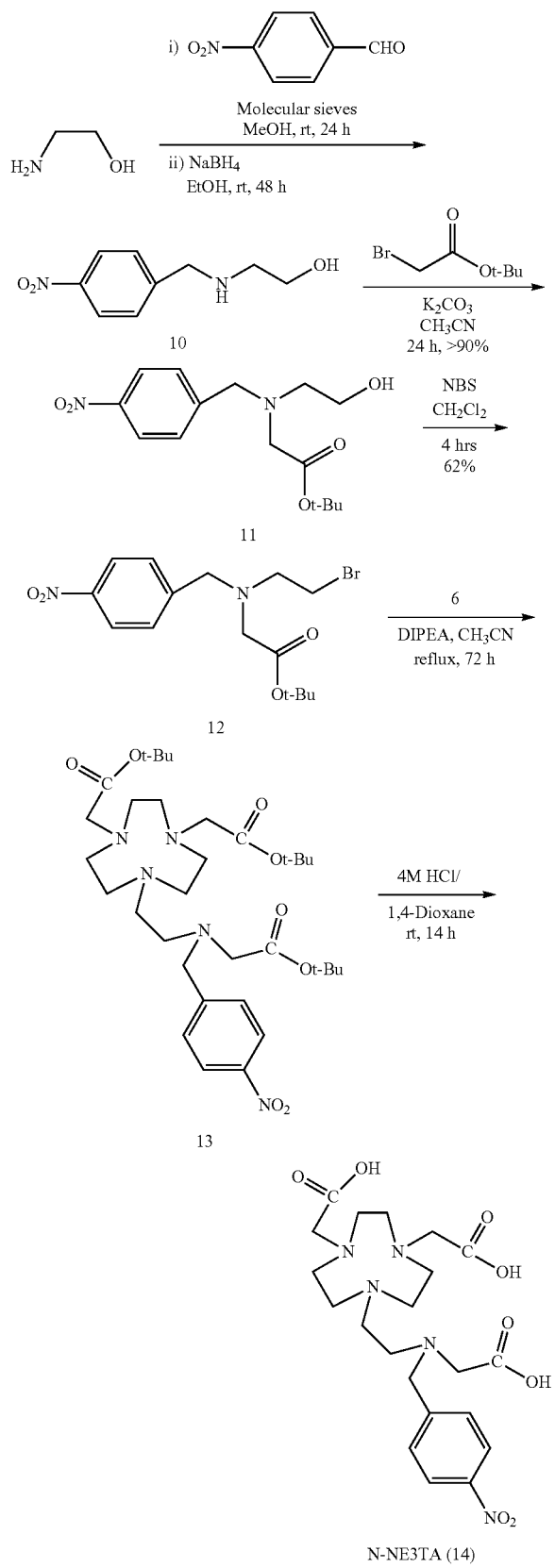
Scheme 10: Synthesis of C-NE3TA-NBD
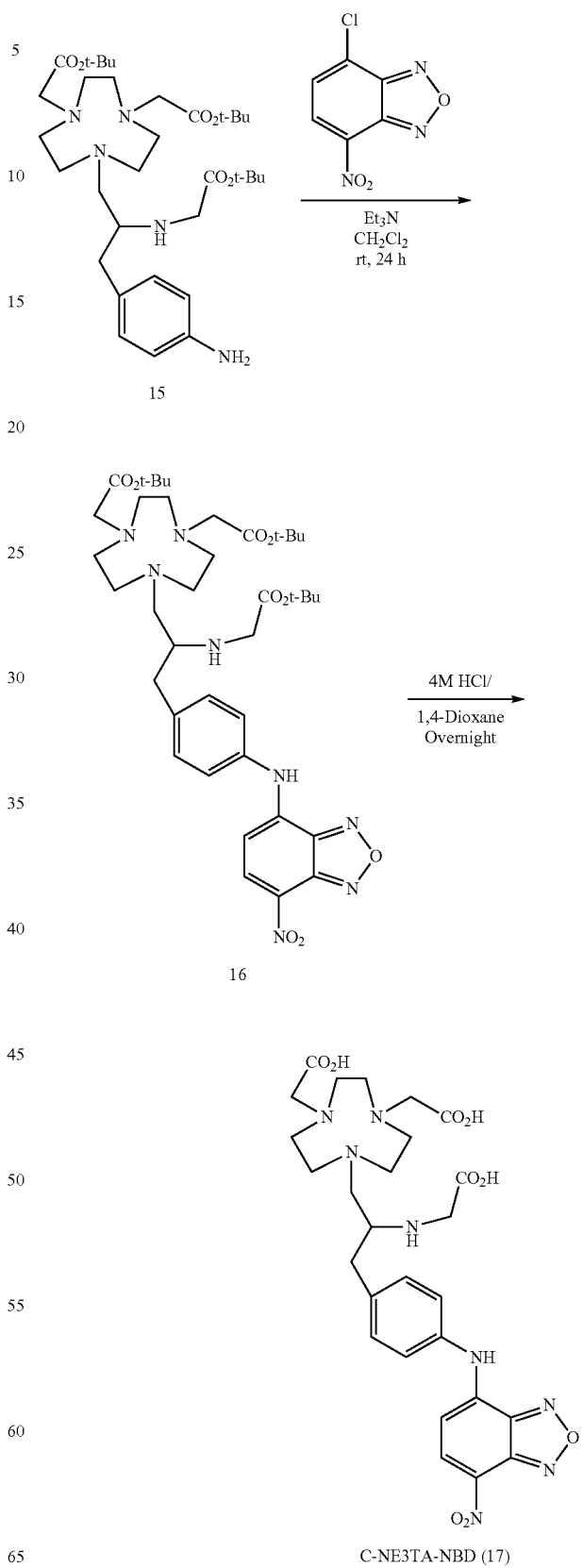

Scheme 11: Synthesis of CA-NE3TA
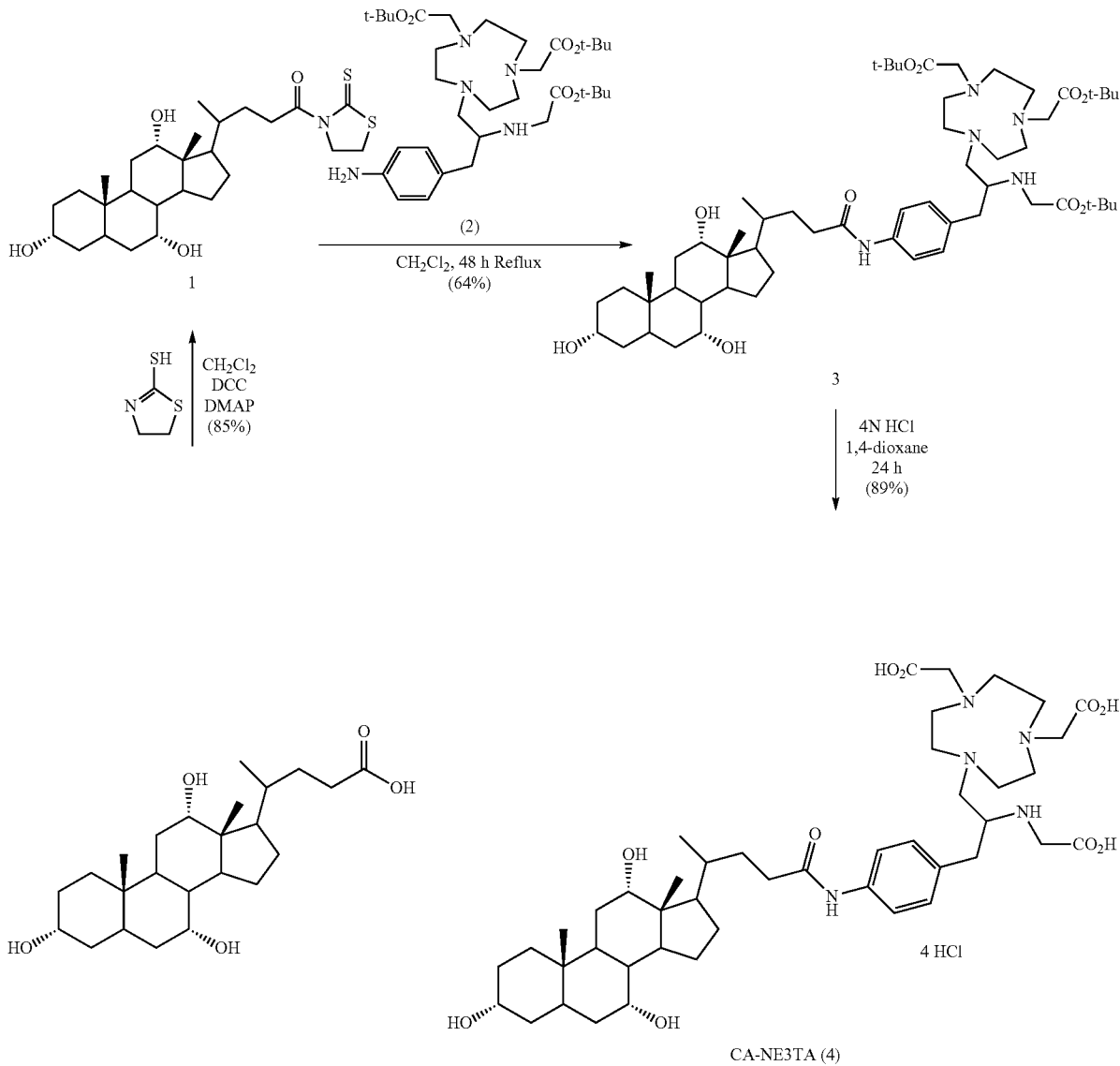
Scheme 12: Synthesis of C-NE3TA
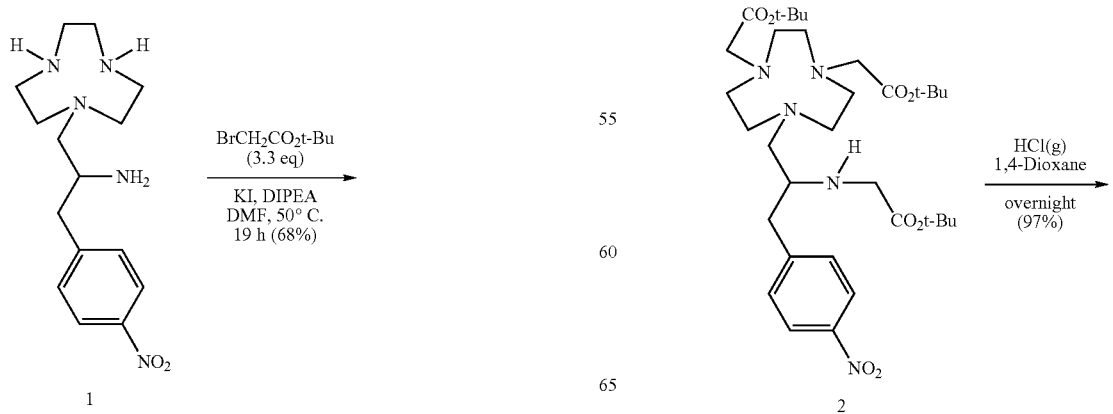

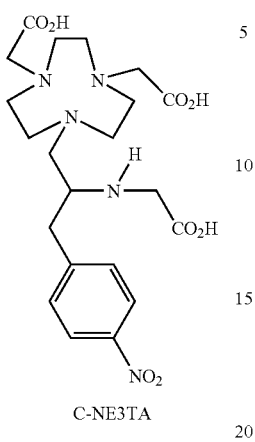
C-NE3TA
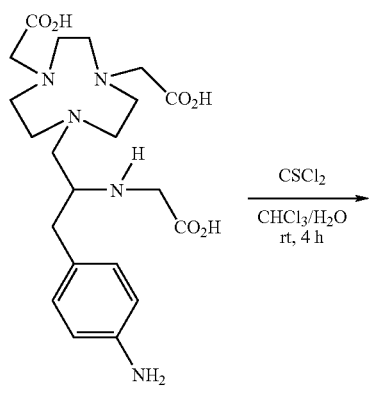
5
Scheme 13: Synthesis of C-NE3TA-NCS
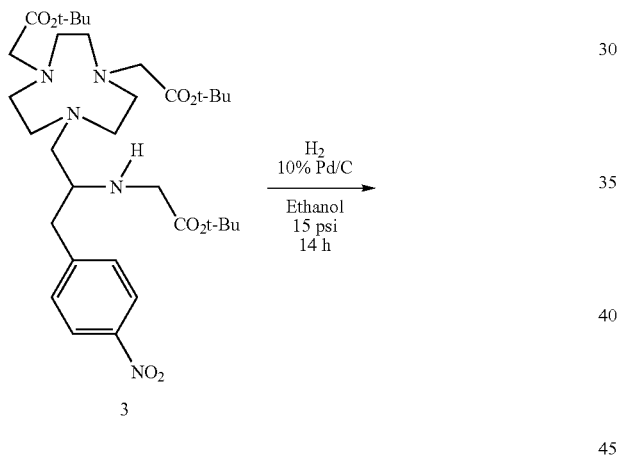
3
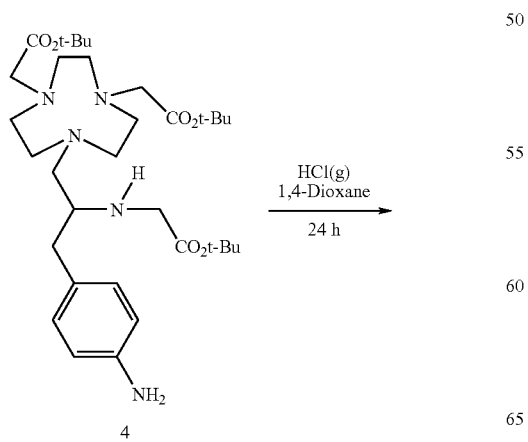
4
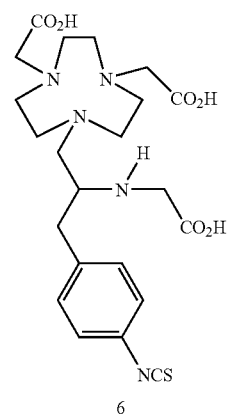
6

Scheme 14: Synthesis of bile acid-based polyaminocarboxylates
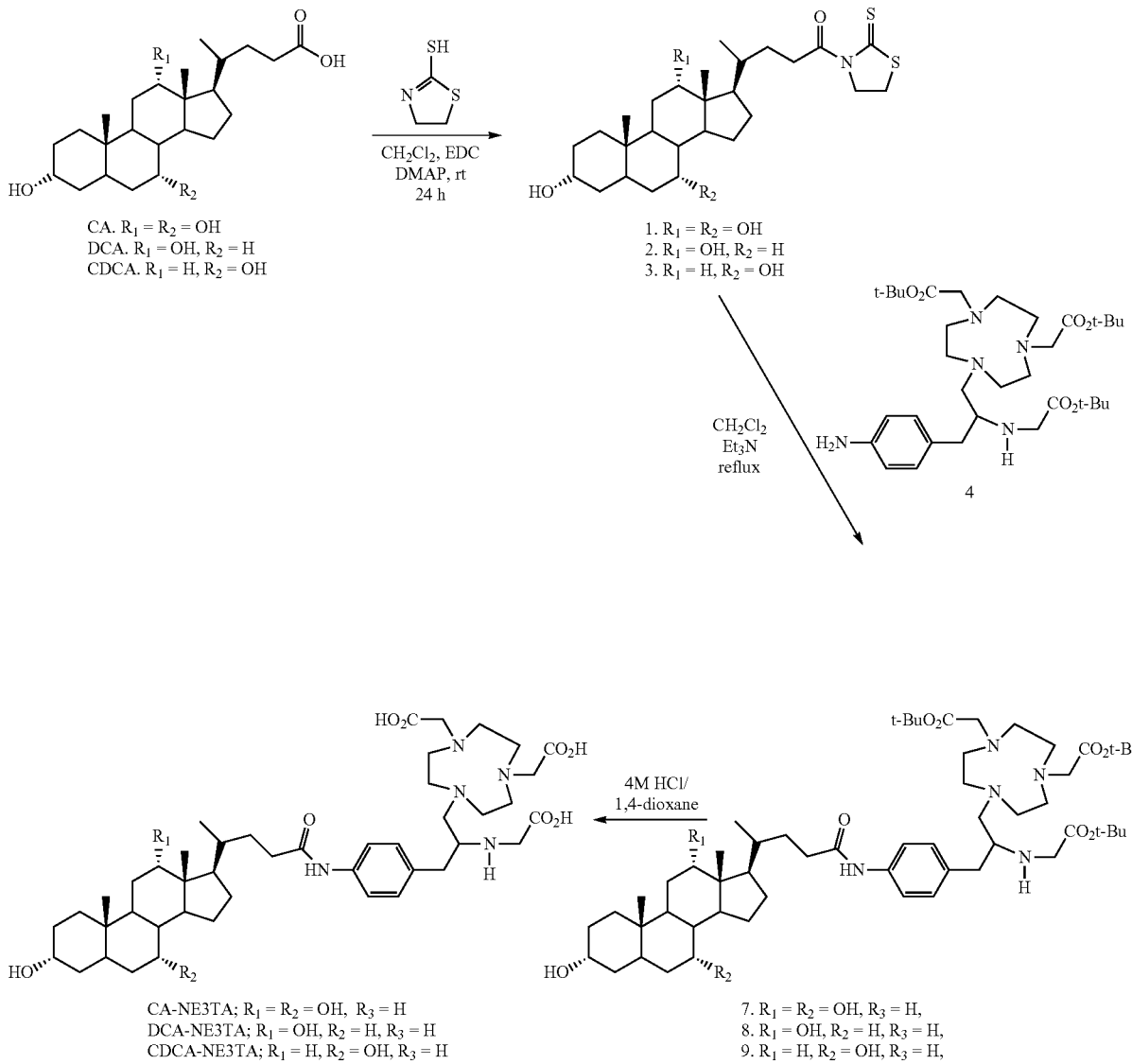
Scheme 15: Synthesis of NBD-CA-NE3TA
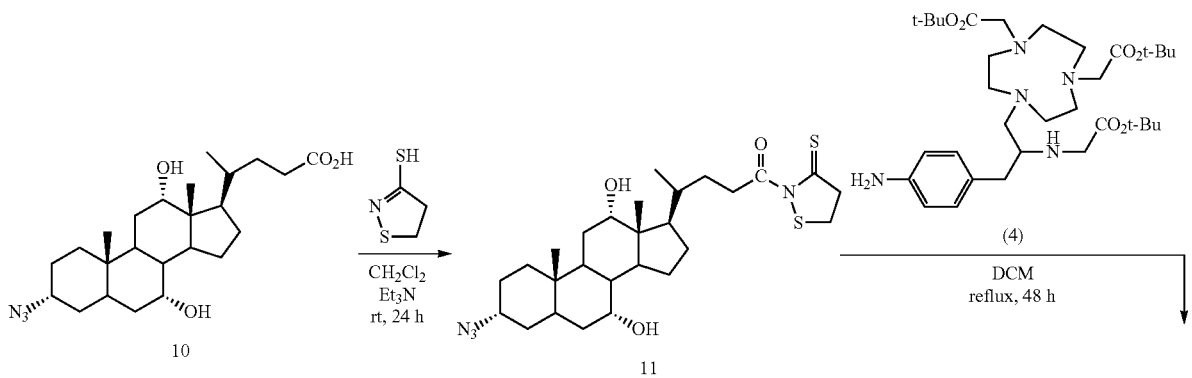

-continued
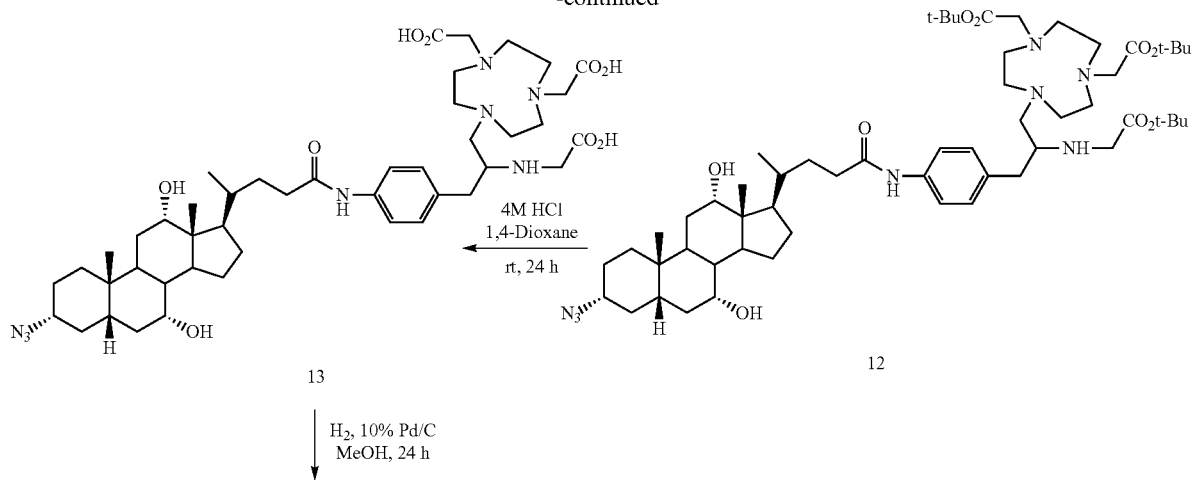
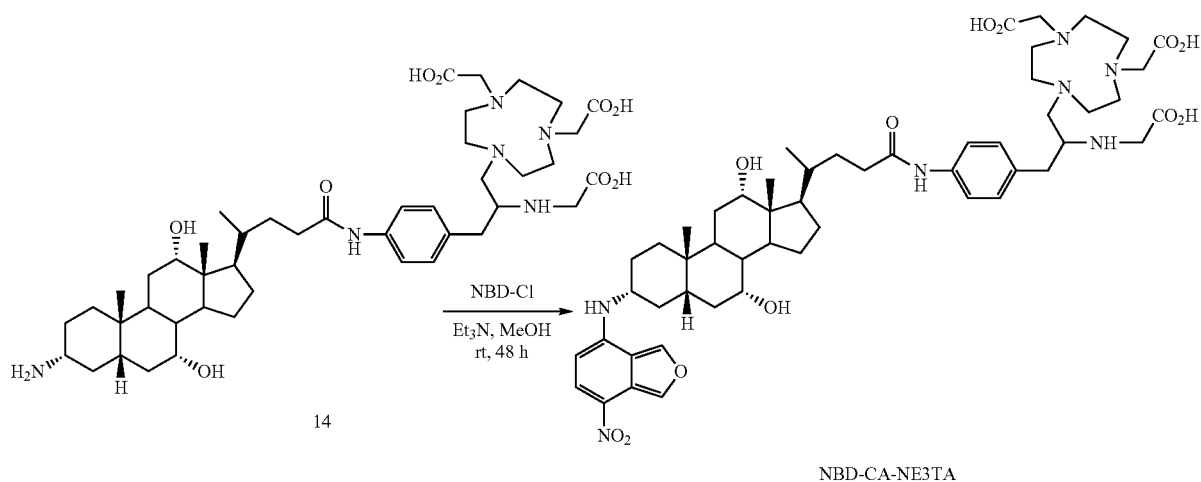
Scheme 16: Improved synthesis of C-NE3TA via reductive amination of 8 with 9
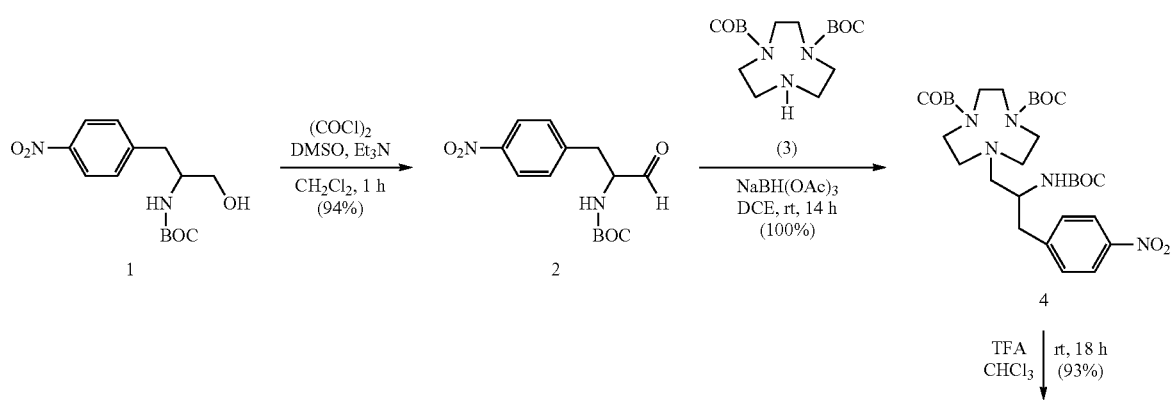

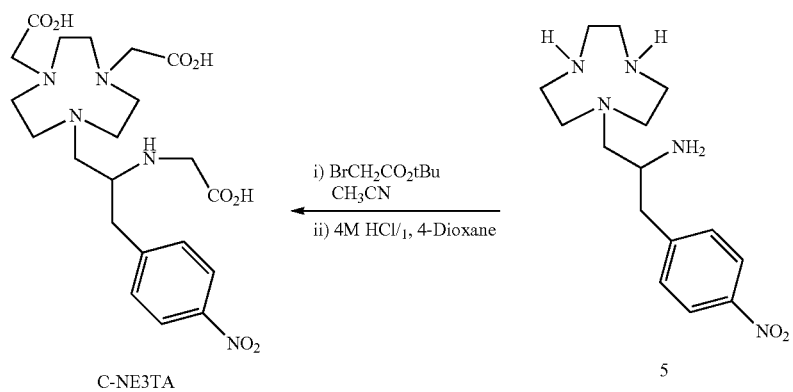
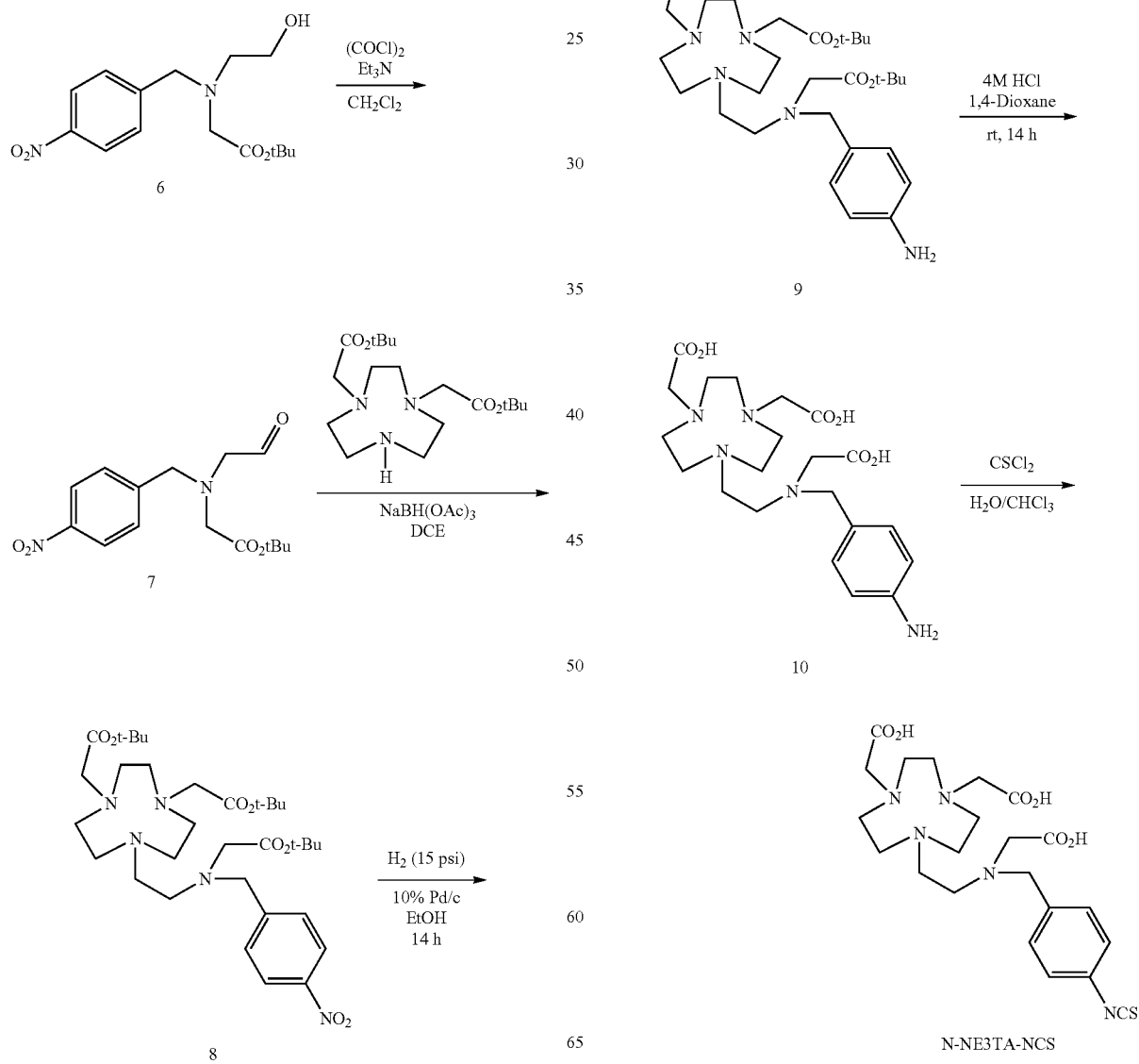
Scheme 17: Synthesis of N-NE3TA-NCS

Scheme 18. Formation of Aziridinum Cations 3 and 3' and ring-opened compounds 4 and 5
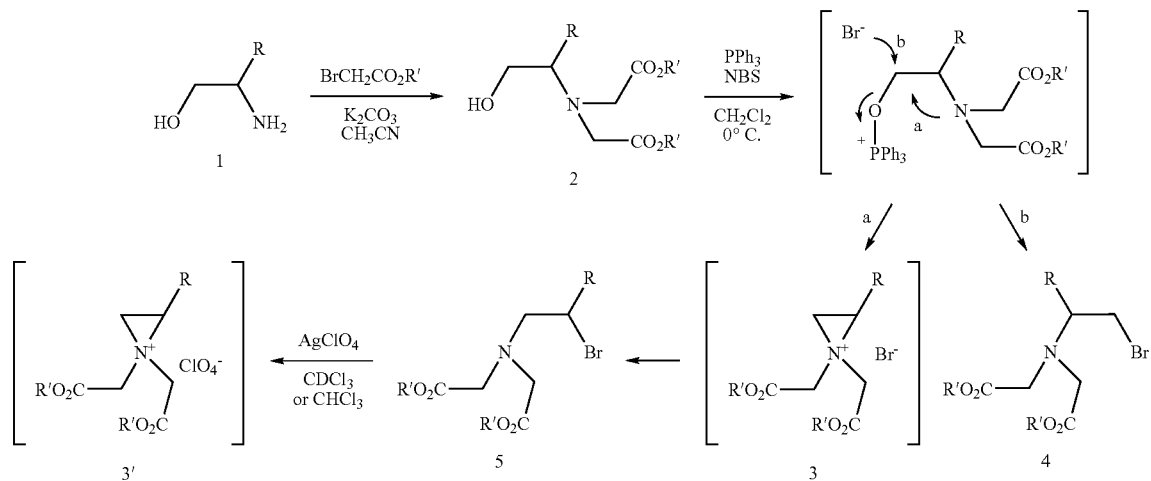
Scheme 19: Regioselective ring opening of aziridinium ions 3 and 4: Synthesis of precursor molecules 7 or 8 bimodal macrocyclic ligands
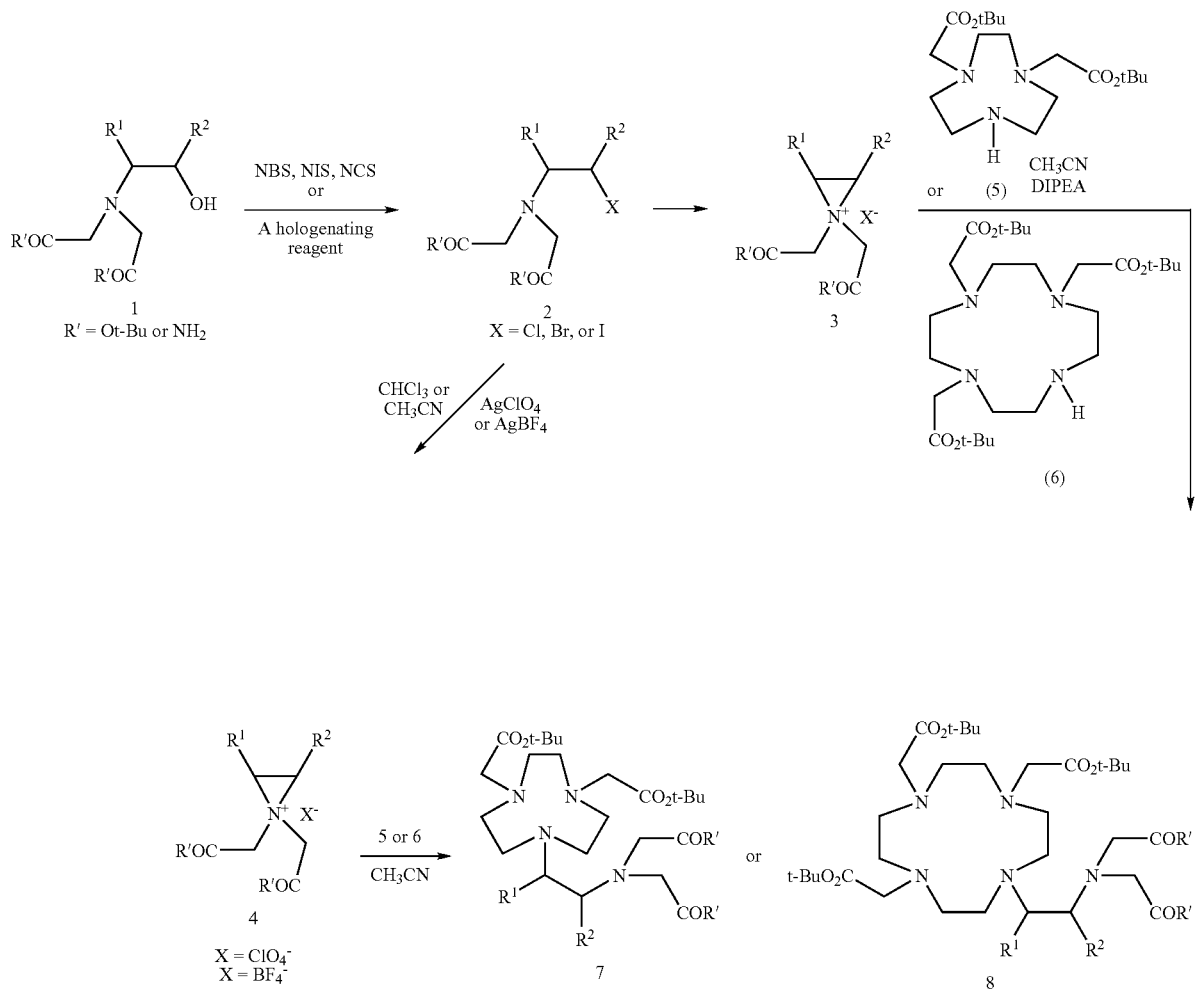

Starting material 1
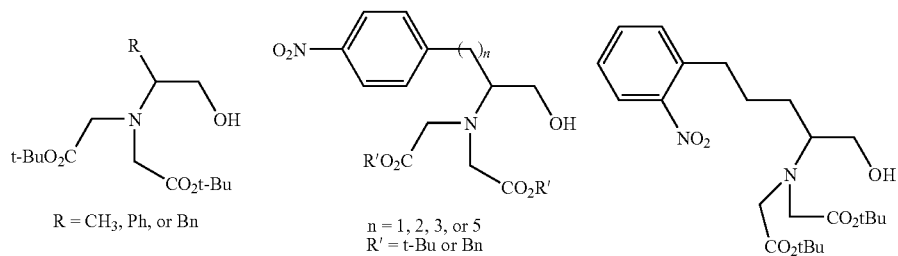
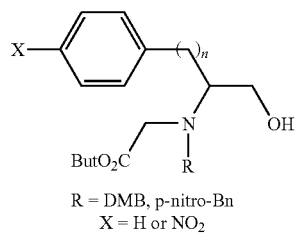
Product 7 and 8
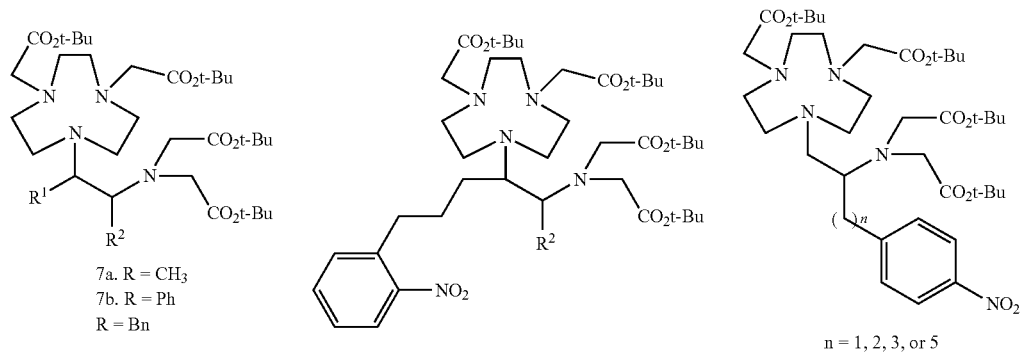
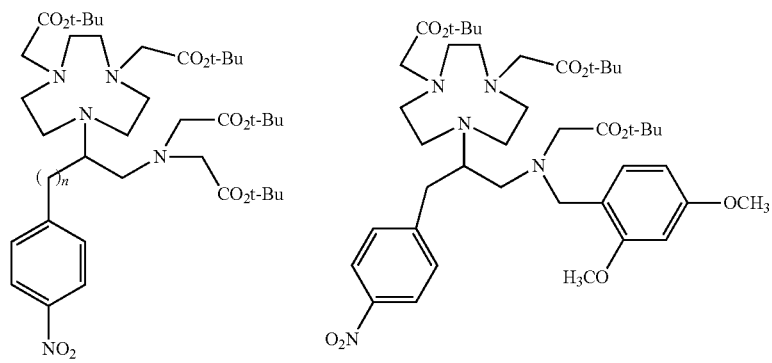
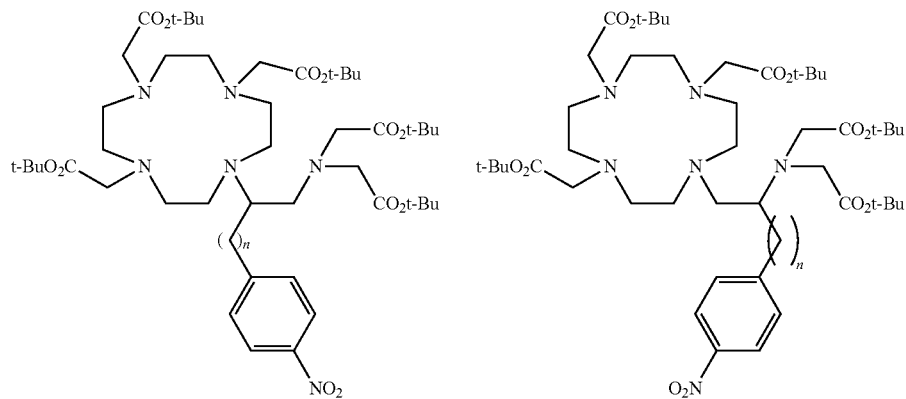

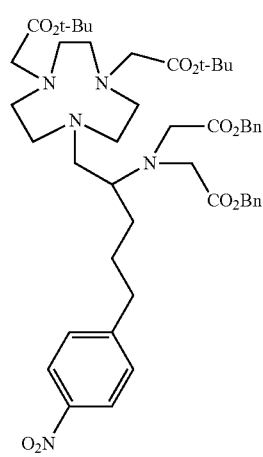
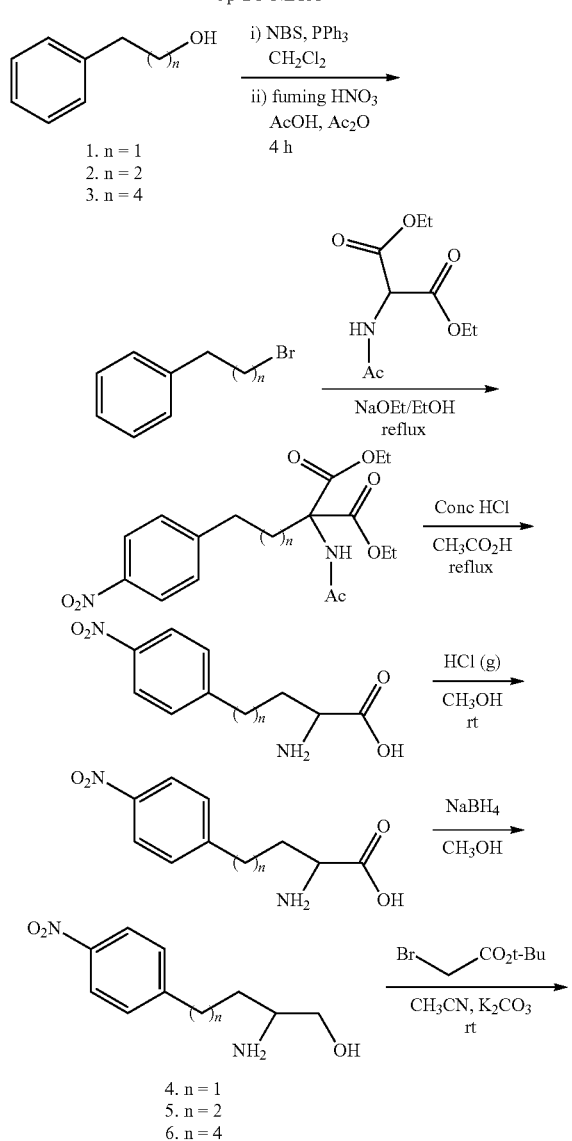
Scheme 20: Efficient Synthesis of 2p-2C-NETA, 3p-2C-NETA, and 5p-2C-NETA
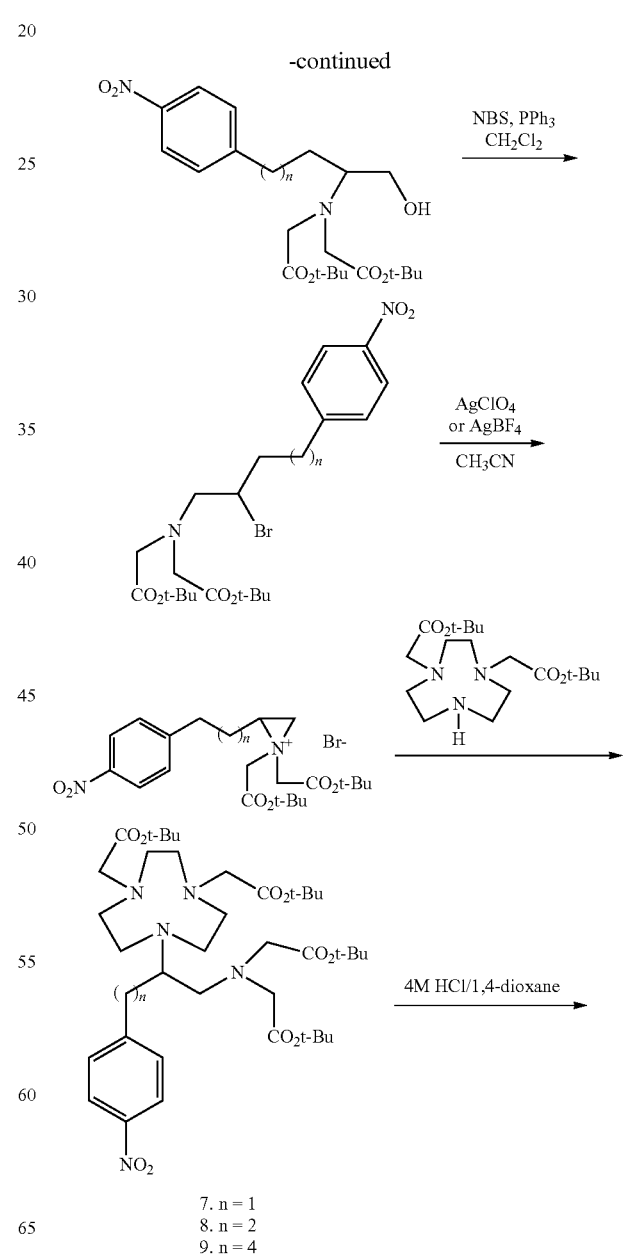

-continued

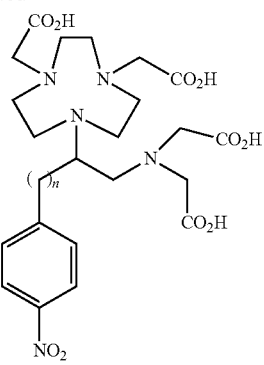

2p-2C-NETA. n = 1
3p-2C-NETA. n = 2
5p-2C=NETA. n = 4

What is claimed is:

1. A compound of formula (III):

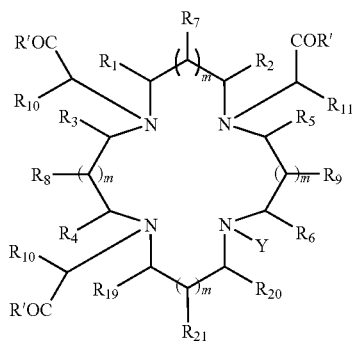

(III)

wherein: R' independently is OH, NH$_2$, or OR", wherein R" independently is alkyl, tert-butyl, allyl, benzyl, or a protecting group; m is 0 or 1; Y is a structure of formula (a-1):

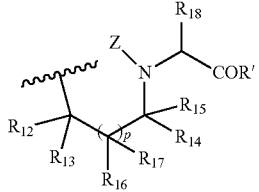

(a-1)

where p is 0 or 1; Z is hydrogen, CHR$_{18}$COR', or a group of formula (a-5), (a-6), or (a-7);

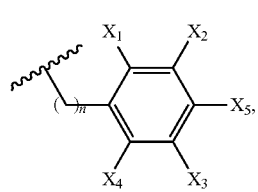

(a-5)

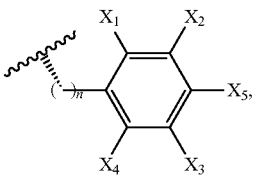

(a-6)

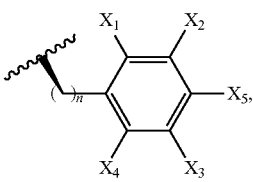

(a-7)

where n is 1-10 and each of X$_1$-X$_5$ independently is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydo, alkylamido, holoalkylamido, an ester containing group, an carbonyl containing group, an amide containing group, a thioamide containing group, or an amino acid-containing group; and each of R$^{1-21}$ independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, hydroxy, carboxyl, carboxyalkyloxy, amine, carboxylic acid, or holoalkylamido, aldehyde, ester, amido, tosyl, phthalimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, a protecting group, or the group of formula (a-5), (a-6), or (a-7); wherein at least one of R$^{1-21}$ comprises the group of formula (a-5), (a-6), or (a-7).

2. The compound according to claim 1, wherein at least one of R$^{1-9}$ or R$^{12-17}$ comprises a cycloalkyl formed with a neighboring carbon.

3. A complex comprising the compound of claim 1 and a metal ion, a radioactive isotope of the metal ion, or a radioactive isotope of carbon, nitrogen, iodine, fluorine, oxygen, or helium.

4. A conjugate comprising the compound of claim 1 and a targeting moiety, a fluorescence moiety, or a nanoparticle.

5. The conjugate according to claim 4, comprising the targeting moiety, wherein the targeting moiety comprises a biomolecule selected from a hormone, a bile acid, an amino acid, a peptide, a peptidomimetic, a protein, a deoxyribonucleic acid (DNA), a ribonucleic acid (RNA), a lipid, an albumin, a receptor molecule, a receptor binding molecule, a hapten, a monoclonal antibody, a polyclonal antibody, a peptide, an aptamer, a folic acid, an estrogen, or a transferrin.

6. A complex comprising the conjugate of claim 4 and a metal ion, a radioactive isotope of the metal ion, or a radioactive isotope of carbon, nitrogen, iodine, fluorine, oxygen, or helium.

7. A pharmaceutical composition comprising the compound of claim 1 and a pharmaceutically acceptable carrier.

8. The compound according to claim 1, wherein m is 0, Z is CHR$_{18}$COR', and at least one of R' of Z or formula (a-1) is not OH.

9. The compound according to claim 1, wherein each of Z and one of R$^{14-15}$ is a compound of the formula of (a-5), (a-6), or (a-7).

10. The compound according to claim 9, wherein at least one of R' of Z or formula (a-1) is $NH_2$.

11. The compound according to claim 1, wherein Z is hydrogen and one of $R^{14-15}$ is a compound of the formula of (a-5), (a-6), or (a-7).

12. The compound according to claim 1, wherein p is 1 and one of $R^{12-17}$ is a compound of the formula of (a-5), (a-6), or (a-7).

13. The compound according to claim 1, wherein $R^2$ is a compound of the formula of (a-5), (a-6), or (a-7).

14. A compound of formula (III-a):

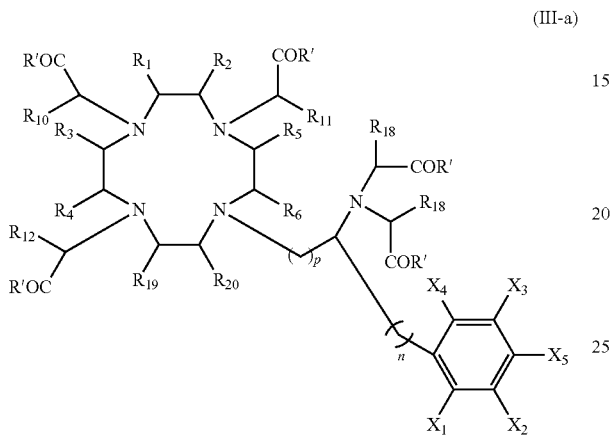

(III-a)

wherein: wherein p is 1 or 2 and n is 1 to 10; R' independently is OH, $NH_2$, or OR", wherein R" independently is alkyl, tert-butyl, allyl, benzyl, or a protecting group; each of $R^{1-6, 10-12, 18-20}$ independently is or includes hydrogen, carboxyalkyl, alkylamido, alkyl, allyl, benzyl, benzyloxyalkyl, cycloalkyl, alkoxy, hydroxyalkyl, aryl, aryloxy, hydroxyaryl, heteroaryl, phenyl, vinyl, alkynyl, alkenyl, furannylalkyl, alkylthioalkyl, arylhydroxyalkyl, indanyl, inolylalkyl, naphthylalkyl, imidazolylalkyl, pyridiylalkyl, benzothiophenylalkyl, thiophenylalkyl, thioalkyl, thioaryl, thiobenzyl, hydroxy, carboxyl, carboxyalkyloxy, amine, carboxylic acid, or holoalkylamido, aldehyde, ester, amido, tosyl, phthalimidyl, trityl, tert-butyloxycarbonyl, carbobenzyloxy, o-nosyl, acetyl, fluoroacetyl, dimethoxybenzyl, p-methoxybenzyl, an amide containing group, a thioamide containing group, an amino acid-containing group, an ester containing group, or a protecting group: and each of $X_1$-$X_5$ independently is or includes hydrogen, halo, cyano, alkyl, hydroxy, nitro, amino, alkylamino, thiocyano, isothiocyano, alkoxy, aryloxy, carboxyl, carboxyalkyl, carboxyalkyloxy, ester, amido, aldehydo, alkylamido, holoalkylamido, an ester containing group, an carbonyl containing group, an amide containing group, a thioamide containing group, or an amino acid-containing group.

15. A method of preparing a compound of claim 1, comprising:
chemically reacting a compound of formula (c-1) with a compound of (d-1) or (d-2)

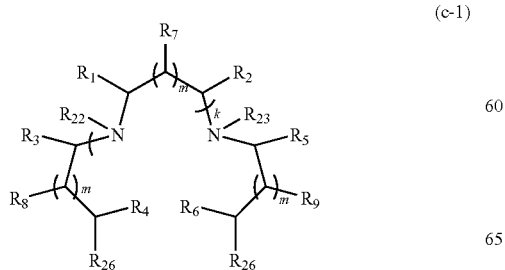

(c-1)

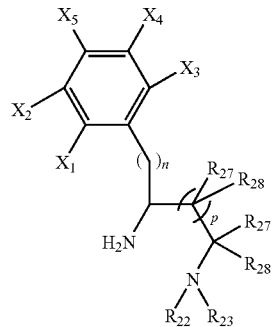

(d-1)

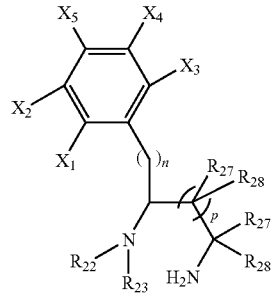

(d-2)

where, k is or 1; m is 0 or 1; n is 1 to 10; p is 0 or 1; $R^{26}$ is a leaving group and includes tosylate, chloride, bromide, mesylate, triflate, or iodide; $R^{27-28}$ is independently is or includes hydrogen, alkyl, allyl, benzyl, cycloalkyl, hydroxyalkyl, aryl, heteroaryl, phenyl, vinyl, or an oxo group; to provide a compound of formula (e-1) or (e-2), where k is 2:

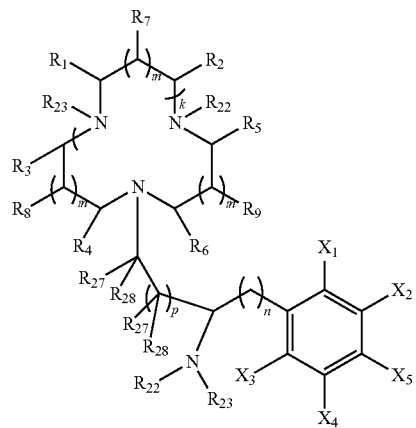

(e-1)

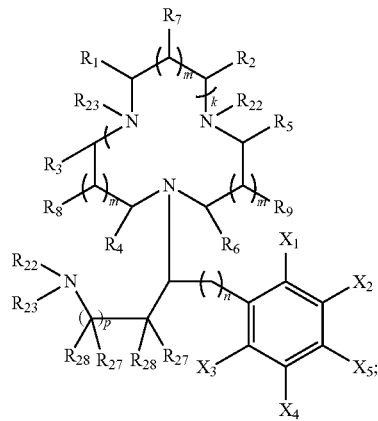

(e-2)

converting a compound of the formula (e-1) or (e-2), wherein $R^{22-23}$ is a protecting group, to a compound of the formula (e-3) or (e-4):

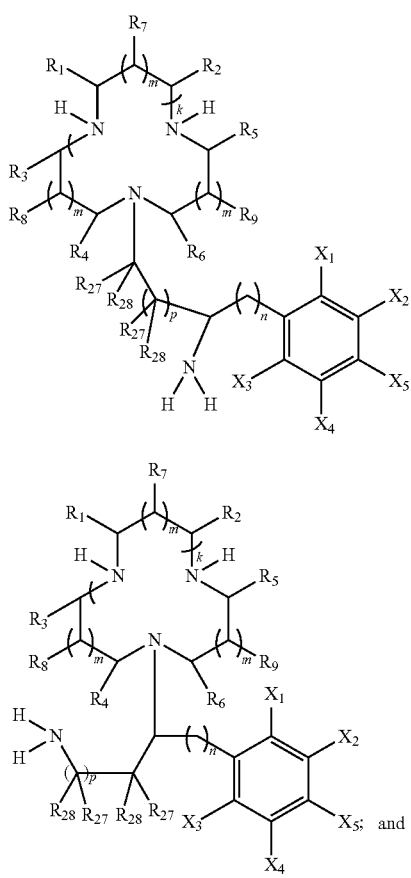

alkylating the compound of the formula (e3) or (e-4) to provide a compound according to formula (III).

16. The compound according to claim 1, wherein one of $R_{14-15}$ is a compound of the formula of (a-5), (a-6), or (a-7).

17. The compound according to claim 1, wherein at least one of R' of Z or formula (a-1) is $NH_2$.

18. The compound according to claim 1, wherein at least one R' of Z or of formula (a-1) is or includes tert-butoxy (O-tert-butyl).

19. The compound according to claim 1, wherein Z includes tert-butyloxycarbonyl and each R' is OR", wherein R" is tert-butyl.

20. The complex of claim 3, wherein the metal ion is selected from the group consisting of Ac, Al, Bi, Pb, Y, Mn, Cr, Fe, Co, Zn, Ni, Tc, Gd, In, Ga, Cu, Re, Sm, Pm, Ho, Zr, a lanthanide, and an actinide.

21. The complex of claim 6, wherein the metal ion is selected from the group consisting of Ac, Al, Bi, Pb, Y, Mn, Cr, Fe, Co, Zn, Ni, Tc, Gd, In, Ga, Cu, Re, Sm, Pm, Ho, Zr, a lanthanide, and an actinide.

22. The compound according to claim 1, wherein one of $R_{12-13}$ is a compound of the formula of (a-5), (a-6), or (a-7).

23. The compound according to claim 1, wherein at least one of: $R^2$ or one of $R^{12-17}$ comprises the group of formula (a-5), (a-6), or (a-7).

24. The compound according to claim 12, wherein Z is hydrogen.

25. The compound according to claim 1, wherein p is 1 and n is 3.

* * * * *